United States Patent
Gray et al.

(10) Patent No.: US 10,711,036 B2
(45) Date of Patent: Jul. 14, 2020

(54) MALT1 INHIBITORS AND USES THEREOF

(71) Applicants: Cornell University, Ithaca, NY (US); Dana-Farber Cancer Institute, Inc., Boston, MA (US); Children's Medical Center Corporation, Boston, MA (US)

(72) Inventors: Nathanael S. Gray, Boston, MA (US); David A. Scott, Newton, MA (US); John Hatcher, Marlborough, MA (US); Spandan Chennamadhavuni, Decatur, GA (US); Ari M. Melnick, New York, NY (US); Lorena Fontan Gabas, New York, NY (US); Hao Wu, Brookline, MA (US); Qi Qiao, Brighton, MA (US); Guangyan Du, Jamaica Plain, MA (US)

(73) Assignees: Cornell University, Ithaca, NY (US); Dana-Farber Cancer Institute, Inc., Boston, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 15/755,951

(22) PCT Filed: Aug. 26, 2016

(86) PCT No.: PCT/US2016/049038
§ 371 (c)(1),
(2) Date: Feb. 27, 2018

(87) PCT Pub. No.: WO2017/040304
PCT Pub. Date: Mar. 9, 2017

(65) Prior Publication Data
US 2018/0251489 A1    Sep. 6, 2018
US 2019/0389904 A2    Dec. 26, 2019

Related U.S. Application Data

(60) Provisional application No. 62/256,672, filed on Nov. 17, 2015, provisional application No. 62/211,629, filed on Aug. 28, 2015.

(51) Int. Cl.
| | |
|---|---|
| C07K 5/11 | (2006.01) |
| A61P 35/02 | (2006.01) |
| C07K 5/103 | (2006.01) |
| C07K 5/065 | (2006.01) |
| C07K 5/078 | (2006.01) |
| C07K 5/062 | (2006.01) |
| C07K 5/097 | (2006.01) |
| C07K 5/02 | (2006.01) |
| A61K 38/07 | (2006.01) |

(Continued)

(52) U.S. Cl.
CPC ............ *C07K 5/1019* (2013.01); *A61K 38/07* (2013.01); *A61P 35/02* (2018.01); *C07K 5/0205* (2013.01); *C07K 5/0606* (2013.01); *C07K 5/06052* (2013.01); *C07K 5/06078* (2013.01); *C07K 5/06139* (2013.01); *C07K 5/0821* (2013.01); *C07K 5/101* (2013.01); *A61K 38/00* (2013.01); *A61K 45/06* (2013.01)

(58) Field of Classification Search
None
See application file for complete search history.

(56) References Cited

U.S. PATENT DOCUMENTS

| | | |
|---|---|---|
| 5,210,272 A | 5/1993 | Palmer et al. |
| 6,291,678 B1 | 9/2001 | Berryman et al. |

(Continued)

FOREIGN PATENT DOCUMENTS

| | | |
|---|---|---|
| WO | WO 2009/060835 A1 | 11/2008 |
| WO | WO 2012/071414 A2 | 5/2012 |

(Continued)

OTHER PUBLICATIONS

Isidro-Llobet et al. Amino Acid-Protecting Groups, Chem Rev. 2009, 109, 2455-2504 (Year: 2009).*

(Continued)

*Primary Examiner* — Christina Bradley
(74) *Attorney, Agent, or Firm* — Wolf, Greenfield & Sacks, P.C.

(57) ABSTRACT

Provided herein are compounds of Formula (I) and pharmaceutical compositions thereof, which may be useful as MALT1 inhibitors. Also provided are for the treatment of proliferative disorders (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease) by administering a compound of Formula (I).

34 Claims, 5 Drawing Sheets
Specification includes a Sequence Listing.

(51) Int. Cl.
*A61K 38/00* (2006.01)
*A61K 45/06* (2006.01)

(56) References Cited

U.S. PATENT DOCUMENTS

| | | | |
|---|---|---|---|
| 6,806,274 | B1 | 10/2004 | Crawley et al. |
| 2015/0291562 | A1 | 10/2015 | Crew et al. |
| 2019/0263785 | A1 | 8/2019 | Melnick et al. |

FOREIGN PATENT DOCUMENTS

| | | |
|---|---|---|
| WO | WO 2014/074815 A1 | 5/2014 |
| WO | WO 2015/181747 A1 | 12/2015 |

OTHER PUBLICATIONS

International Search Report and Written Opinion for PCT/US2016/049038, dated Jan. 19, 2017.
International Preliminary Report on Patentability for PCT/US2016/049038, dated Mar. 15, 2018.
Angliker et al., Synthesis and properties of peptidyl derivatives of arginylfluoromethanes. Biochem J. Dec. 1, 1988;256(2):481-6.
Afonina et al., MALT1—a universal soldier: multiple strategies to ensure NF-κB activation and target gene expression. FEBS Journal 2015;282(17):3286-3297.
Alizadeh et al., Distinct types of diffuse large B-cell lymphoma identified by gene expression profiling. Nature. Feb. 3, 2000;403(6769):503-11.
Baens et al., MALT1 auto-proteolysis is essential for NF-κB-dependent gene transcription in activated lymphocytes. PLoS One. Aug. 8, 2014;9(8):e103774. doi: 10.1371/journal.pone.0103774. eCollection 2014.
Coorneart et al., T cell antigen receptor stimulation induces MALT1 paracaspase-mediated cleavage of the NF-kappaB inhibitor A20. Nat Immunol. Mar. 2008;9(3):263-71. doi: 10.1038/ni1561. Epub Jan. 27, 2008.
Davis et al., Chronic active B-cell-receptor signalling in diffuse large B-cell lymphoma. Nature. Jan. 7, 2010;463(7277):88-92. doi: 10.1038/nature08638.
Fontan et al., MALT1 small molecule inhibitors specifically suppress ABC-DLBCL in vitro and in vivo. Cancer Cell. Dec. 11, 2012;22(6):812-24. doi: 10.1016/j.ccr.2012.11.003.
Hailfinger et al., Essential role of MALT1 protease activity in activated B cell-like diffuse large B-cell lymphoma. PNAS 2009;106(47):19946-19951. https://doi.org/10.1073/pnas.0907511106.
Halifinger et al., Malt1-dependent RelB cleavage promotes canonical NF-κB activation in lymphocytes and lymphoma cell lines. PNAS Aug. 2011;108(35):14596-14601. https://doi.org/10.1073/pnas.1105020108.
Jelesch et al., Cleavage of roquin and regnase-1 by the paracaspase MALT1 releases their cooperatively repressed targets to promote T(H)17 differentiation. Nat Immunol. Nov. 2014;15(11):1079-89. doi: 10.1038/ni.3008. Epub Oct. 5, 2014.
Nagel et al., Pharmacologic inhibition of MALT1 protease by phenothiazines as a therapeutic approach for the treatment of aggressive ABC-DLBCL. Cancer Cell. Dec. 11, 2012;22(6):825-37. doi: 10.1016/j.ccr.2012.11.002.
Nie et al., Conversion of the LIMA1 tumour suppressor into an oncogenic LMO-like protein by API2-MALT1 in MALT lymphoma. Nat. Commun. 2015;6:5908.
Rebeaud et al., The proteolytic activity of the paracaspase MALT1 is key in T cell activation. Nat Immunol. Mar. 2008;9(3):272-81. doi: 10.1038/ni1568. Epub Feb. 10, 2008.
Rosebeck et al., Cleavage of NIK by the API2-MALT1 fusion oncoprotein leads to noncanonical NF-kappaB activation. Science. Jan. 28, 2011;331(6016):468-72. doi: 10.1126/science.1198946.
Rosenwald et al., The use of molecular profiling to predict survival after chemotherapy for diffuse large-B-cell lymphoma. N Engl J Med. Jun. 20, 2002;346(25):1937-47.
Ruefli-Brasse et al., Regulation of NF-kappaB-dependent lymphocyte activation and development by paracaspase. Science. Nov. 28, 2003;302(5650):1581-4. Epub Oct. 23, 2003.
Ruland et al., Differential requirement for Malt1 in T and B cell antigen receptor signaling. Immunity. Nov. 2003;19(5):749-58.
Staal et al., T-cell receptor-induced JNK activation requires proteolytic inactivation of CYLD by MALT1. EMBO J. May 4, 2011;30(9):1742-52. doi: 10.1038/emboj.2011.85. Epub Mar. 29, 2011.
Uehata et al., Malt1-induced cleavage of regnase-1 in CD4(+) helper T cells regulates immune activation. Cell. May 23, 2013;153(5):1036-49. doi: 10.1016/j.cell.2013.04.034.
Extended European Search Report for Application No. EP16842694.8 dated Apr. 3, 2019.
International Search Report and Written Opinion for Application No. PCT/US2017/059234 dated Feb. 20, 2018.
International Preliminary Report on Patentability for Application No. PCT/US2017/059234 dated May 16, 2019.
Arora et al., Cellular proteolytic modification of tumor-suppressor CYLD is critical for the initiation of human T-cell acute lymphoblastic leukemia. Blood Cells Mol Dis. 2015, 54(1):132-138.
Caputo et al., Synthesis of benzothiazole derivatives and their biological evaluation as anticancer agents. Med Chem Res. 2012; 21(9):2644-2651.
Farinha et al., Molecular pathogenesis of mucosa-associated lymphoid tissue lymphoma. J Clin Oncol. Sep. 10, 2005;23(26):6370-8.
Fontan et al., Specific covalent inhibition of MALT1 paracaspase suppresses B cell lymphoma growth. J Clin Invest. Oct. 1, 2018;128(10):4397-4412. doi: 10.1172/JCI99436. Epub Jul. 19, 2018.
Mcguire et al., Pharmacological inhibition of MALT1 protease activity protects mice in a mouse model of multiple sclerosis. J Neuroinflammation. Jul. 21, 2014;11:124. doi: 10.1186/1742-2094-11-124.
Pan et al., MALT1 is required for EGFR-induced NF-κB activation and contributes to EGFR-driven lung cancer progression. Oncogene. Feb. 18, 2016;35(7):919-28. doi: 10.1038/onc.2015.146. Epub May 18, 2015.
Yu et al., Crystal structure of the mucosa-associated lymphoid tissue lymphoma translocation 1 (MALT1) paracaspase region Proc Natl Acad Sci U S A. Dec. 27, 2011;108(52):21004-9. doi: 10.1073/pnas.1111708108. Epub Dec. 7, 2011.

* cited by examiner

SEQUENCE LISTING

```
<160> NUMBER OF SEQ ID NOS: 3

<210> SEQ ID NO 1
<211> LENGTH: 824
<212> TYPE: PRT
<213> ORGANISM: Homo sapiens

<400> SEQUENCE: 1

Met Ser Leu Leu Gly Asp Pro Leu Gln Ala Leu Pro Pro Ser Ala Ala
1               5                   10                  15

Pro Thr Gly Pro Leu Leu Ala Pro Pro Ala Gly Ala Thr Leu Asn Arg
            20                  25                  30

Leu Arg Glu Pro Leu Leu Arg Arg Leu Ser Glu Leu Leu Asp Gln Ala
        35                  40                  45

Pro Glu Gly Arg Gly Trp Arg Arg Leu Ala Glu Leu Ala Gly Ser Arg
    50                  55                  60

Gly Arg Leu Arg Leu Ser Cys Leu Asp Leu Glu Gln Cys Ser Leu Lys
65                  70                  75                  80

Val Leu Glu Pro Glu Gly Ser Pro Ser Leu Cys Leu Leu Lys Leu Met
                85                  90                  95
```

-continued

```
Gly Glu Lys Gly Cys Thr Val Thr Glu Leu Ser Asp Phe Leu Gln Ala
            100                 105                 110
Met Glu His Thr Glu Val Leu Gln Leu Leu Ser Pro Pro Gly Ile Lys
            115                 120                 125
Ile Thr Val Asn Pro Glu Ser Lys Ala Val Leu Ala Gly Gln Phe Val
        130                 135                 140
Lys Leu Cys Cys Arg Ala Thr Gly His Pro Phe Val Gln Tyr Gln Trp
145                 150                 155                 160
Phe Lys Met Asn Lys Glu Ile Pro Asn Gly Asn Thr Ser Glu Leu Ile
                165                 170                 175
Phe Asn Ala Val His Val Lys Asp Ala Gly Phe Tyr Val Cys Arg Val
            180                 185                 190
Asn Asn Asn Phe Thr Phe Glu Phe Ser Gln Trp Ser Gln Leu Asp Val
            195                 200                 205
Cys Asp Ile Pro Glu Ser Phe Gln Arg Ser Val Asp Gly Val Ser Glu
    210                 215                 220
Ser Lys Leu Gln Ile Cys Val Glu Pro Thr Ser Gln Lys Leu Met Pro
225                 230                 235                 240
Gly Ser Thr Leu Val Leu Gln Cys Val Ala Val Gly Ser Pro Ile Pro
                245                 250                 255
His Tyr Gln Trp Phe Lys Asn Glu Leu Pro Leu Thr His Glu Thr Lys
            260                 265                 270
Lys Leu Tyr Met Val Pro Tyr Val Asp Leu Glu His Gln Gly Thr Tyr
            275                 280                 285
Trp Cys His Val Tyr Asn Asp Arg Asp Ser Gln Asp Ser Lys Lys Val
    290                 295                 300
Glu Ile Ile Ile Gly Arg Thr Asp Glu Ala Val Glu Cys Thr Glu Asp
305                 310                 315                 320
Glu Leu Asn Asn Leu Gly His Pro Asp Asn Lys Glu Gln Thr Thr Asp
                325                 330                 335
Gln Pro Leu Ala Lys Asp Lys Val Ala Leu Leu Ile Gly Asn Met Asn
            340                 345                 350
Tyr Arg Glu His Pro Lys Leu Lys Ala Pro Leu Val Asp Val Tyr Glu
            355                 360                 365
Leu Thr Asn Leu Leu Arg Gln Leu Asp Phe Lys Val Val Ser Leu Leu
    370                 375                 380
Asp Leu Thr Glu Tyr Glu Met Arg Asn Ala Val Asp Glu Phe Leu Leu
385                 390                 395                 400
Leu Leu Asp Lys Gly Val Tyr Gly Leu Leu Tyr Tyr Ala Gly His Gly
                405                 410                 415
Tyr Glu Asn Phe Gly Asn Ser Phe Met Val Pro Val Asp Ala Pro Asn
            420                 425                 430
Pro Tyr Arg Ser Glu Asn Cys Leu Cys Val Gln Asn Ile Leu Lys Leu
        435                 440                 445
Met Gln Glu Lys Glu Thr Gly Leu Asn Val Phe Leu Leu Asp Met Cys
            450                 455                 460
Arg Lys Arg Asn Asp Tyr Asp Asp Thr Ile Pro Ile Leu Asp Ala Leu
465                 470                 475                 480
Lys Val Thr Ala Asn Ile Val Phe Gly Tyr Ala Thr Cys Gln Gly Ala
                485                 490                 495
Glu Ala Phe Glu Ile Gln His Ser Gly Leu Ala Asn Gly Ile Phe Met
            500                 505                 510
Lys Phe Leu Lys Asp Arg Leu Leu Glu Asp Lys Lys Ile Thr Val Leu
```

```
                515                 520                 525
Leu Asp Glu Val Ala Glu Asp Met Gly Lys Cys His Leu Thr Lys Gly
    530                 535                 540

Lys Gln Ala Leu Glu Ile Arg Ser Ser Leu Ser Glu Lys Arg Ala Leu
545                 550                 555                 560

Thr Asp Pro Ile Gln Gly Thr Glu Tyr Ser Ala Glu Ser Leu Val Arg
                565                 570                 575

Asn Leu Gln Trp Ala Lys Ala His Glu Leu Pro Glu Ser Met Cys Leu
            580                 585                 590

Lys Phe Asp Cys Gly Val Gln Ile Gln Leu Gly Phe Ala Ala Glu Phe
        595                 600                 605

Ser Asn Val Met Ile Ile Tyr Thr Ser Ile Val Tyr Lys Pro Pro Glu
    610                 615                 620

Ile Ile Met Cys Asp Ala Tyr Val Thr Asp Phe Pro Leu Asp Leu Asp
625                 630                 635                 640

Ile Asp Pro Lys Asp Ala Asn Lys Gly Thr Pro Glu Glu Thr Gly Ser
                645                 650                 655

Tyr Leu Val Ser Lys Asp Leu Pro Lys His Cys Leu Tyr Thr Arg Leu
            660                 665                 670

Ser Ser Leu Gln Lys Leu Lys Glu His Leu Val Phe Thr Val Cys Leu
        675                 680                 685

Ser Tyr Gln Tyr Ser Gly Leu Glu Asp Thr Val Glu Asp Lys Gln Glu
    690                 695                 700

Val Asn Val Gly Lys Pro Leu Ile Ala Lys Leu Asp Met His Arg Gly
705                 710                 715                 720

Leu Gly Arg Lys Thr Cys Phe Gln Thr Cys Leu Met Ser Asn Gly Pro
                725                 730                 735

Tyr Gln Ser Ser Ala Ala Thr Ser Gly Gly Ala Gly His Tyr His Ser
            740                 745                 750

Leu Gln Asp Pro Phe His Gly Val Tyr His Ser His Pro Gly Asn Pro
        755                 760                 765

Ser Asn Val Thr Pro Ala Asp Ser Cys His Cys Ser Arg Thr Pro Asp
    770                 775                 780

Ala Phe Ile Ser Ser Phe Ala His His Ala Ser Cys His Phe Ser Arg
785                 790                 795                 800

Ser Asn Val Pro Val Glu Thr Thr Asp Glu Ile Pro Phe Ser Phe Ser
                805                 810                 815

Asp Arg Leu Arg Ile Ser Glu Lys
            820

<210> SEQ ID NO 2
<211> LENGTH: 813
<212> TYPE: PRT
<213> ORGANISM: Homo sapiens

<400> SEQUENCE: 2

Met Ser Leu Leu Gly Asp Pro Leu Gln Ala Leu Pro Pro Ser Ala Ala
1               5                   10                  15

Pro Thr Gly Pro Leu Leu Ala Pro Pro Ala Gly Ala Thr Leu Asn Arg
            20                  25                  30

Leu Arg Glu Pro Leu Leu Arg Arg Leu Ser Glu Leu Leu Asp Gln Ala
        35                  40                  45

Pro Glu Gly Arg Gly Trp Arg Arg Leu Ala Glu Leu Ala Gly Ser Arg
    50                  55                  60
```

-continued

```
Gly Arg Leu Arg Leu Ser Cys Leu Asp Leu Glu Gln Cys Ser Leu Lys
 65                  70                  75                  80

Val Leu Glu Pro Glu Gly Ser Pro Ser Leu Cys Leu Leu Lys Leu Met
                 85                  90                  95

Gly Glu Lys Gly Cys Thr Val Thr Glu Leu Ser Asp Phe Leu Gln Ala
            100                 105                 110

Met Glu His Thr Glu Val Leu Gln Leu Leu Ser Pro Pro Gly Ile Lys
        115                 120                 125

Ile Thr Val Asn Pro Glu Ser Lys Ala Val Leu Ala Gly Gln Phe Val
    130                 135                 140

Lys Leu Cys Cys Arg Ala Thr Gly His Pro Phe Val Gln Tyr Gln Trp
145                 150                 155                 160

Phe Lys Met Asn Lys Glu Ile Pro Asn Gly Asn Thr Ser Glu Leu Ile
                165                 170                 175

Phe Asn Ala Val His Val Lys Asp Ala Gly Phe Tyr Val Cys Arg Val
            180                 185                 190

Asn Asn Asn Phe Thr Phe Glu Phe Ser Gln Trp Ser Gln Leu Asp Val
        195                 200                 205

Cys Asp Ile Pro Glu Ser Phe Gln Arg Ser Val Asp Gly Val Ser Glu
    210                 215                 220

Ser Lys Leu Gln Ile Cys Val Glu Pro Thr Ser Gln Lys Leu Met Pro
225                 230                 235                 240

Gly Ser Thr Leu Val Leu Gln Cys Val Ala Val Gly Ser Pro Ile Pro
                245                 250                 255

His Tyr Gln Trp Phe Lys Asn Glu Leu Pro Leu Thr His Glu Thr Lys
            260                 265                 270

Lys Leu Tyr Met Val Pro Tyr Val Asp Leu Glu His Gln Gly Thr Tyr
        275                 280                 285

Trp Cys His Val Tyr Asn Asp Arg Asp Ser Gln Asp Ser Lys Lys Val
    290                 295                 300

Glu Ile Ile Ile Asp Glu Leu Asn Asn Leu Gly His Pro Asp Asn Lys
305                 310                 315                 320

Glu Gln Thr Thr Asp Gln Pro Leu Ala Lys Asp Lys Val Ala Leu Leu
                325                 330                 335

Ile Gly Asn Met Asn Tyr Arg Glu His Pro Lys Leu Lys Ala Pro Leu
            340                 345                 350

Val Asp Val Tyr Glu Leu Thr Asn Leu Leu Arg Gln Leu Asp Phe Lys
        355                 360                 365

Val Val Ser Leu Leu Asp Leu Thr Glu Tyr Glu Met Arg Asn Ala Val
370                 375                 380

Asp Glu Phe Leu Leu Leu Leu Asp Lys Gly Val Tyr Gly Leu Leu Tyr
385                 390                 395                 400

Tyr Ala Gly His Gly Tyr Glu Asn Phe Gly Asn Ser Phe Met Val Pro
                405                 410                 415

Val Asp Ala Pro Asn Pro Tyr Arg Ser Glu Asn Cys Leu Cys Val Gln
            420                 425                 430

Asn Ile Leu Lys Leu Met Gln Glu Lys Glu Thr Gly Leu Asn Val Phe
        435                 440                 445

Leu Leu Asp Met Cys Arg Lys Arg Asn Asp Tyr Asp Asp Thr Ile Pro
    450                 455                 460

Ile Leu Asp Ala Leu Lys Val Thr Ala Asn Ile Val Phe Gly Tyr Ala
465                 470                 475                 480

Thr Cys Gln Gly Ala Glu Ala Phe Glu Ile Gln His Ser Gly Leu Ala
```

```
                            485                 490                 495
Asn Gly Ile Phe Met Lys Phe Leu Lys Asp Arg Leu Leu Glu Asp Lys
                    500                 505                 510

Lys Ile Thr Val Leu Leu Asp Glu Val Ala Glu Asp Met Gly Lys Cys
                515                 520                 525

His Leu Thr Lys Gly Lys Gln Ala Leu Glu Ile Arg Ser Ser Leu Ser
            530                 535                 540

Glu Lys Arg Ala Leu Thr Asp Pro Ile Gln Gly Thr Glu Tyr Ser Ala
545                 550                 555                 560

Glu Ser Leu Val Arg Asn Leu Gln Trp Ala Lys Ala His Glu Leu Pro
                565                 570                 575

Glu Ser Met Cys Leu Lys Phe Asp Cys Gly Val Gln Ile Gln Leu Gly
                580                 585                 590

Phe Ala Ala Glu Phe Ser Asn Val Met Ile Ile Tyr Thr Ser Ile Val
            595                 600                 605

Tyr Lys Pro Pro Glu Ile Ile Met Cys Asp Ala Tyr Val Thr Asp Phe
        610                 615                 620

Pro Leu Asp Leu Asp Ile Asp Pro Lys Asp Ala Asn Lys Gly Thr Pro
625                 630                 635                 640

Glu Glu Thr Gly Ser Tyr Leu Val Ser Lys Asp Leu Pro Lys His Cys
                645                 650                 655

Leu Tyr Thr Arg Leu Ser Ser Leu Gln Lys Leu Lys Glu His Leu Val
            660                 665                 670

Phe Thr Val Cys Leu Ser Tyr Gln Tyr Ser Gly Leu Glu Asp Thr Val
        675                 680                 685

Glu Asp Lys Gln Glu Val Asn Val Gly Lys Pro Leu Ile Ala Lys Leu
    690                 695                 700

Asp Met His Arg Gly Leu Gly Arg Lys Thr Cys Phe Gln Thr Cys Leu
705                 710                 715                 720

Met Ser Asn Gly Pro Tyr Gln Ser Ser Ala Ala Thr Ser Gly Gly Ala
                725                 730                 735

Gly His Tyr His Ser Leu Gln Asp Pro Phe His Gly Val Tyr His Ser
            740                 745                 750

His Pro Gly Asn Pro Ser Asn Val Thr Pro Ala Asp Ser Cys His Cys
        755                 760                 765

Ser Arg Thr Pro Asp Ala Phe Ile Ser Ser Phe Ala His His Ala Ser
    770                 775                 780

Cys His Phe Ser Arg Ser Asn Val Pro Val Glu Thr Thr Asp Glu Ile
785                 790                 795                 800

Pro Phe Ser Phe Ser Asp Arg Leu Arg Ile Ser Glu Lys
                805                 810

<210> SEQ ID NO 3
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 3

Met Ala Gly Pro His Pro Val Ile Val Ile Thr Gly Pro His Glu Glu
1               5                   10                  15
```

MALT1 INHIBITORS AND USES THEREOF

RELATED APPLICATIONS

The present application is a national stage filing under 35 U.S.C. § 371 of international PCT application, PCT/US2016/049038, filed Aug. 26, 2016, which claims priority under 35 U.S.C. § 119(e) to U.S. provisional patent applications, U.S. Ser. No. 62/211,629, filed Aug. 28, 2015, and U.S. Ser. No. 62/256,672, filed Nov. 17, 2015, each of which is incorporated herein by reference.

GOVERNMENT SUPPORT

This invention was made with government support under Grant Number R01 CA182736 awarded by the National Institutes of Health. The government has certain rights in the invention.

BACKGROUND

Diffuse large B-cell lymphoma (DLBCL) accounts for about 25% of all lymphoma cases. [1]. Subtypes of DLBCL identified by gene expression profiling include germinal center B-cell-like (GCB) DLBCL, activated B-cell-like (ABC) DLBCL and primary mediastinal B-cell lymphoma (PMBL) [2,3]. Patients with the GCB subtype have a significantly better overall survival compared to those with the ABC subtype. [2,3]

ABC-DLBCL is characterized by its reliance on the oncogenic activation of the NF-κB pathway. [4] Mucosa-associated lymphoid tissue lymphoma translocation protein 1 (MALT1) functions in an essential role in NF-κB signaling downstream of T-cell receptors (TCR) and B-cell receptors (BCR) [5]. MALT1 has also been shown to facilitate lymphocyte proliferation, activation, and cytokine production. [6,7] In NF-κB signaling, MALT1 functions as a scaffold protein and forms a complex, referred to as the CBM complex, with caspase recruitment domain family member 11 (CARD11) and B-cell lymphoma 10 (B-cell 10). Through a mechanism mediated by ubiquination of the CBM complex, multiple downstream NF-κB signals are activated to ultimately induce proteasomal degradation of IκBα and release NF-κB for nuclear translocation. [5]

In addition to the scaffold function, MALT1 contains a caspase-like domain with proteolytic activity for several important substrates in lymphocyte regulation. MALT1 is a paracaspase, which cleaves after an arginine or lysine residues instead of an aspartate as in caspases. [8] Known peptide substrates of MALT1, or fusion protein API2-MALT1, include A20, CYLD, Bcl10, RelB, regnase-1, roquin-1, NIK, LIMA1α, and MALT1. [8-16] API2-MALT1 results from a t(11;18)(q21;q21) translocation, and is detected in up to 55% of patents with MALT associated lymphomas. [17] Cleavage of these peptides by MALT1 results in inactivation of the peptides resulting in a range of effects, including enhancing NF-κB activation, enhancing B-cell adhesion to fibronectin, and promoting cytokine expression and secretion. Through these and other mechanisms the paracaspase activity of MALT1 promotes cell proliferation and survival in lymphomas and autoimmune diseases. [5] Due in particular to the high chemo-resistance and low survival rates associated with ABC-DLBCL there is a need from improved therapeutic agents that target lymphocyte signaling and proliferation pathways such as those mediated by MALT1 paracaspase activity.

SUMMARY OF THE INVENTION

Mucosa-associated lymphoid tissue transformation protein 1 (MALT1) is a key regulator of T-cell and B-cell signaling pathways including NF-κB activation, lymphocyte proliferation, lymphocyte activation, cytokine expression and secretion, and natural killer (NK) receptor activation. MALT1 acts as both a scaffold protein in the signaling chain between T- and B-cell receptors (TCR and BCR) and NF-κB activation, and as a protease for cleavage of several peptides involved in NF-κB regulation and other pathways. Proteolysis is catalyzed by a caspase-like domain with conserved residues Cys464 (C464) and His415, and referred to as a paracaspase domain [5].

Substrates identified for MALT1 protease activity include tumor necrosis factor, alpha-induced protein (A20), B-cell lymphoma 10 (Bcl10), cylindromatosis (CYLD), transcription factor RelB, regnase-1, roquin-1, and roquin-2. Autoproteolysis of MALT1 has also been demonstrated. [16] Additionally, the fusion protein API2-MALT1 (resulting from a t(11;18)(q21;q21) translocation) cleaves NF-κB inducing kinase (NIK) and LIM domain and actin-binding protein 1 (LIMA1α). [5] The paracaspase domain cleaves peptide substrates after an arginine or a lysine. The domain may also require an uncharged amino acid (e.g., serine, proline, cysteine) after the arginine or lysine residue.

A20, CYLD, and RelB are negative regulators of NF-κB activation, thus proteolysis by MALT1 promotes NF-κB activation and NF-κB dependent gene expression. CYLD also negatively regulates c-Jun N-terminal kinase (JNK) signaling. [10] Both A20 and CYLD are deubiquitinases that remove polyubiquitin from proteins of NF-κB signaling pathway such as TRAF2, TRAF6, NEMO, MALT1, and TAK1. [8,10] RelB binds NF-κB subunits RelA and c-Rel, inhibiting transcription of their target genes. [11] The MALT1 fragment produced by auto-proteolysis retains MALT1 proteolysis activity, and cleavage of the Bcl10 binding domain promotes NF-κB activation. [16]

The MALT1 substrates regnase-1, roquin-1 and roquin-2 repress expression of multiple genes by post-transcriptional regulation. Regnase-1 regulates the decay of mRNA for several genes including IL-2, IL-6, c-Rel, and Ox40. [13] Roquins also bind mRNA and repress expression of transcription factors c-Rel, IRF4, IκBNS, and IκBζ, which regulate T-cell differentiation (e.g., Th17) and cytokine expression (e.g., IL-17). [12]

Substrates of API2-MALT1 include NIK and LIMA1α. API2 binding of NIK allows for cleavage of the kinase even at low cellular concentrations, which generates a NIK C-terminal fragment resistant to proteasomal degradation. [14] Sufficient levels of C-terminal fragment promote non-canonical NF-κB activation which leads to up-regulation of genes that enhance B-cell adhesion and apoptosis resistance. Similarly API2-MALT1 cleavage of LIMA1α produces fragments that lose the tumor suppressor function of LIMA1α and lymphocyte proliferation and adhesion. [15]

The proteolytic activity of MALT1 and API2-MALT1 is therefore critical in regulating the oncogenic properties of T- and B-cell lymphocytes. Different subtypes of diffuse large B-cell lymphoma (DLBCL) have different phenotypes for NF-κB activation pathways and NF-κB dependent gene expression. Activation of NF-κB by pathways involving MALT1 proteolytic activity is critical to the proliferation and survival of ABC-DLBCL cells. [18] The irreversible MALT1 inhibitor Z-VRPR-fmk has been demonstrated to reduce ABC-DLBCL viability. Genes known to be upregulated in ABC-DLBCL (e.g., FLIP, A1, A20, IL-6, IL-10) were shown to be down-regulated by MALT1 inhibition. [18]

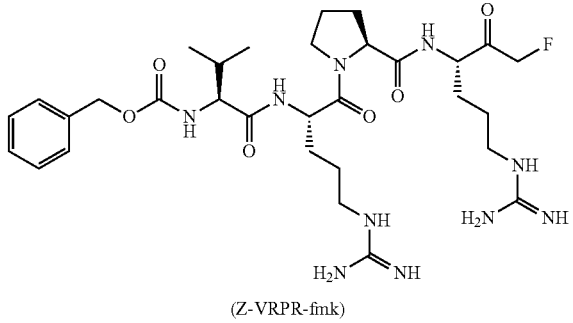 [SMILES: CC(C)[C@H](NC(=O)OCc1ccccc1)C(=O)N[C@@H](CCCNC(=N)N)C(=O)N1CCC[C@H]1C(=O)N[C@@H](CCCNC(=N)N)C(=O)CF]

(Z-VRPR-fmk)

Phenothiazine derivatives (e.g., mepazine, thioridazine, and promazine) have been shown to reversible inhibit MALT1, and display anti-proliferative effects in MALT1-dependent B-cell lymphoma cells. [19] Additionally, MI-2 has been identified as an irreversible MALT1 inhibitor capable of inhibiting ABC-DLBCL cell grown in vitro and in a xenograft mouse model. [20] Additional analog of MI-2 are described in WIPO Application No. PCT/US2013/069141, which is incorporated herein by reference.

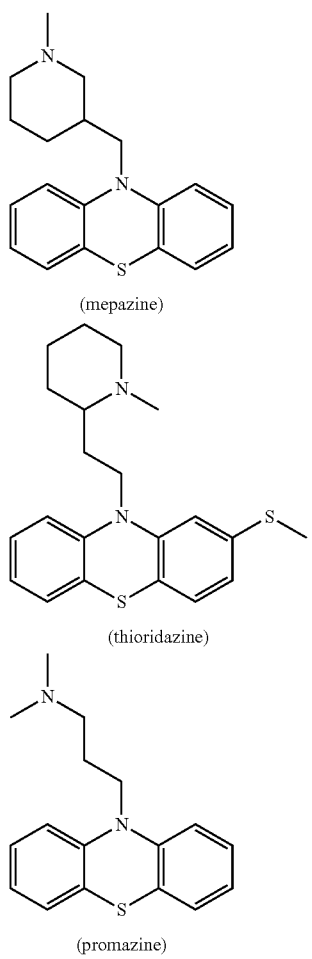

(mepazine)

(thioridazine)

(promazine)

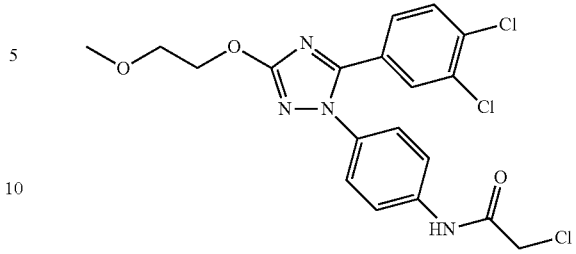

(MI-2)

Compounds provided herein may be inhibitors of MALT1. Also contemplated are compounds that inhibit MALT1 variants, such as fusion proteins API2-MALT1 or IGH-MALT1. They may inhibit the proteolytic activity of MALT1 or a MALT1 fusion protein for cleavage of substrates including, but not limited to, A20, CYLD, Bcl10, RelB, regnase-1, roquin-1, NIK, LIMA1α, and MALT1. The inhibition of MALT1 proteolysis may suppress NF-κB activation, down-regulate expression of NF-κB dependent genes, regulate expression of cytokines (e.g., IL-2, IL-6, IL-8, IL-10), enhance lymphocyte adhesion, enhance lymphocyte apoptosis resistance, and/or enhance lymphocyte proliferation.

In one aspect, provide herein are compound of Formula (I):

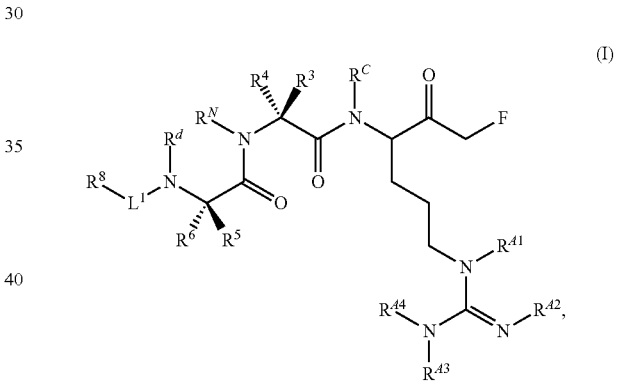

or a pharmaceutically acceptable salt, stereoisomer, tautomer, solvate, hydrate, polymorph, co-crystal, or prodrug thereof, with variable positions defined herein.

In some embodiments, the compound of Formula (I) is a tripeptide (i.e., $L^1$ is a bond). In some embodiments, the compound of Formula (I) is a tripeptide of formula $R^8$—P3-P2-P1-fmk, wherein P3, P2, and P1 are amino acids, fmk is fluoromethylketone, and $R^8$ is as described herein. In some embodiments, each of P3, P2, and P1 is a naturally occurring proteinogenic amino acid. In some embodiments, P1 is arginine. In some embodiments, P2 is proline, serine, or cysteine. In some embodiments, P3 is valine, alanine, isoleucine, or leucine. In some embodiments, P1 is arginine and P2 is proline.

In another aspect, provided herein are pharmaceutical compositions comprising a compound described herein, or a pharmaceutically acceptable salt, stereoisomer, tautomer, solvate, hydrate, polymorph, co-crystal, or prodrug thereof, and optionally a pharmaceutically acceptable excipient. In certain embodiments, the pharmaceutical compositions described herein include a therapeutically or prophylactically effective amount of a compound described herein. The pharmaceutical composition may be useful for treating a proliferative disease in a subject in need thereof, preventing a proliferative disease in a subject in need thereof, inhibiting the activity of a protein kinase in a subject, biological sample, tissue, or cell, and/or inducing apoptosis in a cell. The pharmaceutical composition may contain one or more additional pharmaceutical agents (e.g., anti-proliferative agents, anti-cancer agents).

In another aspect, the present invention provides methods for treating and/or preventing a proliferative disease comprising administering a compound described herein, or a pharmaceutically acceptable salt, stereoisomer, tautomer, solvate, hydrate, polymorph, co-crystal, or prodrug thereof, or a pharmaceutical composition thereof, to a subject in need thereof. In certain embodiments, the proliferative disease is cancer (e.g., leukemia, lymphoma). In some embodiments, the disease is a hematological malignancy. In some embodiments, the disease is diffuse large B-cell lymphoma. In some embodiments, the disease is MALT lymphoma. In certain embodiments, the disease is an autoimmune disease. In certain embodiments, the proliferative disease is benign neoplasm, a disease associated with angiogenesis, an inflammatory disease, or autoinflammatory disease.

In another aspect the present invention provides kits comprising a compound described herein, or a pharmaceutically acceptable salt, stereoisomer, tautomer, solvate, hydrate, polymorph, co-crystal, or prodrug thereof, or a pharmaceutical composition thereof; and instructions for using the compound, or pharmaceutically acceptable salt, stereoisomer, tautomer, solvate, hydrate, polymorph, co-crystal, or prodrug thereof, or the pharmaceutical composition.

In another aspect, provided herein are methods of inhibiting activation of nuclear factor KB (NF-κB) in a subject by administering to the subject a compound described herein, or inhibiting activation of nuclear factor KB (NF-κB) in a biological sample by contacting the biological sample with a compound described herein.

In another aspect, provided herein are methods of inhibiting the activity of mucosa-associated lymphoid tissue lymphoma translation protein 1 (MALT1) or a MALT1 fusion protein in a subject by administering to the subject a compound described herein, or inhibiting the activity of mucosa-associated lymphoid tissue lymphoma translation protein 1 (MALT1) or a MALT1 fusion protein in a biological sample by contacting the biological sample with a compound described herein. In certain embodiments, the method inhibits the protease activity of MALT1. In certain embodiments, the method inhibits the protease activity of a MALT1 fusion protein (e.g., API2-MALT1). In certain embodiments, the method inhibits the protease activity of MALT1 for cleavage of a peptide substrate. In certain embodiments, the peptide substrate is A20, Bcl10, RelB, CYLD, NIK, regnase-1, roquin-1, roquin-2, LIMA1α, or MALT1.

In another aspect, provided herein are methods of inhibiting cell proliferation in a subject by administering to the subject a compound described herein, or inhibiting cell proliferation in a biological sample by contacting the biological sample with a compound described herein. In some embodiments, cell proliferation is inhibited for T-cells. In some embodiments, cell proliferation is inhibited for B-cells. In some embodiments, cell proliferation is inhibited for T-cells and B-cells.

In another aspect, provided herein are methods of inducing apoptosis of a cell in a subject by administering to the subject a compound described herein, or inducing apoptosis of a cell in a biological sample by contacting the biological sample with a compound described herein. In some embodiments, cell is a tumor cell. In some embodiments, the cell is a lymphocyte. In some embodiments, the cell is a T-cell. In some embodiments, the cell is a B-cell.

In another aspect, provided herein are methods of inhibiting adhesion of a cell in a subject by administering to the subject a compound described herein, or inhibiting adhesion of a cell in a biological sample by contacting the biological sample with a compound described herein. In some embodiments, cell is a tumor cell. In some embodiments, the cell is a lymphocyte. In some embodiments, the cell is a T-cell. In some embodiments, the cell is a B-cell.

The details of certain embodiments of the invention are set forth in the Detailed Description of Certain Embodiments, as described below. Other features, objects, and advantages of the invention will be apparent from the Definitions, Examples, Figures, and Claims.

Definitions

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, $5^{th}$ Edition, John Wiley & Sons, Inc., New York, 2001; Larock, Comprehensive Organic Transformations, VCH Publishers, Inc., New York, 1989; and Carruthers, Some Modern Methods of Organic Synthesis, $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H. Tables of Resolving Agents and Optical Resolutions p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⁓ is a single bond where the stereochemistry of the moieties immediately attached thereto is not specified, - - - is absent or a single bond, and === or === is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds may be useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(S) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

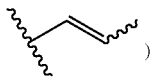)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(S) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(S) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C═C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3-6 membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl (triazinyl). Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5-6 membered, monocyclic heteroaryl. In certain embodiments, the heteroaryl is substituted or unsubstituted, 9-10 membered, bicyclic heteroaryl.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$_{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R, or —NR$^{bb}$C(=O)N(R$^{bb}$)$_2$. In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, or —NO$_2$.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

The term "sulfonyl" refers to a group selected from —SO$_2$N(R$^{bb}$)$_2$, —SO$_2$R, and —SO$_2$OR$^{aa}$, wherein R$^{aa}$ and R$^{bb}$ are as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (–CHO), esters (—CO$_2$R$^{aa}$, —C(=O)SR$^{aa}$), and amides (—C(=O)N(R$^{bb}$)$_2$, —C(=O)NR$^{bb}$SO$_2$R$^{aa}$, —C(=S)N(R$^{bb}$)$_2$), wherein R$^{aa}$ and R$^{bb}$ are as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R, —C(=NR$^{bb}$)R, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. In certain embodiments, the nitrogen protecting group described herein is Bn, Boc, Cbz, Fmoc, trifluoroacetyl, triphenylmethyl, acetyl, tosyl, nosyl, brosyl, mesyl, or triflyl.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R, —C(=NR$^{bb}$)OR, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. In certain embodiments, an oxygen protecting group described herein is silyl, TBDPS, TBDMS, TIPS, TES, TMS, MOM, THP, t-Bu, Bn, allyl, acetyl, pivaloyl, or benzoyl.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, ca-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, o-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

The term "amino acid" includes the natural (naturally occurring) amino acids (e.g. Ala, Arg, Asn, Asp, Cys, selenocysteine, Gln, Glu, Gly, His, Ile, Leu, Lys, Met, Phe, Pro, Ser, Thr, Trp, Tyr, and Val) in D or L form, and unnatural (not naturally occurring) amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, alpha-methyl-alanine, para-benzoylphenylalanine, phenylglycine, propargylglycine, sarcosine, and tert-butylglycine). The term "amino acid" also includes mono-radicals of the natural amino acids and unnatural amino acids. The term "amino acid" also includes di-radicals of the natural amino acids and unnatural amino acids. When the amino acid is a mono-radical, the point of attachment may be at the C-terminus or the N-terminus. When the amino acid is a di-radical, the points of attachment may be at the C-terminus and the N-terminus.

The term "dipeptide" includes two peptidically bound amino acids joined by a peptide bond. The term "dipeptide" also includes mono-radicals of two peptidically bound amino acids joined by a peptide bond. The term "dipeptide" also includes di-radicals of two peptidically bound amino acids joined by a peptide bond. When the dipeptide is a mono-radical, the point of attachment may be at the C-terminus or the N-terminus. When the dipeptide is a di-radical, the points of attachment may be at the C-terminus and the N-terminus.

These and other exemplary substituents are described in more detail in the Detailed Description, Examples, and Claims. The invention is not intended to be limited in any manner by the above exemplary listing of substituents.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-4}$ alkyl, $C_{2-8}$ alkenyl, $C_{2-8}$ alkynyl, aryl, $C_{7-12}$ substituted aryl, and $C_{7-12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, diseases associated with angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF).

"Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated as in the growth of normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple negative breast cancer (TNBC)); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "hematological malignancy" refers to tumors that affect blood, bone marrow, and/or lymph nodes. Exemplary hematological malignancies include, but are not limited to, leukemia, such as acute lymphoblastic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt's lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphomalleukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemiallymphoma as described above; myelodysplasia; and multiple myeloma (MM).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hay fever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for inhibiting MALT1. In certain embodiments, a therapeutically effective amount is an amount sufficient for treating cancer (e.g., lymphoma (e.g., diffuse large B-cell lymphoma, MALT lymphoma)). In certain embodiments, a therapeutically effective amount is an amount sufficient for inhibiting MALT1 and treating cancer (e.g., lymphoma (e.g., diffuse large B-cell lymphoma, MALT lymphoma)).

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a therapeutically effective amount is an amount sufficient for inhibiting MALT1. In certain embodiments, a prophylactically effective amount is an amount sufficient for preventing cancer (e.g., lymphoma (e.g., diffuse large B-cell lymphoma, MALT lymphoma)). In certain embodiments, a prophylactically effective amount is an amount sufficient for inhibiting MALT1 and treating cancer (e.g., lymphoma (e.g., diffuse large B-cell lymphoma, MALT lymphoma)).

As used herein the term "inhibit" or "inhibition" in the context of enzymes, for example, in the context of MALT1, refers to a reduction in the activity of the enzyme. In some embodiments, the activity of the enzyme is an activity for peptide cleavage. For example, in the context of MALT1, the proteolytic activity towards cleavage of a peptide including, but not limited to, A20, Bcl10, RelB, CYLD, NIK, regnase-1, roquin-1, roquin-2, LIMA1α, and MALT1. In some embodiments, the term refers to a reduction of the level of enzyme activity, e.g., MALT1 activity, to a level that is statistically significantly lower than an initial level, which may, for example, be a baseline level of enzyme activity. In some embodiments, the term refers to a reduction of the level of enzyme activity, e.g., MALT1 activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

The term "MALT1" refers to mucosa-associate lymphoid tissue lymphoma translocation protein 1. MALT1 may refer to the RNA and DNA encoding sequences in addition to the protein. MALT1 is a member of the paracaspase family. Human MALT1 is encoded by the MALT1 gene. In some embodiments, a MALT1 inhibitor provided herein is specific for a MALT1 from a specific species, e.g., for human MALT1. The term MALT1 further includes, in some embodiments, sequence variants and mutations (e.g., naturally occurring or synthetic MALT1 sequence variants or mutations), and different MALT1 isoforms. MALT1 fusion proteins from translocations are also included in the term MALT1, and may also be specifically referred to (e.g., API2-MALT1) in some embodiments. In some embodiments, the term MALT1 includes protein or encoding sequences that are homologous to a MALT1 protein or encoding sequence, for example, a protein or encoding sequence having at least 80%, at least 85%, at least 90%, at least 91%, at least 92%, at least 93%, at least 94%, at least 95%, at least 96%, at least 97%, at least 98%, at least 99%, or at least 99.5% sequence identity with a MALT1 sequence, for example, with a MALT1 sequence provided herein. MALT1 protein and encoding gene sequences are well known to those of skill in the art, and exemplary protein sequences include, but are not limited to, the following sequences. Additional MALT1 sequences, e.g., MALT1 homologues from other species, will be apparent to those of skill in the art, and the invention is not limited to the exemplary sequences provided herein.

>gi|58030781|ref|NP_006776.1| mucosa-associated lymphoid tissue lymphoma translocation protein 1 isoform a [*Homo sapiens*]

(SEQ ID NO: 1)

A)
MSLLGDPLQALPPSAAPTGPLLAPPAGATLNRLREPLLRRLSELLDQAPE
GRGWRRLAEL

B)
AGSRGRLRLSCLDLEQCSLKVLEPEGSPSLCLLKLMGEKGCTVTELSDFL
QAMEHTEVLQ

C)
LLSPPGIKITVNPESKAVLAGQFVKLCCRATGHPFVQYQWFKMNKEIPNG
NTSELIFNAV

D)
HVKDAGFYVCRVNNNFTFEFSQWSQLDVCDIPESFQRSVDGVSESKLQIC
VEPTSQKLMP

E)
GSTLVLQCVAVGSPIPHYQWFKNELPLTHETKKLYMVPYVDLEHQGTYWC
HVYNDRDSQD

F)
SKKVEIIIGRTDEAVECTEDELNNLGHPDNKEQTTDQPLAKDKVALLIGN
MNYREHPKLK

G)
APLVDVYELTNLLRQLDFKVVSLLDLTEYEMRNAVDEFLLLLDKGVYGLL
YYAGHGYENF

H)
GNSFMVPVDAPNPYRSENCLCVQNILKLMQEKETGLNVFLLDMCRKRNDY
DDTIPILDAL

I)
KVTANIVFGYATCQGAEAFEIQHSGLANGIFMKFLKDRLLEDKKITVLLD
EVAEDMGKCH

J)
LTKGKQALEIRSSLSEKRALTDPIQGTEYSAESLVRNLQWAKAHELPESM
CLKFDCGVQI

K)
QLGFAAEFSNVMIIYTSIVYKPPEIIMCDAYVTDFPLDLDIDPKDANKGT
PEETGSYLVS

L)
KDLPKHCLYTRLSSLQKLKEHLVFTVCLSYQYSGLEDTVEDKQEVNVGKP
LIAKLDMHRG

M)
LGRKTCFQTCLMSNGPYQSSAATSGGAGHYHSLQDPFHGVYHSHPGNPSN
VTPADSCHCS

N)
RTPDAFISSFAHHASCHFSRSNVPVETTDEIPFSFSDRLRISEK

>gi|278865661|ref|NP_776216.1| mucosa-associated lymphoid tissue lymphoma translocation protein 1 isoform b [*Homo sapiens*]

(SEQ ID NO: 2)

A)
MSLLGDPLQALPPSAAPTGPLLAPPAGATLNRLREPLLRRLSELLDQAPE
GRGWRRLAEL

B)
AGSRGRLRLSCLDLEQCSLKVLEPEGSPSLCLLKLMGEKGCTVTELSDFL
QAMEHTEVLQ

C)
LLSPPGIKITVNPESKAVLAGQFVKLCCRATGHPFVQYQWFKMNKEIPNG
NTSELIFNAV

D)
HVKDAGFYVCRVNNNFTFEFSQWSQLDVCDIPESFQRSVDGVSESKLQIC
VEPTSQKLMP

E)
GSTLVLQCVAVGSPIPHYQWFKNELPLTHETKKLYMVPYVDLEHQGTYWC
HVYNDRDSQD

F)
SKKVEIIIDELNNLGHPDNKEQTTDQPLAKDKVALLIGNMNYREHPKLKA
PLVDVYELTN

G)
LLRQLDFKVVSLLDLTEYEMRNAVDEFLLLLDKGVYGLLYYAGHGYENFG
NSFMVPVDAP

H)
NPYRSENCLCVQNILKLMQEKETGLNVFLLDMCRKRNDYDDTIPILDALK
VTANIVFGYA

I)
TCQGAEAFEIQHSGLANGIFMKFLKDRLLEDKKITVLLDEVAEDMGKCHL
TKGKQALEIR

J)
SSLSEKRALTDPIQGTEYSAESLVRNLQWAKAHELPESMCLKFDCGVQIQ
LGFAAEFSNV

K)
MIIYTSIVYKPPEIIMCDAYVTDFPLDLDIDPKDANKGTPEETGSYLVSK
DLPKHCLYTR

L)
LSSLQKLKEHLVFTVCLSYQYSGLEDTVEDKQEVNVGKPLIAKLDMHRGL
GRKTCFQTCL

M)
MSNGPYQSSAATSGGAGHYHSLQDPFHGVYHSHPGNPSNVTPADSCHCSR
TPDAFISSFA

N)
HHASCHFSRSNVPVETTDEIPFSFSDRLRISEK

BRIEF DESCRIPTION OF THE DRAWINGS

The accompanying drawings, which constitute a part of this specification, illustrate several embodiments of the invention and together with the description, serve to explain the principles of the invention.

DETAILED DESCRIPTION OF CERTAIN EMBODIMENTS

Figure 1A:
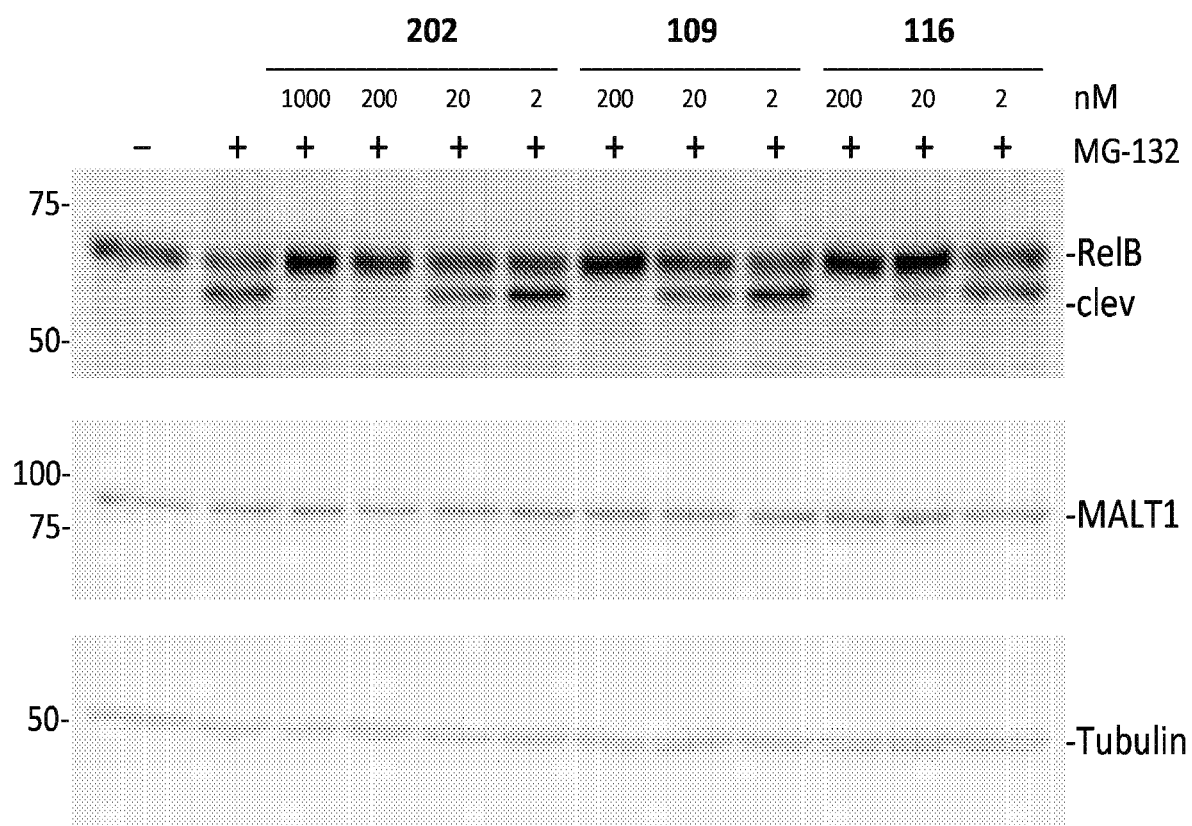
FIG. 1A. Western blots for RelB and MALT1 after 30 minutes pretreatment with indicated doses of compounds or vehicle, followed by proteasome inhibitor MG-132 (5 μM) treatment for 2 hours in OCI-LY3. clev=cleavage product of RelB.

Provided herein are compounds and pharmaceutical compositions that may inhibit MALT1, or a MALT1 variant, such as a fusion protein comprising a MALT1 sequence (e.g., API2-MALT1). The compounds and pharmaceutical compositions may be useful in methods provided herein for the treatment or prevention of proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease).

Compound provided herein may be useful in inhibiting cell proliferation, inducing apoptosis of a cell, or inhibiting cell adhesion in a subject or biological sample. In some embodiments, the cell is a lymphocyte. In some embodiments, the cell is a B-cell. In some embodiments, the cell is a T-cell. The compounds may also be useful inhibiting activation of NF-κB, inhibiting cleavage of A20, Bcl10, RelB, CYLD, NIK, regnase-1, roquin-1, roquin-2, LIMA1α, or MALT1, modulating cytokine production (e.g., inhibiting expression of IL-2, IL-6, IL-8, IL-10, or IL-17), inhibiting lymphocyte adhesion to fibronectin, or up-regulating expression of a gene (e.g. IκBNS, IκBζ, c-Rel, IRF4, IL-2, IL-6, c-Rel, or Ox40).

Without wishing to be bound to any particular theory, the compounds may irreversibly inhibit MALT1, or a variant thereof, by forming a covalent attachment between MALT1 and the inhibitor. In some embodiments, the fluoromethylketone group is able to covalently bind Cys464 of MALT1. The proximity of the fluoromethylketone moiety and Cys464 of MALT1 is shown in a co-crystal structure of the paracaspase binding pocket with compound 101 (See FIG. 3). In some embodiments, the inhibitor is not cleaved by MALT1. In some embodiments, the inhibitor is cleaved by MALT1 (e.g., after the arginine moiety). In some embodiments, the covalently bound inhibitor prevents binding of a MALT1 substrate.

Provided herein are compounds of Formula (I):

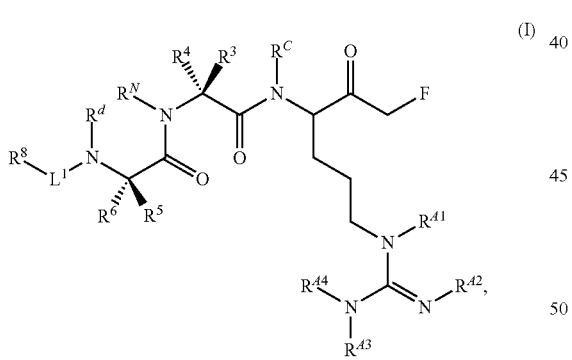

or a pharmaceutically acceptable salt, stereoisomer, tautomer, solvate, hydrate, polymorph, co-crystal, or prodrug thereof, wherein:

$R^3$ is hydrogen, halogen, optionally substituted alkyl, optionally substituted carbocyclyl, optionally substituted heterocyclyl, optionally substituted aryl, or optionally substituted heteroaryl;

$R^4$ is hydrogen, halogen, or optionally substituted alkyl;

$R^N$ is hydrogen, optionally substituted alkyl, optionally substituted acyl, or a nitrogen protecting group;

or $R^N$ and either $R^3$ or $R^4$ are joined to form an optionally substituted heterocyclic ring, or $R^3$ and $R^4$ are joined to form an optionally substituted carbocyclic or optionally substituted heterocyclic ring;

$R^5$ is hydrogen, halogen, optionally substituted alkyl, optionally substituted carbocyclyl, optionally substituted heterocyclyl, optionally substituted aryl, or optionally substituted heteroaryl;

$R^6$ is hydrogen, halogen, optionally substituted alkyl, optionally substituted carbocyclyl, optionally substituted heterocyclyl, optionally substituted aryl, or optionally substituted heteroaryl;

or $R^5$ and $R^6$ are joined to form an optionally substituted carbocyclic or optionally substituted heterocyclic ring;

$R^8$ is optionally substituted alkyl, optionally substituted carbocyclyl, optionally substituted heterocyclyl, —C(=O)$R^{8b}$, —C(=O)O$R^{8a}$, —C(=O)N($R^{8a}$)$_2$, —S(=O)$_2R^{8a}$, or a nitrogen protecting group;

each occurrence of $R^{8a}$ and $R^{8b}$ is independently hydrogen, optionally substituted alkyl, optionally substituted alkenyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^{8a}$, are joined to form an optionally substituted heterocyclic or optionally substituted heteroaryl ring;

$L^1$ is a bond, an amino acid, or a dipeptide;

each of $R^c$ and $R^d$ is independently hydrogen, optionally substituted alkyl, optionally substituted acyl, or a nitrogen protecting group; and each of $R^{A1}$, $R^{A2}$, $R^{A3}$, and $R^{A4}$ is independently hydrogen, optionally substituted alkyl, optionally substituted acyl, optionally substituted sulfonyl, or a nitrogen protecting group, or any two of $R^{A1}$, $R^{A2}$, $R^{A3}$, and $R^{A4}$ are joined to form an optionally substituted heterocyclic or optionally substituted heteroaryl ring.

In certain embodiments, provided herein are compounds of Formula (I):

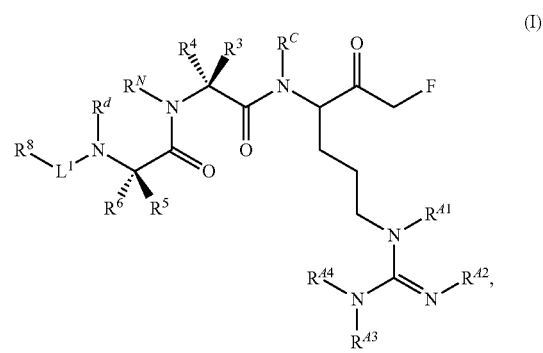

or a pharmaceutically acceptable salt, stereoisomer, tautomer, solvate, hydrate, polymorph, co-crystal, or prodrug thereof, wherein:

$R^3$ is hydrogen, halogen, optionally substituted alkyl, optionally substituted carbocyclyl, optionally substituted heterocyclyl, optionally substituted aryl, or optionally substituted heteroaryl;

$R^4$ is hydrogen, halogen, or optionally substituted alkyl;

$R^N$ is hydrogen, optionally substituted alkyl, optionally substituted acyl, or a nitrogen protecting group;

or $R^N$ and either $R^3$ or $R^4$ are joined to form an optionally substituted heterocyclic ring, or $R^3$ and $R^4$ are joined to form an optionally substituted carbocyclic or optionally substituted heterocyclic ring;

$R^5$ is hydrogen, halogen, or optionally substituted alkyl;

R⁶ is hydrogen, halogen, optionally substituted alkyl, optionally substituted carbocyclyl, optionally substituted heterocyclyl, optionally substituted aryl, or optionally substituted heteroaryl;

or R⁵ and R⁶ are joined to form an optionally substituted carbocyclic or optionally substituted heterocyclic ring;

R⁸ is optionally substituted alkyl, optionally substituted carbocyclyl, optionally substituted heterocyclyl, —C(=O)R⁸ᵇ, —C(=O)OR⁸ᵃ, —C(=O)N(R⁸ᵃ)₂, —S(=O)₂R⁸ᵃ, or a nitrogen protecting group;

each occurrence of R⁸ᵃ and R⁸ᵇ is independently hydrogen, optionally substituted alkyl, optionally substituted alkenyl, optionally substituted carbocyclyl, optionally substituted heterocyclyl, optionally substituted aryl, optionally substituted heteroaryl, optionally substituted acyl, an oxygen protecting group, or a nitrogen protecting group, or two R⁸ᵃ are joined to form an optionally substituted heterocyclic or optionally substituted heteroaryl ring;

L¹ is a bond, an amino acid, or a dipeptide;

each of Rᶜ and Rᵈ is independently hydrogen, optionally substituted alkyl, optionally substituted acyl, or a nitrogen protecting group; and each of Rᴬ¹, Rᴬ², Rᴬ³, and Rᴬ⁴ is independently hydrogen, optionally substituted alkyl, optionally substituted acyl, optionally substituted sulfonyl, or a nitrogen protecting group, or any two of Rᴬ¹, Rᴬ², Rᴬ³, and Rᴬ⁴ are joined to form an optionally substituted heterocyclic or optionally substituted heteroaryl ring.

In certain embodiments, the compound is of Formula (I):

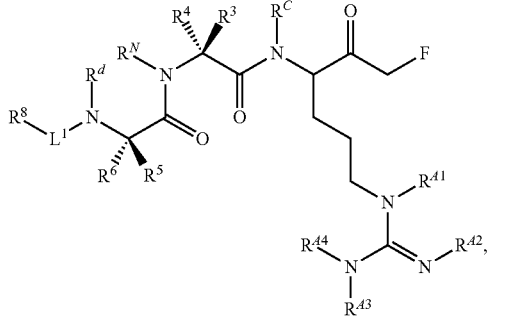

(I)

or a pharmaceutically acceptable salt, wherein:

R³ is hydrogen, halogen, optionally substituted alkyl, optionally substituted carbocyclyl, optionally substituted heterocyclyl, optionally substituted aryl, or optionally substituted heteroaryl;

R⁴ is hydrogen, halogen, or optionally substituted alkyl;

Rᴺ is hydrogen, optionally substituted alkyl, optionally substituted acyl, or a nitrogen protecting group;

or Rᴺ and either R³ or R⁴ are joined to form an optionally substituted heterocyclic ring, or R³ and R⁴ are joined to form an optionally substituted carbocyclic or optionally substituted heterocyclic ring;

R⁵ is hydrogen, halogen, or optionally substituted alkyl;

R⁶ is hydrogen, halogen, optionally substituted alkyl, optionally substituted carbocyclyl, optionally substituted heterocyclyl, optionally substituted aryl, or optionally substituted heteroaryl;

or R⁵ and R⁶ are joined to form an optionally substituted carbocyclic or optionally substituted heterocyclic ring;

R⁸ is optionally substituted alkyl, optionally substituted carbocyclyl, optionally substituted heterocyclyl, —C(=O)R⁸ᵇ, —C(=O)OR⁸ᵃ, —C(=O)N(R⁸ᵃ)₂, —S(=O)₂R⁸ᵃ, or a nitrogen protecting group;

each occurrence of R⁸ᵃ and R⁸ᵇ is independently hydrogen, optionally substituted alkyl, optionally substituted carbocyclyl, optionally substituted heterocyclyl, optionally substituted aryl, optionally substituted heteroaryl, optionally substituted acyl, an oxygen protecting group, or a nitrogen protecting group, or two R⁸ᵃ are joined to form an optionally substituted heterocyclic or optionally substituted heteroaryl ring;

L¹ is a bond, an amino acid, or a dipeptide;

each of Rᶜ and Rᵈ is independently hydrogen, optionally substituted alkyl, optionally substituted acyl, or a nitrogen protecting group; and each of Rᴬ¹, Rᴬ², Rᴬ³, and Rᴬ⁴ is independently hydrogen, optionally substituted alkyl, optionally substituted acyl, optionally substituted sulfonyl, or a nitrogen protecting group, or any two of Rᴬ¹, Rᴬ², Rᴬ³, and Rᴬ⁴ are joined to form an optionally substituted heterocyclic or optionally substituted heteroaryl ring.

In certain embodiments, the compounds is not of formula:

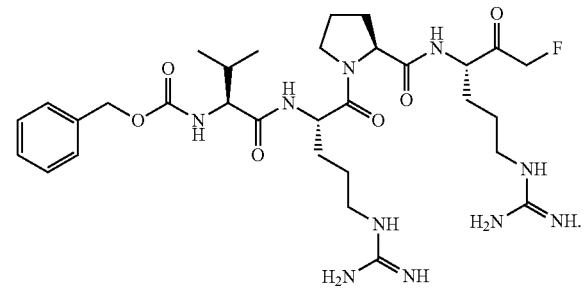 [SMILES: CC(C)[C@H](NC(=O)OCc1ccccc1)C(=O)N[C@@H](CCCNC(=N)N)C(=O)N1CCC[C@H]1C(=O)N[C@@H](CCCNC(=N)N)C(=O)CF]

In certain embodiments, R⁸ is not -L¹-R⁸ᵃ. In certain embodiments, R⁸ is not —C(=O)R⁸ᵇ. In certain embodiments, R⁸ᵇ is not optionally substituted alkyl. In certain embodiments, R⁸ is optionally substituted alkyl, optionally substituted carbocyclyl, optionally substituted heterocyclyl, —C(=O)R⁸ᵇ, —C(=O)OR⁸ᵃ, —C(=O)N(R⁸ᵃ)₂, —S(=O)₂R⁸ᵃ, or a nitrogen protecting group. In certain embodiments, R⁸ is optionally substituted alkyl, optionally substituted carbocyclyl, optionally substituted heterocyclyl, —C(=O)OR⁸ᵃ, —C(=O)N(R⁸ᵃ)₂, —S(=O)₂R⁸ᵃ, or a nitrogen protecting group. In certain embodiments, each of R⁵ and R⁶ is not 3-gunaidinopropyl. In certain embodiments, each of R⁵ and R⁶ is not alkyl substituted with a guanidine or a guanidine derivative. In certain embodiments, each of R³ and R⁴ is not benzyl.

In certain embodiments, the compound of Formula (I) is a stereoisomer of formula:

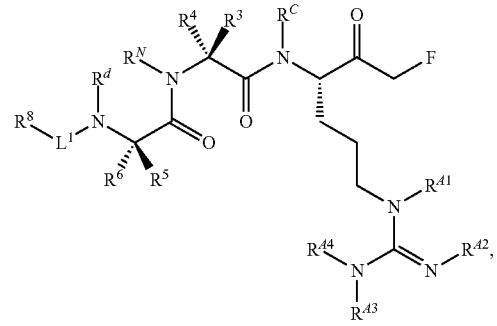

or a pharmaceutically acceptable salt, stereoisomer, tautomer, solvate, hydrate, polymorph, co-crystal, or prodrug thereof.

In certain embodiments, the compound of Formula (I) is a stereoisomer of formula:

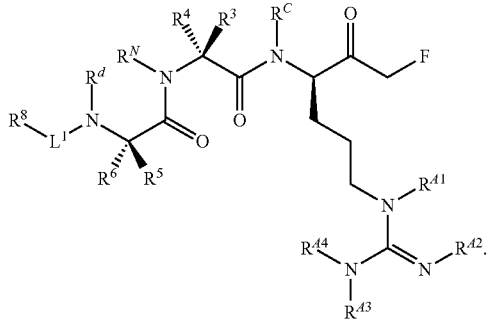

or a pharmaceutically acceptable salt, stereoisomer, tautomer, solvate, hydrate, polymorph, co-crystal, or prodrug thereof.

In certain embodiments, the compound of Formula (I) is of Formula (I-A):

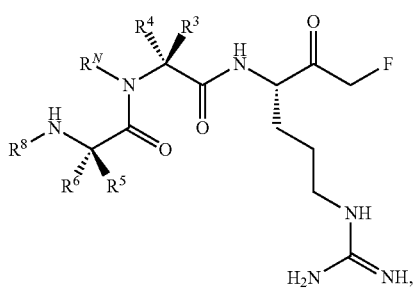

or a pharmaceutically acceptable salt, stereoisomer, tautomer, solvate, hydrate, polymorph, co-crystal, or prodrug thereof.

In certain embodiments, the compound of Formula (I) is of Formula (I-A-1):

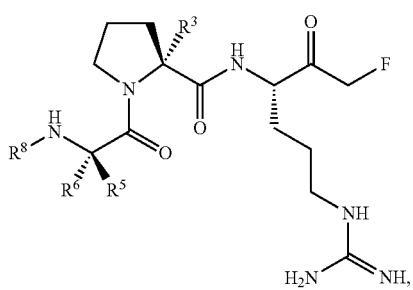

or a pharmaceutically acceptable salt, stereoisomer, tautomer, solvate, hydrate, polymorph, co-crystal, or prodrug thereof.

In certain embodiments, the compound of Formula (I) is of Formula (I-A-2):

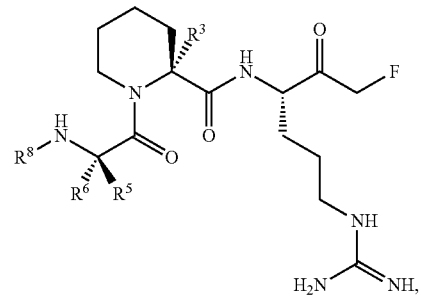

or a pharmaceutically acceptable salt, stereoisomer, tautomer, solvate, hydrate, polymorph, co-crystal, or prodrug thereof.

In certain embodiments, the compound of Formula (I) is of Formula (I-A-3):

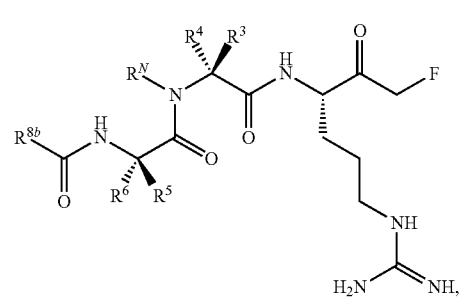

or a pharmaceutically acceptable salt, stereoisomer, tautomer, solvate, hydrate, polymorph, co-crystal, or prodrug thereof.

In certain embodiments, the compound of Formula (I) is of Formula (I-B):

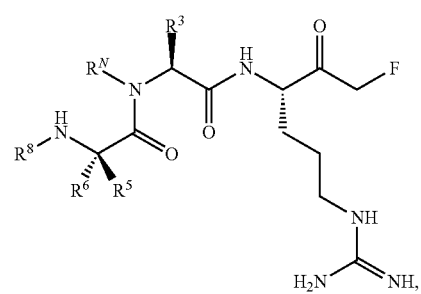

or a pharmaceutically acceptable salt, stereoisomer, tautomer, solvate, hydrate, polymorph, co-crystal, or prodrug thereof.

In certain embodiments, the compound of Formula (I) is of Formula (I-B-1):

(I-B-1)

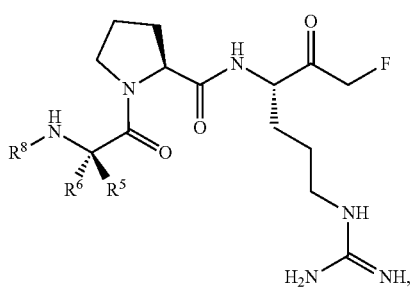

or a pharmaceutically acceptable salt, stereoisomer, tautomer, solvate, hydrate, polymorph, co-crystal, or prodrug thereof.

In certain embodiments, the compound of Formula (I) is of Formula (I-B-2):

(I-B-2)

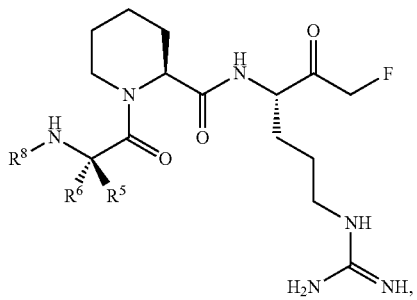

or a pharmaceutically acceptable salt, stereoisomer, tautomer, solvate, hydrate, polymorph, co-crystal, or prodrug thereof.

In certain embodiments, the compound of Formula (I) is of Formula (I-B-3):

(I-B-3)

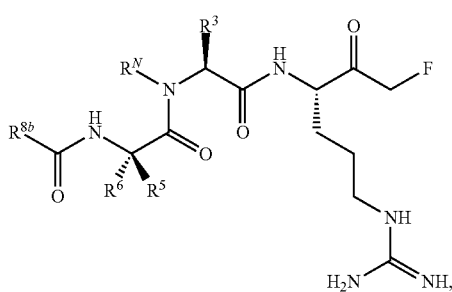

or a pharmaceutically acceptable salt, stereoisomer, tautomer, solvate, hydrate, polymorph, co-crystal, or prodrug thereof.

In certain embodiments, the compound of Formula (I) is of Formula (I-C):

(I-C)

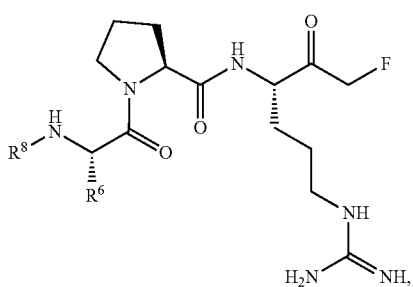

or a pharmaceutically acceptable salt, stereoisomer, tautomer, solvate, hydrate, polymorph, co-crystal, or prodrug thereof.

In certain embodiments, the compound of Formula (I) is of Formula (I-C-1):

(I-C-1)

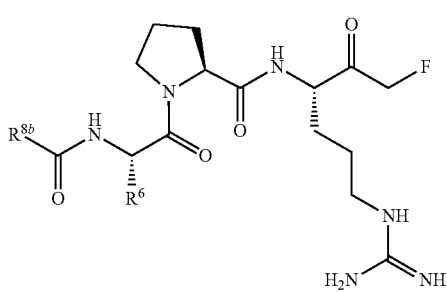

or a pharmaceutically acceptable salt, stereoisomer, tautomer, solvate, hydrate, polymorph, co-crystal, or prodrug thereof.

In certain embodiments, the compound of Formula (I) is of Formula (I-D):

(I-D)

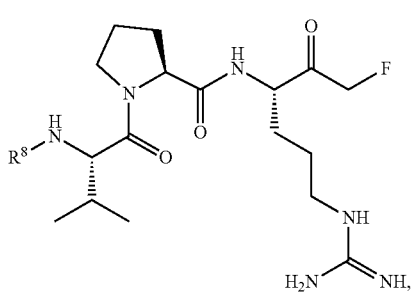

or a pharmaceutically acceptable salt, stereoisomer, tautomer, solvate, hydrate, polymorph, co-crystal, or prodrug thereof.

In certain embodiments, the compound of Formula (I) is of Formula (I-D-1):

(I-D-1)

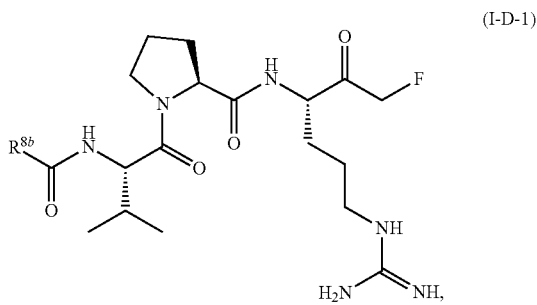

or a pharmaceutically acceptable salt, stereoisomer, tautomer, solvate, hydrate, polymorph, co-crystal, or prodrug thereof.

In certain embodiments, the carbon to which $R^3$ and $R^4$ is chiral. In some embodiments, the carbon to which $R^3$ and $R^4$ is attached is in the (S)-configuration. In some embodiments, the carbon to which $R^3$ and $R^4$ is attached is in the (R)-configuration.

In certain embodiments, $R^3$ and $R^N$ are joined to form an optionally substituted heterocyclic ring. In certain embodiments, $R^3$ and $R^N$ are joined to form an optionally substituted azetidine ring. In certain embodiments, $R^3$ and $R^N$ are joined to form an optionally substituted pyrrolidene ring. In certain embodiments, $R^3$ and $R^N$ are joined to form an optionally substituted oxazole or thiozole ring. In certain embodiments, $R^3$ and $R^N$ are joined to form an optionally substituted oxazolidine ring. In certain embodiments, $R^3$ and $R^N$ are joined to form an optionally substituted thiazolidine ring. In certain embodiments, $R^3$ and $R^N$ are joined to form an optionally substituted piperidine ring. In certain embodiments, $R^3$ and $R^N$ are joined to form an optionally substituted morpholine ring. In certain embodiments, $R^4$ and $R^N$ are joined to form an optionally substituted heterocyclic ring. In certain embodiments, $R^4$ and $R^N$ are joined to form an optionally substituted pyrrolidene ring. In certain embodiments, $R^4$ and $R^N$ are joined to form an optionally substituted piperidine ring. In certain embodiments, $R^3$ and $R^4$ are joined to form an optionally substituted carbocyclic or optionally substituted heterocyclic ring. In certain embodiments, $R^3$ and $R^4$ are joined to form an optionally substituted cyclopropyl, cyclobutyl, cyclopentyl, or cyclohexyl ring. In certain embodiments, no combination of $R^3$, $R^4$ and $R^N$ is joined. In certain embodiments, the heterocyclic ring formed by joining $R^3$ and $R^N$ is substituted with one or more (e.g., 1, 2, 3, 4, 5, or 6), as valency permits, substituents (e.g., substituents independently selected form the group consisting of halogen, substituted and unsubstituted $C_{1-6}$ alkyl, —$OR^{8a}$ (e.g., —OH), and —CN).

In certain embodiments, $R^3$ and $R^N$ are taken together as a moiety of formula:

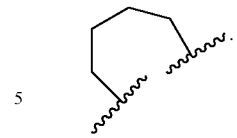

In certain embodiments, $R^3$ and $R^N$ are taken together as a moiety of formula:

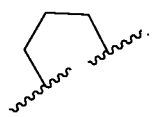 [SMILES: *CCC*]

In certain embodiments, $R^3$ and $R^N$ are taken together as a moiety of formula:

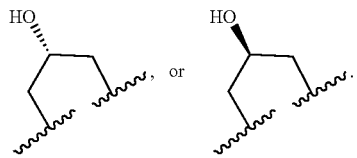

In certain embodiments, $R^4$ and $R^N$ are taken together as a moiety of formula:

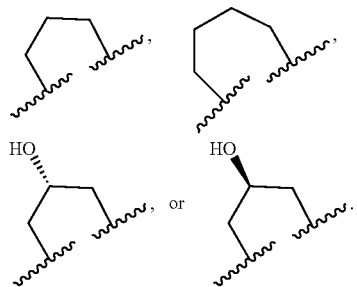

As generally defined herein $R^3$ is hydrogen, halogen, optionally substituted alkyl, optionally substituted carbocyclyl, optionally substituted heterocyclyl, optionally substituted aryl, or optionally substituted heteroaryl.

In some embodiments, $R^3$ is hydrogen. In some embodiments, $R^3$ is a non-hydrogen group. In certain embodiments, $R^3$ is halogen. In certain embodiments, $R^3$ is —F. In certain embodiments, $R^3$ is —Cl, —Br, or —I.

In certain embodiments, $R^3$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^3$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^3$ is methyl. In certain embodiments, $R^3$ is ethyl, propyl, or butyl. In certain embodiments, $R^3$ is substituted methyl (e.g., methyl substituted with 1, 2, or 3 substituents independently selected from the group consisting of halogen and —$OR^{8a}$ (e.g., —OH). In certain embodiments, $R^3$ is —$CH_2OH$. In certain embodiments, $R^3$ is haloalkyl, e.g., —$CHF_2$, —$CHCl_2$, —$CH_2CHF_2$, —$CH_2CHCl_2$. In certain embodiments, $R^3$ is perhaloalkyl, e.g., —$CF_3$, —$CF_2CF_3$, —$CCl_3$.

In certain embodiments, $R^3$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^3$ is unsubstituted carbocyclyl, e.g., unsubstituted $C_{3-6}$ carbocyclyl. In some embodiments, $R^3$ is cyclopropyl, cyclobutyl, cyclopentyl, or cyclohexyl. In certain embodiments, $R^3$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^3$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^3$ is optionally substituted aryl, e.g., optionally substituted phenyl. In certain embodiments, $R^3$ is unsubstituted aryl, e.g., unsubstituted phenyl. In certain embodiments, $R^3$ is optionally substituted heteroaryl, e.g., optionally substituted 5-6 membered heteroaryl, or optionally substituted 9-10 membered bicyclic heteroaryl. In certain embodiments, $R^3$ is unsubstituted heteroaryl, e.g., unsubstituted 5-6 membered heteroaryl, or unsubstituted 9-10 membered bicyclic heteroaryl. In certain embodiments, $R^3$ is optionally substituted aralkyl, e.g., optionally substituted benzyl. In certain embodiments, $R^3$ is optionally substituted heteroaralkyl, e.g., methyl substituted with an optionally substituted 5-6 membered heteroaryl ring. In certain embodiments, $R^3$ is unsubstituted aralkyl, e.g., unsubstituted benzyl. In certain embodiments, $R^3$ is unsubstituted heteroaralkyl, e.g., methyl substituted with an unsubstituted 5-6 membered heteroaryl ring.

In certain embodiments, $R^3$ is of formula:

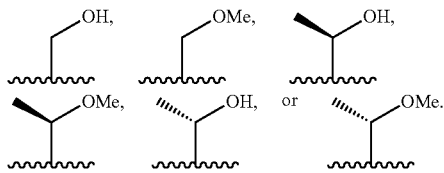

In certain embodiments, $R^3$ is of formula:

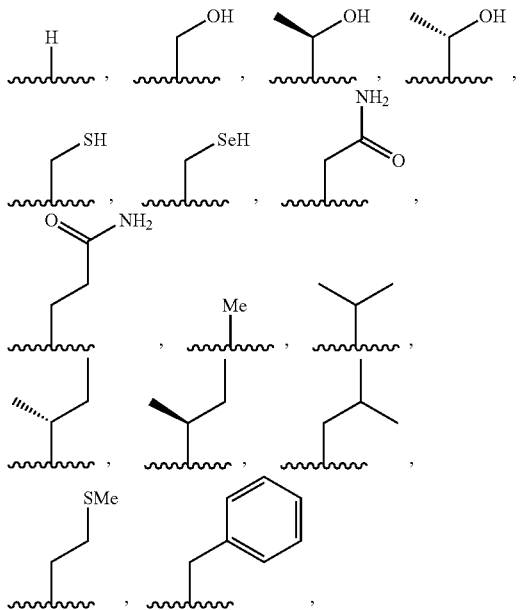

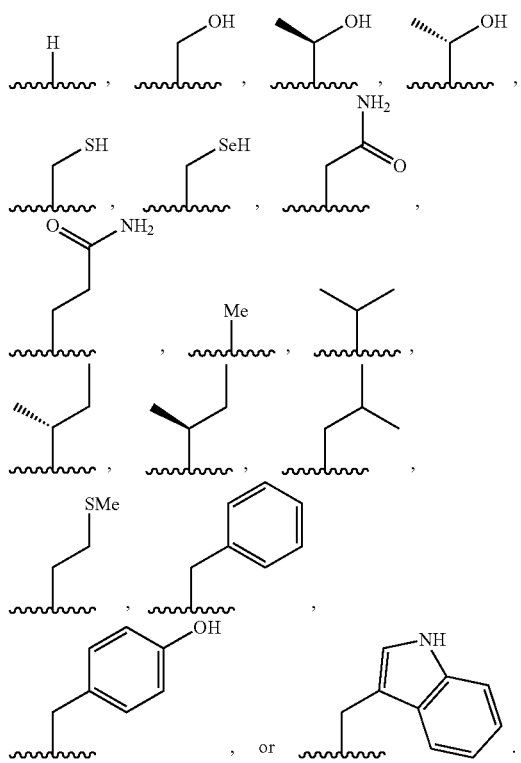

In certain embodiments, $R^3$ is of formula:

As generally defined herein, $R^4$ is hydrogen, halogen, or optionally substituted alkyl. In some embodiments, $R^4$ is hydrogen. In some embodiments, $R^4$ is a non-hydrogen group. In certain embodiments, $R^4$ is halogen. In certain embodiments, $R^4$ is —F. In certain embodiments, $R^4$ is —Cl, —Br, or —I.

In certain embodiments, $R^4$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^4$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^4$ is methyl. In certain embodiments, $R^4$ is substituted methyl (e.g., methyl substituted with 1, 2, or 3 substituents independently selected from the group consisting of halogen and —$OR^{8a}$ (e.g., —OH). In certain embodiments, $R^4$ is —$CH_2OH$. In certain embodiments, $R^4$ is ethyl, propyl, or butyl. In certain embodiments, $R^4$ is haloalkyl, e.g., —$CHF_2$, —$CHCl_2$, —$CH_2CHF_2$, —$CH_2CHCl_2$. In certain embodiments, $R^4$ is perhaloalkyl, e.g., —$CF_3$, —$CF_2CF_3$, —$CCl_3$.

In certain embodiments, $R^4$ is of formula:

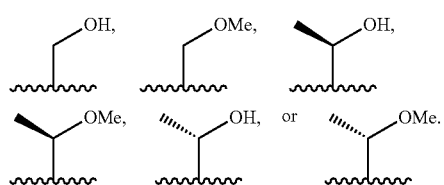

In certain embodiments, $R^4$ is of formula:

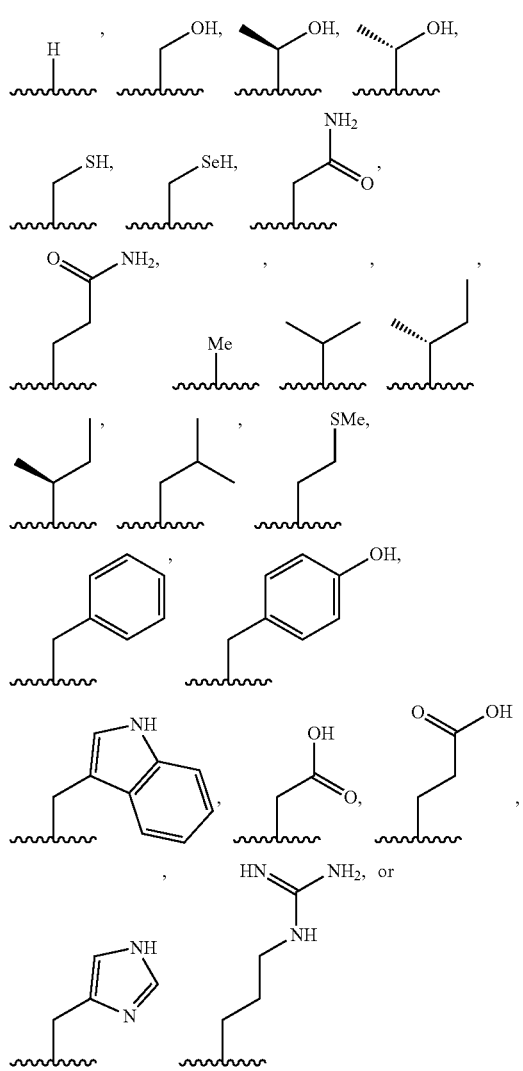

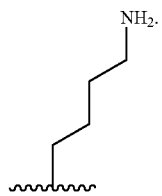

In certain embodiments, $R^4$ is of formula:

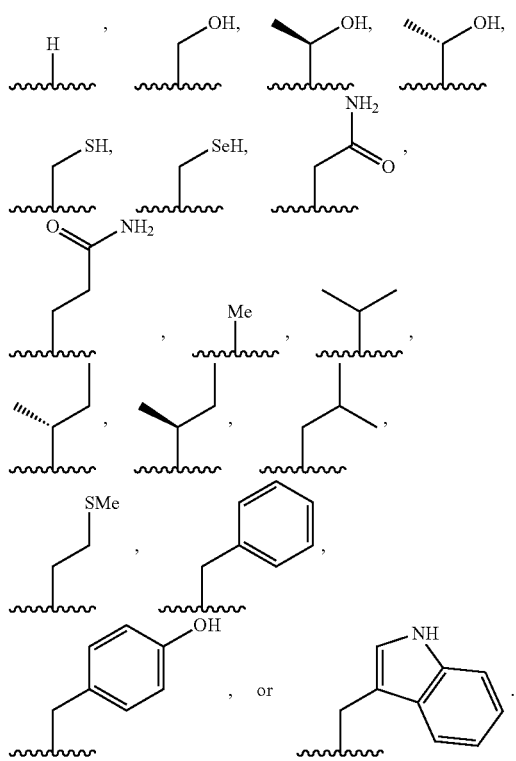

As generally defined herein, $R^N$ is hydrogen, optionally substituted alkyl, optionally substituted acyl, or a nitrogen protecting group. In some embodiments, $R^N$ is hydrogen. In some embodiments, $R^N$ is a non-hydrogen group.

In certain embodiments, $R^N$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^N$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^N$ is methyl. In certain embodiments, $R^N$ is ethyl, propyl, or butyl.

In certain embodiments, $R^N$ is optionally substituted acyl, e.g., —CHO, —$CO_2H$, or —C(=O)$NH_2$. In certain embodiments, $R^N$ is —C(=O)$R^f$, —C(=O)$OR^f$, —C(=O)NH($R^f$), or —C(=O)N($R^f$)$_2$, wherein each occurrence of $R^f$ is independently hydrogen, optionally substituted alkyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^f$ are joined to form an optionally substituted heterocyclic or optionally substituted heteroaryl ring. In certain embodiments, $R^N$ is —C(=O)$R^f$, and $R^f$ is optionally substituted alkyl, e.g., —C(=O)Me. In certain embodiments, $R^N$ is —C(=O)$R^f$, and $R^f$ is optionally substituted alkenyl. In certain embodiments, $R^N$ is —C(=O)$R^f$, and $R^f$ is optionally substituted carbocyclyl, heterocyclyl, aryl, or heteroaryl. In certain embodiments, $R^N$ is —C(=O)O$R^f$, and $R^f$ is optionally substituted alkyl. In certain embodiments, $R^N$ is —C(=O)O$R^f$, and $R^f$ is optionally substituted alkenyl. In certain embodiments, $R^N$ is —C(=O)O$R^f$, and $R^f$ is optionally substituted carbocyclyl, heterocyclyl, aryl, or heteroaryl. In certain embodiments, $R^N$ is —C(=O)N($R^f$)$_2$, and at least one $R^f$ is optionally substituted alkyl. In certain embodiments, $R^N$ is —C(=O)NH$R^f$, and $R^f$ is optionally substituted alkyl. In certain embodiments, $R^N$ is —C(=O)NH$R^f$, and $R^f$ is optionally substituted alkenyl. In certain embodiments, $R^N$ is —C(=O)NH$R^f$, and $R^f$ is optionally substituted carbocyclyl, heterocyclyl, aryl, or heteroaryl.

In certain embodiments, $R^N$ is a nitrogen protecting group. In some embodiments, $R^N$ is Bn, Boc, Cbz, Fmoc, trifluoroacetyl, triphenylmethyl, acetyl, tosyl, nosyl, brosyl, mesyl, or triflyl.

In certain embodiments, the carbon to which $R^5$ and $R^6$ is chiral. In some embodiments, the carbon to which $R^5$ and $R^6$ is attached is in the (S)-configuration. In some embodiments, the carbon to which $R^5$ and $R^6$ is attached is in the (R)-configuration.

In certain embodiments, $R^5$ and $R^6$ are joined to form an optionally substituted carbocyclic or optionally substituted heterocyclic ring. In certain embodiments, $R^5$ and $R^6$ are joined to form an optionally substituted, 3-6 membered, monocyclic carbocyclic ring. In certain embodiments, $R^5$ and $R^6$ are joined to form an optionally substituted, cyclopropyl, cyclobutyl, cyclopentyl, or cyclohexyl ring. In certain embodiments, $R^5$ and $R^6$ are joined to form an optionally substituted, 3-6 membered, monocyclic heterocyclic ring. In certain embodiments, $R^5$ and $R^6$ are joined to form an optionally substituted tetrahydropyran ring.

In certain embodiments, $R^5$ and $R^6$ are not joined. In certain embodiments, $R^5$ is optionally substituted alkyl, e.g., optionally substituted $C_{1-12}$ alkyl. In certain embodiments, $R^5$ is unsubstituted alkyl, e.g., unsubstituted $C_{1-12}$ alkyl.

As generally defined herein $R^6$ is hydrogen, halogen, optionally substituted alkyl, optionally substituted carbocyclyl, optionally substituted heterocyclyl, optionally substituted aryl, or optionally substituted heteroaryl.

In some embodiments, $R^6$ is hydrogen. In some embodiments, $R^6$ is a non-hydrogen group. In certain embodiments, $R^6$ is halogen. In certain embodiments, $R^6$ is —F. In certain embodiments, $R^6$ is —Cl, —Br, or —I.

In certain embodiments, $R^6$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^6$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^6$ is methyl. In certain embodiments, $R^6$ is ethyl, propyl, or butyl. In certain embodiments, $R^6$ is haloalkyl, e.g., —CHF$_2$, —CHCl$_2$, —CH$_2$CHF$_2$, —CH$_2$CHCl$_2$. In certain embodiments, $R^6$ is perhaloalkyl, e.g., —CF$_3$, —CF$_2$CF$_3$, —CCl$_3$.

In certain embodiments, $R^6$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^6$ is unsubstituted carbocyclyl, e.g., unsubstituted $C_{3-6}$ carbocyclyl. In some embodiments, $R^6$ is cyclopropyl, cyclobutyl, cyclopentyl, or cyclohexyl. In certain embodiments, $R^6$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^6$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^6$ is optionally substituted aryl, e.g., optionally substituted phenyl. In certain embodiments, $R^6$ is unsubstituted aryl, e.g., unsubstituted phenyl. In certain embodiments, $R^6$ is optionally substituted heteroaryl, e.g., optionally substituted 5-6 membered heteroaryl, or optionally substituted 9-10 membered bicyclic heteroaryl. In certain embodiments, $R^6$ is unsubstituted heteroaryl, e.g., unsubstituted 5-6 membered heteroaryl, or unsubstituted 9-10 membered bicyclic heteroaryl. In certain embodiments, $R^6$ is optionally substituted aralkyl, e.g., optionally substituted benzyl. In certain embodiments, $R^6$ is optionally substituted heteroaralkyl, e.g., methyl substituted with an optionally substituted 5-6 membered heteroaryl ring. In certain embodiments, $R^6$ is unsubstituted aralkyl, e.g., unsubstituted benzyl. In certain embodiments, $R^6$ is unsubstituted heteroaralkyl, e.g., methyl substituted with an unsubstituted 5-6 membered heteroaryl ring.

In certain embodiments, $R^6$ is of formula:

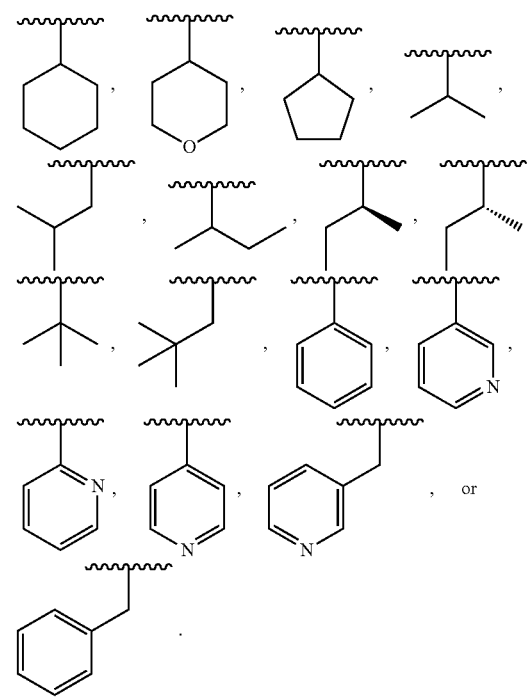

In certain embodiments, $R^6$ is of formula:

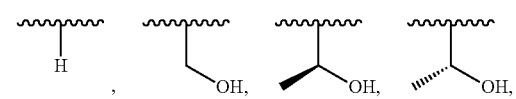

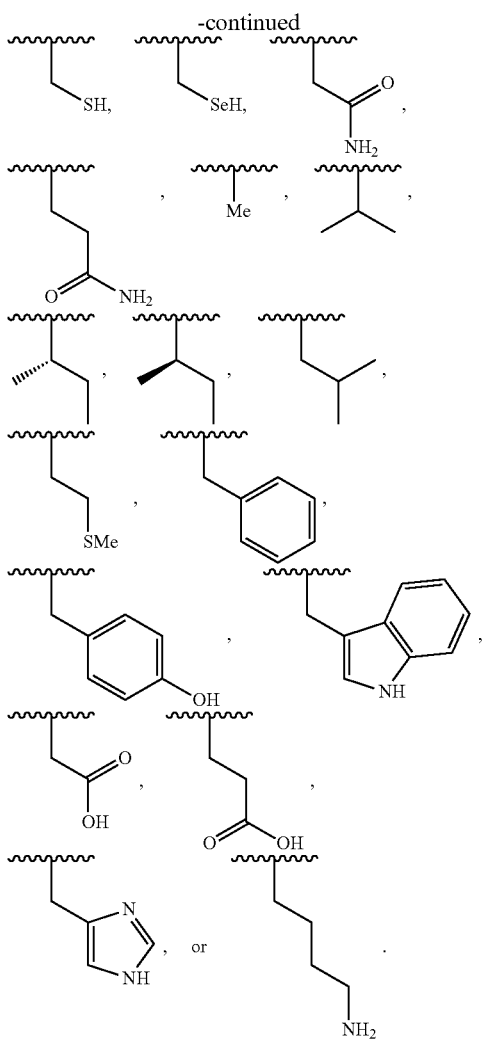

As generally defined herein, R⁵ is hydrogen, halogen, optionally substituted alkyl, optionally substituted carbocyclyl, optionally substituted heterocyclyl, optionally substituted aryl, or optionally substituted heteroaryl. In certain embodiments, R⁵ is hydrogen, halogen, or optionally substituted alkyl. In some embodiments, R⁵ is hydrogen. In some embodiments, R⁵ is a non-hydrogen group. In certain embodiments, R⁵ is halogen. In certain embodiments, R⁵ is —F. In certain embodiments, R⁵ is —Cl, —Br, or —I.

In certain embodiments, R⁵ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, R⁵ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, R⁵ is methyl. In certain embodiments, R⁵ is ethyl, propyl, or butyl. In certain embodiments, R⁵ is haloalkyl, e.g., —CHF₂, —CHCl₂, —CH₂CHF₂, —CH₂CHCl₂. In certain embodiments, R⁵ is perhaloalkyl, e.g., —CF₃, —CF₂CF₃, —CCl₃.

In certain embodiments, R⁵ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, R⁵ is unsubstituted carbocyclyl, e.g., unsubstituted $C_{3-6}$ carbocyclyl. In some embodiments, R⁵ is cyclopropyl, cyclobutyl, cyclopentyl, or cyclohexyl.

In certain embodiments, R⁵ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, R⁵ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, R⁵ is optionally substituted aryl, e.g., optionally substituted phenyl. In certain embodiments, R⁵ is unsubstituted aryl, e.g., unsubstituted phenyl.

In certain embodiments, R⁵ is optionally substituted heteroaryl, e.g., optionally substituted 5-6 membered monocyclic heteroaryl, or optionally substituted 9-10 membered bicyclic heteroaryl. In certain embodiments, R⁵ is unsubstituted heteroaryl, e.g., unsubstituted 5-6 membered monocyclic heteroaryl, or unsubstituted 9-10 membered bicyclic heteroaryl.

In certain embodiments, R⁵ is optionally substituted aralkyl, e.g., optionally substituted benzyl. In certain embodiments, R⁵ is optionally substituted heteroaralkyl, e.g., methyl substituted with an optionally substituted 5-6 membered monocyclic heteroaryl ring. In certain embodiments, R⁵ is unsubstituted aralkyl, e.g., unsubstituted benzyl. In certain embodiments, R⁵ is unsubstituted heteroaralkyl, e.g., methyl substituted with an unsubstituted 5-6 membered monocyclic heteroaryl ring.

In certain embodiments, R⁵ is of formula:

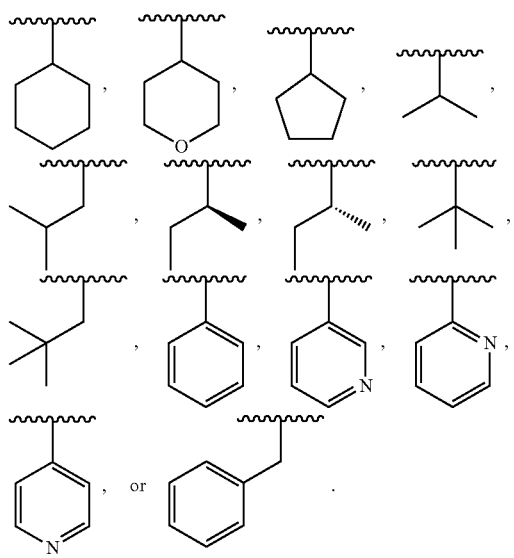

In certain embodiments, R⁵ is of formula:

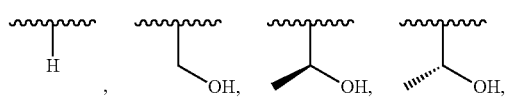

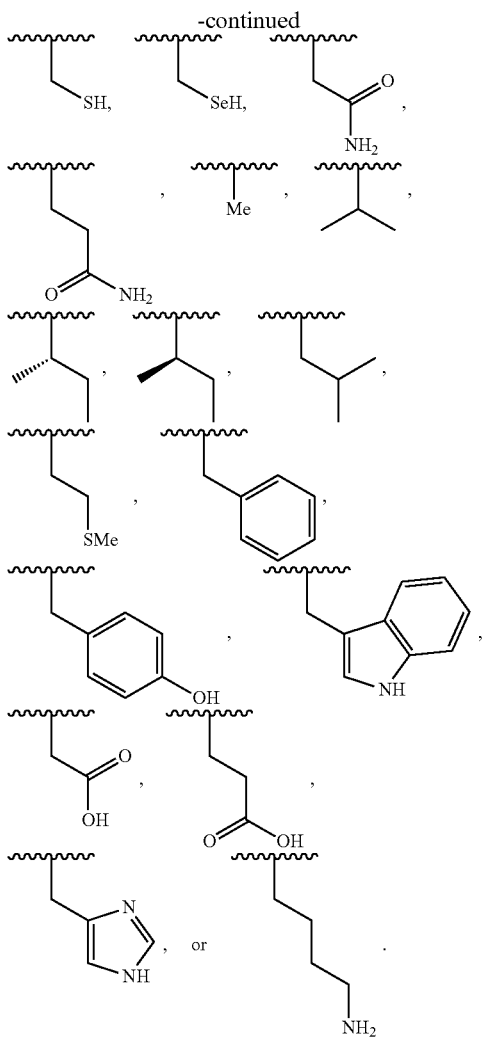

As generally defined herein, $R^8$ is optionally substituted alkyl, optionally substituted carbocyclyl, optionally substituted heterocyclyl, —C(=O)$R^{8b}$, —C(=O)O$R^{8a}$, —C(=O)N($R^{8a}$)$_2$, —S(=O)$_2R^{8a}$.

In certain embodiments, $R^8$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^8$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^8$ is methyl. In certain embodiments, $R^8$ is ethyl, propyl, or butyl. In certain embodiments, $R^8$ is haloalkyl, e.g., —CHF$_2$, —CHCl$_2$, —CH$_2$CHF$_2$, —CH$_2$CHCl$_2$. In certain embodiments, $R^8$ is perhaloalkyl, e.g., —CF$_3$, —CF$_2$CF$_3$, —CCl$_3$. In certain embodiments, $R^8$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^8$ is unsubstituted carbocyclyl, e.g., unsubstituted $C_{3-6}$ carbocyclyl. In some embodiments, $R^8$ is cyclopropyl, cyclobutyl, cyclopentyl, or cyclohexyl. In certain embodiments, $R^8$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^8$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^8$ is —C(=O)$R^{8b}$, wherein $R^{8b}$ is hydrogen, optionally substituted alkyl, optionally substituted carbocyclyl, optionally substituted heterocyclyl, optionally substituted aryl, optionally substituted heteroaryl, or optionally substituted acyl. In certain embodiments, $R^8$ is —C(=O)$R^{8b}$, wherein $R^{8b}$ is hydrogen, optionally substituted carbocyclyl, optionally substituted heterocyclyl, optionally substituted aryl, optionally substituted heteroaryl, or optionally substituted acyl. In certain embodiments, $R^8$ is —C(=O)$R^{8b}$, and $R^{8b}$ is optionally substituted alkyl, e.g., —C(=O)Me. In certain embodiments, $R^8$ is —C(=O)$R^{8b}$, and $R^{8b}$ is optionally substituted alkenyl. In certain embodiments, $R^8$ is —C(=O)$R^{8b}$, and $R^{8b}$ is optionally substituted carbocyclyl, heterocyclyl, aryl, or heteroaryl.

In certain embodiments, $R^8$ is —C(=O)$R^{8b}$, wherein $R^{8b}$ is optionally substituted alkenyl. In certain embodiments, $R^8$ is —C(=O)O$R^{8a}$, wherein $R^{8a}$ is optionally substituted alkenyl.

In certain embodiments, $R^8$ is —C(=O)O$R^{8a}$, wherein $R^{8a}$ is independently hydrogen, optionally substituted alkyl, optionally substituted carbocyclyl, optionally substituted heterocyclyl, optionally substituted aryl, optionally substituted heteroaryl, optionally substituted acyl, or an oxygen protecting group. In certain embodiments, $R^8$ is —C(=O)O$R^{8a}$, and $R^{8a}$ is optionally substituted alkyl. In certain embodiments, $R^8$ is —C(=O)O$R^{8a}$, and $R^{8a}$ is optionally substituted alkenyl. In certain embodiments, $R^8$ is —C(=O)O$R^{8a}$, and $R^{8a}$ is optionally substituted carbocyclyl, heterocyclyl, aryl, or heteroaryl.

In certain embodiments, $R^8$ is —C(=O)N($R^{8a}$)$_2$, wherein each $R^{8a}$ is independently hydrogen, optionally substituted alkyl, optionally substituted carbocyclyl, optionally substituted heterocyclyl, optionally substituted aryl, optionally substituted heteroaryl, optionally substituted acyl, a nitrogen protecting group, or two $R^{8a}$ are joined to form an optionally substituted heterocyclic or optionally substituted heteroaryl ring. In certain embodiments, $R^8$ is —C(=O)N($R^{8a}$)$_2$, and at least one $R^{8a}$ is optionally substituted alkyl. In certain embodiments, $R^8$ is —C(=O)NH$R^{8a}$, and $R^{8a}$ is optionally substituted alkyl. In certain embodiments, $R^8$ is —C(=O)NH$R^{8a}$, and $R^{8a}$ is optionally substituted alkenyl. In certain embodiments, $R^8$ is —C(=O)NH$R^{8a}$, and $R^{8a}$ is optionally substituted carbocyclyl, heterocyclyl, aryl, or heteroaryl.

In certain embodiments, $R^8$ is optionally substituted sulfonyl, e.g., —S(=O)$_2$OH. In certain embodiments, $R^8$ is —S(=O)$_2R^{8a}$, wherein $R^{8a}$ is hydrogen, optionally substituted alkyl, optionally substituted carbocyclyl, optionally substituted heterocyclyl, optionally substituted aryl, or optionally substituted heteroaryl. In certain embodiments, $R^8$ is —S(=O)$_2R^{8a}$, and $R^{8a}$ is optionally substituted alkyl, e.g., —S(=O)$_2$Me. In certain embodiments, $R^8$ is —S(=O)$_2R^{aa}$, and $R^{8a}$ is optionally substituted carbocyclyl, heterocyclyl, aryl, or heteroaryl.

In certain embodiments, $R^8$ is a nitrogen protecting group. In some embodiments, $R^8$ is Bn, Boc, Cbz, Fmoc, trifluoroacetyl, triphenylmethyl, acetyl, tosyl, nosyl, brosyl, mesyl, or triflyl.

In certain embodiments, $R^8$ is of formula:

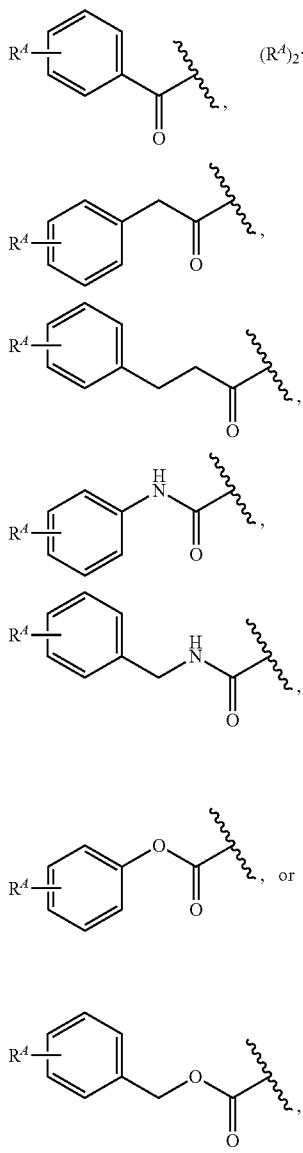

wherein each instance of $R^A$ is independently hydrogen, halogen, optionally substituted alkyl, optionally substituted carbocyclyl, cyano, optionally substituted heterocyclyl, optionally substituted aryl, optionally substituted heteroaryl, or optionally substituted acyl, or two $R^A$ attached to neighboring atoms are joined to form an optionally substituted aryl or optionally substituted heteroaryl ring.

In certain embodiments, at least one $R^A$ is hydrogen. In certain embodiments, each $R^A$ is hydrogen. In certain embodiments, at least one $R^A$ is halogen. In certain embodiments, each $R^A$ is halogen. In certain embodiments, at least one $R^A$ is substituted or unsubstituted alkyl (e.g., substituted or unsubstituted $C_{1-6}$ alkyl). In certain embodiments, each $R^A$ is independently hydrogen, halogen, or substituted or unsubstituted $C_{1-6}$ alkyl. In certain embodiments, each $R^A$ is independently halogen or substituted or unsubstituted $C_{1-6}$ alkyl.

In certain embodiments, $R^8$ is of formula:

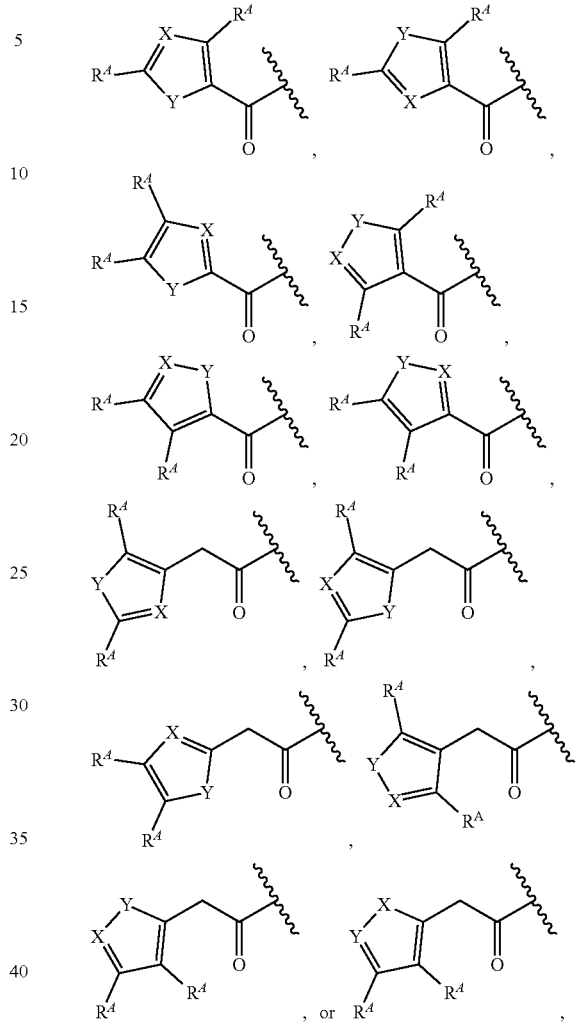

wherein X is N or $CR^A$; Y is O, S, $NR^A$, or $C(R^A)_2$; and each occurrence of $R^A$ is hydrogen, halogen, optionally substituted alkyl, optionally substituted carbocyclyl, optionally substituted heterocyclyl, optionally substituted aryl, optionally substituted heteroaryl, optionally substituted acyl, or a nitrogen protecting group, or two $R^A$ attached to neighboring atoms are joined to form an optionally substituted aryl or optionally substituted heteroaryl ring.

In certain embodiments, $R^8$ is of formula:

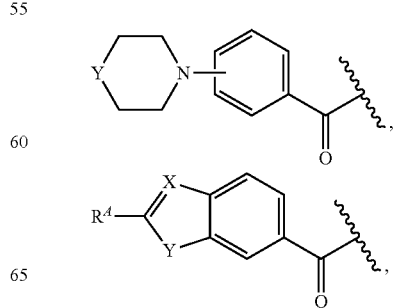

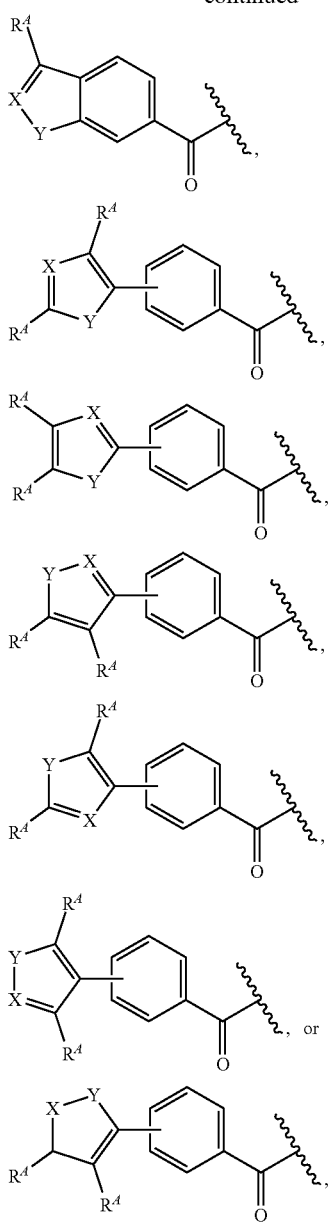

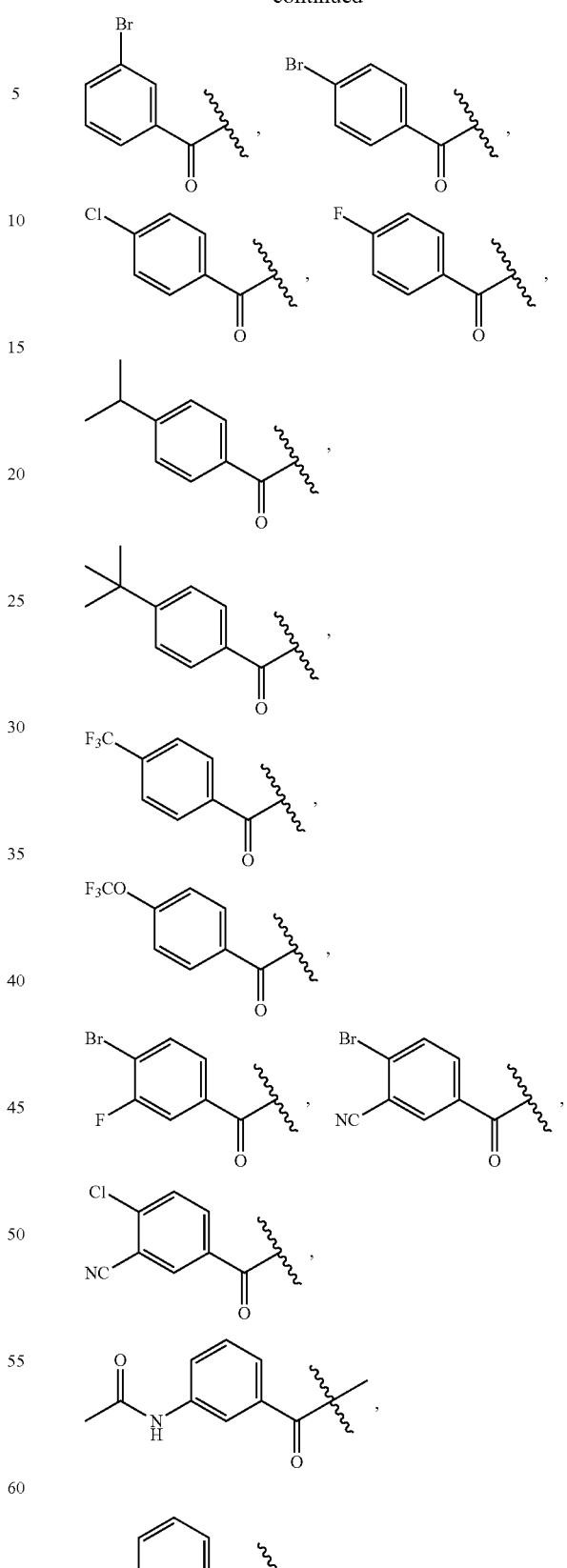

wherein X is N or CR$^A$; Y is O, S, NR, or C(R$^A$)$_2$; and each occurrence of R$^A$ is hydrogen, optionally substituted alkyl, optionally substituted carbocyclyl, optionally substituted heterocyclyl, optionally substituted aryl, optionally substituted heteroaryl, optionally substituted acyl, or a nitrogen protecting group, or two R$^A$ attached to neighboring atoms are joined to form an optionally substituted aryl or optionally substituted heteroaryl ring.

In certain embodiments, R$^8$ is of formula:

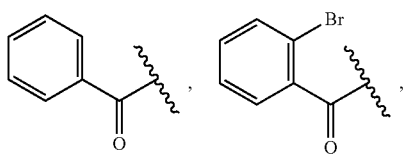

-continued
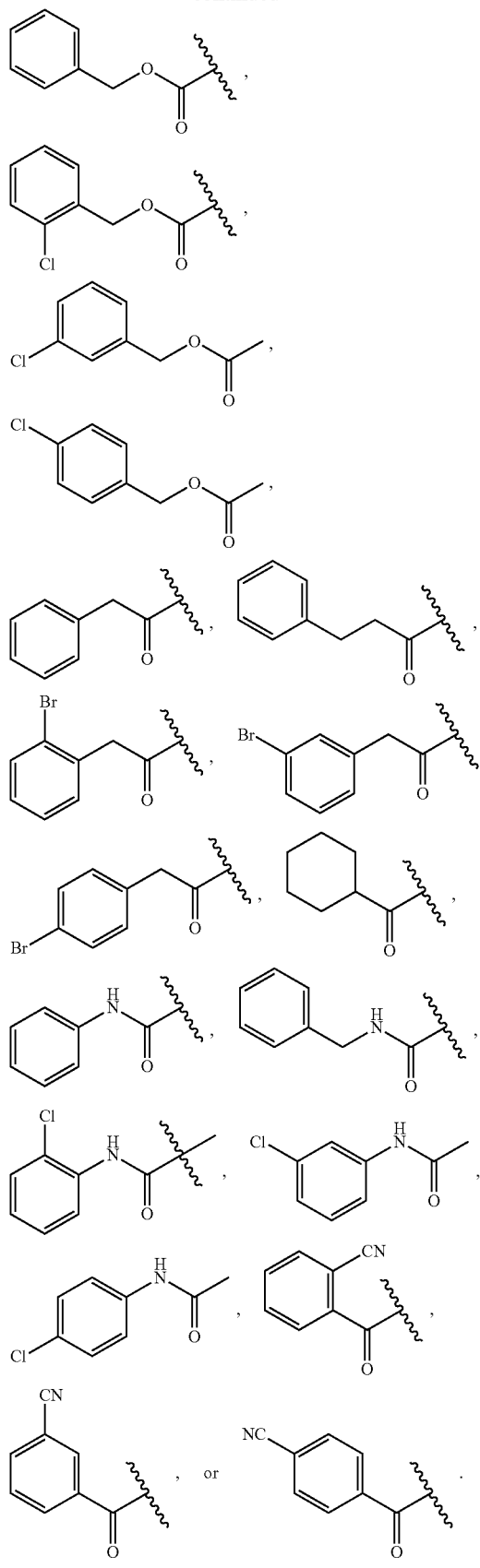
In certain embodiments, R[8] is of formula:
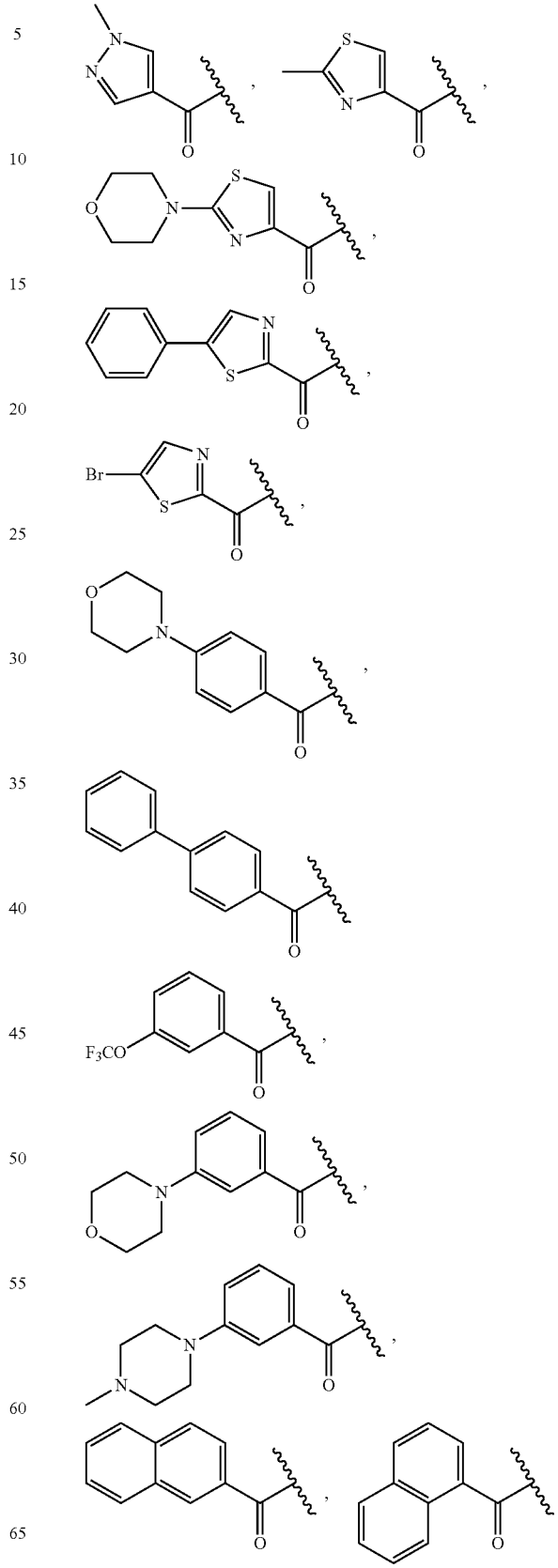

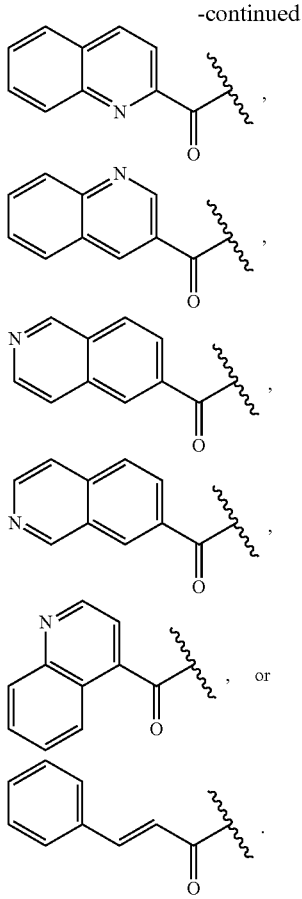

In certain embodiments, $R^8$ is of formula:

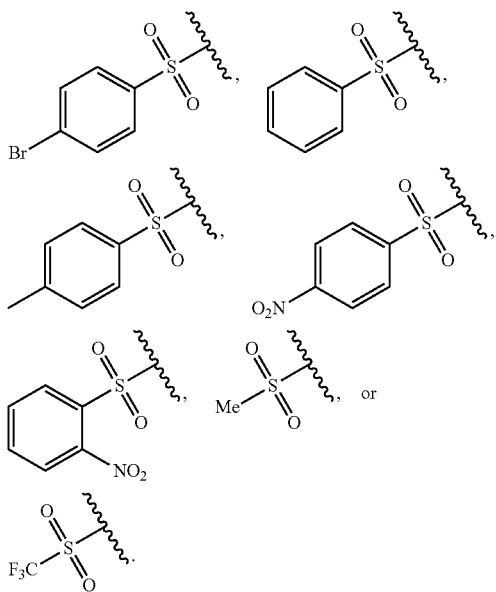

As generally defined herein, $L^1$ is a bond, an amino acid, or a dipeptide. In certain embodiments, $L^1$ is an L natural amino acid. In certain embodiments, $L^1$ is a D natural amino acid. In certain embodiments, $L^1$ is an unnatural amino acid. In certain embodiments, $L^1$ is a dipeptide of two natural amino acids that are independently L or D. In certain embodiments, $R^8$ is $-L^1-R^{8a}$, and $L^1$ is an amino acid (e.g., a peptidically bound amino acid). In certain embodiments, $R^8$ is $-L^1-R^{8a}$, and $L^1$ is a dipeptide (e.g., two peptidically bound amino acids joined by a peptide bond).

In certain embodiments, $L^1$ is of formula:

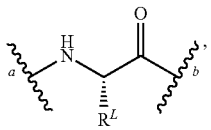

wherein a is attached to $R^{8a}$ and b is attached to the nitrogen attached to $R^d$, and $R^L$ is hydrogen, halogen, optionally substituted alkyl, optionally substituted carbocyclyl, optionally substituted heterocyclyl, optionally substituted aryl, or optionally substituted heteroaryl. In some embodiments, $R^L$ is a side chain of a naturally occurring amino acid selected from glycine, cysteine, selenocysteine, serine, threonine, asparagine, glutamine, alanine, isoleucine, leucine, methionine, phenylalanine, tyrosine, tryptophan, arginine, histidine, lysine, aspartate, or glutamate.

In certain embodiments, $L^1$ is of formula:

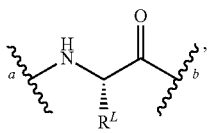

wherein a is attached to $R^8$ and b is attached to the nitrogen attached to $R^d$, and $R^L$ is hydrogen, halogen, optionally substituted alkyl, optionally substituted carbocyclyl, optionally substituted heterocyclyl, optionally substituted aryl, or optionally substituted heteroaryl. In some embodiments, $R^L$ is a side chain of a naturally occurring amino acid (e.g., glycine, cysteine, selenocysteine, serine, threonine, asparagine, glutamine, alanine, isoleucine, leucine, methionine, phenylalanine, tyrosine, tryptophan, arginine, histidine, lysine, aspartate, or glutamate).

In certain embodiments, $L^1$ is of formula:

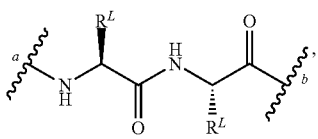

wherein a is attached to $R^{8a}$ and b is attached to the nitrogen attached to $R^d$, and each $R^L$ is independently hydrogen, halogen, optionally substituted alkyl, optionally substituted carbocyclyl, optionally substituted heterocyclyl, optionally substituted aryl, or optionally substituted heteroaryl. In some embodiments, each $R^L$ is independently a side chain of a naturally occurring amino acid selected from glycine, cysteine, selenocysteine, serine, threonine, asparagine, glutamine, alanine, isoleucine, leucine, methionine, phenylalanine, tyrosine, tryptophan, arginine, histidine, lysine, aspartate, or glutamate.

In certain embodiments, $L^1$ is of formula:

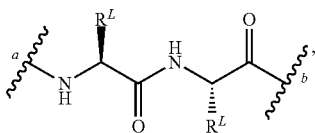

wherein a is attached to $R^8$ and b is attached to the nitrogen attached to $R^d$, and each $R^L$ is independently hydrogen, halogen, optionally substituted alkyl, optionally substituted carbocyclyl, optionally substituted heterocyclyl, optionally substituted aryl, or optionally substituted heteroaryl. In some embodiments, each $R^L$ is independently a side chain of a naturally occurring amino acid (e.g., glycine, cysteine, selenocysteine, serine, threonine, asparagine, glutamine, alanine, isoleucine, leucine, methionine, phenylalanine, tyrosine, tryptophan, arginine, histidine, lysine, aspartate, or glutamate). In certain embodiments, two instances of $R^L$ are the same. In certain embodiments, two instances of $R^L$ are different from each other.

As generally defined herein $R^c$ and $R^d$ is independently hydrogen, optionally substituted alkyl, optionally substituted acyl, or a nitrogen protecting group. In certain embodiments, $R^c$ is hydrogen. In certain embodiments, $R^d$ is hydrogen. In certain embodiments, both $R^c$ and $R^d$ are hydrogen. In certain embodiments, $R^c$ is hydrogen and $R^d$ is a non-hydrogen group (e.g., methyl). In certain embodiments, $R^c$ is a non-hydrogen group (e.g., methyl) and $R^d$ is hydrogen. In certain embodiments, both $R^c$ and $R^d$ are non-hydrogen group (e.g., methyl).

In certain embodiments, $R^c$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^c$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^c$ is methyl. In certain embodiments, $R^c$ is ethyl, propyl, or butyl.

In certain embodiments, $R^d$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^d$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^d$ is methyl. In certain embodiments, $R^d$ is ethyl, propyl, or butyl.

In certain embodiments, $R^c$ is optionally substituted acyl, e.g., —CHO, —$CO_2H$, or —C(=O)$NH_2$. In certain embodiments, $R^c$ is —C(=O)$R^f$, —C(=O)$OR^f$, —C(=O)NH($R^f$), or —C(=O)N($R^f$)$_2$, wherein each occurrence of $R^f$ is independently hydrogen, optionally substituted alkyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^f$ are joined to form an optionally substituted heterocyclic or optionally substituted heteroaryl ring. In certain embodiments, $R^c$ is —C(=O)$R^f$, and $R^f$ is optionally substituted alkyl, e.g., —C(=O)Me. In certain embodiments, $R^c$ is —C(=O)$R^f$, and $R^f$ is optionally substituted alkenyl. In certain embodiments, $R^c$ is —C(=O)$R^f$, and $R^f$ is optionally substituted carbocyclyl, heterocyclyl, aryl, or heteroaryl. In certain embodiments, $R^c$ is —C(=O)$OR^f$, and $R^f$ is optionally substituted alkyl. In certain embodiments, $R^c$ is —C(=O)$OR^f$, and $R^f$ is optionally substituted alkenyl. In certain embodiments, $R^c$ is —C(=O)$OR^f$, and $R^f$ is optionally substituted carbocyclyl, heterocyclyl, aryl, or heteroaryl. In certain embodiments, $R^c$ is —C(=O)N($R^f$)$_2$, and at least one $R^f$ is optionally substituted alkyl. In certain embodiments, $R^c$ is —C(=O)NH$R^f$, and $R^f$ is optionally substituted alkyl. In certain embodiments, $R^c$ is —C(=O)NH$R^f$, and $R^f$ is optionally substituted alkenyl. In certain embodiments, $R^c$ is —C(=O)NH$R^f$, and $R^f$ is optionally substituted carbocyclyl, heterocyclyl, aryl, or heteroaryl.

In certain embodiments, $R^c$ is a nitrogen protecting group. In some embodiments, $R^c$ is Bn, Boc, Cbz, Fmoc, trifluoroacetyl, triphenylmethyl, acetyl, tosyl, nosyl, brosyl, mesyl, or triflyl.

In certain embodiments, $R^d$ is optionally substituted acyl, e.g., —CHO, —$CO_2H$, or —C(=O)$NH_2$. In certain embodiments, $R^d$ is —C(=O)$R^f$, —C(=O)$OR^f$, —C(=O)NH($R^f$), or —C(=O)N($R^f$)$_2$, wherein each occurrence of $R^f$ is independently hydrogen, optionally substituted alkyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^f$ are joined to form an optionally substituted heterocyclic or optionally substituted heteroaryl ring. In certain embodiments, $R^d$ is —C(=O)$R^f$, and $R^f$ is optionally substituted alkyl, e.g., —C(=O)Me. In certain embodiments, $R^d$ is —C(=O)$R^f$, and $R^f$ is optionally substituted alkenyl. In certain embodiments, $R^d$ is —C(=O)$R^f$, and $R^f$ is optionally substituted carbocyclyl, heterocyclyl, aryl, or heteroaryl. In certain embodiments, $R^d$ is —C(=O)$OR^f$, and $R^f$ is optionally substituted alkyl. In certain embodiments, $R^d$ is —C(=O)$OR^f$, and $R^f$ is optionally substituted alkenyl. In certain embodiments, $R^d$ is —C(=O)$OR^f$, and $R^f$ is optionally substituted carbocyclyl, heterocyclyl, aryl, or heteroaryl. In certain embodiments, $R^d$ is —C(=O)N($R^f$)$_2$, and at least one $R^f$ is optionally substituted alkyl. In certain embodiments, $R^d$ is —C(=O)NH$R^f$, and $R^f$ is optionally substituted alkyl. In certain embodiments, $R^d$ is —C(=O)NH$R^f$, and $R^f$ is optionally substituted alkenyl. In certain embodiments, $R^d$ is —C(=O)NH$R^f$, and $R^f$ is optionally substituted carbocyclyl, heterocyclyl, aryl, or heteroaryl.

In certain embodiments, $R^d$ is a nitrogen protecting group. In some embodiments, $R^d$ is Bn, Boc, Cbz, Fmoc, trifluoroacetyl, triphenylmethyl, acetyl, tosyl, nosyl, brosyl, mesyl, or triflyl.

As generally defined herein independently hydrogen, optionally substituted alkyl, optionally substituted acyl, optionally substituted sulfonyl, or a nitrogen protecting group, or any two of $R^{41}$, $R^{42}$, $R^{43}$, and $R^{44}$ are joined to form an optionally substituted heterocyclic or optionally substituted heteroaryl ring.

In certain embodiments, $R^{41}$ and $R^{42}$ are joined to form an optionally substituted heterocyclic ring. In certain embodiments, $R^{41}$ and $R^{43}$ or $R^{44}$ are joined to form an optionally substituted heterocyclic ring. In certain embodiments, $R^{42}$ and $R^{43}$ or $R^{44}$ are joined to form an optionally substituted heterocyclic ring. In certain embodiments, $R^{43}$ and $R^{44}$ are joined to form an optionally substituted heterocyclic ring. In certain embodiments, none of $R^{41}$, $R^{42}$, $R^{43}$, and $R^{44}$ are joined to form a ring.

In certain embodiments, each of $R^{41}$, $R^{42}$, $R^{43}$, and $R^{44}$ is hydrogen. In certain embodiments, each of $R^{41}$, $R^{42}$, and $R^{43}$ is hydrogen, and $R^{44}$ is a non-hydrogen group. In certain embodiments, each of $R^{41}$, $R^{43}$, and $R^{44}$ is hydrogen, and $R^{A2}$ is a non-hydrogen group. In certain embodiments, $R^{A1}$ and $R^{A3}$ are hydrogen, and $R^{A2}$ and $R^{A4}$ are non-hydrogen groups.

In certain embodiments, at least one of $R^{A1}$, $R^{A2}$, $R^{A3}$, or $R^{A4}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one of $R^{A1}$, $R^{A2}$, $R^{A3}$, or $R^{A4}$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, at least one of $R^{A1}$, $R^{A2}$, $R^{A3}$, or $R^{A4}$ is methyl. In certain embodiments, at least one of $R^{A1}$, $R^{A2}$, $R^{A3}$, or $R^{A4}$ is ethyl, propyl, or butyl.

In certain embodiments, at least one of $R^{A1}$, $R^{A2}$, $R^{A3}$, or $R^{A4}$ is optionally substituted acyl, e.g., —CHO, —CO$_2$H, or —C(=O)NH$_2$. In certain embodiments, at least one of $R^{A1}$, $R^{A2}$, $R^{A3}$, or $R^{A4}$ is —C(=O)R$^f$, —C(=O)OR$^f$, —C(=O)NH(R$^f$), or —C(=O)N(R$^f$)$_2$, wherein each occurrence of R$^f$ is independently hydrogen, optionally substituted alkyl, optionally substituted carbocyclyl, optionally substituted heterocyclyl, optionally substituted aryl, optionally substituted heteroaryl, optionally substituted acyl, an oxygen protecting group, or a nitrogen protecting group, or two R$^f$ are joined to form an optionally substituted heterocyclic or optionally substituted heteroaryl ring. In certain embodiments, at least one of $R^{A1}$, $R^{A2}$, $R^{A3}$, or $R^{A4}$ is —C(=O)R$^f$, and R$^f$ is optionally substituted alkyl, e.g., —C(=O)Me. In certain embodiments, at least one of $R^{A1}$, $R^{A2}$, $R^{A3}$, or $R^{A4}$ is —C(=O)R$^f$, and R$^f$ is optionally substituted alkenyl. In certain embodiments, at least one of $R^{A1}$, $R^{A2}$, $R^{A3}$, or $R^{A4}$ is —C(=O)R$^f$, and R$^f$ is optionally substituted carbocyclyl, heterocyclyl, aryl, or heteroaryl. In certain embodiments, at least one of $R^{A1}$, $R^{A2}$, $R^{A3}$, or $R^{A4}$ is —C(=O)OR$^f$, and R$^f$ is optionally substituted alkyl. In certain embodiments, at least one of $R^{A1}$, $R^{A2}$, $R^{A3}$, or $R^{A4}$ is —C(=O)OR$^f$, and R$^f$ is optionally substituted alkenyl. In certain embodiments, at least one of $R^{A1}$, $R^{A2}$, $R^{A3}$, or $R^{A4}$ is —C(=O)OR$^f$, and R$^f$ is optionally substituted carbocyclyl, heterocyclyl, aryl, or heteroaryl. In certain embodiments, at least one of $R^{A1}$, $R^{A2}$, $R^{A3}$, or $R^{A4}$ is —C(=O)N(R$^f$)$_2$, and at least one R$^f$ is optionally substituted alkyl. In certain embodiments, at least one of $R^{A1}$, $R^{A2}$, $R^{A3}$, or $R^{A4}$ is —C(=O)NHR$^f$, and R$^f$ is optionally substituted alkyl. In certain embodiments, at least one of $R^{A1}$, $R^{A2}$, $R^{A3}$, or $R^{A4}$ is —C(=O)NHR$^f$, and R$^f$ is optionally substituted alkenyl. In certain embodiments, at least one of $R^{A1}$, $R^{A2}$, $R^{A3}$, or $R^{A4}$ is —C(=O)NHR$^f$, and R$^f$ is optionally substituted carbocyclyl, heterocyclyl, aryl, or heteroaryl.

In certain embodiments, at least one of $R^{A1}$, $R^{A2}$, $R^{A3}$, or $R^{A4}$ is optionally substituted sulfonyl, e.g., —S(=O)$_2$OH. In certain embodiments, at least one of $R^{A1}$, $R^{A2}$, $R^{A3}$, or $R^{A4}$ is —S(=O)$_2$R$^f$, wherein R$^f$ is hydrogen, optionally substituted alkyl, optionally substituted carbocyclyl, optionally substituted heterocyclyl, optionally substituted aryl, or optionally substituted heteroaryl. In certain embodiments, at least one of $R^{A1}$, $R^{A2}$, $R^{A3}$, or $R^{A4}$ is —S(=O)$_2$R$^f$, and R$^f$ is optionally substituted alkyl, e.g., —S(=O)$_2$Me. In certain embodiments, at least one of $R^{A1}$, $R^{A2}$, $R^{A3}$, or $R^{A4}$ is —S(=O)$_2$R$^f$, and R$^f$ is optionally substituted carbocyclyl, heterocyclyl, aryl, or heteroaryl.

In certain embodiments, at least one of $R^{A1}$, $R^{A2}$, $R^{A3}$, or $R^{A4}$ is a nitrogen protecting group. In some embodiments, $R^{A4}$ is a nitrogen protecting group. In some embodiments, $R^{A2}$ is a nitrogen protecting group. In some embodiments, $R^{A2}$ is a nitrogen protecting group, and $R^{A4}$ is a nitrogen protecting group. In some embodiments, the nitrogen protecting group is selected from the group consisting of selected from the group consisting of tosyl, 2,2,5,7,8-pentamethylchroman-6-yl, 2,2,4,5,7-pentamethyl-2,3-dihydrobenzofuran-5-sulfonyl, mesityl-2-sulfonyl, 4-methoxy-2,3,6-trimethylphenylsulfonyl, 1,2-dimethylindole-3-sulfonyl, tert-butoxycarbonyl, 5-dibenzosuberenyl, 5-dibenzosuberyl, 2-methoxy-5-dibenzosuberyl, trifluoroacetyl, benzyloxycarbonyl, allyloxycarbonyl, and —NO$_2$.

In certain embodiments, the guanidine moiety is of formula:

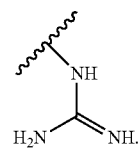

In certain embodiments, the guanidine moiety is of formula:

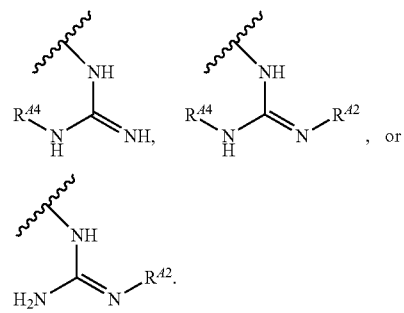

In certain embodiments, the guanidine moiety is of formula:

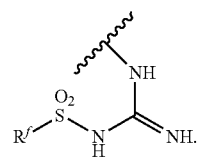

In certain embodiments, the guanidine moiety is of formula:

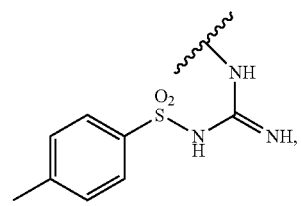

-continued
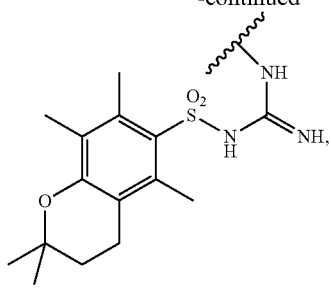
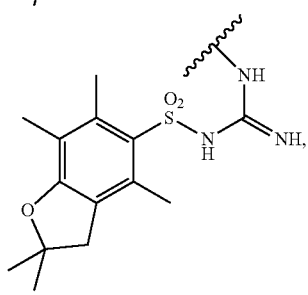
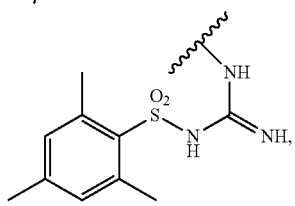
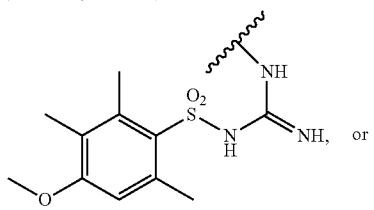, or
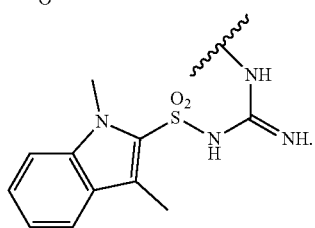
In certain embodiments, the guanidine moiety is of formula:
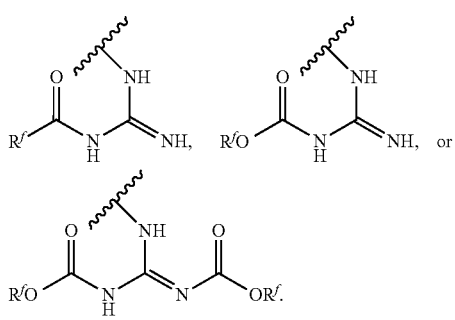
In certain embodiments, the guanidine moiety is of formula:
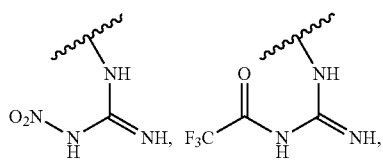
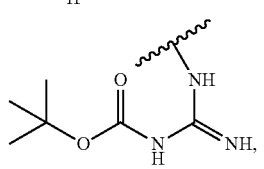
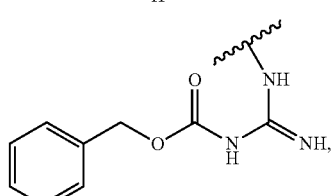
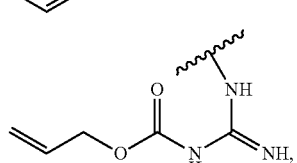
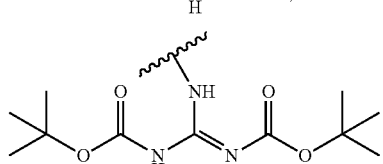
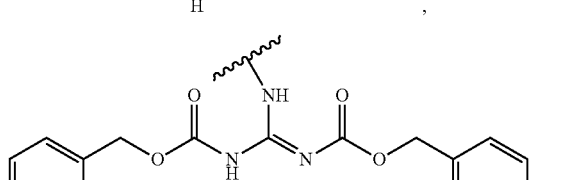, 
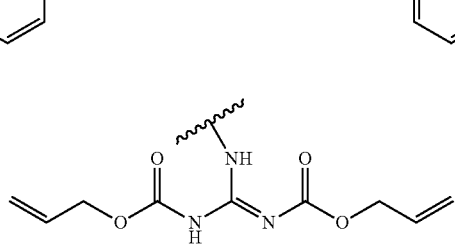, or
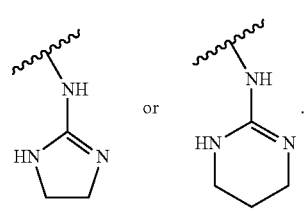 [SMILES: *NC1=NCCN1 ; *NC1=NCCCN1].
In certain embodiments, the guanidine moiety is of formula:
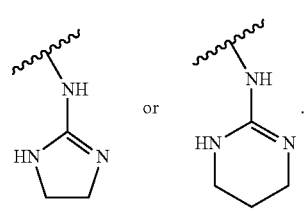 [SMILES: *NC1=NCCN1 ; *NC1=NCCCN1]
In certain embodiments, the compound is a compound listed in Table 1, or a pharmaceutically acceptable salt, stereoisomer, or tautomer thereof.

Table 1. Exemplary compounds of Formula (I)
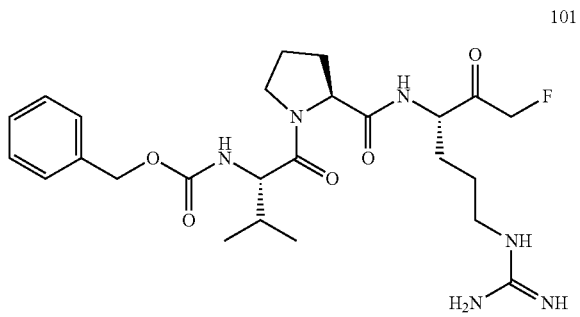
101
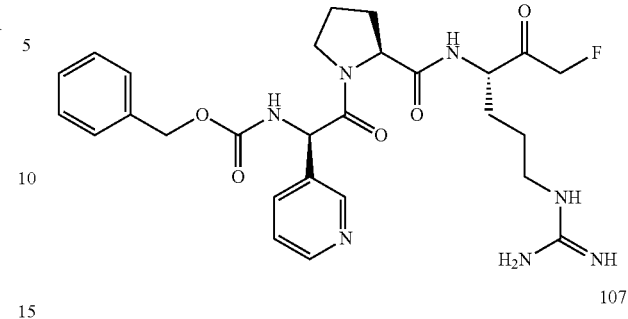
106
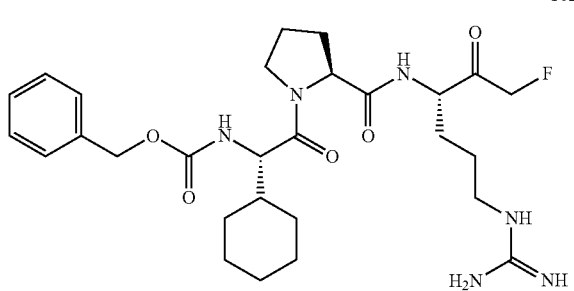
102
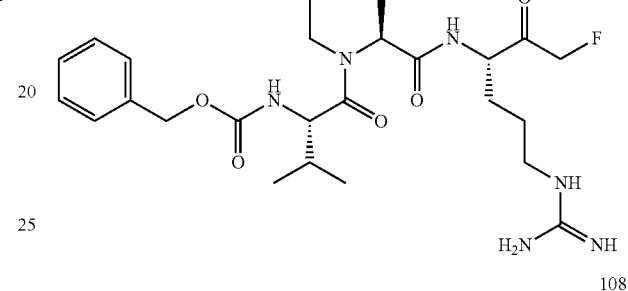
107
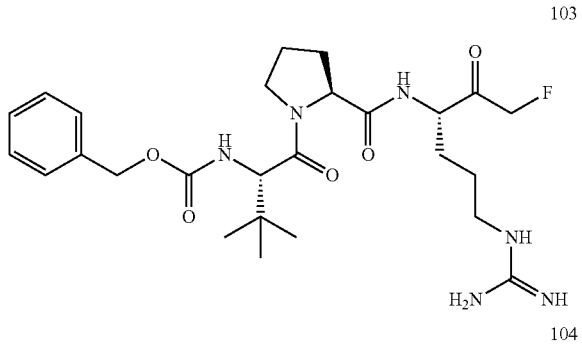
103
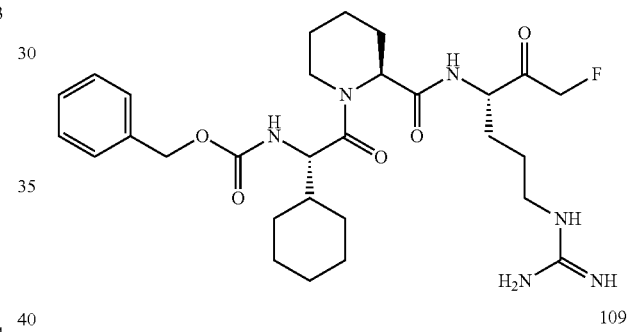
108
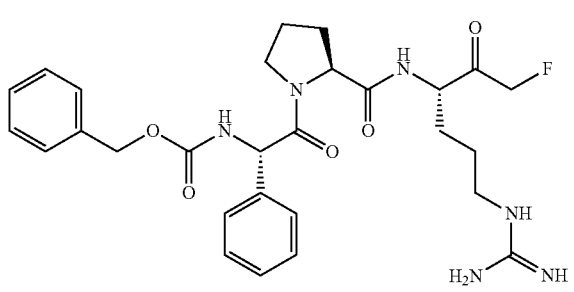
104
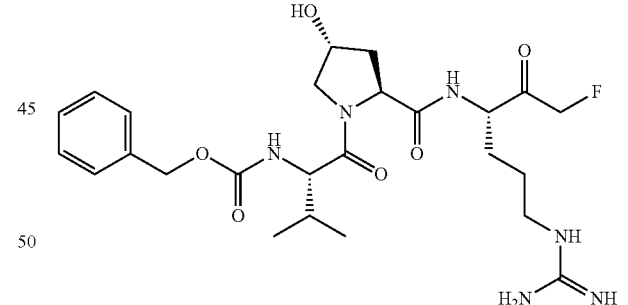
109
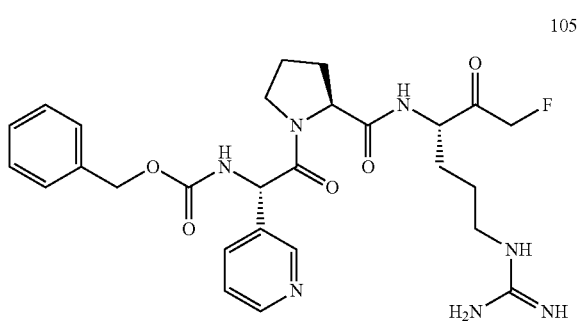
105
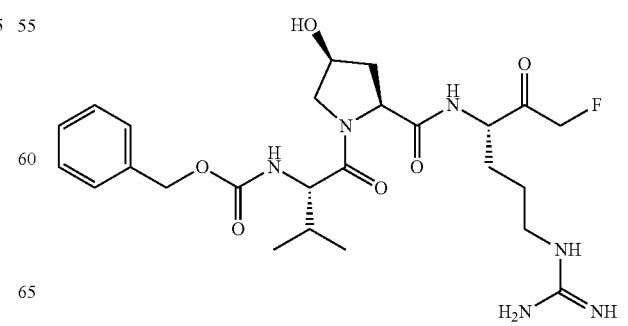
110

111 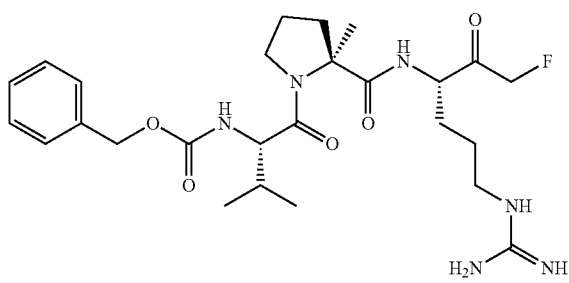
112 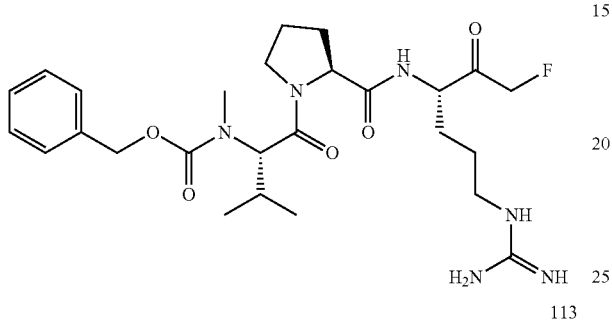
113 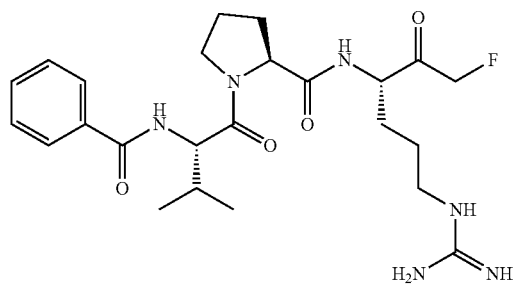
114 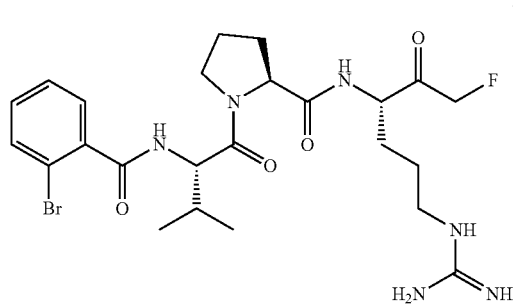
115 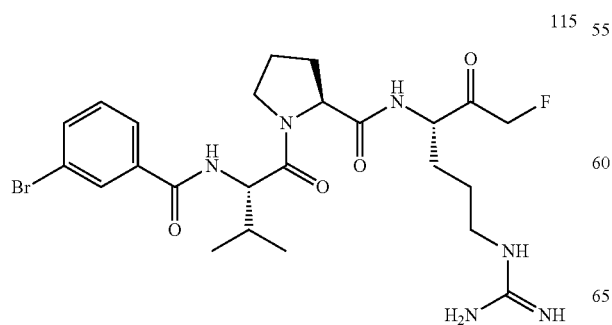
116 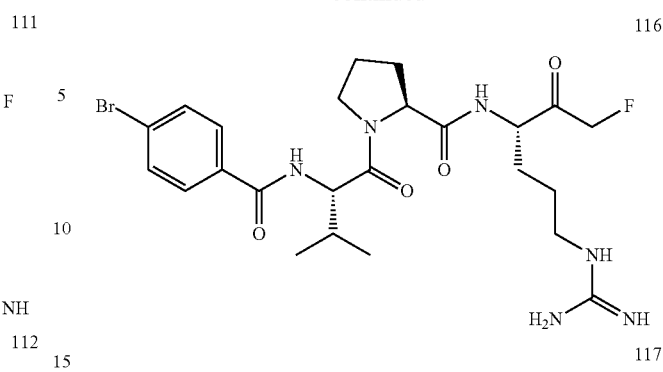
117 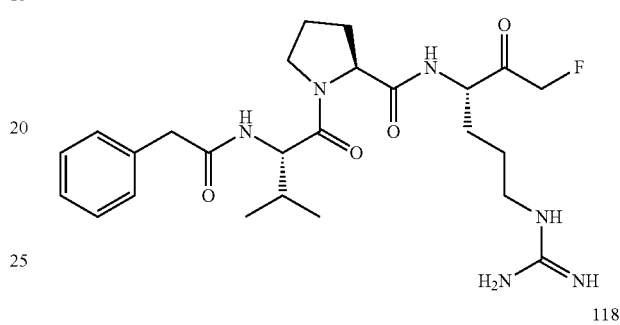
118 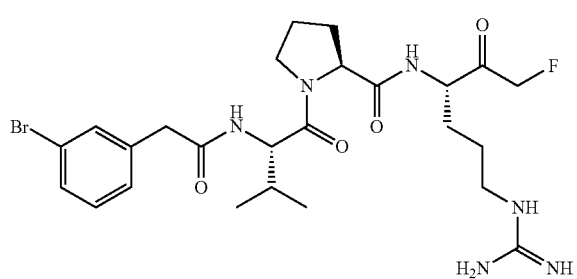
119 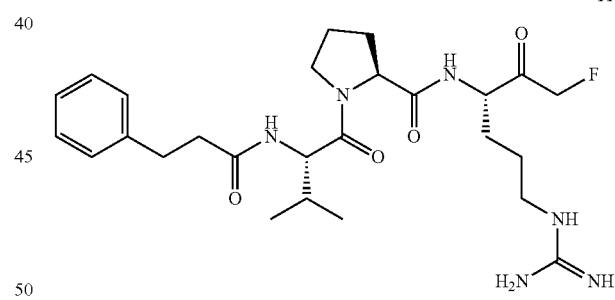
120 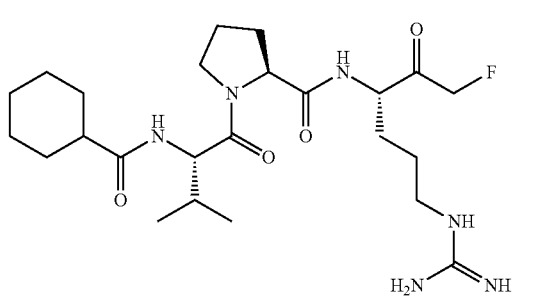

121
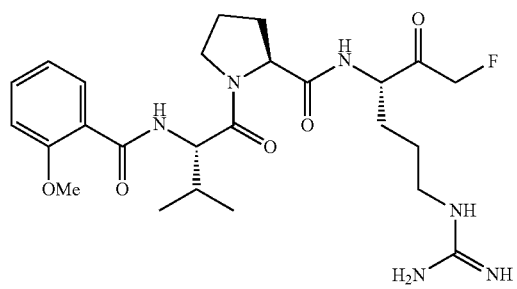
122
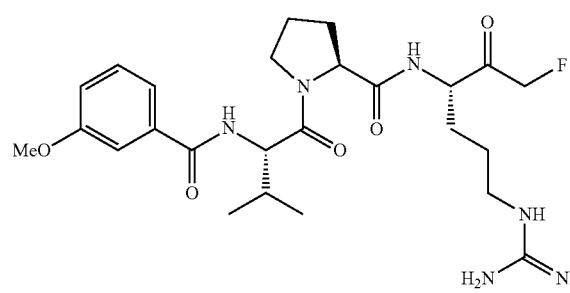
123
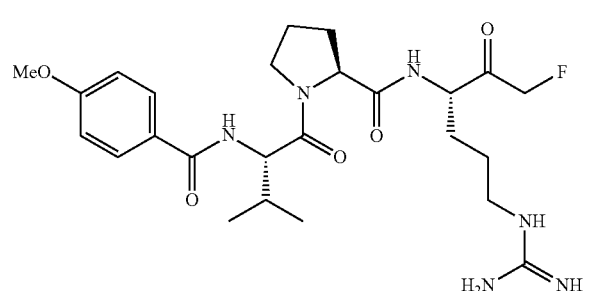
124
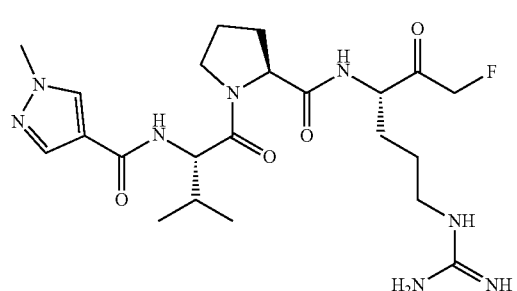
125
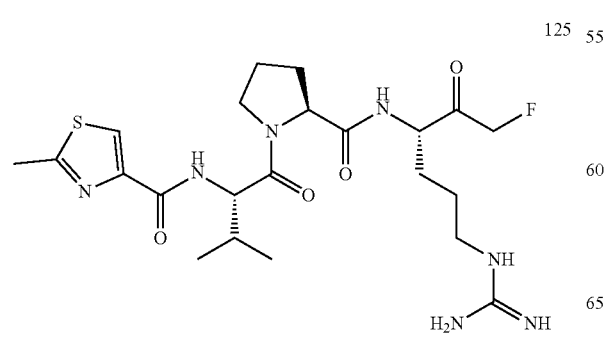
126
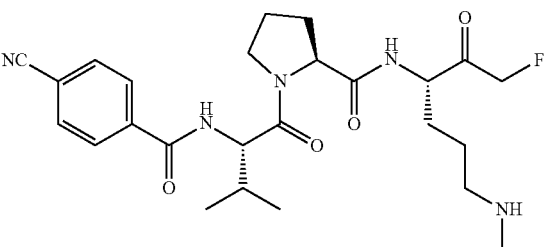
127
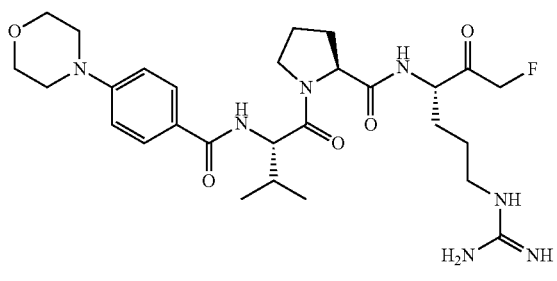
128
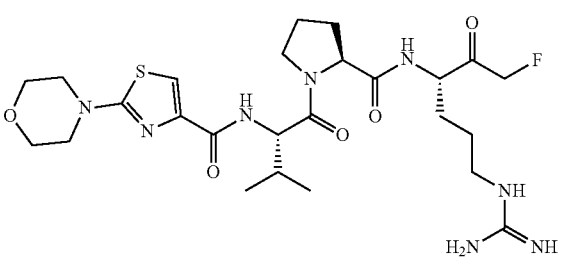
129
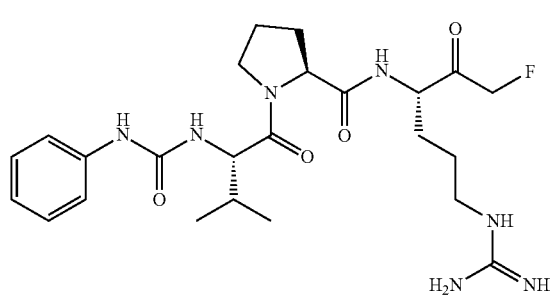
130
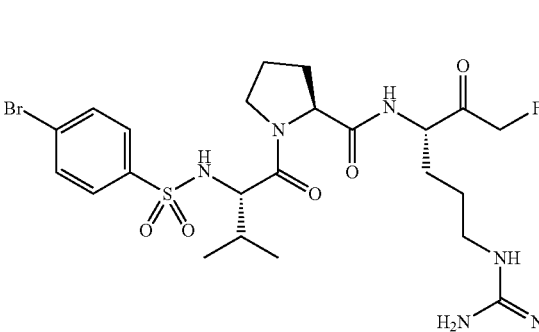

Table 2. Exemplary compounds of Formula (I)
201
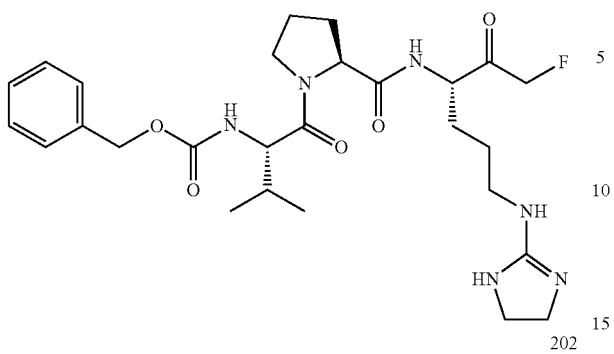
202
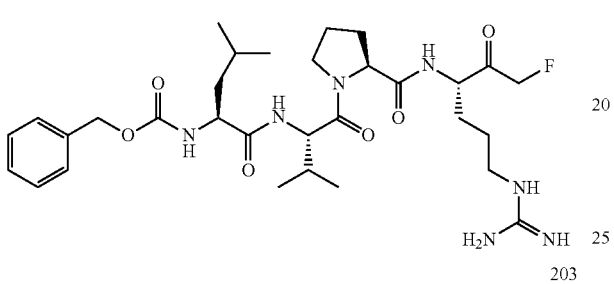
203
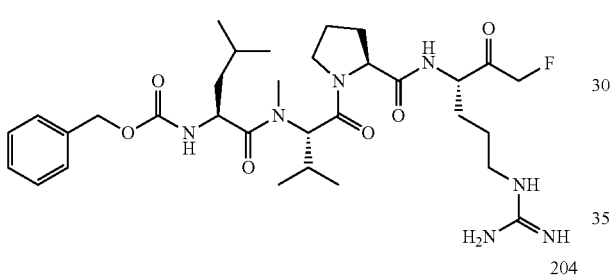
204
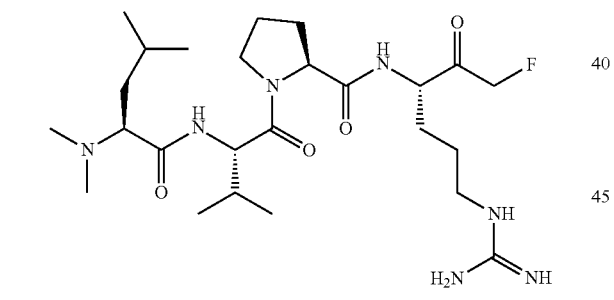
205
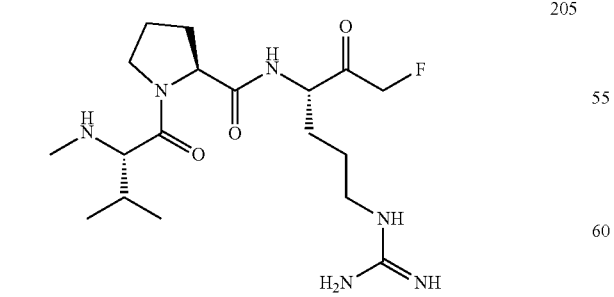
131
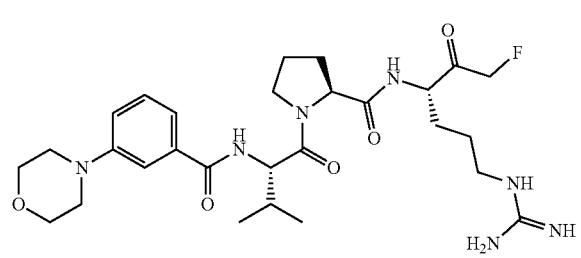
132
133
134
135
In certain embodiments, the compound is a compound listed in Table 2, or a pharmaceutically acceptable salt, stereoisomer, or tautomer thereof.

136
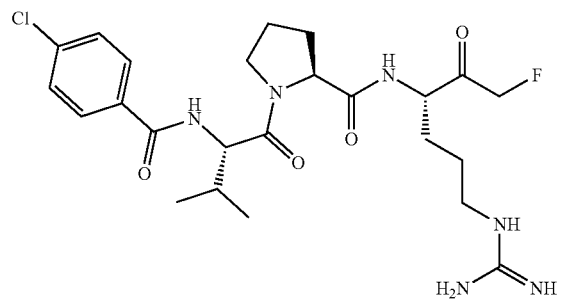
137
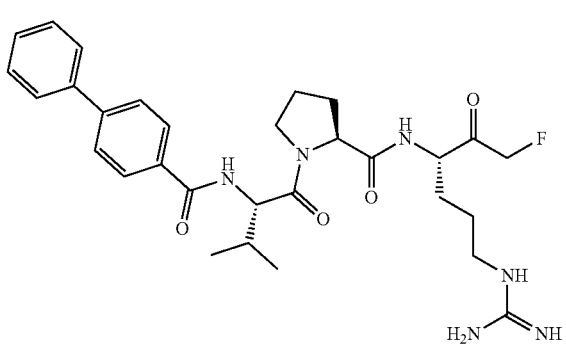
138
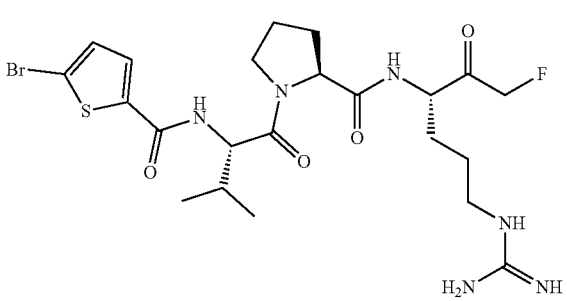
139
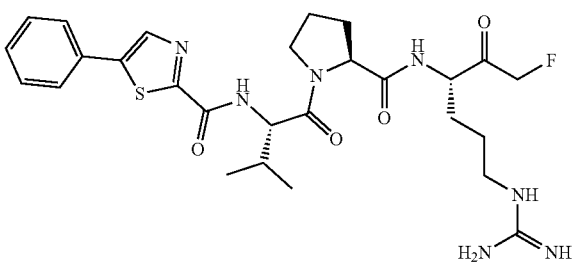
140
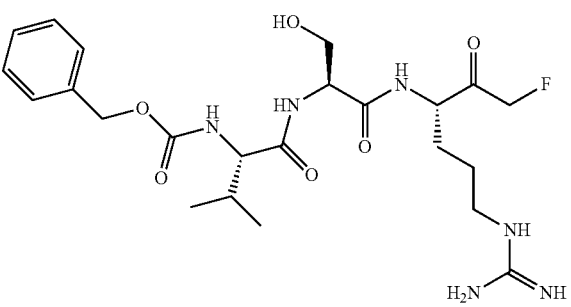
141
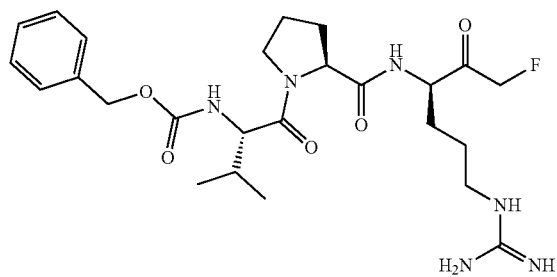
142
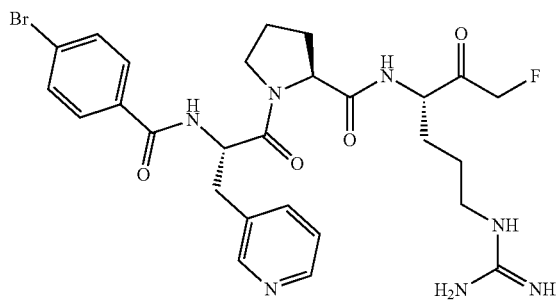
143
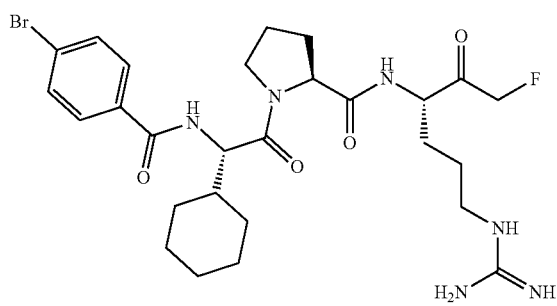
144
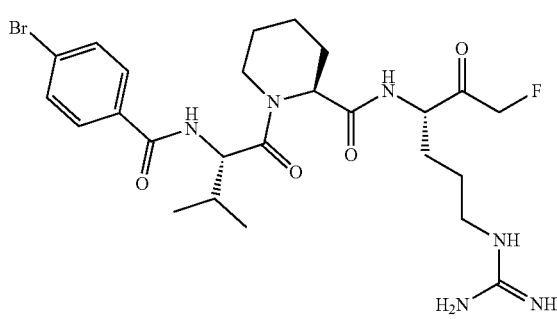
145
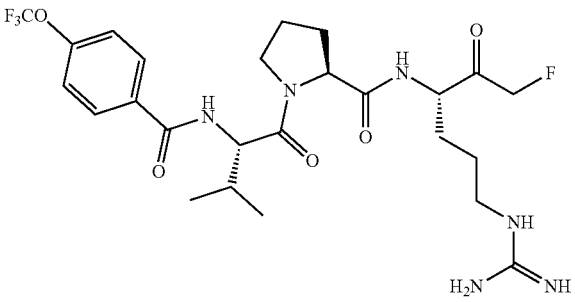

146
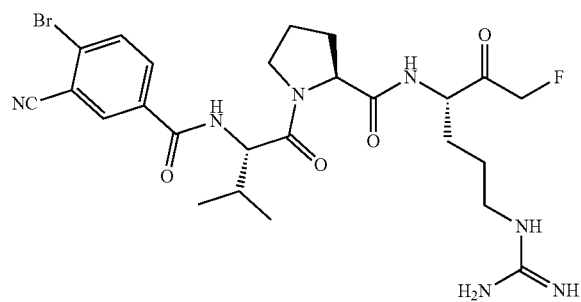
147
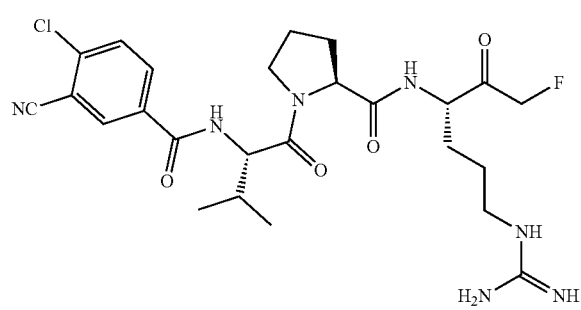
148
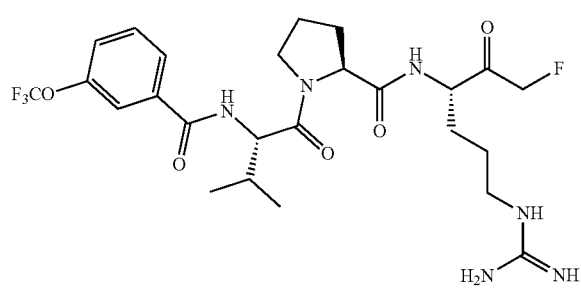
149
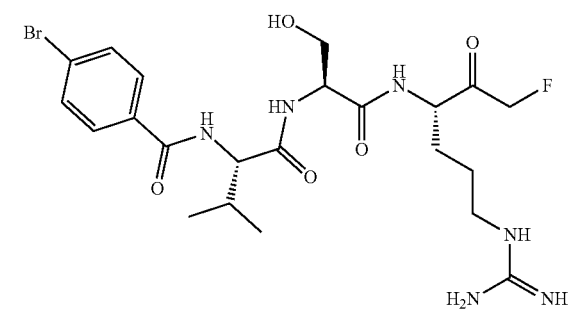
150
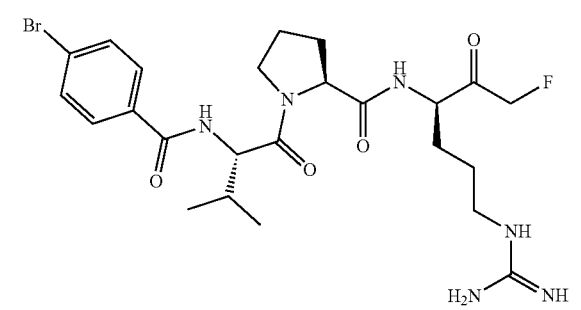
151
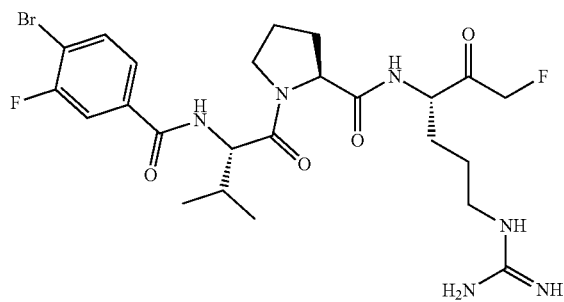
152
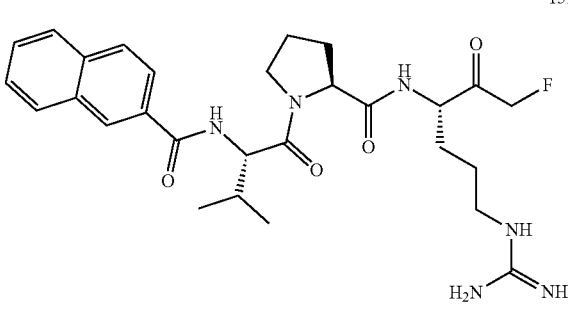
153
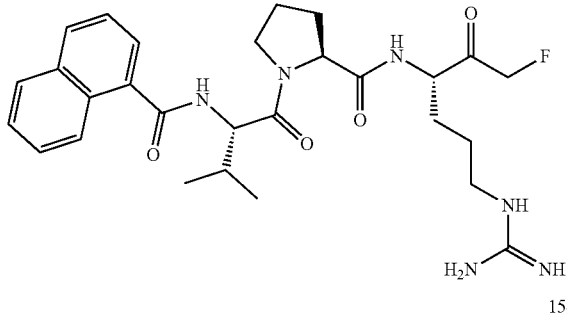
154
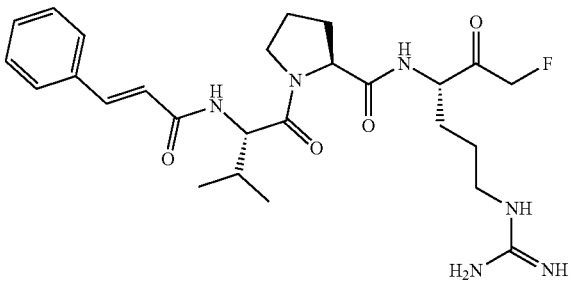
155
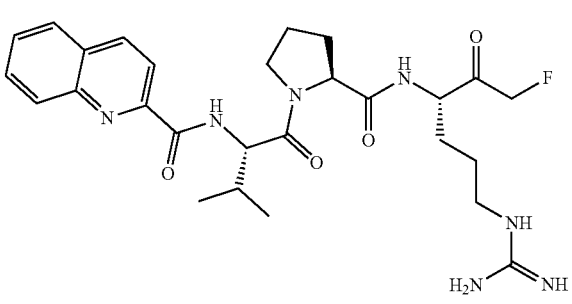

81
-continued
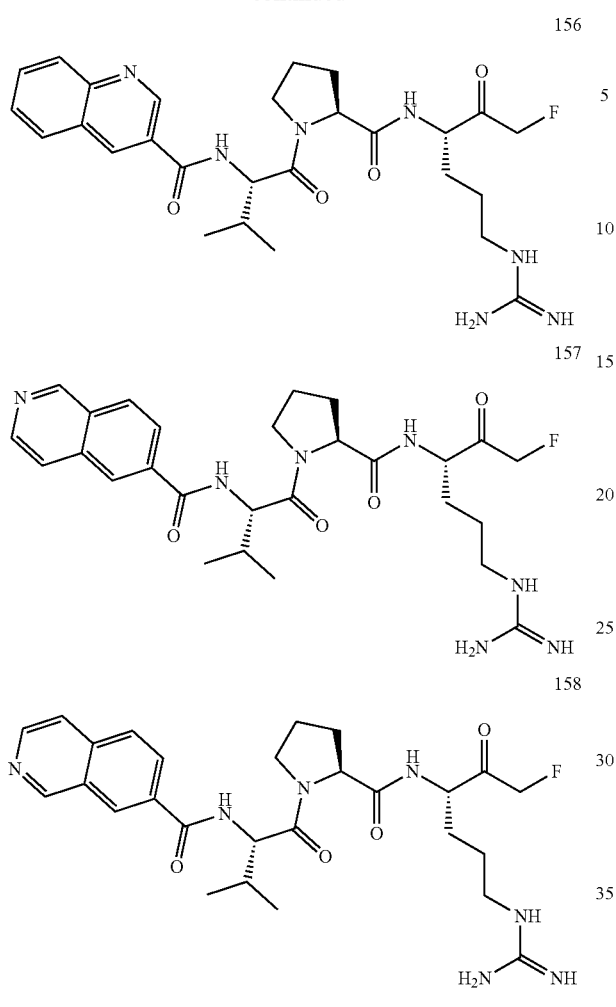
82
-continued
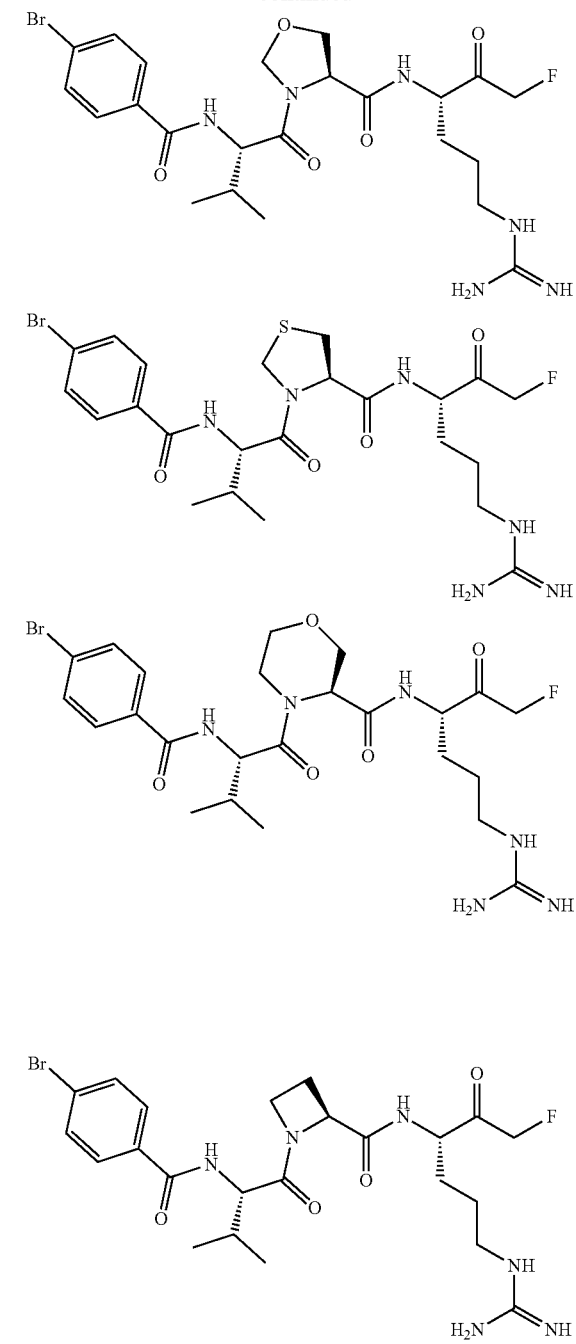
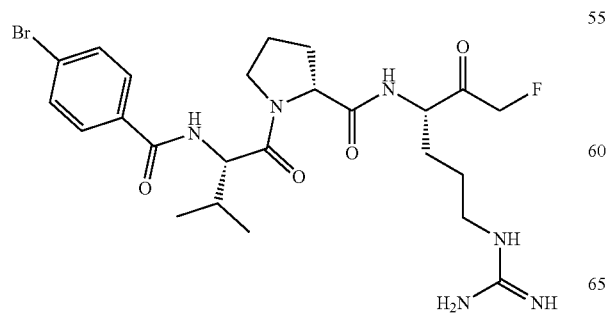

83
-continued
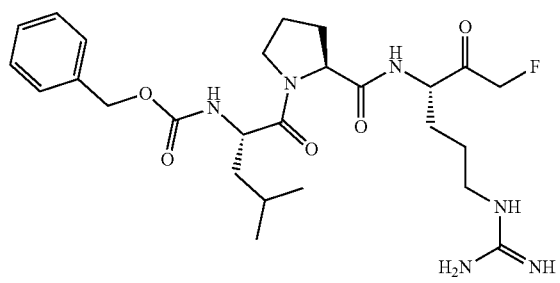
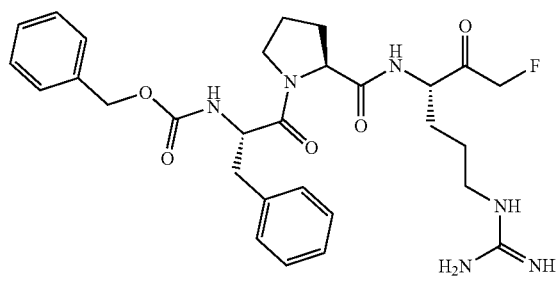
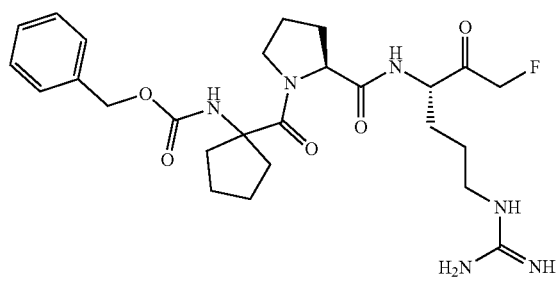
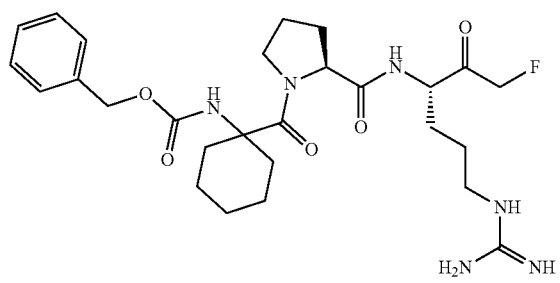
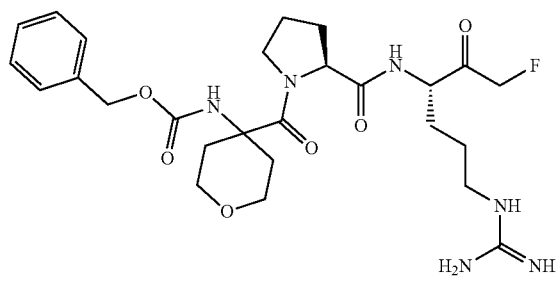
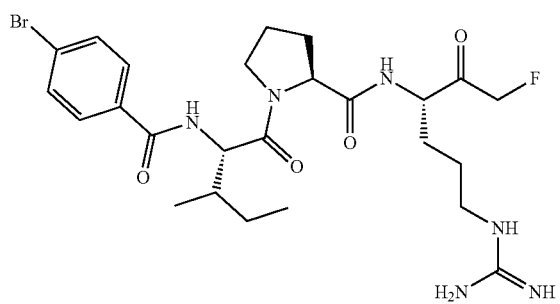
84
-continued
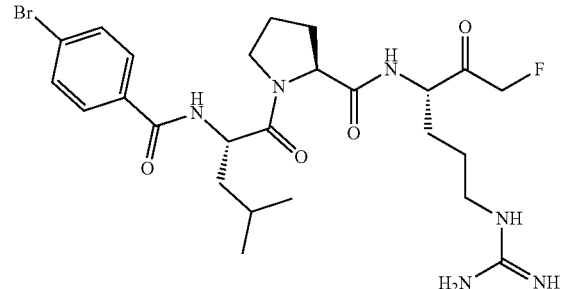
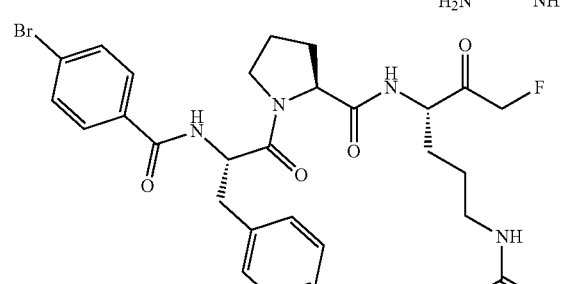
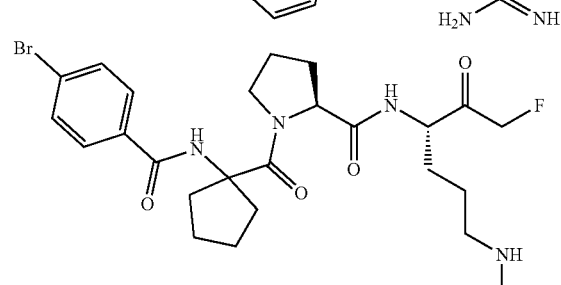
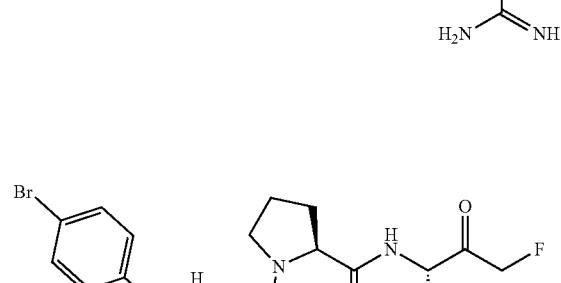
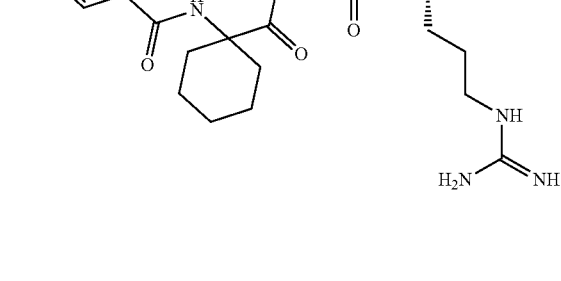
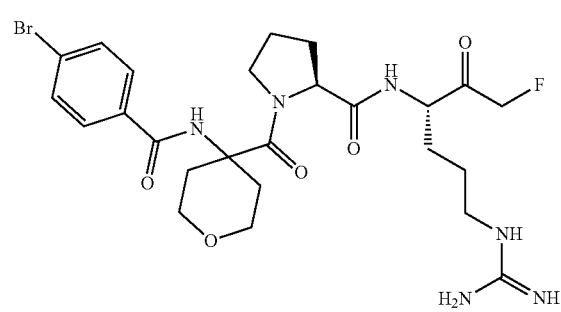

-continued
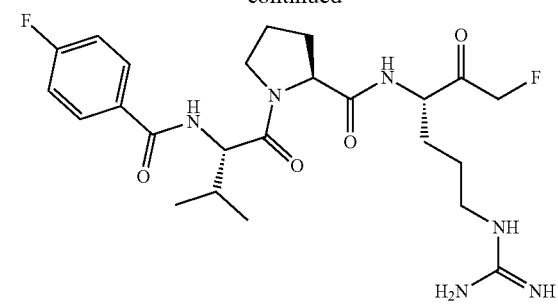
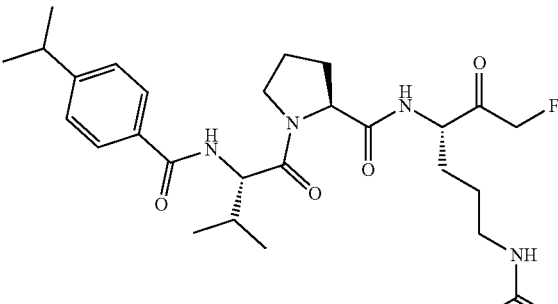
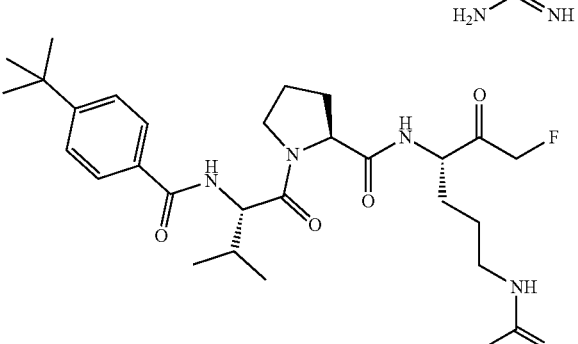
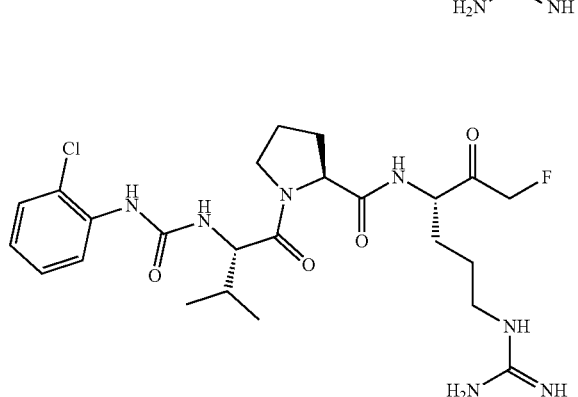
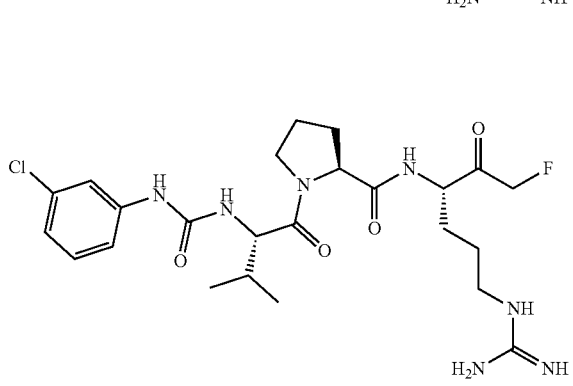
-continued
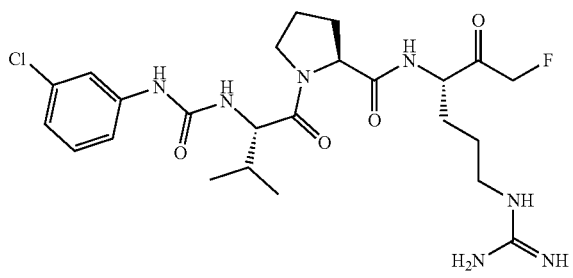
In certain embodiments, the compound described herein is of the formula:
160
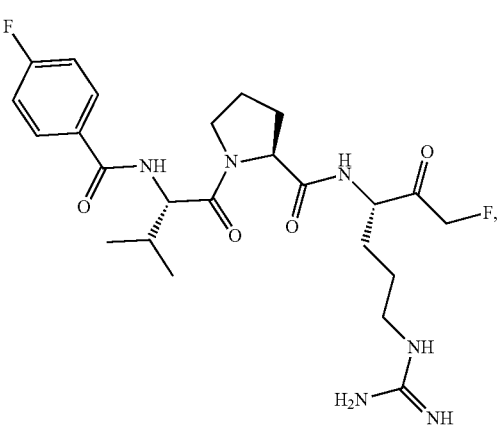

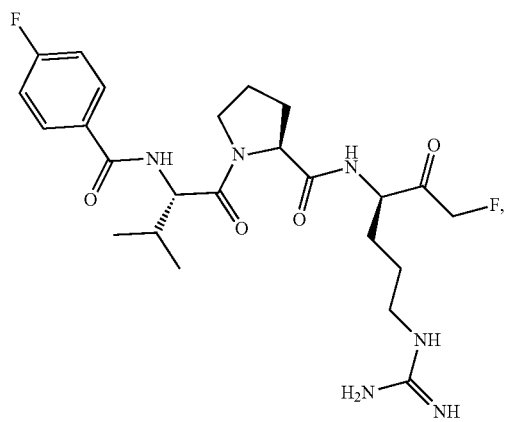
161
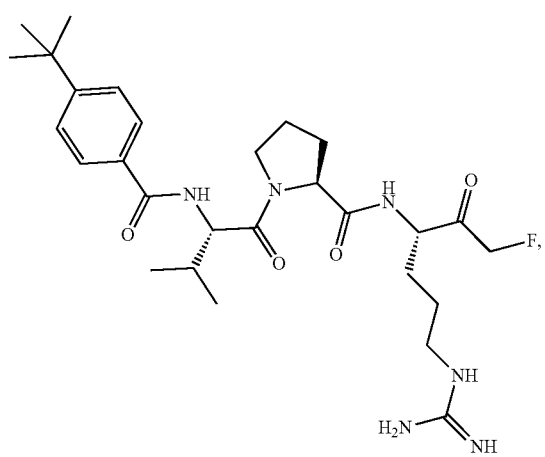
162
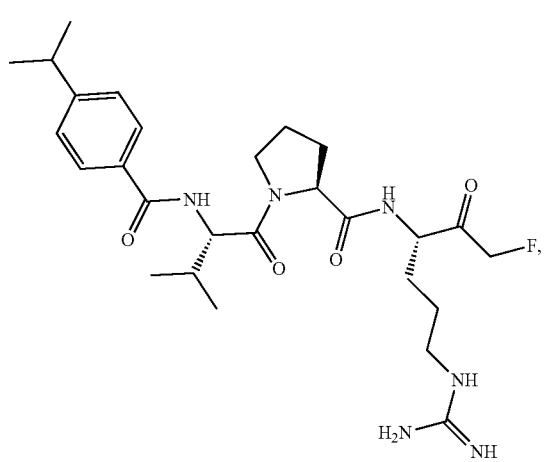
163
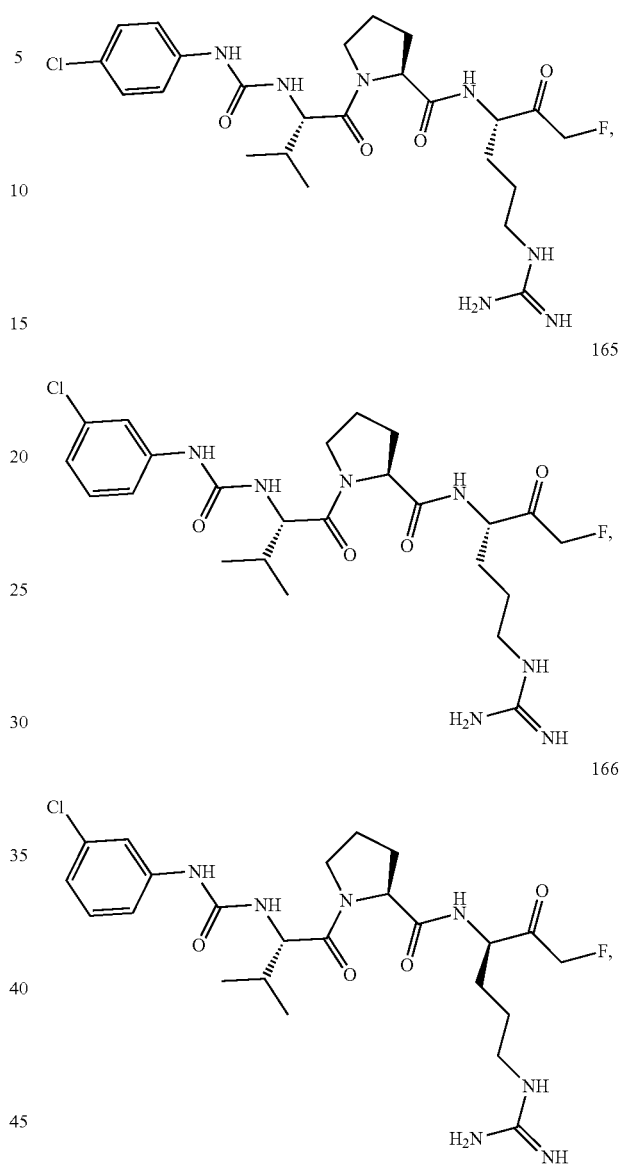
164
165
166
167

89
-continued
168
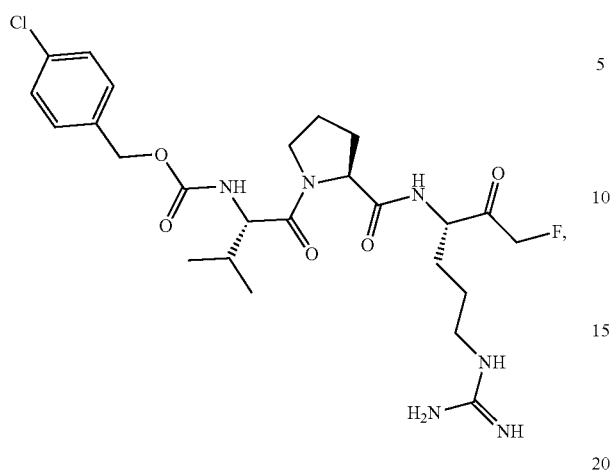
169
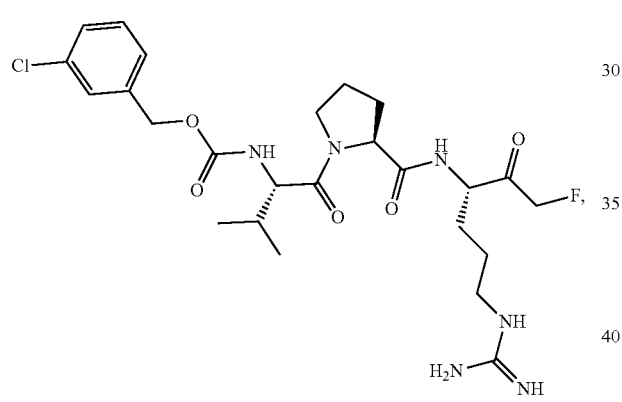
170
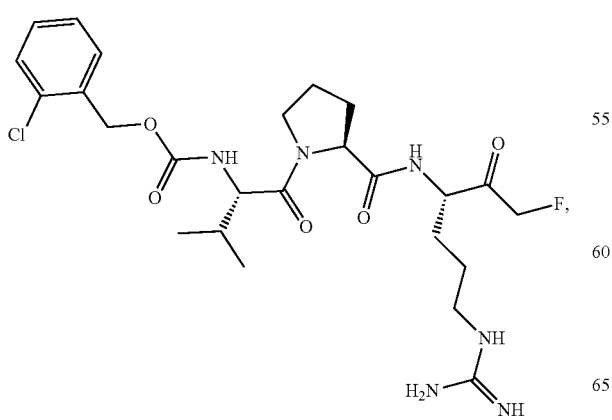
90
-continued
171
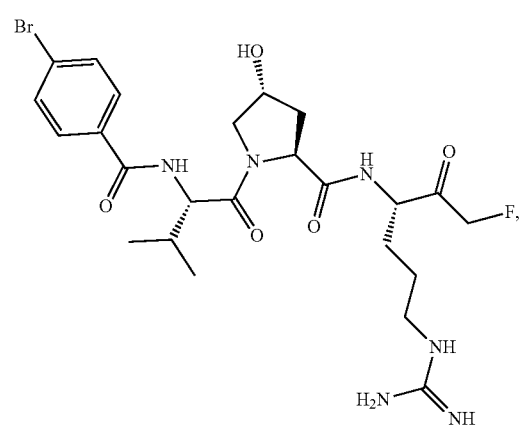
172
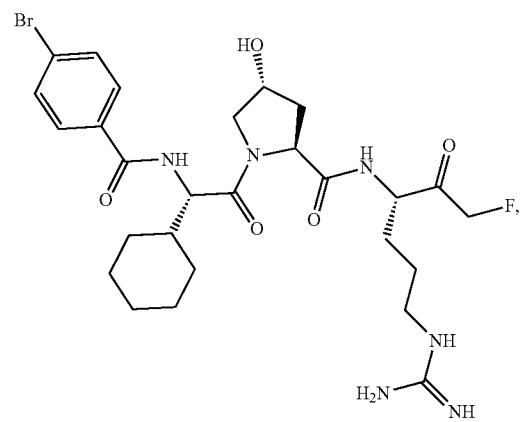
173
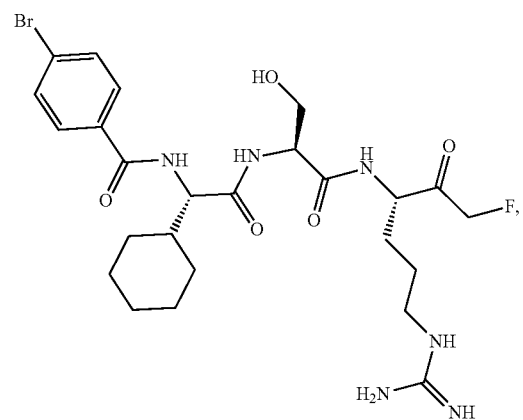

91
-continued
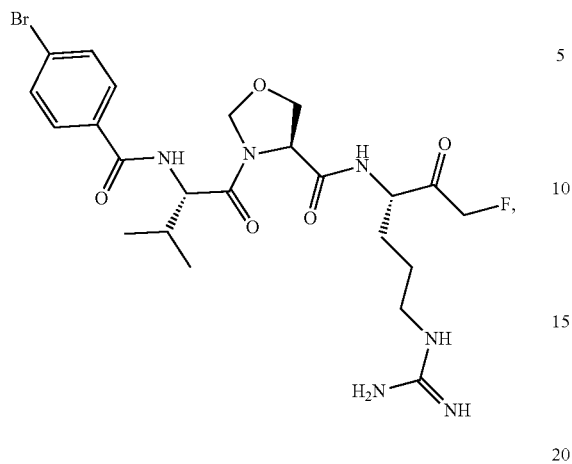
174
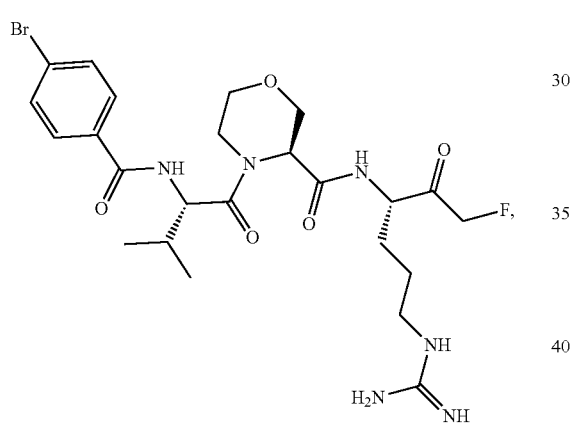
175
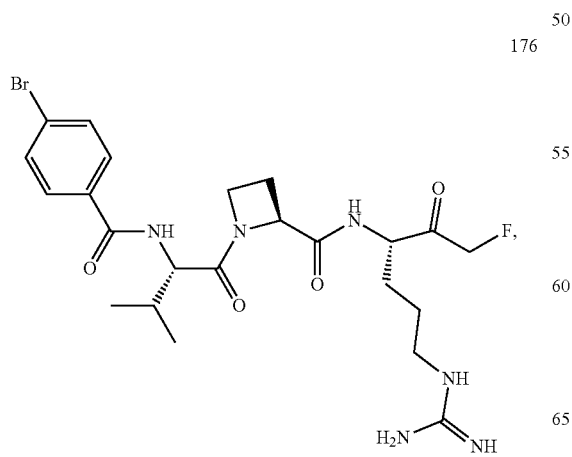
176
92
-continued
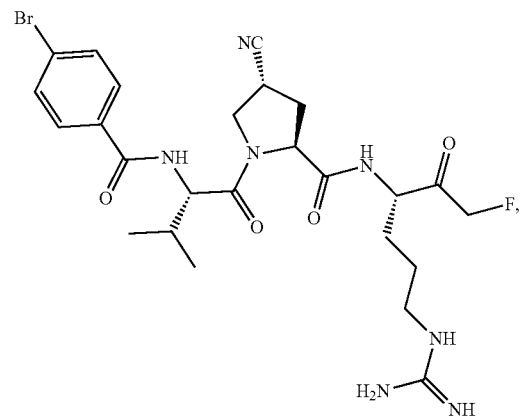
177
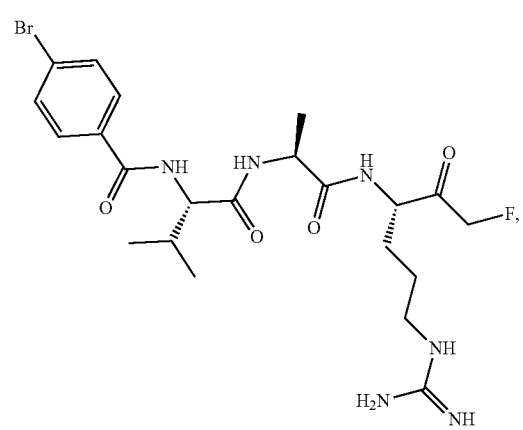
178
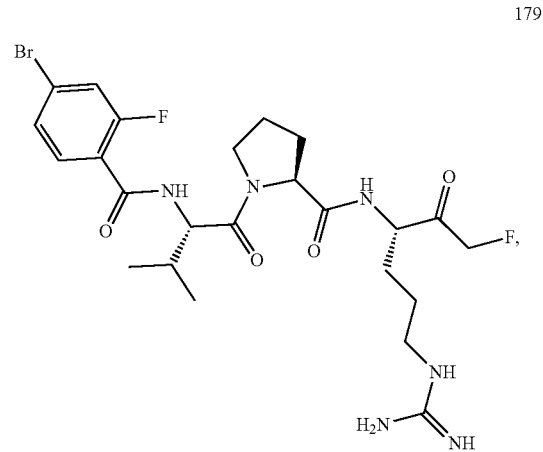
179

93 94
180
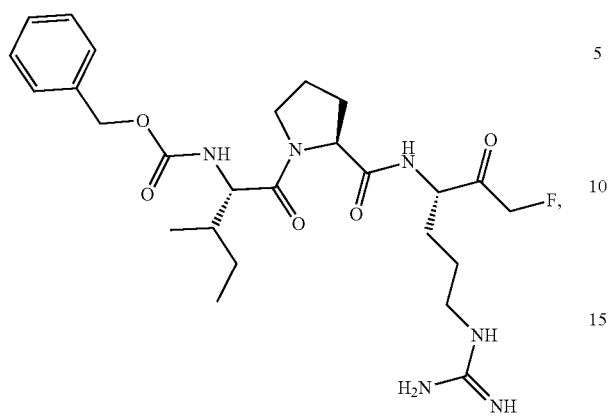
183
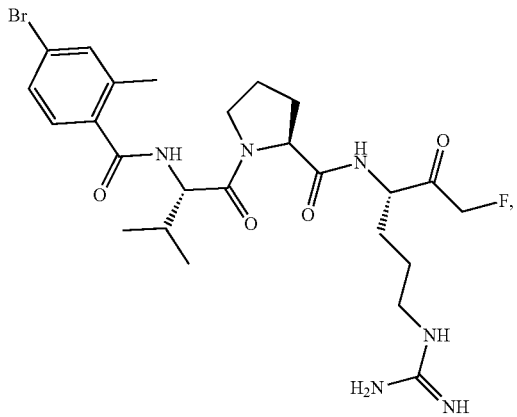
181
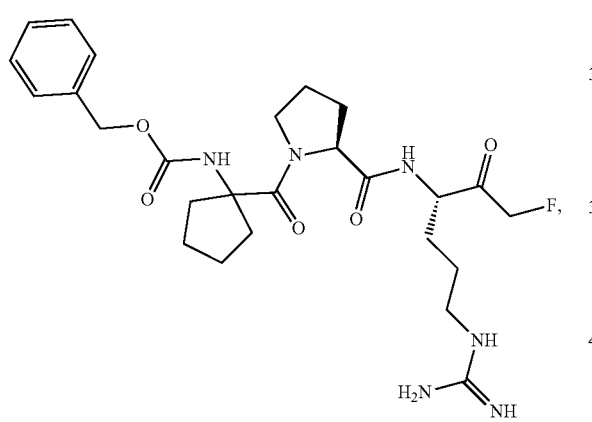
184
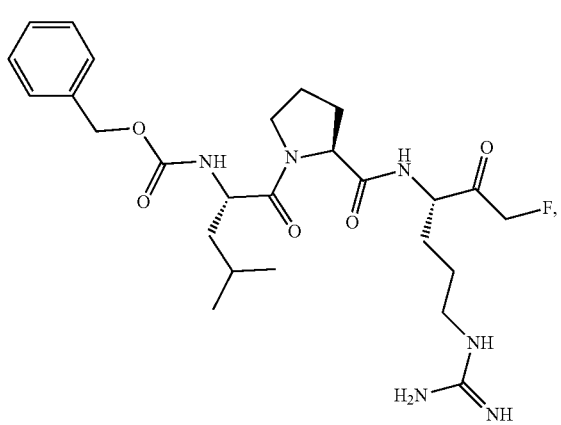
182
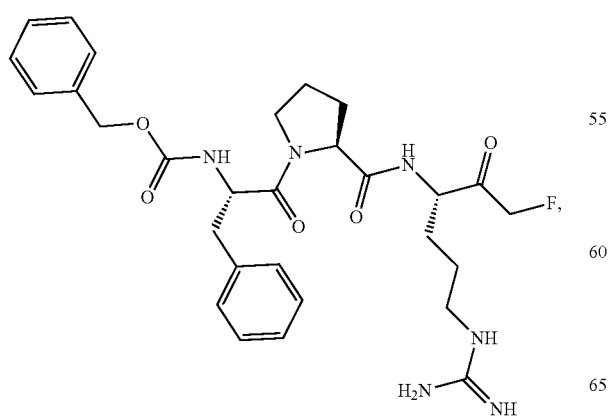
185
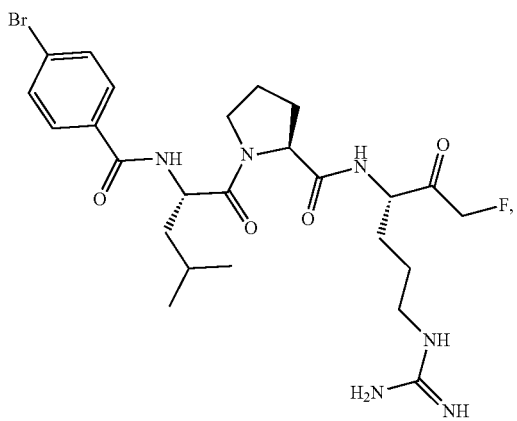

95

-continued

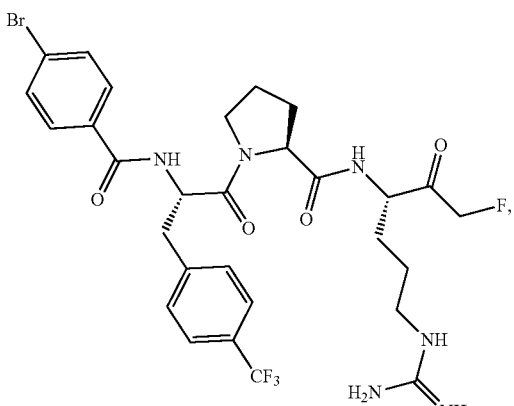

186

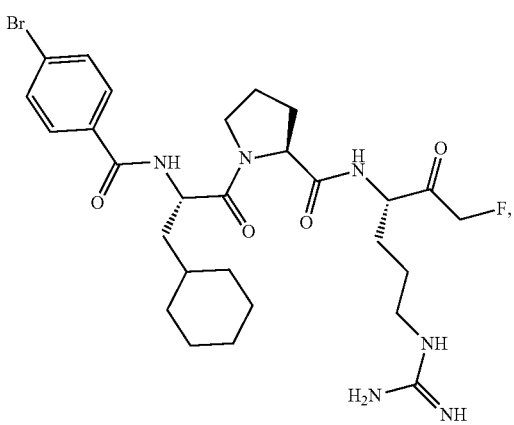

187 or a pharmaceutically acceptable salt, stereoisomer, tautomer, solvate, hydrate, polymorph, co-crystal, or prodrug thereof.

In certain embodiments, the compound described herein is compound 172, or a pharmaceutically acceptable salt, stereoisomer, or tautomer thereof. In certain embodiments, the compound described herein is compound 171, or a pharmaceutically acceptable salt, stereoisomer, or tautomer thereof. In certain embodiments, the compound described herein is compound 135, or a pharmaceutically acceptable salt, stereoisomer, or tautomer thereof. In certain embodiments, the compound described herein is compound 174, or a pharmaceutically acceptable salt, stereoisomer, or tautomer thereof. In certain embodiments, the compound described herein is compound 116, or a pharmaceutically acceptable salt, stereoisomer, or tautomer thereof. In certain embodiments, the compound described herein is compound 143, or a pharmaceutically acceptable salt, stereoisomer, or tautomer thereof. In certain embodiments, the compound described herein is compound 173, or a pharmaceutically acceptable salt, stereoisomer, or tautomer thereof. In certain embodiments, the compound described herein is compound 149, or a pharmaceutically acceptable salt, stereoisomer, or tautomer thereof. In certain embodiments, the compound described herein is compound 151, or a pharmaceutically acceptable salt, stereoisomer, or tautomer thereof. In certain embodiments, the compound described herein is compound 177, or a pharmaceutically acceptable salt, stereoisomer, or tautomer thereof.

96

In certain embodiments, a compound described herein is a pharmaceutically acceptable salt, stereoisomer, tautomer, solvate, hydrate, polymorph, co-crystal, or prodrug of a formula described herein.

Methods of Preparing the Compounds

Compounds described herein may be synthesized according to the schemes described below and procedures presented in the Examples. The reagents and conditions described are intended to be exemplary and are not limiting. As appreciated by one of skill in the art, various analogs may be prepared by modifying the synthetic reactions such as using different starting materials, different reagents, and different reaction conditions (e.g., temperature, solvent, concentration, etc.).

In one aspect, provided herein are methods for the preparation of a compound of Formula (I) and intermediates thereto. Exemplary synthetic methods are shown in Schemes 1 and 2. Unless otherwise stated, variables depicted in the schemes below are as generally described herein for compounds of Formula (I).

Scheme 1.

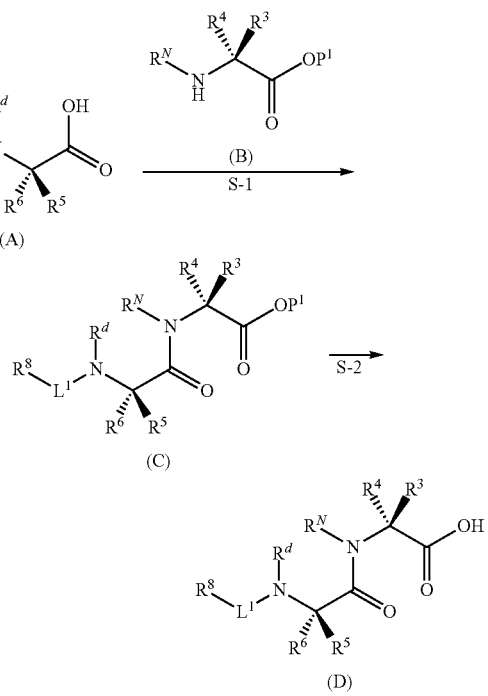

$P^1$ is optionally substituted alkyl, optionally substituted alkenyl, optionally substituted acyl, or an oxygen protecting group.

Step S-1 comprises coupling an amino acid of Formula (B) with an amino acid ester of Formula (B), to form a dipeptide ester of Formula (C). All methods of peptide coupling are contemplated. In certain embodiments, the step of coupling is performed in the presence of a carboxyl activating agent. In certain embodiments, the carboxyl activating agent is a carbodiimide. In some embodiments, the carbodiimide is dicyclohexylcarbodiimide (DCC), diisopropylcarbodiimide (DIC), or 1-ethyl-3-(3-dimethylaminopropyl)carbodiimide (EDAC), or a derivative thereof. In certain embodiments, the carboxyl activating agent is a triazole. In some embodiments, the triazole is 1-hydroxybenzotriazole (HOBt), 1-hydroxy-7-azabenzotriazole (HOAt), 2-cyano-2-(hydroxyimino)acetate), HBTU, HATU, HCTU, TBTU, or PyBOP, or a derivative thereof. In certain embodiments, the step of coupling is performed in the presence of a base. In some embodiments, the base is a non-nucleophilic base. In some embodiments, the base is an amine. In some embodiments, the base is trimethyl amine, triethyl amine, diisopropyl ethyl amine (DIPEA), tetramethylpiperidine, 1,8-diazabicycloundec-7-ene (DBU), lutidene, or 2,6-di-tert-butylpyridine. In some embodiments, the coupling is performed in a solvent comprising DMF. In certain embodiments, $P^1$ is unsubstituted $C_{1-6}$ alkyl. In certain embodiments, $P^1$ is methyl, ethyl, propyl, or butyl. In some embodiments, $P^1$ is methyl. In certain embodiments, $P^1$ is an oxygen protecting group. In certain embodiments, the oxygen protecting group is silyl, TBDPS, TBDMS, TIPS, TES, TMS, MOM, THP, t-Bu, Bn, allyl, acetyl, pivaloyl, or benzoyl.

Step S-2 comprises converting the ester of a dipeptide ester of Formula (C) to a carboxylic acid of Formula (D). In certain embodiments, the step of converting is an acid hydrolysis of the ester. In certain embodiments, the step of converting is a base hydrolysis of the ester. In certain embodiments, the step of converting is performed in the presence of a base. In some embodiments, the base is a hydroxide, carbonate, or phosphate salt. In some embodiments, the base is lithium hydroxide, sodium hydroxide, or potassium hydroxide.

Step S-3 comprises coupling a dipeptide ester of Formula (C) with an arginine analog of Formula (E). All methods of peptide coupling are contemplated. In some embodiments, the carbodiimide is dicyclohexylcarbodiimide (DCC), disoproylcarbodiimide (DIC), or 1-ethyl-3-(3-dimethylaminopropyl)carbodiimide (EDAC), or a derivative thereof. In certain embodiments, the carboxyl activating agent is a triazole. In some embodiments, the triazole is 1-hydroxybenzotriazole (HOBt), 1-hydroxy-7-azabenzotriazole (HOAt), 2-cyano-2-(hydroxyimino)acetate), HBTU, HATU, HCTU, TBTU, or PyBOP, or a derivative thereof. In certain embodiments, the step of coupling is performed in the presence of a base. In some embodiments, the base is a non-nucleophilic base. In some embodiments, the base is an amine. In some embodiments, the base is trimethyl amine, triethyl amine, diisopropyl ethyl amine (DIPEA), tetramethylpiperidine, 1,8-diazabicycloundec-7-ene (DBU), lutidene, or 2,6-di-tert-butylpyridine. In some embodiments, the coupling is performed in a solvent comprising DMF.

In certain embodiments, the arginine analog of Formula (E) is a protected arginine (e.g., $R^{44}$ is protecting group, $R^{44}$ and $R^{42}$ are protecting groups). In some embodiments, each of $R^{41}$, $R^{42}$, $R^{43}$, and $R^{44}$ is hydrogen. In some embodiments, at least one of $R^{41}$, $R^{42}$, $R^{43}$, and $R^{44}$ is a non-hydrogen group. In some embodiments, the step of coupling (D) and (E) further comprises deprotecting the guanidine group (i.e., removing a non-hydrogen group from $R^{41}$, $R^{42}$, $R^{43}$, or $R^{44}$, or a combination thereof). In some embodiments, the guanidine moiety (e.g., in a compound of Formula (E) is of formula:

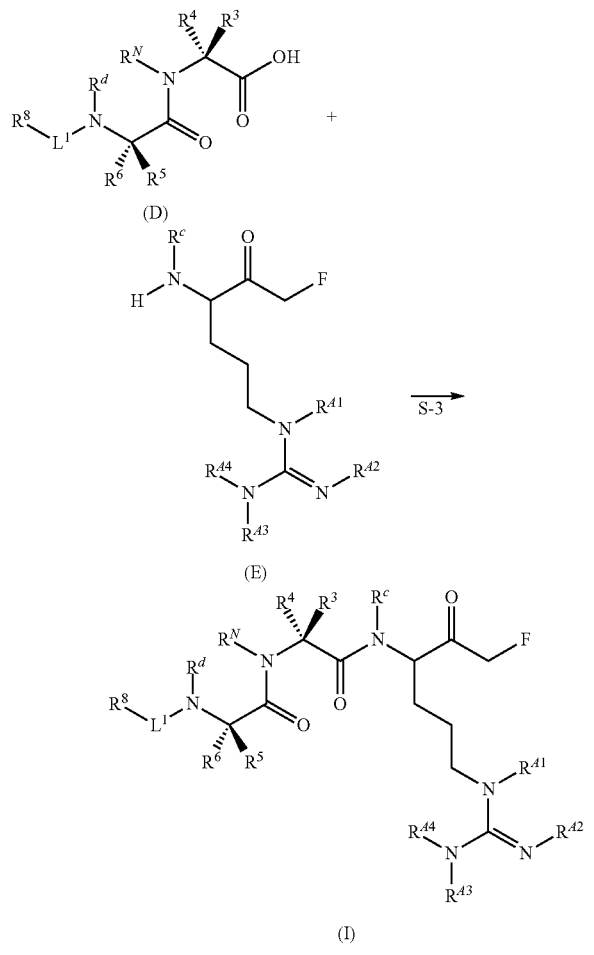

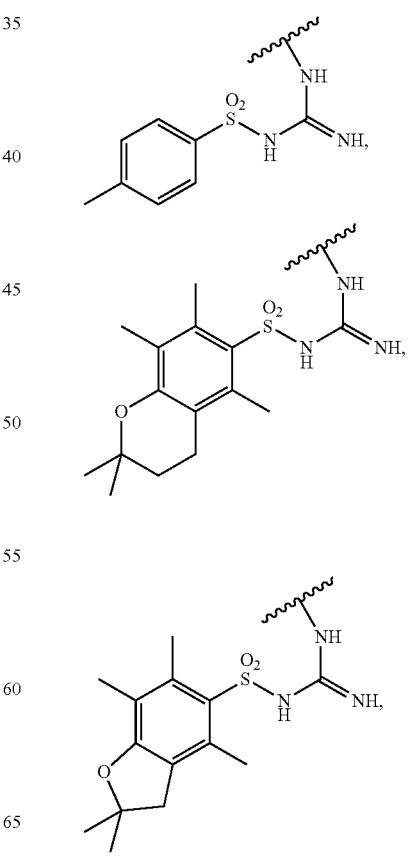

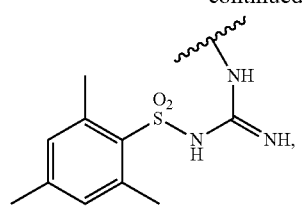
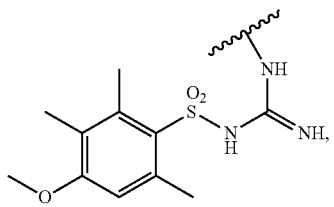
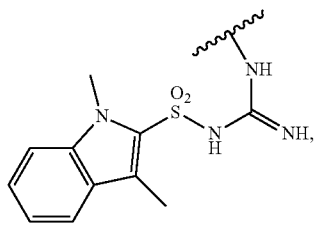
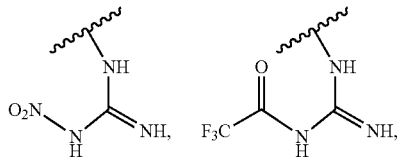
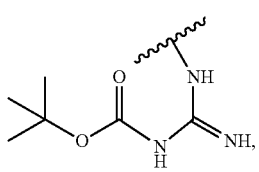
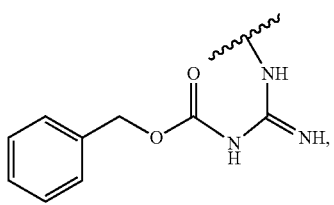
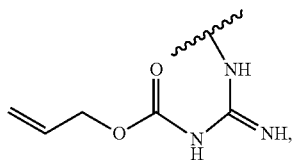
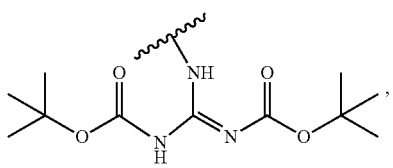
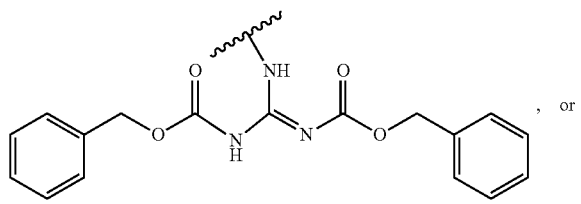, or

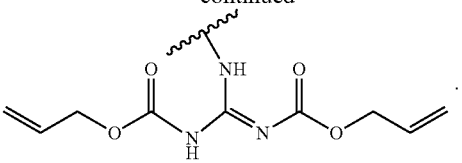

The method of preparing a compound of Formula (I) or an intermediate thereto may optionally further comprise one or more steps of protecting a nitrogen, oxygen, or sulfur atom, or deprotecting a nitrogen, oxygen, or sulfur atom. In certain embodiments, the step of deprotecting or protecting comprises replacing group $R^8$ or -$L^1$-$R^8$. In certain embodiments, the step of deprotecting or protecting comprises replacing group $R^N$. In certain embodiments, the step of deprotecting or protecting comprises replacing group $R^c$. In certain embodiments, the step of deprotecting or protecting comprises replacing group $R^d$. In certain embodiments, the step of deprotecting or protecting comprises replacing group $R^{A1}$. In certain embodiments, the step of deprotecting or protecting comprises replacing group $R^{A2}$. In certain embodiments, the step of deprotecting or protecting comprises replacing group $R^{A3}$. In certain embodiments, the step of deprotecting or protecting comprises replacing group $R^{A4}$.

In one aspect, provided herein is a method of preparing a compound of Formula (I):

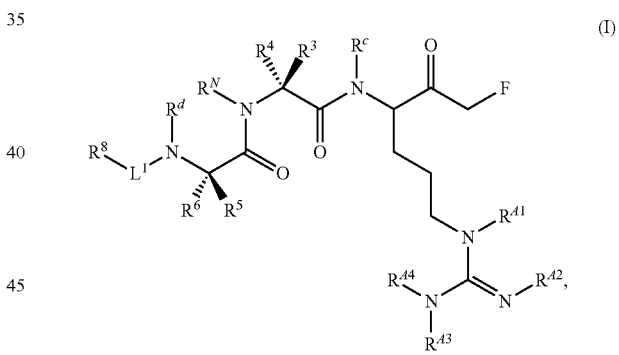

(I)

or a pharmaceutically acceptable salt, stereoisomer, or tautomer thereof, the method comprising coupling a carboxylic acid of Formula (D):

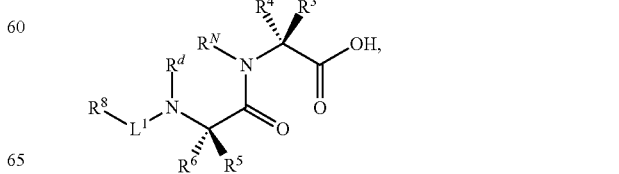

(D)

or a salt thereof, and a compound of Formula (E):

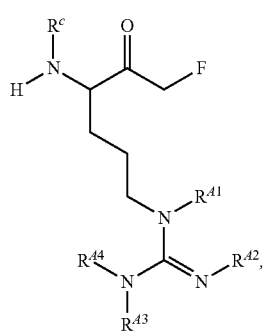

or a salt thereof, wherein $R^3$, $R^4$, $R^N$, $R^5$, $R^6$, $R^8$, $L^1$, $R^c$, $R^d$, $R^{A1}$, $R^{A2}$, $R^{A3}$, and $R^{A4}$ are as defined herein.

In certain embodiments, the method of preparing a compound of Formula (I) further comprises converting an ester of Formula (C):

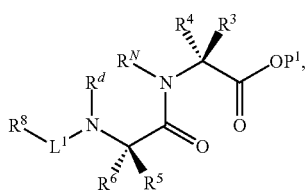

or a salt thereof, to a carboxylic acid of Formula (D), wherein $P^1$ is optionally substituted alkyl, optionally substituted acyl, or an oxygen protecting group.

In certain embodiments, the method of preparing a compound of Formula (I) further comprises coupling a compound of Formula (A):

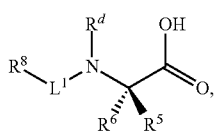

or a salt thereof, and a compound of Formula (B):

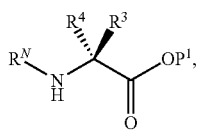

or a salt thereof, to yield an ester of Formula (C).

Pharmaceutical Compositions and Administration

The present invention also provides pharmaceutical compositions comprising a compound described herein (e.g., a compound of Formula (I)), or a pharmaceutically acceptable salt, solvate, hydrate, polymorph, co-crystal, tautomer, stereoisomer, or prodrug thereof, and optionally a pharmaceutically acceptable excipient. In certain embodiments, the pharmaceutical composition described herein comprises a compound of Formula (I), or a pharmaceutically acceptable salt, stereoisomer, or tautomer thereof, and a pharmaceutically acceptable excipient. In certain embodiments, the pharmaceutical composition is useful for treating a patient with a proliferative disease. In certain embodiments, the pharmaceutical composition is useful for treating a patient with cancer. In certain embodiments, the pharmaceutical composition is useful for treating a patient with a lymphoma. In certain embodiments, the pharmaceutical composition is useful for treating a patient with a leukemia. In certain embodiments, the pharmaceutical composition is useful for treating a patient with Hodgkin's lymphoma, Burkitt's lymphoma, non-Hodgkin's lymphoma, diffuse large B-cell lymphoma, or MALT lymphoma. In certain embodiments, the pharmaceutical composition is useful for treating a patient with diffuse large B-cell lymphoma.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease) in a subject in need thereof. In certain embodiments, the effective amount is an amount effective for preventing a proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease) in a subject in need thereof. In certain embodiments, the effective amount is an amount effective for reducing the risk of developing a proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease) in a subject in need thereof. In certain embodiments, the effective amount is an amount effective for inhibiting MALT1 in a subject. In certain embodiments, the effective amount is an amount effective for inhibiting a MALT1 fusion protein (e.g. API2-MALT1) in a subject. In certain embodiments, the effective amount is an amount effective for inhibiting the cleavage of A20, Bcl10, RelB, CYLD, NIK, regnase-1, roquin-1, roquin-2, LIMA1α, or MALT1 in a subject. In certain embodiments, the effective amount is an amount effective for inhibiting secretion of IL-6 in a subject.

In certain embodiments, the effective amount is an amount effective for inhibiting MALT1 by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting MALT1 by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for a range of inhibition between a percentage described in this paragraph and another percentage described in this paragraph, inclusive.

Pharmaceutical compositions described herein can be prepared by any method known in the art of pharmacology. In general, such preparatory methods include bringing the compound described herein (i.e., the "active ingredient")

into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(S) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(S) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting MALT1), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which are different from the compound described herein and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

DLBCLs display a large mutational burden that affects multiple protein coding genes. Because of that, single-agent therapy would not be expected to eradicate disease. ABC-DLBCLs are more resistant to current chemotherapy regimens. For instance, ABC-DLBCL is less responsive to the standard of care, R-CHOP, with 40% 3-year progression free survival versus 74% for GCB-DLBCL. Combination therapy, e.g. R-CHOP, may be useful for treating and/or preventing DLBCLs. It is possible that MALT1 inhibition could sensitize ABC-DLBCLs to R-CHOP by disrupting cell survival signaling through NF-κB. It is also possible that MALT1-targeted therapy could synergistically kill lymphoma cells when a MALT1 inhibitor is combined with other more upstream BCR pathway inhibitors that might complement MALT1 inhibition. For example, inhibiting phosphatidylinositol-4,5-bisphosphate 3-kinase (PI3K), spleen tyrosine kinase (SYK), or Bruton's tyrosine kinase (BTK) could allow the inhibition of pathways parallel to NF-κB like mitogen-activated protein kinase (MAPK), JNK, or NFAT (nuclear factor of activated T cells) to further inhibit survival and proliferation signals. Inhibitors of these proteins include: PI3K inhibitors BEZ235, BKM120, GDC-0941, BYL719 or CAL-101; SYK inhibitors R-406 or Fostamatinib; BTK inhibitors Ibrutinib or CC-292. Other potential targets for MALT1 combination therapy in ABC-DLBCL include other oncogenes frequently deregulated in this subtype of lymphoma: BCL2, BCL6, and MYC. BCL2 is frequently amplified and overexpressed in ABC-DLBCL. Several agents have been developed to inhibit BCL2 and its antiapoptotic family members, including small-molecule BH3-mimetic compounds such as ABT-737 and obatoclax. Simultaneous inhibition of MALT1 and BCL2 would be expected to reduce NF-κB activation and induce apoptosis, with potential to synergistically kill lymphoma cells. The BCL6 gene is also frequently translocated or mutated, resulting in its deregulated expression in ABC-DLBCL, where it suppresses cell-cycle checkpoint genes as well as terminal differentiation through repression of PRDM1 and other genes. Peptidomimetic and small-molecule inhibitors of BCL6 that disrupt its ability to form repression complexes have potent antilymphoma activity against DLBCLs, including ABC-DLBCLs. BCL6 inhibitors do not seem to induce toxic effects in animals, supporting the suitability of their use in combinatorial regimens. Concurrent inhibition of MALT1 paracaspase activity and BCL6 would be expected to simultaneously attenuate NF-κB activation and promote checkpoint growth suppression and apoptosis. MYC is frequently overexpressed in DLBCL. Deregulated expression of MYC affects many cellular processes, including proliferation, differentiation, and metabolism. An inhibitor of the bromodomain-containing protein 4 (BRD4), JQ1 downregulates MYC transcription, resulting in downregulation of MYC-induced target genes. JQ1 caused cell-cycle arrest and cellular senescence in multiple myeloma, Burkitt lymphoma, and acute myeloid leukemia. Combination of MALT1 inhibition with JQ1 is expected to synergistically collaborate to kill lymphoma by concomitantly affecting fundamental pathways for cell proliferation. Around 30% of ABC-DLBCLs display activating mutations of MYD88 that in a large proportion of the cases coexist with B-cell receptor activating mutations, therefore combination of MALT1 inhibition with TLR 7/8/9 antagonist or inhibition of MYD88 or its downstream targets IRAK1 and IRAK4 is expected to synergistically kill lymphoma by parallel inhibition of the two pathways. Hsp90 is a heat shock protein required for survival of cancer cells and in particular DLBCL. There are several inhibitors of Hsp90 in clinical trials including 17-N-Allylamino-17-demethoxygeldanamycin (17AAG) and PUH71. Hsp90 inhibition has been shown to inhibit NF-κB signaling at various levels and concomitant treatment with MALT1 inhibition is expected to have additive or synergistic effect in killing DLBCL.

In certain embodiments, the additional pharmaceutical agent is a pharmaceutical agent useful for treating and/or preventing a proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-diabetic agents, anti-proliferative agents, anti-cancer agents, anti-angiogenesis agents, anti-inflammatory agents, anti-bacterial agents, anti-viral agents, cardiovascular agents, and pain-relieving agents. In certain embodiments, the additional pharmaceutical agent is an anti-cancer agent. In certain embodiments, the additional pharmaceutical agent is an anti-proliferative agent. In certain embodiments, the additional pharmaceutical agent is an anti-angiogenesis agent. In certain embodiments, the additional pharmaceutical agent is an anti-inflammatory agent. In certain embodiments, the additional pharmaceutical agent inhibits MALT1.

In certain embodiments, the compounds described herein or pharmaceutical compositions can be administered in combination with an anti-cancer therapy including, but not limited to, transplantation (e.g., bone marrow transplantation, stem cell transplantation), surgery, radiation therapy, immunotherapy, and chemotherapy.

In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is an anti-lymphoma agent. In certain embodiments, the additional pharmaceutical agent is an anti-myelodysplasia agent. In certain embodiments, the additional pharmaceutical agent is an agent listed elsewhere herein.

In certain embodiments, the additional pharmaceutical agent is rituximab, cyclophosphamide, hydroxydaunorubicin, vincristine, prednisone, prednisolone, lenalidomide, etoposide, or bortezomib, or a combination thereof. In certain embodiments, the additional pharmaceutical agent is a proteasome inhibitor (e.g., bortezomib). In certain embodiments, the compound or pharmaceutical composition described herein is administered in combination with a chemotherapy regimen, such as CHOP or R-CHOP. CHOP comprises administration of cyclophosphamide, hydroxydaunorubicin, vincristine (ONCOVIN), and prednisone or prednisolone. R-CHOP adds rituximab to the CHOP regimen.

In certain embodiments, the additional pharmaceutical agent is an upstream-BCR-pathway inhibitor. In certain embodiments, the additional pharmaceutical agent is a PI3K inhibitor (e.g., BEZ235, BKM120, GDC-0941, BYL719, CAL-101, or a pharmaceutically acceptable salt, solvate, hydrate, polymorph, co-crystal, tautomer, stereoisomer, isotopically labeled derivative, or prodrug thereof). In certain embodiments, the PI3K inhibitor is tozasertib, GSK1059615, PX866, LY294002, SF1126, XL147, XL765, BGT226, BAY80946, BAY841236, GDC-0941, GDC-0032, GDC-0980, GDC-0941, PX-866, GSK2126458, INK1117, ZSTK474, PWT33597, AEZS-136, PKI-587, PF-4691502, PF-05212384, wortmannin, demethoxyviridin, pictilisib, idelalisib, IPI-145, or a pharmaceutically acceptable salt, solvate, hydrate, polymorph, co-crystal, tautomer, stereoisomer, isotopically labeled derivative, or prodrug thereof. In certain embodiments, the additional pharmaceutical agent is a SYK inhibitor (e.g., Staurosporine (antibiotic AM-2282), BAY 61-3606 (SYK Inhibitor IV), Piceatannol (astringinin), R406, PKC-412, R788 (Fostamatinib), 2-(2-aminoethylamino)-4-(3-trifluoromethylanilino)-pyrimidine-5-carboxamide (SYK Inhibitor II), MNS (SYK Inhibitor III), (2-oxomorpholin-4-yl)-acetic acid, PRT062607 (P505-15, BIIB057), Entospletinib (GS-9973), PRT318, P505-15, ER-27139, R112, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is a BTK inhibitor (e.g., GDC-0834, CGI-560, CGI-1746, HM-71224, CC-292 (AVL-292), ONO-4059, CNX-774, LFM-A13, PCI-32765 (Imbruvica), QL47, BGB-3111, ACP-196, Ibrutinib, LMA-13 (α-cyano-β-hydroxy-β-methyl-N-(2,5dibromophenyl)propenamide), DDE11, C132765, AVL-292, AVL-101, PRN1008, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is a MAPK inhibitor (e.g., AMG548, AS1940477, CBS3830, Dilmapimod (SB-6813123), Doramapimod (BIRB-796), FR-167653, JLU1124, LASSBio-998, Losmapimod (GW856553), LY2228820, LY3007113, ML3403, Pamapimod, PD-98059 (PD098059), PD-169316, PH-797804, R-130823, RO3201195, RPR-200765A, RPR-203494, RWJ-67657, SB-202190, SB-203580, SB-239063, SB-242235, SCIO-323, SD-282, Semapimod (CNI-1493), Soblidotin (TZT-1027), TAK-715, Talmapimod (SCIO-469), UO126, UR-13756, VX-702, VX-745, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is a JNK inhibitor (e.g., AS007149, AS601245, Berberine, CDDO-Me (Triterpenoid), Curcumin, DA-125, DIM, echinocystic acid, Eupalmerin acetate, Isoobtusilactone A, Mangostin, Norcantharidin, Plumbagin, Rocaglamide, SAMC, SP-600125 (anthrapyrazolone), SP600129, Tanzisertib (CC-930), Tetrahydroxyquinone, Vitamin E succinate, XG-102 (D-JNKI-1), RWJ 67657, CC-401, Bentamapimod, Aloisine A, AEG 3482, BI 78D3, SU 3327, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is a NFAT inhibitor (e.g., VIVIT peptide, MAGPHPVIVITGPHEE (SEQ ID NO: 3), cyclosporin-A (CsA), FK506, Tacrolimus, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is a BCL2 inhibitor (e.g., ABT-737, ABT 263 (Navitoclax), Gossypol, (−)-Epigallocatechin gallate, Obatoclax, Licochalcone A, HA14-1, TW-37, EM20-25, 4-methoxy-2-[2-(5-methoxy-2-nitrosophenyl)ethyl]-1-nitrosobenzene, Nilotinib-d3, YC137, ABT 737-d8, ABT 263-d8, 2-Methoxy-antimycin A3, ABT-199 (Venetoclax, GDC-0199), Gambogic acid, Nilotinib, Obatoclax (GX15-070), UMI-77, Sabutoclax, AT101, BAM7, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is a BCL6 inhibitor (e.g., 2-((5Z)-5-(5-bromo-2-oxo-1H-indol-3-ylidene)-4-oxo-2-sulfanylidene-1,3-thiazolidin-3-yl)butanedioic acid (CID5721353), or a pharmaceutically acceptable salt, solvate, hydrate, polymorph, co-crystal, tautomer, stereoisomer, isotopically labeled derivative, or prodrug thereof). In certain embodiments, the additional pharmaceutical agent is a MYC inhibitor (e.g., F3680 (10058-F4), Omomyc, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is a bromodomain-containing protein inhibitor (e.g., bromodomain-containing protein 2 (BRD2) inhibitor, bromodomain-containing protein 3 (BRD3) inhibitor, bromodomain-containing protein 4 (BRD4) inhibitor, TBP (TATA box binding protein)-associated factor protein (TAF) inhibitor, CREB-binding protein (CBP) inhibitor, or E1A binding protein p300 (EP300) inhibitor). In certain embodiments, the bromodomain-containing protein inhibitor is JQ1, or a pharmaceutically acceptable salt, solvate, hydrate, polymorph, co-crystal, tautomer, stereoisomer, isotopically labeled derivative, or prodrug thereof. In certain embodiments, the bromodomain-containing protein inhibitor is I-BET 151, I-BET 762, OTX-015, TEN-010, CPI-203, CPI-0610, RVX-208, LY294002, BMS-986158, GSK525762, or a pharmaceutically acceptable salt, solvate, hydrate, polymorph, co-crystal, tautomer, stereoisomer, isotopically labeled derivative, or prodrug thereof. In certain embodiments, the additional pharmaceutical agent is a TLR 7/8/9 antagonist (e.g., IRS 661, IRS 954, Chloroquine (NBP2-29386), Quinacrine (NBP2-29385), IMO-8400, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is a MYD88 inhibitor (e.g., Pepinh-MYD, ST 2825, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is an IRAK1 inhibitor (e.g., 1-(2-(4-Morpholinyl)ethyl)-2-(3-nitrobenzoylamino)benzimidazole, Pacritinib, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is an IRAK4 inhibitor (e.g., 1-(2-(4-Morpholinyl)ethyl)-2-(3-nitrobenzoylamino)benzimidazole, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is a Hsp90 inhibitor (e.g., Tanespimycin (17-N-allylamino-17-demethoxygeldanamycin (17-AAG)), Luminespib (AUY-922, NVP-AUY922), 17-DMAG (Alvespimycin), Ganetespib (STA-9090), VER155008, PUH71, HSP990 (NVP-HSP990), BIIB021, AICAR, Geldanamycin, IPI-504, Radicicol, Herbimycin A, Gedunin, Celastrol, *Celastrus scandens*, NVP-AUY922, Novobiocin, Macbecin I, MPC-3100, CAY10607, 17-GMB-APA-GA, 17-AEP-GA, 17-DMAP-GA, KW-2478, NVP-BEP800, AT13387, Nelfinavir, Novobiocin, or a pharmaceutically acceptable salt, solvate, hydrate, polymorph, co-crystal, tautomer, stereoisomer, isotopically labeled derivative, or prodrug thereof). In certain embodiments, the additional pharmaceutical agent is BEZ235, BKM120, GDC-0941, BYL719, CAL-101, R-406, Fostamatinib, Ibrutinib, CC-292, ABT-737, obatoclax, JQ1, 17AAG, PUH71, or a pharmaceutically acceptable salt, solvate, hydrate, polymorph, co-crystal, tautomer, stereoisomer, isotopically labeled derivative, or prodrug thereof.

Also encompassed by the disclosure are kits (e.g., pharmaceutical packs). The kits provided may comprise a pharmaceutical composition or compound described herein and optionally a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease) in a subject in need thereof. In certain embodiments, the kits are useful for preventing a proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease) in a subject in need thereof. In certain embodiments, the kits are useful for reducing the risk of developing proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease) in a subject in need thereof. In certain embodiments, the kits are useful for inhibiting MALT1, or a MALT1 fusion protein (e.g., API2-MALT1) in a subject.

In certain embodiments, a kit described herein further includes instructions for using the kit (e.g., instructions for using the compound or pharmaceutical composition included in the kit, such as instructions for administering the compound or pharmaceutical composition to a subject in need thereof). A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease) in a subject in need thereof. In certain embodiments, the kits and instructions provide for preventing a proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease) in a subject in need thereof. In certain embodiments, the kits and instructions provide for reducing the risk of developing proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease) in a subject in need thereof. In certain embodiments, the kits and instructions provide for inhibiting MALT1 in a subject or in an infectious microorganism. A kit described herein may include one or more additional pharmaceutical agents described herein as a separate composition.

Methods of Treatment and Uses

The present invention also provides methods for the treatment or prevention of a proliferative disease. In certain embodiments, the proliferative disease is cancer. In certain embodiments, the disease in an autoimmune disease. In certain embodiments, the proliferative disease is benign neoplasm, a disease associated with angiogenesis, an inflammatory disease, an autoinflammatory disease, or an autoimmune disease. In certain embodiments, the cancer is a lymphoma. In certain embodiments, the cancer is a leukemia. In certain embodiments, the cancer is Hodgkin's lymphoma. In certain embodiments, the cancer is non-Hodgkin's lymphoma. In certain embodiments, the cancer is Burkitt's lymphoma. In certain embodiments, the cancer is diffuse large B-cell lymphoma (DLBCL). In certain embodiments, the cancer is MALT lymphoma. In some embodiments, the cancer is germinal center B-cell-like diffuse large B-cell lymphoma (GCB-DLBCL) or primary mediastinal B-cell lymphoma (PMBL). In some embodiments, the cancer is activated B-cell-like diffuse large B-cell lymphoma (ABC-DLBCL).

The compounds described herein (e.g., compounds of Formula (I)) may exhibit a therapeutic and/or preventative effect in the treatment of proliferative diseases (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease) and/or may exhibit a therapeutic or preventative effect superior to existing agents for treatment of a proliferative disease. Additionally, the compounds described herein (e.g., compounds of Formula (I)) may exhibit inhibitory activity towards mucosa-associated lymphoid tissue lymphoma translocation protein 1 (MALT1) or a MALT1 fusion protein (e.g., API2-MALT1); may exhibit the ability to inhibit cleavage of a peptide selected from A20, Bcl10, RelB, CYLD, NIK, regnase-1, roquin-1, roquin-2, LIMA1α, and MALT1; may exhibit the ability to inhibit activation of nuclear factor-KB (NF-κB); may exhibit the ability to down-regulate expression of a gene selected from FLIP, A1, A20, IL-2, IL-6, IL-10 or STAT3; may exhibit the ability to inhibit phosphorylation of STAT3; may inhibit T-cell or B-cell activation and/or may inhibit T-cell or B-cell proliferation.

The compounds described herein (e.g., compounds of Formula (I)) may exhibit selective inhibition of MALT1 or a MALT1 fusion protein (e.g., API2-MALT1) versus inhibition of other proteins. In certain embodiments, the compound of Formula (I) selectively inhibits MALT1 or API2-MALT1 over another protease. In certain embodiments, the compound of Formula (I) selectively inhibits MALT1 or API2-MALT1 over another paracaspase. In certain embodiments, the selectivity versus inhibition of another protein is between about 2 fold and about 10 fold. In certain embodiments, the selectivity is between about 10 fold and about 50 fold. In certain embodiments, the selectivity is between about 50 fold and about 100 fold. In certain embodiments, the selectivity is between about 100 fold and about 500 fold. In certain embodiments, the selectivity is between about 500 fold and about 1000 fold. In certain embodiments, the selectivity is between about 1000 fold and about 5000 fold. In certain embodiments. In certain embodiments, the selectivity is between about 5000 fold and about 10000 fold. In certain embodiments, or at least about 10000 fold.

The present invention provides methods that may be useful for the treatment of an proliferative disease by administering a compound described herein, or pharmaceutically acceptable salt, solvate, hydrate, polymorph, co-crystal, tautomer, stereoisomer, or prodrug thereof, or pharmaceutical composition thereof, to a subject in need thereof. In certain embodiments, the compound is administered as a pharmaceutically acceptable salt, stereoisomer, or tautomer thereof. In certain embodiments, the compound is administered as a pharmaceutically acceptable salt of the compound. In certain embodiments, the compound is administered as a specific stereoisomer or mixture of stereoisomers of the compound. In certain embodiments, the compound is administered as a specific tautomer or mixture of tautomers of the compound. In certain embodiments, the compound is administered as a pharmaceutical composition as described herein comprising the compound.

The present invention also provides uses of the inventive compounds, and pharmaceutically acceptable salts, solvates, hydrates, polymorphs, co-crystals, tautomers, stereoisomers, prodrugs, and pharmaceutical compositions thereof, in the manufacture of medicaments for the treatment and prevention of a proliferative disease. In certain embodiments, the proliferative disease is cancer. In certain embodiments, the proliferative disease is benign neoplasm, a disease associated with angiogenesis, an inflammatory disease, an auto-inflammatory disease, or an autoimmune disease. In certain embodiments, the cancer is a lymphoma. In certain embodiments, the cancer is a leukemia. In certain embodiments, the cancer is Hodgkin's lymphoma. In certain embodiments, the cancer is non-Hodgkin's lymphoma. In certain embodiments, the cancer is Burkitt's lymphoma. In certain embodiments, the cancer is diffuse large B-cell lymphoma (DLBCL). In certain embodiments, the cancer is MALT lymphoma. In some embodiments, the cancer is germinal center B-cell-like diffuse large B-cell lymphoma (GCB-DLBCL) or primary mediastinal B-cell lymphoma (PMBL). In some embodiments, the cancer is activated B-cell-like diffuse large B-cell lymphoma (ABC-DLBCL).

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the proliferative disease to be treated or prevented using the compounds described herein is cancer. All types of cancers disclosed herein or known in the art are contemplated as being within the scope of the invention. In certain embodiments, the proliferative disease is a cancer associated with or dependent on MALT1. In certain embodiments, the proliferative disease is a cancer associated with or dependent on a MALT1 fusion protein (e.g., API2-MALT1). In certain embodiments, the proliferative disease is a cancer associated with dependence on B-cell lymphoma 10 (Bcl10). In certain embodiments, the proliferative disease is a cancer associated with dependence on caspase recruitment domain-containing protein (CARD1). In certain embodiments, the proliferative disease is a cancer associated with dependence on NF-κB. Exemplary cancers include, but are not limited to, hematological malignancies. Additional exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple negative breast cancer (TNBC)); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In certain embodiments, the cancer is a hematological malignancy. Exemplary hematological malignancies include, but are not limited to, leukemia, such as acute lymphoblastic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt's lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

In certain embodiments, the disease is an autoimmune disease. Exemplary autoimmune diseases include, but are not limited to, glomerulonephritis, Goodpasture's syndrome, necrotizing vasculitis, lymphadenitis, peri-arteritis *nodosa*, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

In certain embodiments, the disease is a cancer associated with a viral infection. In some embodiments, the disease is a cancer resulting from infection with an oncovirus. In some embodiments, the oncovirus is hepatitis A, hepatitis B, hepatitis C, human T-lymphotropic virus (HTLV), human papillomavirus (HPV), Kaposi's sarcoma-associated herpesvirus (HHV-8), Merkel cell polyomavirus, or Epstein-Barr virus (EBV). In some embodiments, the disease is human T-lymphotropic virus. In some embodiments, the disease is Kaposi's sarcoma-associated herpesvirus. In some embodiments, the disease is Epstein-Barr virus. Leukemias and lymphomas which may be associated with an oncoviral include: for HTLV, adult T-cell leukemia; for HHV-8, Castleman's disease and primary effusion lymphoma; and for EBV, Burkitt's lymphoma, Hogdkin's lymphoma, and post-transplant lymphoproliferative disease.

In another aspect, provided herein are methods of down-regulating expression of a gene in a subject by administering to the subject a compound described herein (e.g., a compound of Formula (I)), or down-regulating expression of a gene in a biological sample by contacting the biological sample with a compound described herein (e.g., a compound of Formula (I)). In some embodiments, the gene which is down-regulated is a NF-κB dependent gene. Genes which may be down-regulated include, but are not limited to, FLIP, A1, A20, IL-2, IL-6, IL-8, IL-10 and STAT3.

In another aspect, provided herein are methods of inhibiting cell proliferation in a subject by administering to the subject a compound described herein (e.g., a compound of Formula (I)), or inhibiting cell proliferation in a biological sample by contacting the biological sample with a compound described herein (e.g., a compound of Formula (I)). In some embodiments, cell proliferation is inhibited for T-cells. In some embodiments, cell proliferation is inhibited for B-cells. In some embodiments, cell proliferation is inhibited for T-cells and B-cells.

In another aspect, provided herein are methods of inducing apoptosis of a cell in a subject by administering to the subject a compound described herein (e.g., a compound of Formula (I)), or inducing apoptosis of a cell in a biological sample by contacting the biological sample with a compound described herein (e.g., a compound of Formula (I)). In some embodiments, cell is a tumor cell. In some embodiments, the cell is a lymphocyte. In some embodiments, the cell is a T-cell. In some embodiments, the cell is a B-cell.

In another aspect, provided herein are methods of inhibiting adhesion of a cell in a subject by administering to the subject a compound described herein (e.g., a compound of Formula (I)), or inhibiting adhesion of a cell in a biological sample by contacting the biological sample with a compound described herein (e.g., a compound of Formula (I)). In some embodiments, cell is a tumor cell. In some embodiments, the cell is a lymphocyte. In some embodiments, the cell is a T-cell. In some embodiments, the cell is a B-cell.

In another aspect, provided herein are methods of inhibiting activation of T-cells or B-cells in a subject by administering to the subject a compound described herein (e.g., a compound of Formula (I)), or inhibiting activation of T-cells or B-cells in a biological sample by contacting the biological sample with a compound described herein (e.g., a compound of Formula (I)).

In another aspect, provided herein are methods of inhibiting activation of nuclear factor KB (NF-κB) in a subject by administering to the subject a compound described herein (e.g., a compound of Formula (I)), or inhibiting activation of nuclear factor KB (NF-κB) in a biological sample by contacting the biological sample with a compound described herein (e.g., a compound of Formula (I)).

In another aspect, provided herein are methods of inhibiting the activity of mucosa-associated lymphoid tissue lymphoma translation protein 1 (MALT1) or a MALT1 fusion protein in a subject by administering to the subject a compound described herein (e.g., a compound of Formula (I)), or inhibiting the activity of mucosa-associated lymphoid tissue lymphoma translation protein 1 (MALT1) or a MALT1 fusion protein in a biological sample by contacting the biological sample with a compound described herein (e.g., a compound of Formula (I)). In certain embodiments, the method inhibits the protease activity of MALT1. In certain embodiments, the method inhibits the protease activity of a MALT1 fusion protein (e.g., API2-MALT1). In certain embodiments, the method inhibits the protease activity of MALT1 or a MALT1 fusion protein for cleavage of a peptide substrate. In certain embodiments, the peptide substrate is A20, Bcl10, RelB, CYLD, NIK, regnase-1, roquin-1, roquin-2, LIMA1α, or MALT1. The inhibitor may selectively inhibit the protease activity of MALT1 or a MALT1 fusion protein for cleavage of a first peptide substrate over protease activity for cleavage of a second peptide substrate. In some embodiments, the first and/or second substrate is A20, Bcl10, RelB, CYLD, NIK, regnase-1, roquin-1, roquin-2, LIMA1α, or MALT1. In certain embodiments, the selectivity is between about 1.25 fold and about 5 fold. In certain embodiments, the selectivity is between about 5 fold and about 10 fold. In certain embodiments, the selectivity is between about 10 fold and about 25 fold. In certain embodiments, the selectivity is between about 25 fold and about 50 fold. In certain embodiments, the selectivity is between about 50 fold and about 100 fold. In certain embodiments, the selectivity is between about 100 fold and about 250 fold. In certain embodiments. In certain embodiments, the selectivity is between about 250 fold and about 500 fold. In certain embodiments, the selectivity is between about 500 fold and about 1000 fold. In certain embodiments, or at least about 1000 fold.

In another aspect, provided herein are methods of modulating cytokine production in a subject by administering to the subject a compound described herein (e.g., a compound of Formula (I)), or modulating cytokine production in a biological sample by contacting the biological sample with a compound described herein (e.g., a compound of Formula (I)). In some embodiments, the method inhibits production of a cytokine selected from IL-2, IL-6, IL-8, IL-10, or IL-17. In some embodiments, the method promotes production of a cytokine selected from IL-2, IL-6, IL-8, IL-10, or IL-17. In some embodiments, the method inhibits production of cytokines in T-cells. In some embodiments, the method inhibits production of cytokines in B-cells.

In another aspect, provided herein are methods of inhibiting phosphorylation of a c-Jun N-terminal kinase (JNK) in a subject by administering to the subject a compound described herein (e.g., a compound of Formula (I)), or inhibiting phosphorylation of a c-Jun N-terminal kinase (JNK) in a biological sample by contacting the biological sample with a compound described herein (e.g., a compound of Formula (I)).

In another aspect, provided herein are methods of inhibiting lymphocyte adhesion to fibronectin in a subject by administering to the subject a compound described herein (e.g., a compound of Formula (I)), or inhibiting lymphocyte adhesion to fibronectin in a biological sample by contacting the biological sample with a compound described herein (e.g., a compound of Formula (I)).

In another aspect, provided herein are methods of up-regulating expression of a gene by administering to the subject a compound described herein (e.g., a compound of Formula (I)), or up-regulating expression of a gene in a biological sample by contacting the biological sample with a compound described herein (e.g., a compound of Formula (I)). In some embodiments, the gene encodes a transcription factor or transcriptional regulator. In some embodiments, the transcription factor is c-Rel or IRF4. In some embodiments, the transcription factor is IκBNS or IκBζ. In some embodiments, the gene encodes a cytokine (e.g., IL-17). In some embodiments, the gene is up-regulating by inhibiting degradation of a mRNA. In some embodiments, the mRNA is encoding a T-cell effector gene. In some embodiments, the mRNA is encoding a gene selected from IL-2, IL-6, c-Rel, or Ox40.

In another aspect, provided herein are methods of inhibiting phosphorylation of STAT3 in a subject by administering to the subject a compound described herein (e.g., a compound of Formula (I)), or inhibiting phosphorylation of STAT3 in a biological sample by contacting the biological sample with a compound described herein (e.g., a compound of Formula (I)).

Certain methods described herein, may further comprise administering one or more additional pharmaceutical agents in combination with the compounds described herein, or administration of the compounds described herein may be combined with other treatment methods, e.g., an anti-cancer therapy. In certain embodiments, the compounds described herein or pharmaceutical compositions can be administered in combination with an anti-cancer therapy including, but not limited to, transplantation (e.g., bone marrow transplantation, stem cell transplantation), surgery, radiation therapy, immunotherapy, and chemotherapy. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a proliferative disease (e.g., cancer (e.g., non-Hodgkin's lymphoma, diffuse large B-cell lymphoma, MALT lymphoma), benign neoplasm, a disease associated with angiogenesis, an autoimmune disease, an inflammatory disease, an autoinflammatory disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-diabetic agents, anti-proliferative agents, anti-cancer agents, anti-angiogenesis agents, anti-inflammatory agents, anti-bacterial agents, anti-viral agents, cardiovascular agents, and pain-relieving agents. In certain embodiments, the additional pharmaceutical agent is an anti-cancer agent. In certain embodiments, the additional pharmaceutical agent is an anti-proliferative agent. In certain embodiments, the additional pharmaceutical agent is an anti-angiogenesis agent. In certain embodiments, the additional pharmaceutical agent is an anti-inflammatory agent. In certain embodiments, the additional pharmaceutical agent inhibits MALT1. In certain embodiments, the additional pharmaceutical agent is an anti-cancer agent. In certain embodiments, the additional pharmaceutical agent is an anti-leukemia agent. In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia Chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is an anti-myelodysplasia agent. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), or a combination thereof.

In certain embodiments, the additional pharmaceutical agent is an anti-macroglobulinemia agent. In certain embodiments, the additional pharmaceutical agent is LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof.

In certain embodiments, the additional pharmaceutical agent is rituximab, cyclophosphamide, hydroxydaunorubicin, vincristine, prednisone, prednisolone, lenalidomide, etoposide, or bortezomib, or a combination thereof. In certain embodiments, the additional pharmaceutical agent is a proteasome inhibitor (e.g., bortezomib). In certain embodiments, the compound or pharmaceutical composition described herein is administered in combination with a chemotherapy regimen, such as CHOP or R-CHOP. CHOP comprises administration of cyclophosphamide, hydroxydaunorubicin, vincristine (ONCOVIN), prednisone, prednisolone, or rituximab.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Synthesis of the Compounds

Exemplary compounds of Formula (I) were prepared according to the Schemes E1 to E4. Generally, the sequence begins with preparation of a dipeptide ester (e.g., DE-101) by coupling of two protected amino acids. Hydrolysis of the ester affords a dipeptide acid (e.g., DA-101), which is coupled with an arginine analog followed by deprotection to give the Compound of Formula (I) (e.g., 101).

Compounds 101-111 were prepared according to Scheme E1. For Compound 101, N-((benzyloxy)carbonyl) protected valine and proline methyl ester were combined, and the methyl ester deprotected with base to give the dipeptide acid Z-VP. The second peptide bond was formed by coupling Pmc-arginine-fmk with the dipeptide acid. Deprotection of the guanidine with TFA afforded compound 101 (Z-VPR-fmk). Compounds 102-111 were made by an analogous route with different amino acids in place of valine or proline, or both.

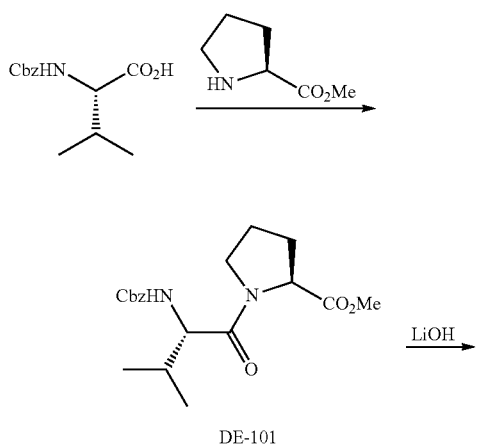

Scheme E1.

DE-101

127
-continued

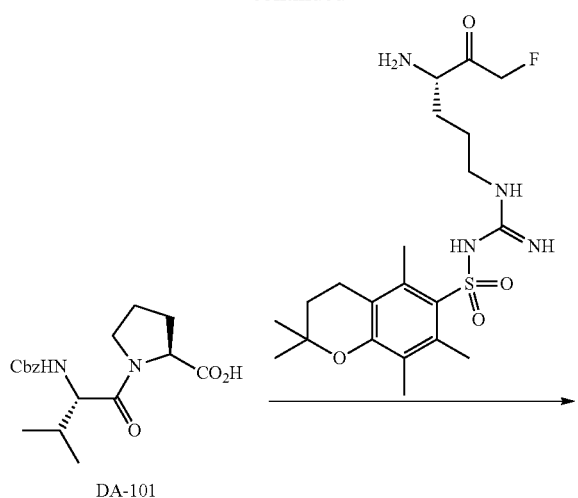

DA-101

128
Benzyl ((S)-1-((S)-2-(((S)-1-fluoro-6-guanidino-2-oxohexan-3-yl)carbamoyl)pyrrolidin-1-yl)-3-methyl-1-oxobutan-2-yl)carbamate 2,2,2-trifluoroacetate (Compound 101)

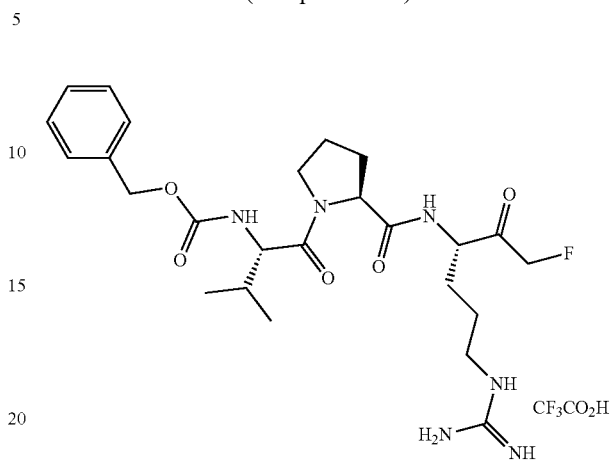

(S)—N—(N-(4-amino-6-fluoro-5-oxohexyl)carbamimidoyl)-2,2,5,7,8-pentamethylchromane-6-sulfonamide 2,2,2-trifluoroacetate (PmcR-fmk, 0.10 g, 0.175 mmol), HATU (0.166 g, 0.438 mmol) and DIPEA (0.38 mL, 2.19 mmol) were added to a solution of ((benzyloxy)carbonyl)-L-valyl-L-proline (0.084 g, 0.241 mmol) in DMF (3 mL) and the mixture was stirred for 10 minutes. The reaction mixture was purified by reverse-phase HPLC (10-100% CH$_3$CN in H$_2$O) and the resulting brown oil was dissolved in a mixture of 90% TFA in DCM (30 mL) and stirred for 1 hour. The solvent was removed under reduced pressure and the residue purified by reverse-phase HPLC (1-50% CH$_3$CN in H$_2$O) to give a brown oil (0.018 g, 16% yield over 2 steps). $^1$H NMR (500 MHz, d$_6$-DMSO) δ 8.51 (d, 1H), 7.48 (t, 1H), 7.42 (d, 1H), 7.36 (m, 5H), 5.21 (dd, 1H), 5.12 (dd, 1H), 5.05 (d, 1H), 4.99 (d, 1H), 4.31 (m, 1H), 4.20 (m, 1H), 4.05 (m, 1H), 3.75 (m, 1H), 3.58 (m, 1H), 3.09 (m, 2H), 2.09 (m, 1H), 1.90 (m, 3H), 1.78 (m, 2H), 1.48 (m, 3H), 0.91 (d, 3H), 0.88 (s, 3H); $^{19}$F NMR (500 MHz) δ −232.48 (t, 1F); MS (m/z): 521.4 [M+1]+.

((Benzyloxy)carbonyl)-L-valyl-L-proline (DA-101)

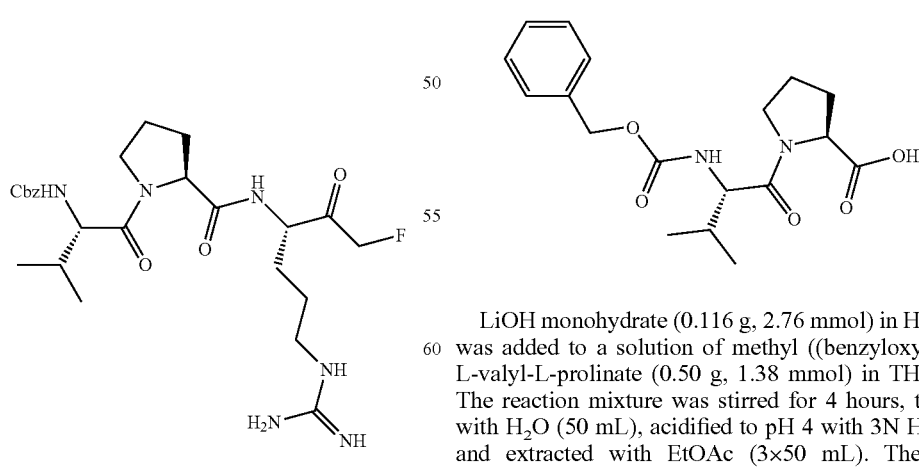

LiOH monohydrate (0.116 g, 2.76 mmol) in H$_2$O (20 mL) was added to a solution of methyl ((benzyloxy)carbonyl)-L-valyl-L-prolinate (0.50 g, 1.38 mmol) in THF (50 mL). The reaction mixture was stirred for 4 hours, then diluted with H$_2$O (50 mL), acidified to pH 4 with 3N HCl solution and extracted with EtOAc (3×50 mL). The combined organic layer was washed with brine, dried (MgSO$_4$) and concentrated to give a white solid (0.45 g, 94% yield). MS (m/z): 348.3 [M+1]$^+$.

Methyl ((benzyloxy)carbonyl)-L-valyl-L-prolinate (DE-101)

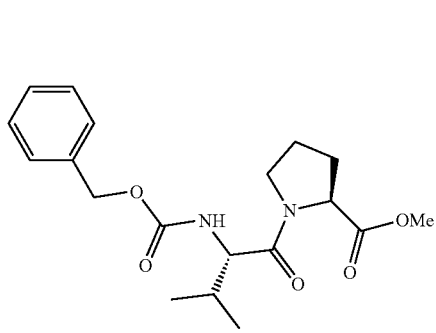 [SMILES: COC(=O)[C@@H]1CCCN1C(=O)[C@@H](NC(=O)OCc1ccccc1)C(C)C]

HATU (3.03 g, 7.95 mmol) and DIPEA (3.46 mL, 19.9 mmol) were added to a solution of ((benzyloxy)carbonyl)-L-valine (1.0 g, 3.98 mmol) and methyl L-prolinate (0.51 g, 3.98 mmol) in DCM (75 mL). The reaction mixture was stirred for 30 minutes, then quenched with water (50 mL) and extracted with DCM (3×50 mL). The combined organic layer was washed with brine, dried (MgSO$_4$) and concentrated. The residue was purified by column chromatography (10-40% EtOAc in Hexanes) to give a colorless oil (1.31 g, 91% yield). MS (m/z): 363.8 [M+1]$^+$.

Scheme E2.

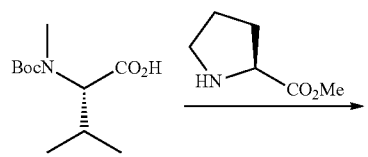

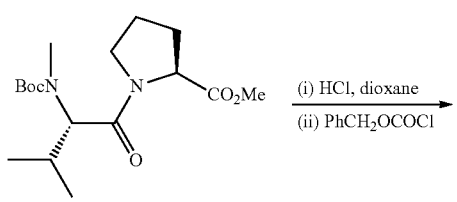

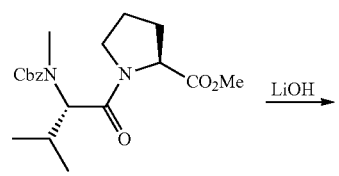

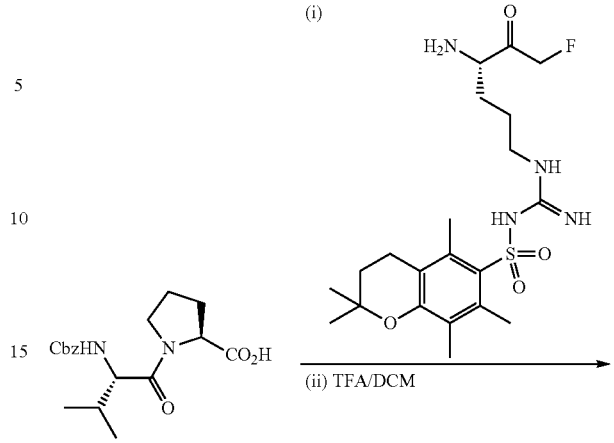

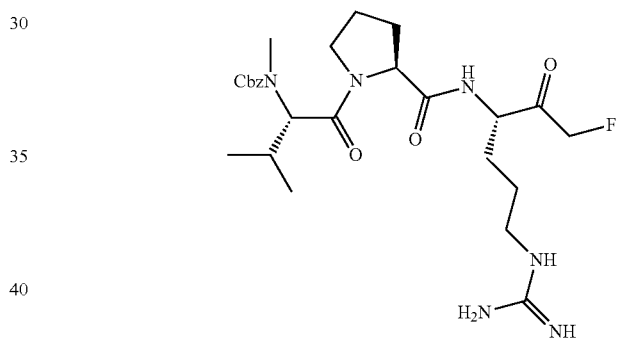

Compound 112 was made according to Scheme E2. N-methyl-N-tert-butyloxycarbonyl was coupled with proline methyl ester. The Boc groups was removed and replaced with N-((benzyloxy)carbonyl). Base hydrolysis of the ester gave dipeptide acid DA-112, which was coupled with PmcR-fmk and deprotected to give compound 112 (Cbz-N-Me-VPR-fmk).

Figure 4:
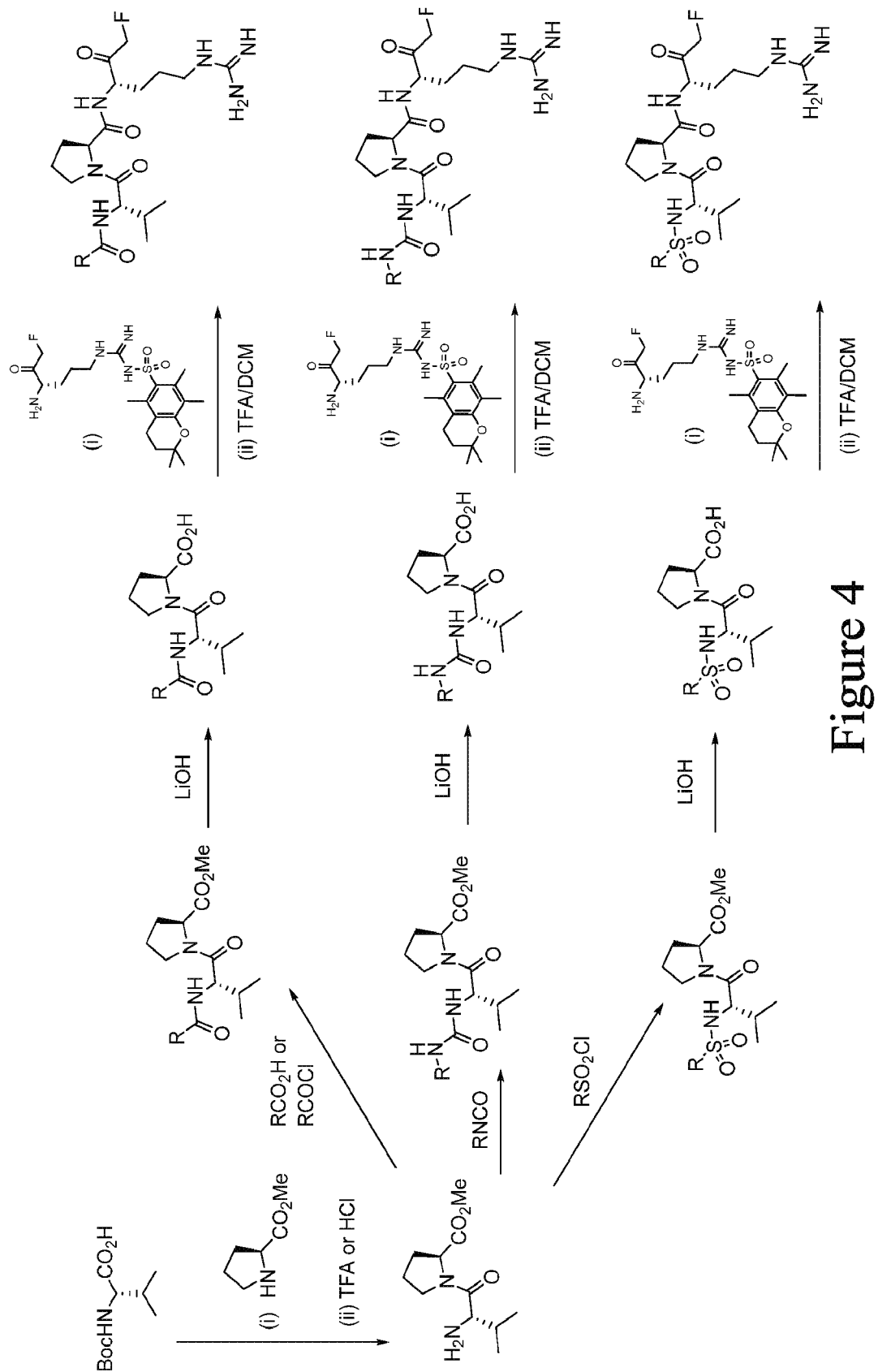
FIG. 4 shows Scheme E3.

Compounds 113 to 130 with various R$^8$ groups were made according to Scheme E3 (FIG. 4). N-tert-butyloxycarbonyl-valine and methyl L-prolinate were coupled and the Boc group removed to give methyl L-valyl-L-prolinate. Amides were formed by reaction with acids (RCO$_2$H) or acyl chloride (RCOCl), ureas by reaction with isocyanates (RNCO), and sulfonamides by reaction with sulfonyl chloride (RSO$_2$Cl). Analogously to Compound 101, the proline methyl ester was hydrolyzed and the dipeptide acids coupled with Pmc-R-fmk.

Compounds 131 to 159 were prepared by similar methods to those described in Schemes E2 and E3. Compounds 141 and 150 were prepared from the corresponding dipeptide acids and the Pmc-R-fmk intermediate prepared from the D-arginine.

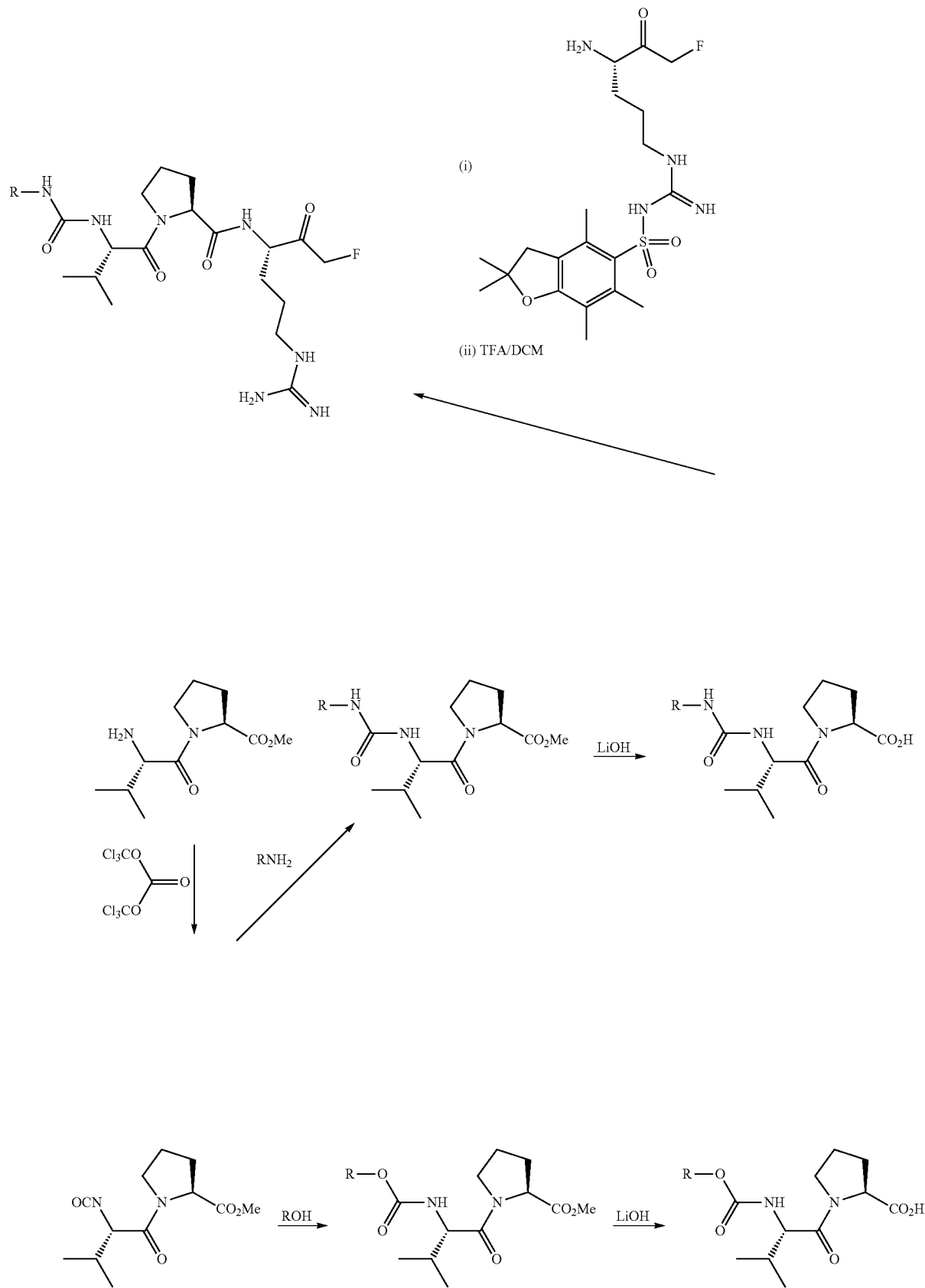

-continued

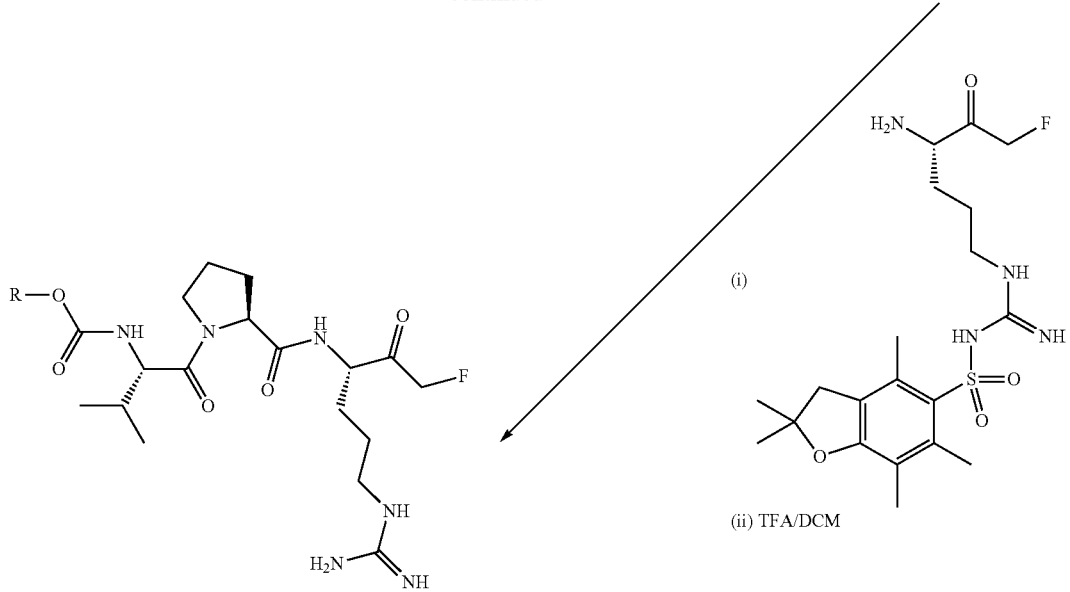

(i)

(ii) TFA/DCM

Scheme E6

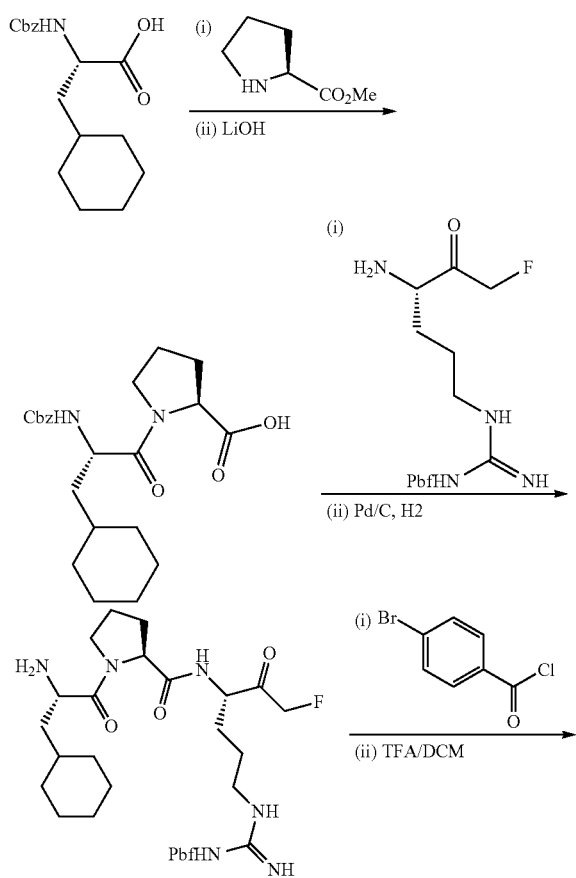

-continued

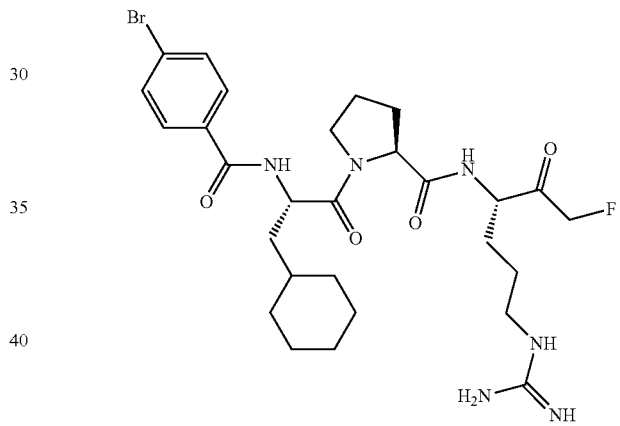

Compounds 160 to 186 were prepared by similar methods to those described in Schemes E2, E3, and E13 from the corresponding dipeptide acids and (S)—N—(N-(4-amino-6-fluoro-5-oxohexyl)carbamimidoyl)-2,2,5,7,8-pentamethylchromane-6-sulfonamide or the Pbf-protected arginine fluoromethyl ketone: (S)—N—(N-(4-amino-6-fluoro-5-oxohexyl)carbamimidoyl)-2,2,4,6,7-pentamethyl-2,3-dihydrobenzofuran-5-sulfonamide. Compounds 161 and 166 were prepared from the corresponding dipeptide acids and the Pbf-R-fmk intermediate derived from D-arginine. Compound 187 was prepared as described in Scheme E6.

Compounds 101 to 187 are listed in Table E1 with mass spectrometry data and the corresponding dipeptide acid or amine used in their preparation.

TABLE E1
Characterization data for compounds 101 to 187.
| Compound | Formula/Name | m/z [M + 1]+ | Dipeptide acid |
|---|---|---|---|
| 101 | 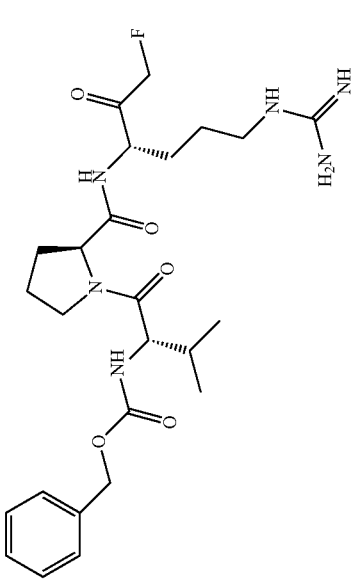<br>Benzyl ((S)-1-((S)-2-(((S)-1-fluoro-6-guanidino-2-oxohexan-3-yl)carbamoyl)pyrrolidin-1-yl)-3-methyl-1-oxobutan-2-yl)carbamate 2,2,2-trifluoroacetate | 521.4 | DA-101 |
| 102 | 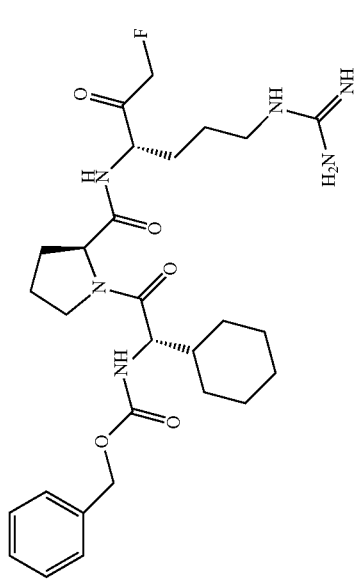<br>Benzyl ((S)-1-cyclohexyl-2-((S)-2-(((S)-1-fluoro-6-guanidino-2-oxohexan-3-yl)carbamoyl)pyrrolidin-1-yl)-2-oxoethyl)carbamate | 561.5 | DA-102 |

TABLE E1-continued

Characterization data for compounds 101 to 187.

| Compound | Formula/Name | m/z [M + 1]⁺ | Dipeptide acid |
|---|---|---|---|
| 103 | Benzyl ((S)-1-((S)-2-(((S)-1-fluoro-6-guanidino-2-oxohexan-3-yl)carbamoyl)pyrrolidin-1-yl)-3,3-dimethyl-1-oxobutan-2-yl)carbamate | 535.5 | DA-103 |
| 104 | Benzyl ((S)-1-((S)-2-(((S)-1-fluoro-6-guanidino-2-oxohexan-3-yl)carbamoyl)pyrrolidin-1-yl)-2-oxo-1-phenylethyl)carbamate | 555.3 | DA-104 |

TABLE E1-continued

Characterization data for compounds 101 to 187.

| Compound | Formula/Name | m/z [M + 1]+ | Dipeptide acid |
|---|---|---|---|
| 105 | Benzyl ((S)-2-((S)-2-(((S)-1-fluoro-6-guanidino-2-oxohexan-3-yl)carbamoyl)pyrrolidin-1-yl)-2-oxo-1-(pyridin-3-yl)ethyl)carbamate (Stereochemistry assigned based upon activity) | 556.6 | DA-105 |
| 106 | Benzyl ((R)-2-((S)-2-(((S)-1-fluoro-6-guanidino-2-oxohexan-3-yl)carbamoyl)pyrrolidin-1-yl)-2-oxo-1-(pyridin-3-yl)ethyl)carbamate (Stereochemistry assigned based upon activity) | — | DA-105 |

TABLE E1-continued

Characterization data for compounds 101 to 187.

| Compound | Formula/Name | m/z [M + 1]⁺ | Dipeptide acid |
|---|---|---|---|
| 107 | Benzyl ((S)-1-((S)-2-(((S)-1-fluoro-6-guanidino-2-oxohexan-3-yl)carbamoyl)piperidin-1-yl)-3-methyl-1-oxobutan-2-yl)carbamate | 535.9 | DA-107 |
| 108 | Benzyl ((S)-1-cyclohexyl-2-((S)-2-(((S)-1-fluoro-6-guanidino-2-oxohexan-3-yl)carbamoyl)piperidin-1-yl)-2-oxoethyl)carbamate | 575.8 | DA-108 |

TABLE E1-continued

Characterization data for compounds 101 to 187.

| Compound | Formula/Name | m/z [M + 1]+ | Dipeptide acid |
|---|---|---|---|
| 109 | Benzyl ((S)-1-((2S,4R)-2-(((S)-1-fluoro-6-guanidino-2-oxohexan-3-yl)carbamoyl)-4-hydroxypyrrolidin-1-yl)-3-methyl-1-oxobutan-2-yl)carbamate | 537.7 | DA-109 |
| 110 | Benzyl ((S)-1-((2S,4S)-2-((((S)-1-fluoro-6-guanidino-2-oxohexan-3-yl)carbamoyl)-4-hydroxypyrrolidin-1-yl)-3-methyl-1-oxobutan-2-yl)carbamate | 537.4 | DA-110 |

TABLE E1-continued

Characterization data for compounds 101 to 187.

| Compound | Formula/Name | m/z [M + 1]+ | Dipeptide acid |
|---|---|---|---|
| 111 | Benzyl ((S)-1-((S)-2-(((S)-1-fluoro-6-guanidino-2-oxohexan-3-yl)carbamoyl)-2-methylpyrrolidin-1-yl)-3-methyl-1-oxobutan-2-yl)carbamate | 535.7 | DA-111 |
| 112 | Benzyl ((S)-1-((S)-2-(((S)-1-fluoro-6-guanidino-2-oxohexan-3-yl)carbamoyl)pyrrolidin-1-yl)-3-methyl-1-oxobutan-2-yl)(methyl)carbamate | 535.7 | DA-112 |

TABLE E1-continued
Characterization data for compounds 101 to 187.
| Compound | Formula/Name | m/z [M + 1]⁺ | Dipeptide acid |
|---|---|---|---|
| 113 | 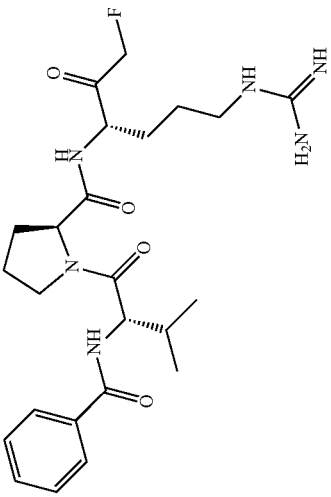<br>(S)-1-(Benzoyl-L-valyl)-N-((S)-1-fluoro-6-guanidino-2-oxohexan-3-yl)pyrrolidine-2-carboxamide | 491.3 | DA-113 |
| 114 | 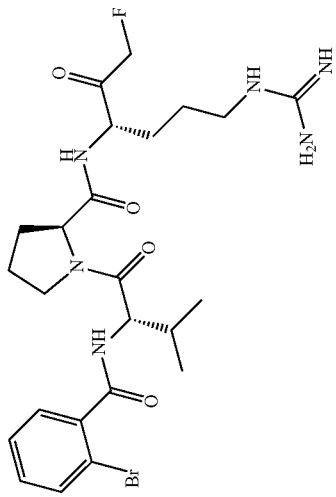<br>(S)-1-((2-Bromobenzoyl)-L-valyl)-N-((S)-1-fluoro-6-guanidino-2-oxohexan-3-yl)pyrrolidine-2-carboxamide | 571.4 | DA-114 |

TABLE E1-continued
Characterization data for compounds 101 to 187.
| Compound | Formula/Name | m/z [M + 1]+ | Dipeptide acid |
|---|---|---|---|
| 115 | 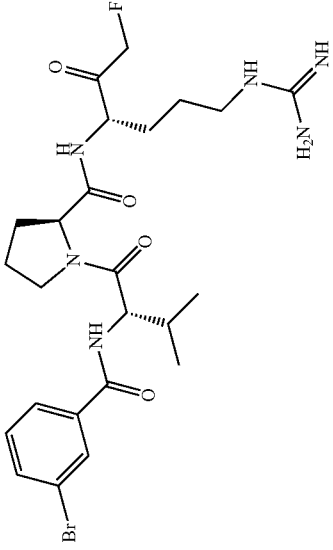<br>(S)-1-((3-Bromobenzoyl)-L-valyl)-N-((S)-1-fluoro-6-guanidino-2-oxohexan-3-yl)pyrrolidine-2-carboxamide | 569.3 | DA-115 |
| 116 | 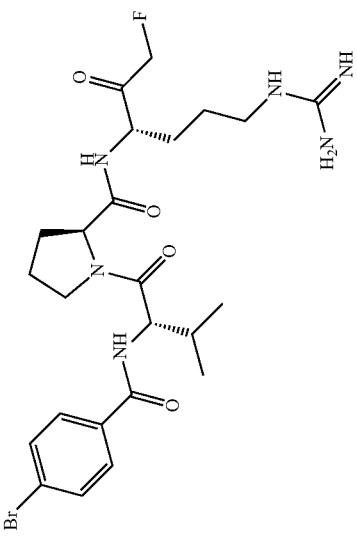<br>(S)-1-(((4-Bromobenzoyl)-L-valyl)-N-((S)-1-fluoro-6-guanidino-2-oxohexan-3-yl)pyrrolidine-2-carboxamide | 569.4 | DA-116 |

TABLE E1-continued

Characterization data for compounds 101 to 187.

| Compound | Formula/Name | m/z [M + 1]+ | Dipeptide acid |
|---|---|---|---|
| 117 | (S)-N-((S)-1-Fluoro-6-guanidino-2-oxohexan-3-yl)-1-((2-phenylacetyl)-L-valyl)pyrrolidine-2-carboxamide | 505.4 | DA-117 |
| 118 | (S)-1-((2-(3-Bromophenyl)acetyl)-L-valyl)-N-((S)-1-fluoro-6-guanidino-2-oxohexan-3-yl)pyrrolidine-2-carboxamide | 585.4 | DA-118 |

TABLE E1-continued
Characterization data for compounds 101 to 187.
| Compound | Formula/Name | m/z [M + 1]+ | Dipeptide acid |
|---|---|---|---|
| 119 | 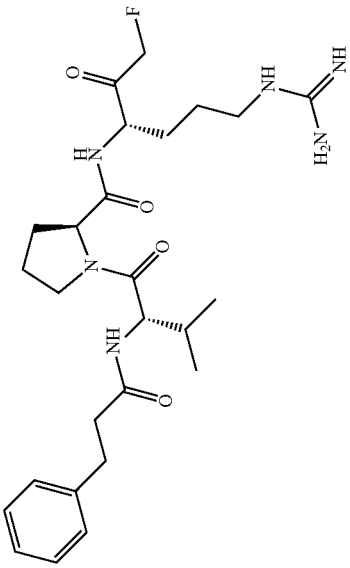 (S)-N-((S)-1-Fluoro-6-guanidino-2-oxohexan-3-yl)-1-((3-phenylpropanoyl)-L-valyl)pyrrolidine-2-carboxamide | 519.6 | DA-119 |
| 120 | 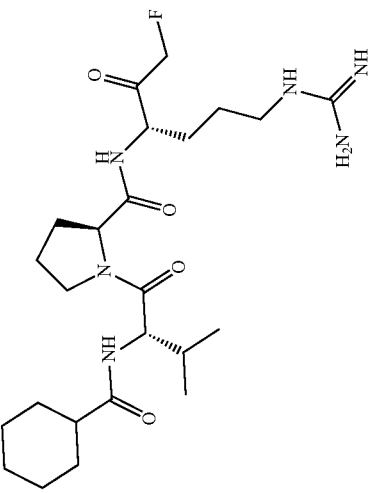 (S)-1-((Cylcohexanecarbonyl)-L-valyl)-N-((S)-1-fluoro-6-guanidino-2-oxohexan-3-yl)pyrrolidine-2-carboxamide | 497.4 | DA-120 |

TABLE E1-continued
Characterization data for compounds 101 to 187.
| Compound | Formula/Name | m/z [M + 1]+ | Dipeptide acid |
|---|---|---|---|
| 121 | 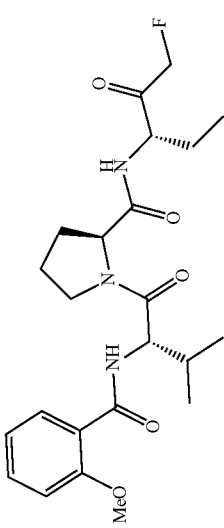<br>(S)-N-((S)-1-Fluoro-6-guanidino-2-oxohexan-3-yl)-1-((2-methoxybenzoyl)-L-valyl)pyrrolidine-2-carboxamide | 521.5 | DA-121 |
| 122 | 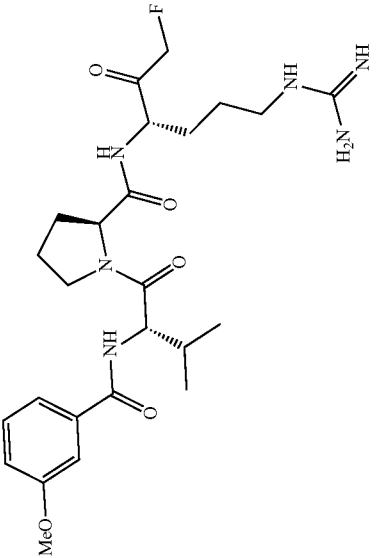<br>(S)-N-((S)-1-Fluoro-6-guanidino-2-oxohexan-3-yl)-1-((3-methoxybenzoyl)-L-valyl)pyrrolidine-2-carboxamide | 521.7 | DA-122 |

TABLE E1-continued
Characterization data for compounds 101 to 187.
| Compound | Formula/Name | m/z [M + 1]+ | Dipeptide acid |
|---|---|---|---|
| 123 | 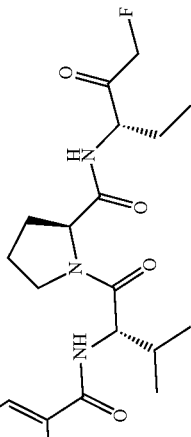<br>(S)-N-((S)-1-Fluoro-6-guanidino-2-oxohexan-3-yl)-1-((4-methoxybenzoyl)-L-valyl)pyrrolidine-2-carboxamide | 521.6 | DA-123 |
| 124 | 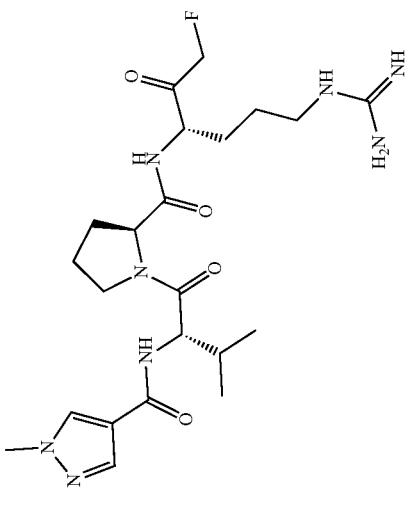<br>N-((S)-1-((S)-2-(((S)-1-Fluoro-6-guanidino-2-oxohexan-3-yl)carbamoyl)pyrrolidin-1-yl)-3-methyl-1-oxobutan-2-yl)-1-methyl-1H-pyrazole-4-carboxamide | 495.6 | DA-124 |

TABLE E1-continued
Characterization data for compounds 101 to 187.
| Compound | Formula/Name | m/z [M + 1]+ | Dipeptide acid |
|---|---|---|---|
| 125 | 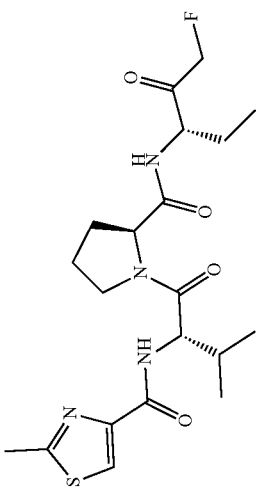  N-((S)-1-((S)-2-(((S)-1-Fluoro-6-guanidino-2-oxohexan-3-yl)carbamoyl)pyrrolidin-1-yl)-3-methyl-1-oxobutan-2-yl)-2-methylthiazole-4-carboxamide | 521.5 | DA-125 |
| 126 | 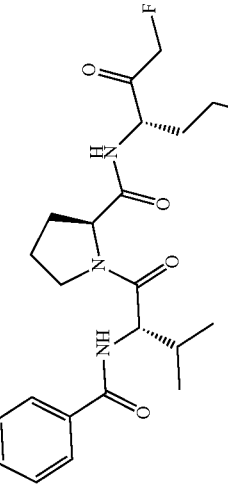  (S)-1-((4-Cyanobenzoyl)-L-valyl)-N-((S)-1-fluoro-6-guanidino-2-oxohexan-3-yl)pyrrolidine-2-carboxamide | 516.1 | DA-126 |

TABLE E1-continued

Characterization data for compounds 101 to 187.

| Compound | Formula/Name | m/z [M + 1]+ | Dipeptide acid |
|---|---|---|---|
| 127 | (S)-N-((S)-1-Fluoro-6-guanidino-2-oxohexan-3-yl)-1-(((4-morpholinobenzoyl)-L-valyl)pyrrolidine-2-carboxamide | 576.8 | DA-127 |

TABLE E1-continued
Characterization data for compounds 101 to 187.
| Compound | Formula/Name | m/z [M + 1]+ | Dipeptide acid |
|---|---|---|---|
| 128 | 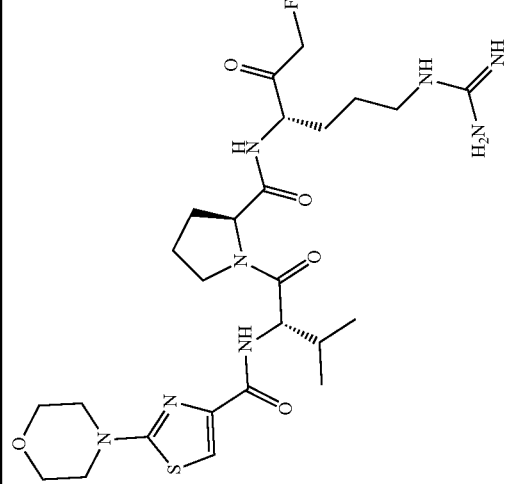<br>N-((S)-1-(((S)-2-(((S)-1-Fluoro-6-guanidino-2-oxohexan-3-yl)carbamoyl)pyrrolidin-1-yl)-2-oxobutan-2-yl)-2-morpholinothiazole-4-carboxamide | 583.4 | DA-128 |

TABLE E1-continued

Characterization data for compounds 101 to 187.

| Compound | Formula/Name | m/z [M + 1]+ | Dipeptide acid |
|---|---|---|---|
| 129 | (S)-N-((S)-1-Fluoro-6-guanidino-2-oxohexan-3-yl)-1-((phenylcarbamoyl)-L-valyl)pyrrolidine-2-carboxamide | 506.3 | DA-129 |
| 130 | (S)-1-(((4-Bromophenyl)sulfonyl)-L-valyl)-N-((S)-1-fluoro-6-guanidino-2-oxohexan-3-yl)pyrrolidine-2-carboxamide | 606.1 | DA-130 |

TABLE E1-continued
Characterization data for compounds 101 to 187.
| Compound | Formula/Name | m/z [M + 1]+ | Dipeptide acid |
|---|---|---|---|
| 131 | 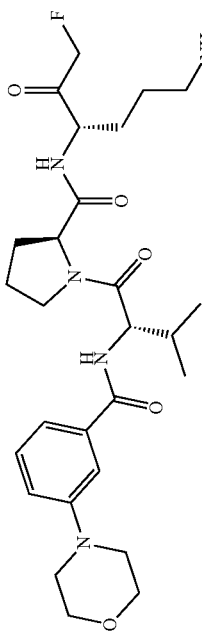<br>(S)-N-((S)-1-fluoro-6-guanidino-2-oxohexan-3-yl)-1-(((3-morpholinobenzoyl)-L-valyl)pyrrolidine-2-carboxamide | 576.8 | DA-131 |
| 132 | 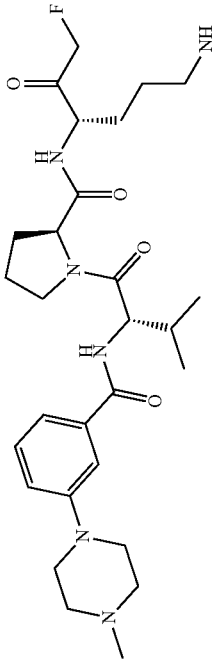<br>(S)-N-((S)-1-fluoro-6-guanidino-2-oxohexan-3-yl)-1-(((3-(4-methylpiperazine-1-yl)benzoyl)-L-valyl)pyrrolidine-2-carboxamide | 589.8 | DA-132 |

TABLE E1-continued
Characterization data for compounds 101 to 187.
| Compound | Formula/Name | m/z [M + 1]+ | Dipeptide acid |
|---|---|---|---|
| 133 | 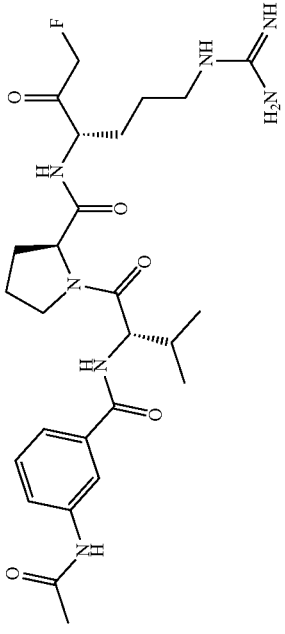<br>(S)-1-((3-acetamidobenzoyl)-L-valyl)-N-((S)-1-fluoro-6-guanidino-2-oxohexan-3-yl)pyrrolidine-2-carboxamide | 548.5 | DA-133 |
| 134 | 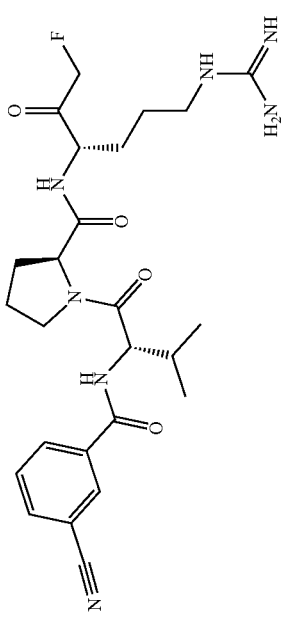<br>(S)-1-((3-cyanobenzoyl)-L-valyl)-N-((S)-1-fluoro-6-guanidino-2-oxohexan-3-yl)pyrrolidine-2-carboxamide | 516.5 | DA-134 |

TABLE E1-continued
Characterization data for compounds 101 to 187.
| Compound | Formula/Name | m/z [M + 1]+ | Dipeptide acid |
|---|---|---|---|
| 135 | 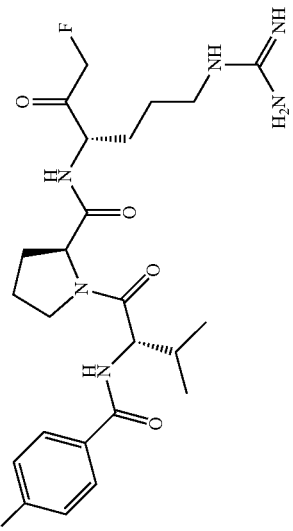<br>(S)-N-((S)-1-fluoro-6-guanidino-2-oxohexan-3-yl)-1-((4-(trifluoromethyl)benzoyl)-L-valyl)pyrrolidine-2-carboxamide | 559.6 | DA-135 |
| 136 | 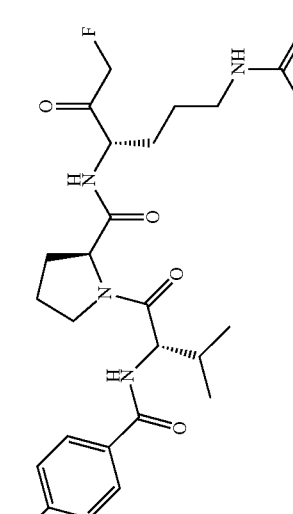<br>(S)-1-((4-chlorobenzoyl)-L-valyl)-N-((S)-1-fluoro-6-guanidino-2-oxohexan-3-yl)pyrrolidine-2-carboxamide | 525.6 | DA-136 |

TABLE E1-continued

Characterization data for compounds 101 to 187.

| Compound | Formula/Name | m/z [M + 1]+ | Dipeptide acid |
|---|---|---|---|
| 137 | (S)-1-(([1,1'-biphenyl]-4-carbonyl)-L-valyl)-N-((S)-1-fluoro-6-guanidino-2-oxohexan-3-yl)pyrrolidine-2-carboxamide | 567.7 | DA-137 |
| 138 | (S)-1-((5-bromothiophene-2-carbonyl)-L-valyl)-N-((S)-1-fluoro-6-guanidino-2-oxohexan-3-yl)pyrrolidine-2-carboxamide | 575.6 | DA-138 |

TABLE E1-continued
Characterization data for compounds 101 to 187.
| Compound | Formula/Name | m/z [M + 1]+ | Dipeptide acid |
|---|---|---|---|
| 139 | 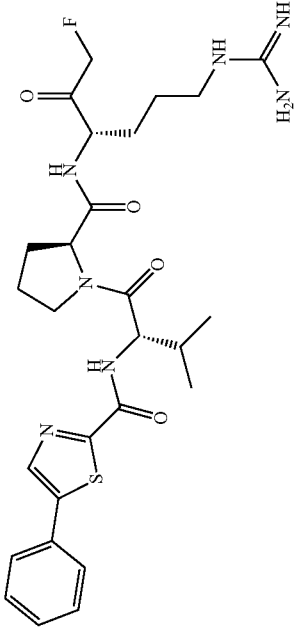<br>N-((S)-1-((S)-2-(((S)-1-fluoro-6-guanidino-2-oxohexan-3-yl)carbamoyl)pyrrolidin-1-yl)-3-methyl-1-oxobutan-2-yl)-5-phenylthiazole-2-carboxamide | 574.7 | DA-139 |
| 140 | 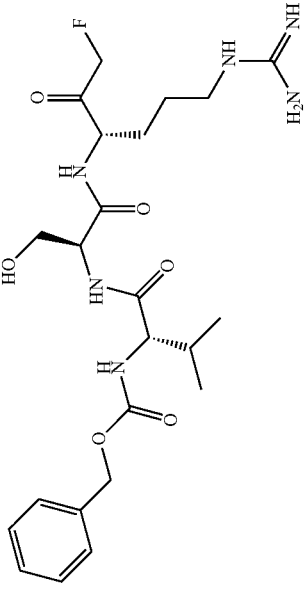<br>benzyl ((S)-1-(((S)-1-((S)-1-fluoro-6-guanidino-2-oxohexan-3-yl)amino)-3-hydoxy-1-oxopropan-2-yl)amino)-3-methyl-1-oxobutan-2-yl)carbamate | 511.6 | DA-140 |

TABLE E1-continued
Characterization data for compounds 101 to 187.
| Compound | Formula/Name | m/z [M + 1]+ | Dipeptide acid |
|---|---|---|---|
| 141 | 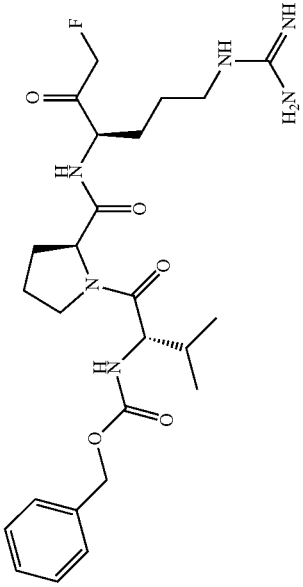<br>benzyl ((S)-1-((S)-2-(((R)-1-fluoro-6-guanidino-2-oxohexan-3-yl)carbamoyl)pyrrolidin-1-yl)-3-methyl-1-oxobutan-2-yl)carbamate | 521.6 | DA-101 |
| 142 | 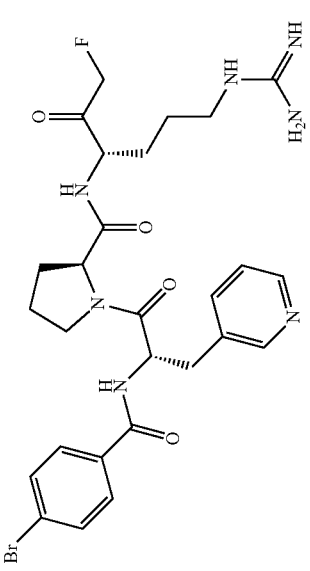<br>(S)-1-((S)-2-(4-bromobenzamido)-3-(pyridin-3-yl)propanoyl)-N-((S)-1-fluoro-6-guanidino-2-oxohexan-3-yl)pyrrolidine-2-carboxamide | 620.7 | DA-142 |

TABLE E1-continued
Characterization data for compounds 101 to 187.
| Compound | Formula/Name | m/z [M + 1]⁺ | Dipeptide acid |
|---|---|---|---|
| 143 | 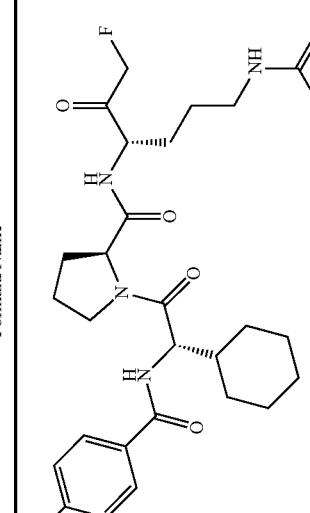<br>(S)-1-((S)-2-(4-bromobenzamido)-2-cyclohexylacetyl)-N-((S)-1-fluoro-6-guanidino-2-oxohexan-3-yl)pyrrolidine-2-carboxamide | 609.7 | DA-143 |
| 144 | 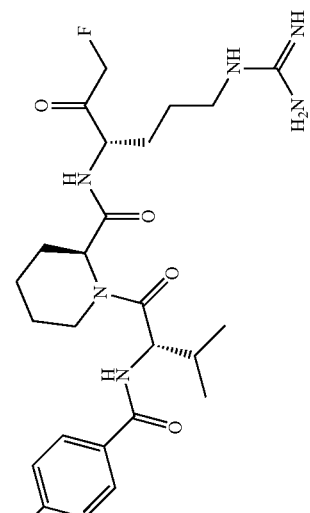<br>(S)-1-((4-bromobenzoyl)-L-valyl)-N-((S)-1-fluoro-6-guanidino-2-oxohexan-3-yl)piperidine-2-carboxamide | 583.7 | DA-144 |

TABLE E1-continued
Characterization data for compounds 101 to 187.
| Compound | Formula/Name | m/z [M + 1]+ | Dipeptide acid |
|---|---|---|---|
| 145 | 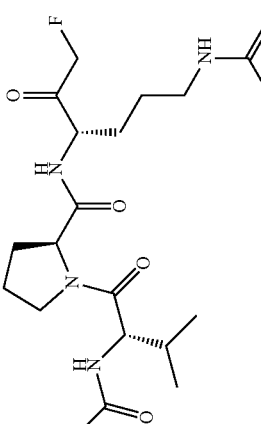<br>(S)-N-((S)-1-fluoro-6-guanidino-2-oxohexan-3-yl)-1-((4-(trifluoromethoxy)benzoyl)-L-valyl)pyrrolidine-2-carboxamide | 575.6 | DA-145 |
| 146 | 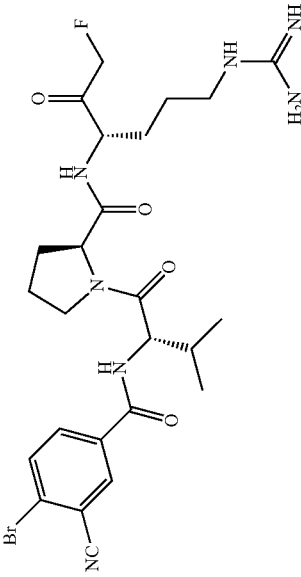<br>(S)-1-((4-bromo-3-cyanobenzoyl)-L-valyl)-N-((S)-1-fluoro-6-guanidino-2-oxohexan-3-yl)pyrrolidine-2-carboxamide | 596.7 | DA-146 |

TABLE E1-continued
Characterization data for compounds 101 to 187.
| Compound | Formula/Name | m/z [M + 1]+ | Dipeptide acid |
|---|---|---|---|
| 147 | 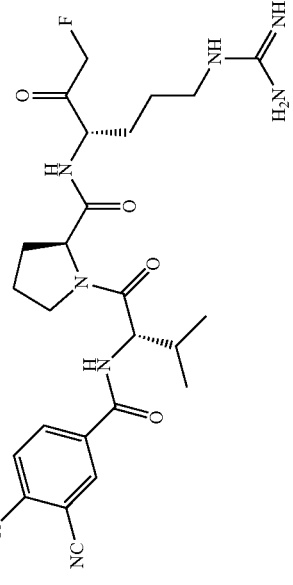<br>(S)-1-((4-chloro-3-cyanobenzoyl)-L-valyl)-N-((S)-1-fluoro-6-guanidino-2-oxohexan-3-yl)pyrrolidine-2-carboxamide | 550.7 | DA-147 |
| 148 | 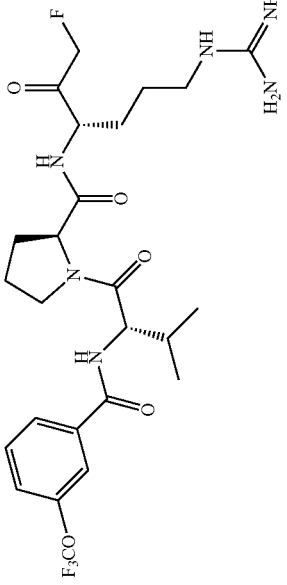<br>(S)-N-((S)-1-fluoro-6-guanidino-2-oxohexan-3-yl)-1-((3-(trifluoromethoxy)benzoyl)-L-valyl)pyrrolidine-2-carboxamide | 575.6 | DA-148 |

TABLE E1-continued

Characterization data for compounds 101 to 187.

| Compound | Formula/Name | m/z [M + 1]+ | Dipeptide acid |
|---|---|---|---|
| 149 | 4-bromo-N-((S)-1-(((S)-1-fluoro-6-guanidino-2-oxohexan-3-yl)amino)-3-hydroxy-1-oxopropan-2-yl)amino)-3-methyl-1-oxobutan-2-yl)benzamide | 559.5 | DA-149 |
| 150 | (S)-1-((4-bromobenzoyl)-L-valyl)-N-((R)-1-fluoro-6-guanidino-2-oxohexan-3-yl)pyrrolidine-2-carboxamide | 571.4 | DA-116 |

TABLE E1-continued
Characterization data for compounds 101 to 187.
| Compound | Formula/Name | m/z [M + 1]+ | Dipeptide acid |
|---|---|---|---|
| 151 | 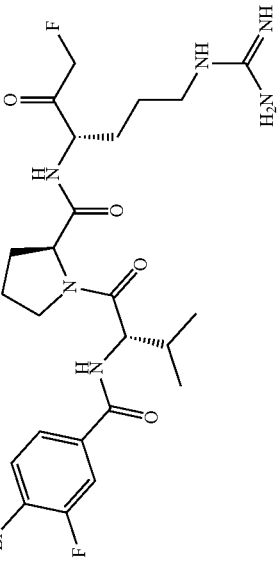<br>(S)-1-((4-bromo-3-fluorobenzoyl)-L-valyl)-N-((S)-1-fluoro-6-guanidino-2-oxohexan-3-yl)pyrrolidine-2-carboxamide | 589.6 | DA-151 |
| 152 | 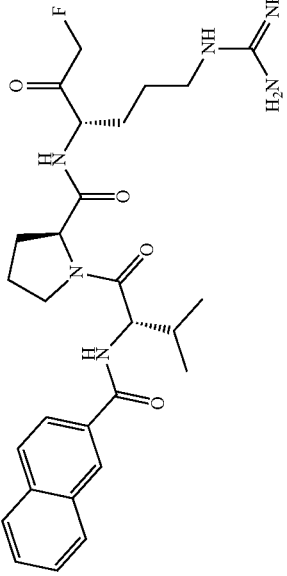<br>(S)-1-((2-naphthoyl)-L-valyl)-N-((S)-1-fluoro-6-guanidino-2-oxohexan-3-yl)pyrrolidine-2-carboxamide | 541.5 | DA-152 |

TABLE E1-continued

Characterization data for compounds 101 to 187.

| Compound | Formula/Name | m/z [M + 1]+ | Dipeptide acid |
|---|---|---|---|
| 153 | (S)-1-((1-naphthoyl)-L-valyl)-N-((S)-1-fluoro-6-guanidino-2-oxohexan-3-yl)pyrrolidine-2-carboxamide | 541.4 | DA-153 |
| 154 | (S)-1-(cinnamoyl-L-valyl)-N-((S)-1-fluoro-6-guanidino-2-oxohexan-3-yl)pyrrolidine-2-carboxamide | 517.6 | DA-154 |

TABLE E1-continued
Characterization data for compounds 101 to 187.
| Compound | Formula/Name | m/z [M + 1]⁺ | Dipeptide acid |
|---|---|---|---|
| 155 | 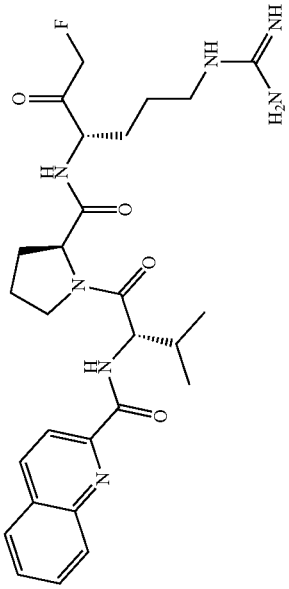<br>N-((S)-1-((S)-2-(((S)-1-fluoro-6-guanidino-2-oxohexan-3-yl)carbamoyl)pyrrolidin-1-yl)-3-methyl-1-oxobutan-2-yl)quinoline-2-carboxamide | 542.7 | DA-155 |
| 156 | 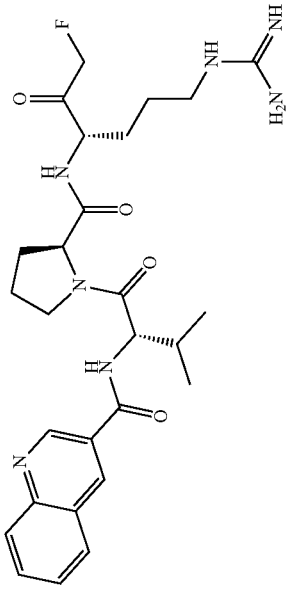<br>N-((S)-1-((S)-2-(((S)-1-fluoro-6-guanidino-2-oxohexan-3-yl)carbamoyl)pyrrolidin-1-yl)-3-methyl-1-oxobutan-2-yl)quinoline-3-carboxamide | 542.8 | DA-156 |

TABLE E1-continued
Characterization data for compounds 101 to 187.
| Compound | Formula/Name | m/z [M + 1]+ | Dipeptide acid |
|---|---|---|---|
| 157 | 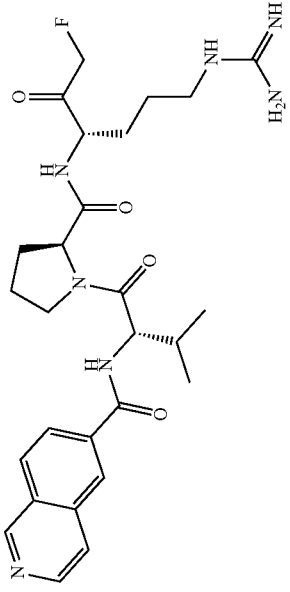<br>N-((S)-1-((S)-2-(((S)-1-fluoro-6-guanidino-2-oxohexan-3-yl)carbamoyl)pyrrolidin-1-yl)-3-methyl-1-oxobutan-2-yl)isoquinoline-6-carboxamide | 542.7 | DA-157 |
| 158 | 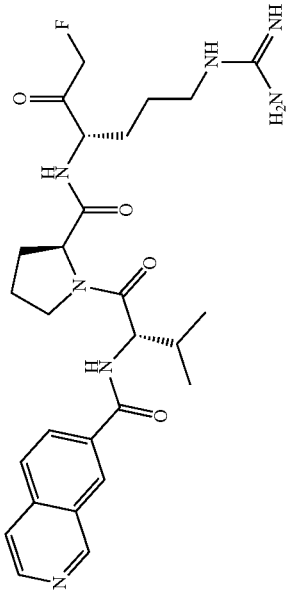<br>N-((S)-1-((S)-2-(((S)-1-fluoro-6-guanidino-2-oxohexan-3-yl)carbamoyl)pyrrolidin-1-yl)-3-methyl-1-oxobutan-2-yl)isoquinoline-7-carboxamide | 542.6 | DA-158 |

TABLE E1-continued
Characterization data for compounds 101 to 187.
| Compound | Formula/Name | m/z [M + 1]+ | Dipeptide acid |
|---|---|---|---|
| 159 | 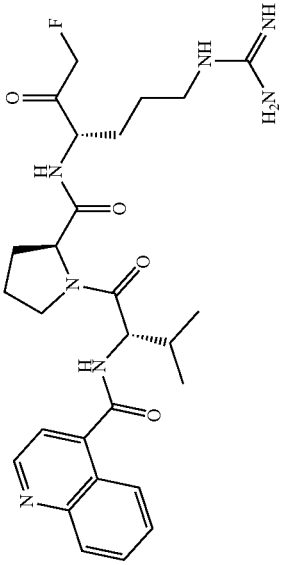<br>N-((S)-1-((S)-2-(((S)-1-fluoro-6-guanidino-2-oxohexan-3-yl)carbamoyl)pyrrolidin-1-yl)-3-methyl-1-oxobutan-2-yl)quinoline-4-carboxamide | 542.5 | DA-159 |
| 160 | 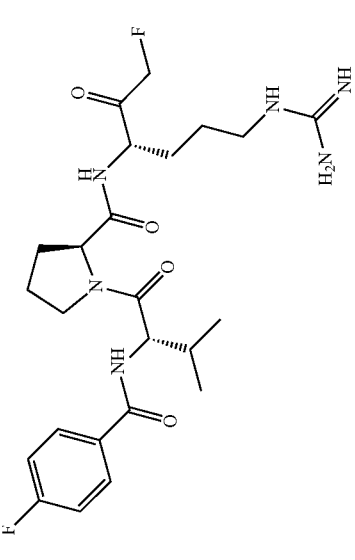<br>(S)-N-((S)-1-Fluoro-6-guanidino-2-oxohexan-3-yl)-1-((4-fluorobenzoyl)-L-valyl)pyrrolidine-2-carboxamide | 509.35 | DA-160 |

TABLE E1-continued
Characterization data for compounds 101 to 187.
| Compound | Formula/Name | m/z [M + 1]+ | Dipeptide acid |
|---|---|---|---|
| 161 | 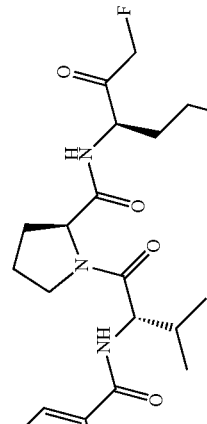<br>(S)-N-((R)-1-Fluoro-6-guanidino-2-oxohexan-3-yl)-1-((4-fluorobenzoyl)-L-valyl)pyrrolidine-2-carboxamide | — | DA-160 |
| 162 | 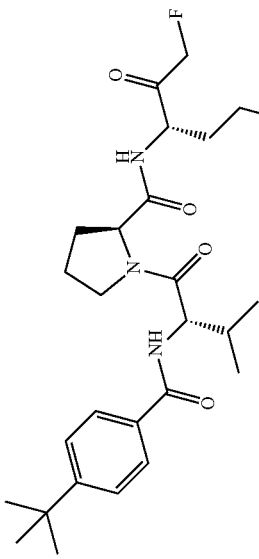<br>(S)-1-((4-tert-Butyl)benzoyl)-L-valyl)-N-((S)-1-fluoro-6-guanidino-2-oxohexan-3-yl)pyrrolidine-2-carboxamide | 546.97 | DA-162 |

TABLE E1-continued
Characterization data for compounds 101 to 187.
| Compound | Formula/Name | m/z [M + 1]+ | Dipeptide acid |
|---|---|---|---|
| 163 | 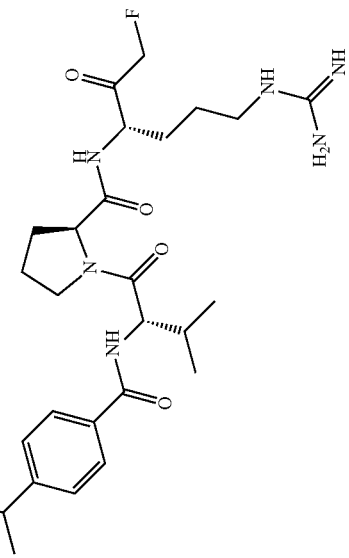<br>(S)-N-((S)-1-Fluoro-6-guanidino-2-oxohexan-3-yl)-1-(((4-isopropylbenzoyl)-L-valyl)pyrrolidine-2-carboxamide | 532.73 | DA-163 |
| 164 | 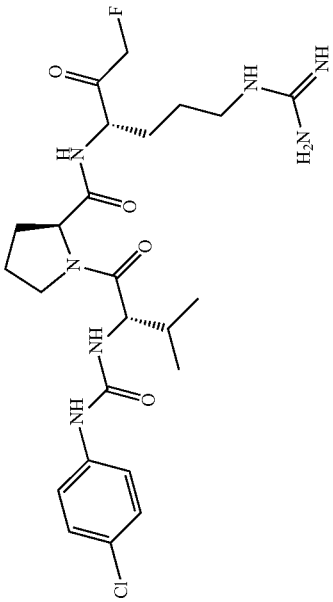<br>(S)-1-(((4-Chlorophenyl)carbamoyl)-L-valyl)-N-((S)-1-fluoro-6-guanidino-2-oxohexan-3-yl)pyrrolidine-2-carboxamide | 540.4 | DA-164 |

TABLE E1-continued
Characterization data for compounds 101 to 187.
| Compound | Formula/Name | m/z [M + 1]⁺ | Dipeptide acid |
|---|---|---|---|
| 165 | 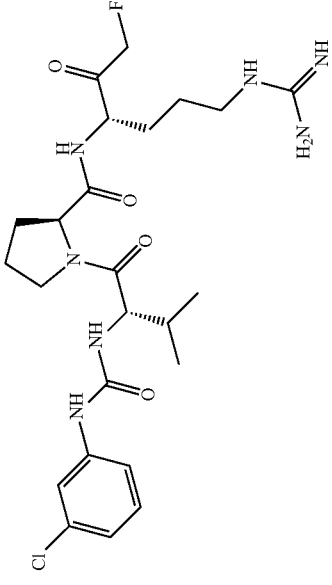<br>(S)-1-(((3-Chlorophenyl)carbamoyl)-L-valyl)-N-((S)-1-fluoro-6-guanidino-2-oxohexan-3-yl)pyrrolidine-2-carboxamide | 540.55 | DA-165 |
| 166 | 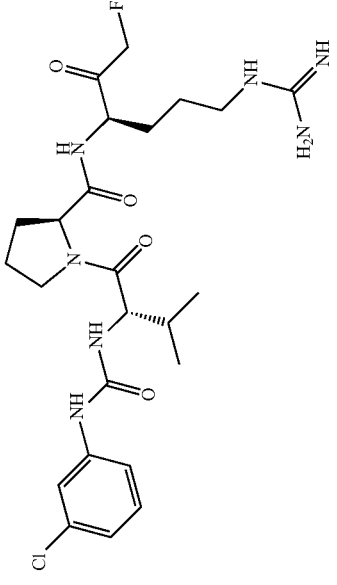<br>(S)-1-(((3-Chlorophenyl)carbamoyl)-L-valyl)-N-((R)-1-fluoro-6-guanidino-2-oxohexan-3-yl)pyrrolidine-2-carboxamide | — | DA-165 |

TABLE E1-continued
Characterization data for compounds 101 to 187.
| Compound | Formula/Name | m/z [M + 1]⁺ | Dipeptide acid |
|---|---|---|---|
| 167 | 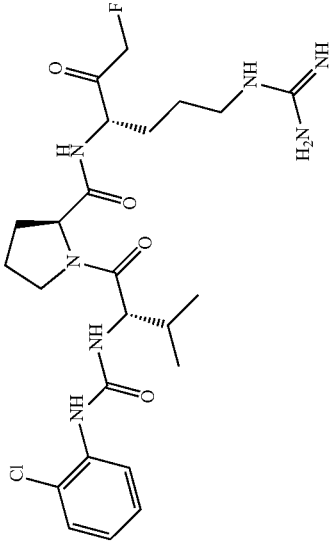<br>(S)-1-(((2-Chlorophenyl)carbamoyl)-L-valyl)-N-((S)-1-fluoro-6-guanidino-2-oxohexan-3-yl)pyrrolidine-2-carboxamide | 539.69 | DA-167 |
| 168 | 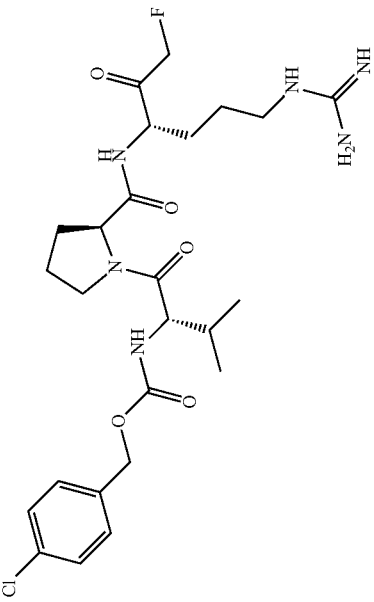<br>4-Chlorobenzyl (((S)-1-((S)-2-(((S)-1-fluoro-6-guanidino-2-oxohexan-3-yl)carbamoyl)pyrrolidin-1-yl)-3-methyl-1-oxobutan-2-yl)carbamate | 554.77 | DA-168 |

TABLE E1-continued

Characterization data for compounds 101 to 187.

| Compound | Formula/Name | m/z [M + 1]+ | Dipeptide acid |
|---|---|---|---|
| 169 | 3-Chlorobenzyl ((S)-1-((S)-2-(((S)-1-fluoro-6-guanidino-2-oxohexan-3-yl)carbamoyl)pyrrolidin-1-yl)-3-methyl-1-oxobutan-2-yl)carbamate | 555.50 | DA-169 |
| 170 | -2Chlorobenzyl ((S)-1-((S)-2-(((S)-1-fluoro-6-guanidino-2-oxohexan-3-yl)carbamoyl)pyrrolidin-1-yl)-3-methyl-1-oxobutan-2-yl)carbamate | 555.4 | DA-160 |

TABLE E1-continued

Characterization data for compounds 101 to 187.

| Compound | Formula/Name | m/z [M + 1]+ | Dipeptide acid |
|---|---|---|---|
| 171 | (2S,4R)-1-((4-Bromobenzoyl)-L-valyl)-N-((S)-1-fluoro-6-guanidino-2-oxohexan-3-yl)-4-hydroxypyrrolidine-2-carboxamide | 587.5 | DA-171 |
| 172 | (2S,4R)-1-((S)-2-(4-Bromobenzamido)-2-cyclohexylacetyl)-N-((S)-1-fluoro-6-guanidino-2-oxohexan-3-yl)-4-hydroxypyrrolidine-2-carboxamide | 624.51 | DA-172 |

TABLE E1-continued

Characterization data for compounds 101 to 187.

| Compound | Formula/Name | m/z [M + 1]+ | Dipeptide acid |
|---|---|---|---|
| 173 | 4-Bromo-N-((S)-1-cyclohexyl-2-(((S)-1-(((S)-1-fluoro-6-guanidino-2-oxohexan-3-yl)amino)-3-hydroxy-1-oxopropan-2-yl)amino)-2-oxoethyl)benzamide | 601.5 | DA-173 |
| 174 | (S)-3-((4-Bromobenzoyl)-L-valyl)-N-((S)-1-fluoro-6-guanidino-2-oxohexan-3-yl)oxazolidine-4-carboxamide | 571.24 | DA-174 |

TABLE E1-continued

Characterization data for compounds 101 to 187.

| Compound | Formula/Name | m/z [M + 1]+ | Dipeptide acid |
|---|---|---|---|
| 175 | (S)-4-((4-Bromobenzoyl)-L-valyl)-N-((S)-1-fluoro-6-guanidino-2-oxohexan-3-yl)morpholine-3-carboxamide | 587.34 | DA-175 |
| 176 | (S)-1-((4-Bromobenzoyl)-L-valyl)-N-((S)-1-fluoro-6-guanidino-2-oxohexan-3-yl)azetidine-2-carboxamide | 555.29 | DA-176 |

TABLE E1-continued
Characterization data for compounds 101 to 187.
| Compound | Formula/Name | m/z [M + 1]+ | Dipeptide acid |
|---|---|---|---|
| 177 | 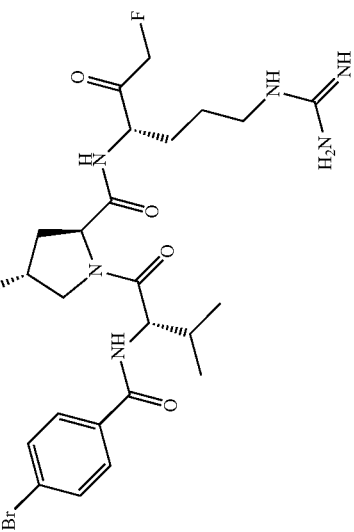<br>(2S,4R)-1-((S)-1-((4-Bromobenzoyl)-L-valyl)-4-N-((S)-1-fluoro-6-guanidino-2-oxohexan-3-yl)pyrrolidine-2-carboxamide | 594.34 | DA-177 |
| 178 | 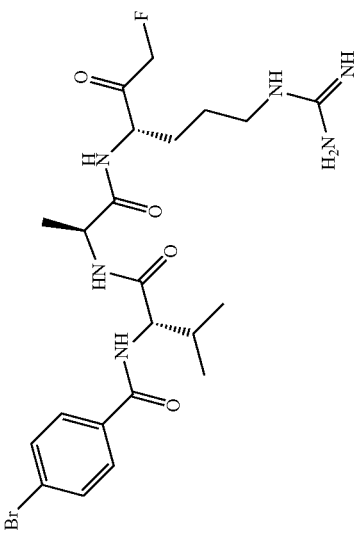<br>4-Bromo-N-((S)-1-(((S)-1-(((S)-1-fluoro-6-guanidino-2-oxohexan-3-yl)amino)-1-oxopropan-2-yl)amino)-3-methyl-1-oxobutan-2-yl)benzamide | 543.32 | DA-178 |

TABLE E1-continued

Characterization data for compounds 101 to 187.

| Compound | Formula/Name | m/z [M + 1]+ | Dipeptide acid |
|---|---|---|---|
| 179 | (S)-1-((4-Bromo-2-fluorobenzoyl)-L-valyl)-N-((S)-1-fluoro-6-guanidino-2-oxohexan-3-yl)pyrrolidine-2-carboxamide | 587.3 | DA-179 |
| 180 | Benzyl ((2S,3R)-1-((S)-2-(((S)-1-fluoro-6-guanidino-2-oxohexan-3-yl)carbamoyl)pyrrolidin-1-yl)-3-methyl-1-oxopentan-2-yl)carbamate | 535.2 | DA-170 |

TABLE E1-continued

Characterization data for compounds 101 to 187.

| Compound | Formula/Name | m/z [M + 1]+ | Dipeptide acid |
|---|---|---|---|
| 181 | Benzyl (1-((S)-2-(((S)-1-fluoro-6-guanidino-2-oxohexan-3-yl)carbamoyl)pyrrolidin-1-carbonyl)cyclopentyl)carbamate | 533 | DA-181 |
| 182 | Benzyl ((S)-1-((S)-2-(((S)-1-fluoro-6-guanidino-2-oxohexan-3-yl)carbamoyl)pyrrolidin-1-yl)-1-oxo-3-phenylpropan-2-yl)carbamate | 569.1 | DA-182 |

TABLE E1-continued
Characterization data for compounds 101 to 187.
| Compound | Formula/Name | m/z [M + 1]+ | Dipeptide acid |
|---|---|---|---|
| 183 | 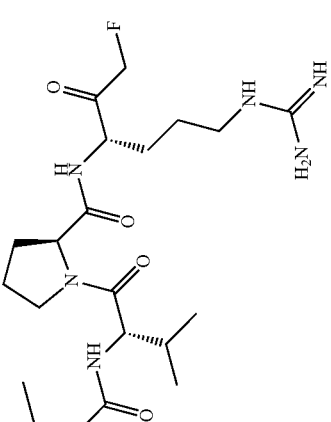<br>(S)-1-((4-Bromo-2-methylbenzoyl)-L-valyl)-N-((S)-1-fluoro-6-guanidino-2-oxohexan-3-yl)pyrrolidine-2-carboxamide | 583.4 | DA-183 |
| 184 | 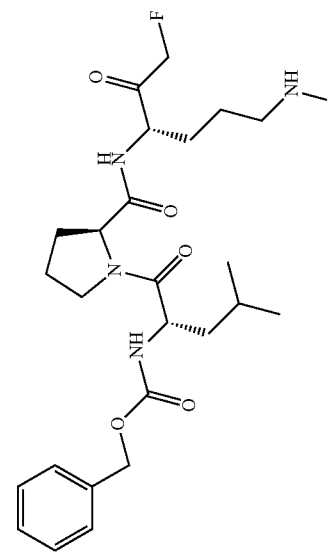<br>Benzyl ((S)-1-((S)-2-(((S)-1-fluoro-6-guanidino-2-oxohexan-3-yl)carbamoyl)pyrrolidin-1-yl)-4-methyl-1-oxopentan-2-yl)carbamate | 535.2 | DA-184 |

TABLE E1-continued
Characterization data for compounds 101 to 187.
| Compound | Formula/Name | m/z [M + 1]+ | Dipeptide acid |
|---|---|---|---|
| 185 | 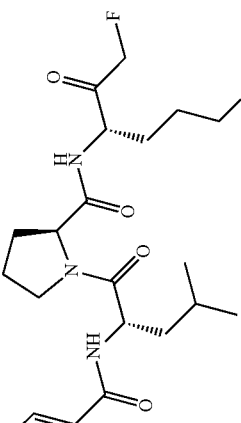<br>(S)-1-((4-Bromobenzoyl)-L-leucyl)-N-((S)-1-fluoro-6-guanidino-2-oxohexan-3-yl)pyrrolidine-2-carboxamide | 583.4 | DA-185 |
| 186 | 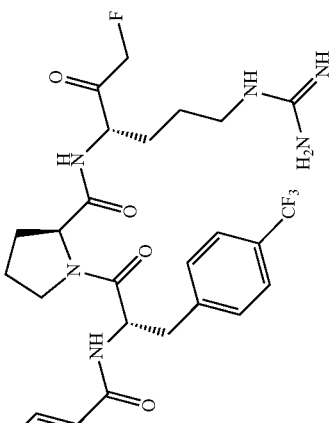<br>(S)-1-((S)-2-(4-Bromobenzamido)-3-(4-(trifluoromethyl)phenyl)propanoyl)-N-((S)-1-fluoro-6-guanidino-2-oxohexan-3-yl)pyrrolidine-2-carboxamide | 685.4 | DA-186 |

TABLE E1-continued
Characterization data for compounds 101 to 187.
| Compound | Formula/Name | m/z [M + 1]$^+$ | Dipeptide acid |
|---|---|---|---|
| 187 | 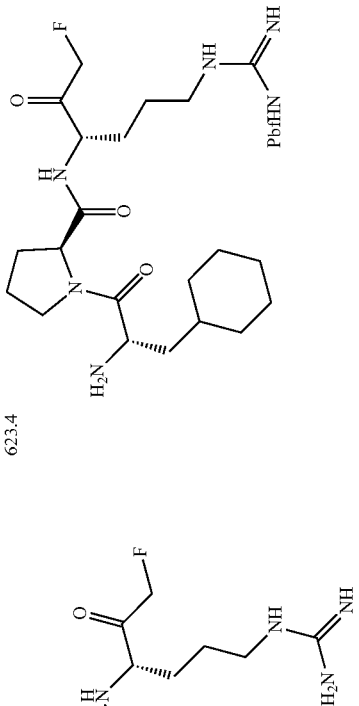<br>(S)-1-((S)-2-(4-Bromobenzamido)-3-cyclohexylpropanoyl)-N-((S)-1-fluoro-6-guanidino-2-oxohexan-3-yl)pyrrolidine-2-carboxamide | 623.4 | 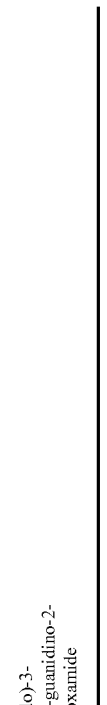 |

The dipeptide acid intermediates were prepared in a similar manner to ((benzyloxy)carbonyl)-L-valyl-L-proline (DA-101), and are listed in Table E2, along with characterization data and the corresponding dipeptide ester from which they were prepared.

TABLE E2

Characterization data for dipeptide acids intermediates.

| Dipeptide Acid | Formula/Name | ¹H NMR (ppm; 500 MHz, d₆-DMSO; or 400 MHz, CDCl3*) | m/z [M + 1]⁺ | Dipeptide ester |
|---|---|---|---|---|
| DA-101 | ((Benzyloxy)carbonyl)-L-valyl-L-proline (DA-101) | — | 389.4 | DE-101 |
| DA-102 | ((S)-2-(((Benzyloxy)carbonyl)amino)-2-cyclohexylacetyl)-L-proline | — | 389.4 | DE-102 |
| DA-103 | ((S)-2-(((Benzyloxy)carbonyl)amino)-3,3-dimethylbutanoyl)-L-proline | — | 363.5 | DE-103 |
| DA-104 | ((S)-2-(((Benzyloxy)carbonyl)amino)-2-phenylacetyl)-L-proline | — | 383.4 | DE-104 |

TABLE E2-continued

| | | | | |
|---|---|---|---|---|
| DA-105 | 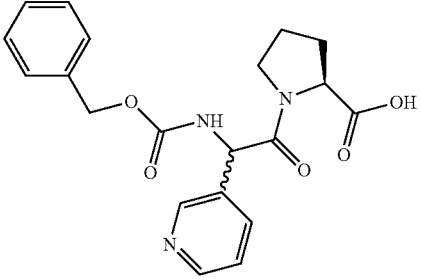<br>(2-(((Benzyloxy)carbonyl)amino)-2-<br>(pyridin-3-yl)acetyl)-L-proline | — | 398.2 | DE-105 |
| DA-107 | 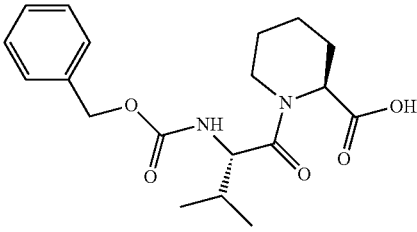<br>(S)-1-(((Benzyloxy)carbonyl)-L-<br>valyl)piperidine-2-carboxylic acid | — | 363.3 | DE-107 |
| DA-108 | 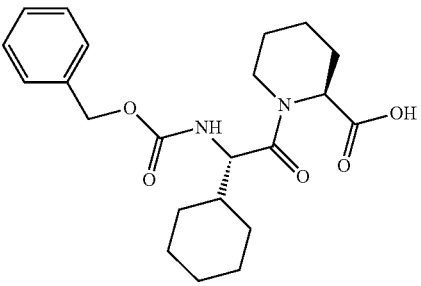<br>(S)-1-((S)-<br>(((Benzyloxy)carbonyl)amino)-2-<br>cyclohexylacetyl)piperidine-2-<br>carboxylic acid | — | 403.8 | DE-108 |
| DA-109 | 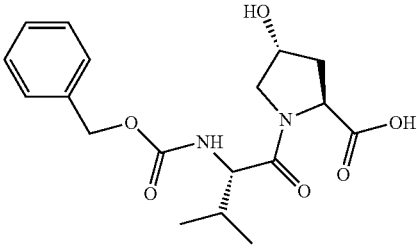<br>(2S,4R)-2-(((Benzyloxy)carbonyl)-L-<br>valyl)-4-hydroxypyrrolidine-2-<br>carboxylic acid | 12.29 (br s, 1H), 7.47 (d, 1H), 7.35 (m, 5H), 5.04 (d, 1H), 4.98 (d, 1H), 4.29 (m, 2H), 4.01 (m, 2H), 3.30 (m, 1H), 2.31 (m, 1H), 1.94 (m, 1H), 1.80 (m, 1H), 0.95 (d, 3H), 0.89 (d, 3H) | 365.8 | DE-109 |

TABLE E2-continued

| | | | | |
|---|---|---|---|---|
| DA-110 | 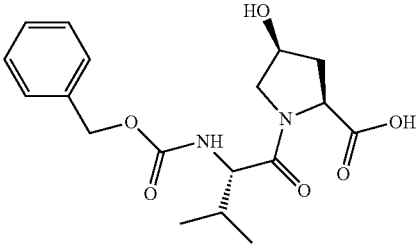<br>(2S,4S)-1-(((Benzyloxy)carbonyl)-L-valyl)-4-hydroxypyrrolidine-2-carboxylic acid | 12.37 (br s, 1H), 7.39 (d, 1H), 7.35 (m, 5H), 5.17 (d, 1H), 5.05 (d, 1H), 4.99 (d, 1H), 4.34 (m, 1H), 4.26 (m, 1H), 4.07 (m, 1H), 3.65 (m, 2H), 2.10 (m, 1H), 1.95 (d, 2H), 0.92 (d, 3H), 087 (d, 3H) | 365.3 | DE-1110 |
| DA-111 | 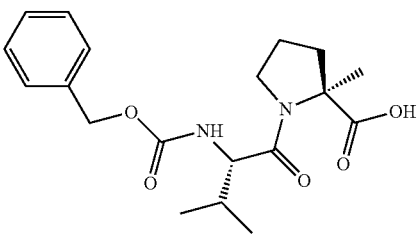<br>(S)-1-(((Benzyloxy)carbonyl)-L-valyl)-2-methylpyrrolidine-2-carboxylic acid | 12.20 (br s, 1H), 7.42 (d, 1H), 7.32 (m, 5H), 5.02 (s, 2H), 3.99 (m, 1H), 4.86 (m, 1H), 3.601 (m, 1H), 2.02 (m, 1H), 1.94 (m, 3H), 1.81 (m, 1H), 1.37 (s, 3H), 0.90 (d, 3H), 0.87 (d, 3H) | 363.1 | DE-111 |
| DA-112 | 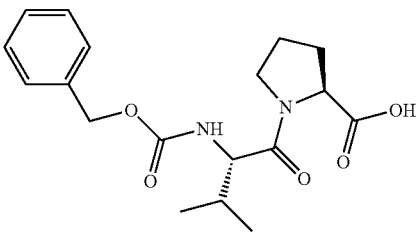<br>N-((Benzyloxy)carbonyl)-N-methyl-L-valyl-L-proline | — | 363.5 | DE-112 |
| DA-113 | 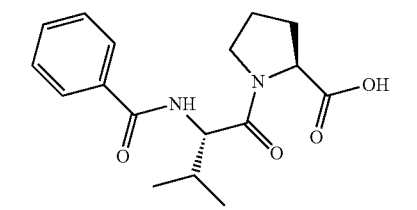<br>Benzoyl-L-valyl-L-proline | — | 319.3 | DE-113 |
| DA-114 | 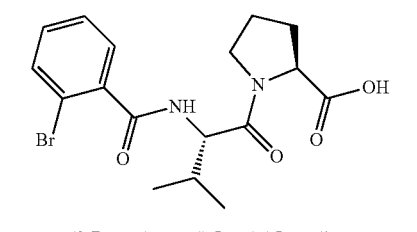<br>(2-Bromobenzoyl)-L-valyl-L-proline | — | 397.3 | DE-114 |

TABLE E2-continued

| | | | | |
|---|---|---|---|---|
| DA-115 | (3-Bromobenzoyl)-L-valyl-L-proline | — | 399.3 | DE-115 |
| DA-116 | (4-Bromobenzoyl)-L-valyl-L-proline | — | 397.3 | DE-116 |
| DA-117 | (2-Phenylacetyl)-L-valyl-L-proline | — | 333.3 | DE-117 |
| DA-118 | (2-(3-Bromophenyl)acetyl)-L-valyl-L-proline | — | 411.3 | DE-118 |
| DA-119 | (3-Phenylpropanoyl)-L-valyl-L-proline | — | 347.4 | DE-119 |
| DA-120 | (Cyclohexanecarbonyl)-L-valyl-L-proline | — | 325.4 | DE-120 |

TABLE E2-continued

| | | | | |
|---|---|---|---|---|
| DA-121 | (2-Methoxybenzoyl)-L-valyl-L-proline | — | 349.3 | DE-121 |
| DA-122 | (3-Methoxybenzoyl)-L-valyl-L-proline | — | 349.5 | DE-122 |
| DA-123 | (4-Methoxybenzoyl)-L-valyl-L-proline | — | 349.3 | DE-123 |
| DA-124 | (1-Methyl-1H-pyrazole-4-carbonyl)-L-valyl-L-proline | 8.21 (s, 1H), 8.14 (d, 1H), 7.91 (s, 1H), 4.42 (m, 1H), 4.24 (m, 1H), 3.92 (m, 1H), 3.84 (s, 3H), 3.63 (m, 1H), 2.15 (m, 1H), 2.10 (m, 1H), 1.91 (m, 2H), 1.86 (m, 1H), 0.97 (d, 3H), 0.92 (d, 3H) | 323.7 | DE-124 |
| DA-125 | (2-Methylthiazole-4-carbonyl)-L-valyl-L-proline | 12.50 (br s, 1H), 8.14 (s, 1H), 7.89 (d, 1H), 4.62 (m, 1H), 4.27 (m, 1H), 3.78 (m, 1H), 3.64 (m, 1H), 2.71 (s, 3H), 2.21 (m, 1H), 2.11 (m, 1H), 1.93 (m, 2H), 1.84 (m, 1H), 0.99 (d, 3H), 0.89 (d, 3H) | 340.3 | DE-125 |

TABLE E2-continued

| | | | | |
|---|---|---|---|---|
| DA-126 | 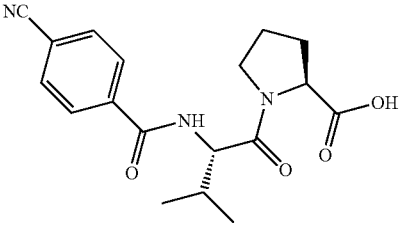<br>(4-Cyanobenzoyl)-L-valyl-L-proline | 12.44 (br s, 1H), 8.86 (d, 1H), 8.04 (d, 2H), 7.95 (d, 2H), 4.47 (m, 1H), 4.25 (m, 1H), 3.95 (m, 1H), 3.67 (m, 1H), 2.17 (m, 2H), 1.95 (m, 2H), 1.86 (m, 1H), 1.02 (d, 3H), 0.97 (d, 3H) | 344.4 | DE-126 |
| DA-127 | 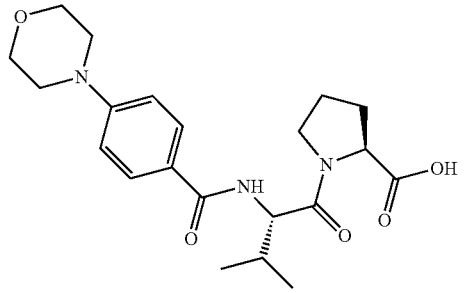<br>(4-Morpholinobenzoyl)-L-valyl-L-proline | 12.25 (br s, 1H), 8.20 (d, 1H), 7.82 (d, 2H), 6.95 (d, 2H), 4.45 (m, 1H), 4.25 (m, 1H), 3.96 (m, 1H), 3.73 (m, 4H), 3.64 (m, 1H), 3.21 (m, 4H), 2.14 (m, 2H), 1.92 (m, 2H), 1.84 (m, 1H), 0.99 (d, 3H), 0.94 (d, 3H) | 404.2 | DE-127 |
| DA-128 | 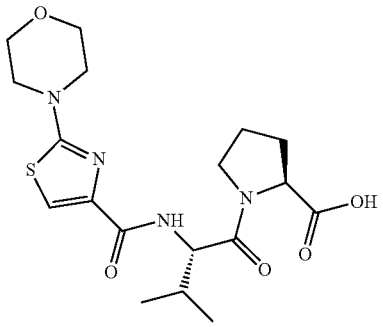<br>(2-Morpholinothiazole-4-carbonyl)-L-valyl-L-proline | 12.26 (br s, 1H), 7.77 (d, 1H), 7.49 (s, 1H), 4.57 (m, 1H), 4.26 (m, 1H), 3.80 (m, 1H), 3.72 (m, 4H), 3.63 (m, 1H), 3.43 (m, 4H), 2.18 (m, 1H), 2.09 (m, 1H), 1.93 (s, 2H), 1.84 (m, 1H), 0.97 (d, 3H), 0.87 (d, 3H) | 411.5 | DE-128 |
| DA-129 | 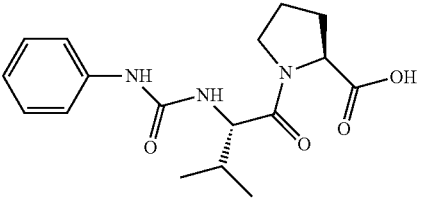<br>(Phenylcarbamoyl)-L-valyl-L-proline | 12.13 (br s, 1H), 8.63 (s, 1H), 7.36 (d, 2H), 7.21 (m, 2H), 6.89 (m, 1H), 6.40 (d, 1H), 4.33 (m, 1H), 4.27 (m, 1H), 3.76 (m, 1H), 3.60 (m, 1H), 2.18 (m, 1H), 1.91 (m, 3H), 1.84 (m, 1H), 0.96 (d, 3H), 0.90 (d, 3H) | 334.6 | DE-129 |
| DA-130 | 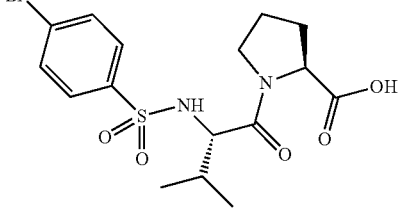<br>((4-Bromophenyl)sulfonyl)-L-valyl-L-proline | — | 434.5 | DE-130 |

TABLE E2-continued
| | | | | |
|---|---|---|---|---|
| DA-131 | 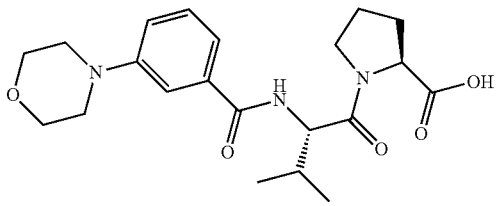 (3-Morpholinobenzoyl)-L-valyl-L-proline | — | 404.6 | DE-131 |
| DA-132 | 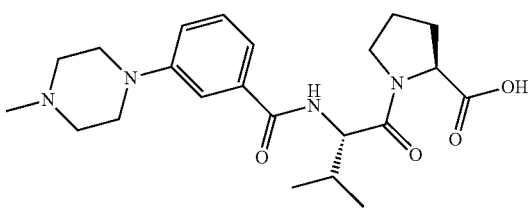 (3-(4-Methylpiperazine-1-yl)benzoyl)-L-valyl-L-proline | — | 417.5 | DE-132 |
| DA-133 | 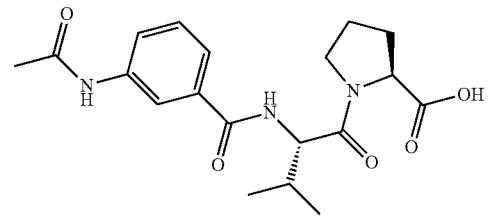 (3-Acetamidobenzoyl)-L-valyl-L-proline | — | 376.6 | DE-133 |
| DA-134 | 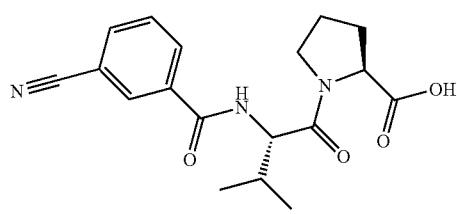 (3-Cyanobenzoyl)-L-valyl-L-proline | — | — | DE-134 |
| DA-135 | 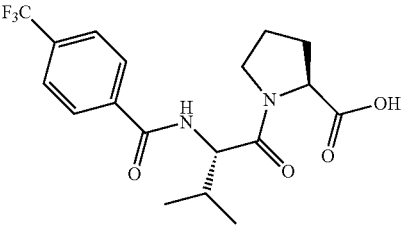 (4-(Trifluoromethyl)benzoyl)-L-valyl-L-proline | — | 387.5 | DE-135 |

TABLE E2-continued
| | | | | |
|---|---|---|---|---|
| DA-136 | 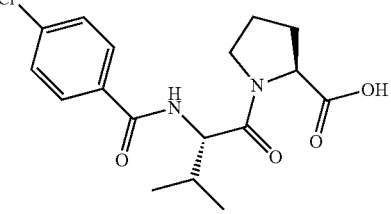 (4-Chlorobenzoyl)-L-valyl-L-proline | — | 353.5 | DE-136 |
| DA-137 | 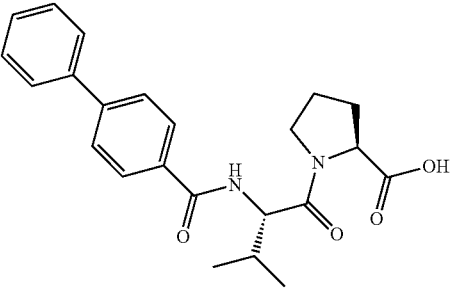 ([1,1'-Biphenyl]-4-carbonyl)-L-valyl-L-proline | — | 395.6 | DE-137 |
| DA-138 | 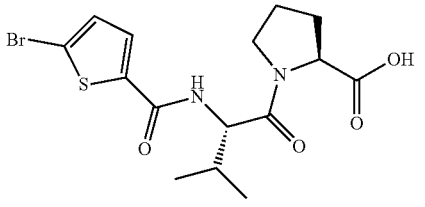 (5-Bromothiophene-2-carbonyl)-L-valyl-L-proline | — | 405.3 | DE-138 |
| DA-139 | 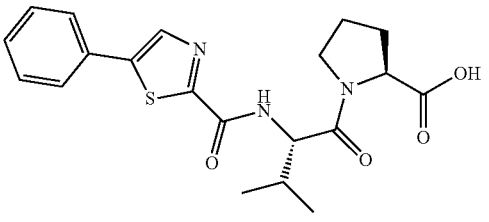 (5-Phenylthiazole-2-carbonyl)-L-valyl-L-proline | — | 402.5 | DE-139 |
| DA-140 | 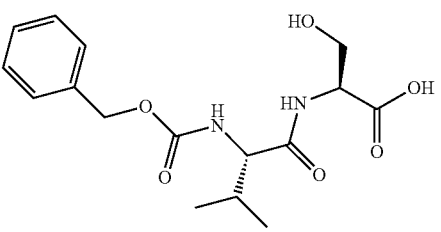 ((Benzyloxy)carbonyl)-L-valyl-L-serine | — | 339.5 | DE-140 |

TABLE E2-continued
| | | | | |
|---|---|---|---|---|
| DA-142 | 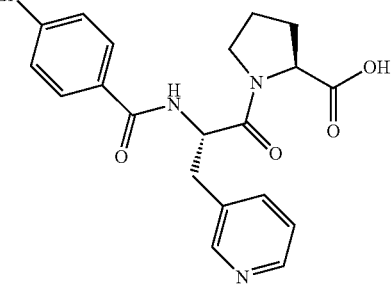 ((S)-2-(4Bromobenzamido)-3-(pyridin-3-yl)propanoyl)-L-proline | — | 447.6 | DE-142 |
| DA-143 | 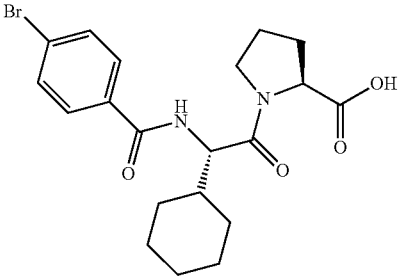 ((S)-2-(4-Bromobenzamido)-2-cyclohexylacetyl)-L-proline | — | 439.8 | DE-143 |
| DA-144 | 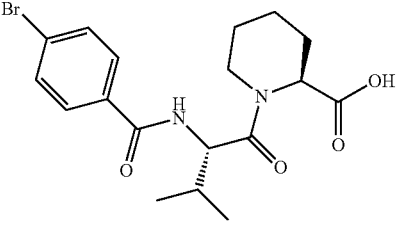 (S)-1-((4-Bromobenzoyl)-L-valyl)piperidine-2-carboxylic acid | — | 413.5 | DE-144 |
| DA-145 | 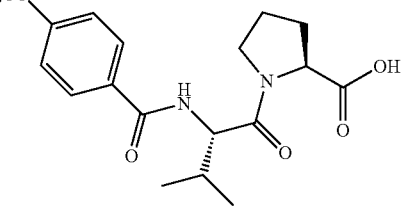 (4-(Trifluoromethoxy)benzoyl)-L-valyl-L-proline | — | 403.6 | DE-145 |
| DA-146 | 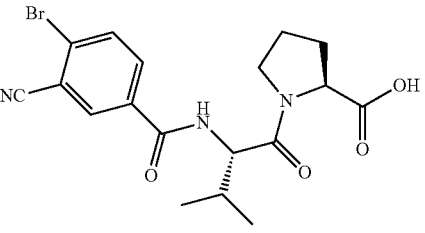 (4-Bromo-3-cyanobenzoyl)-L-valyl-L-proline | — | 424.2 | DE-146 |

TABLE E2-continued
| | | | | |
|---|---|---|---|---|
| DA-147 | 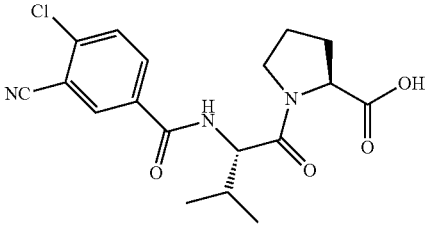 (4-Chloro-3-cyanobenzoyl)-L-valyl-L-proline | — | 378.8 | DE-147 |
| DA-148 | 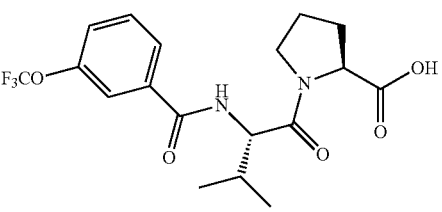 (3-(Triflouromethoxy)benzoyl(-L-valyl-L-proline | — | 403.6 | DE-148 |
| DA-149 | 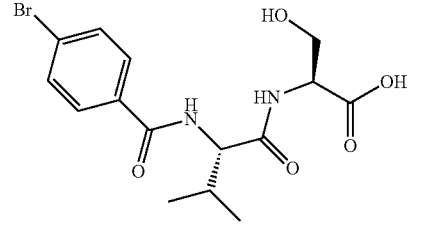 (4-Bromobenzoyl)-L-valyl-L-serine | — | 389.4 | DE-149 |
| DA-151 | 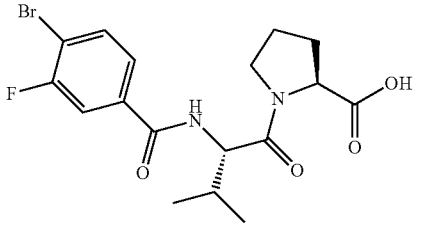 (4-Bromo-3-fluorobenzoyl)-L-valyl-L-proline | — | 417.4 | DE-151 |
| DA-152 | 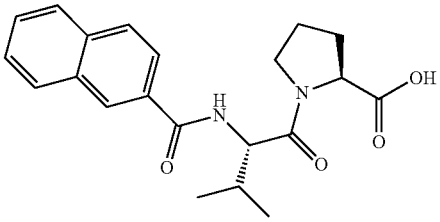 (2-Naphthoyl)-L-valyl-L-proline | — | 369.6 | DE-152 |

TABLE E2-continued

| | | | | |
|---|---|---|---|---|
| DA-153 | (1-Naphthoyl)-L-valyl-L-proline | — | 369.8 | DE-153 |
| DA-154 | Cinnamoyl-L-valyl-L-proline | — | 345.7 | DE-154 |
| DA-155 | (Quinoline-2-carbonyl)-L-valyl-L-proline | — | 370.4 | DE-155 |
| DA-156 | (Quinoline-3-carbonyl)-L-valyl-L-proline | — | 370.8 | DE-156 |
| DA-157 | (Isoquinoline-6-carbonyl)-L-valyl-L-proline | — | 370.6 | DE-157 |

TABLE E2-continued

| | | | | |
|---|---|---|---|---|
| DA-158 | 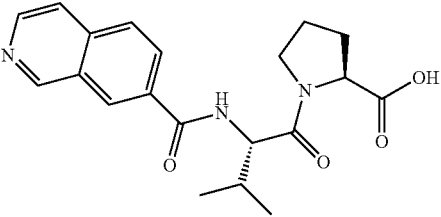<br>(Isoquinoline-7-carbonyl)-L-valyl-L-proline | — | 370.9 | DE-158 |
| DA-159 | 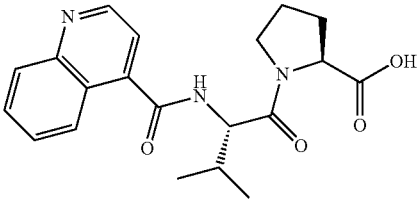<br>(Quinoline-4-carbonyl)-L-valyl-L-proline | — | 370.6 | DE-159 |
| DA-160 | 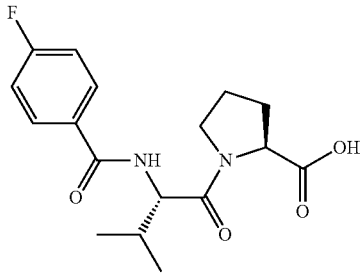<br>(4-Fluorobenzoyl)-L-valyl-L-proline | (400 MHz, CDCl$_3$): 7.84 (m, 2H), 7.22 (d, 1H), 7.10 (m, 2H), 4.82 (m, 1H), 4.57 (m, 1H), 3.99 (m, 1H), 3.75 (m, 1H), 2.19 (m, 3H), 2.07 (m, 2H), 1.07 (d, 3H), 1.02 (d, 3H) * | 337.41 | DE-160 |
| DA-162 | 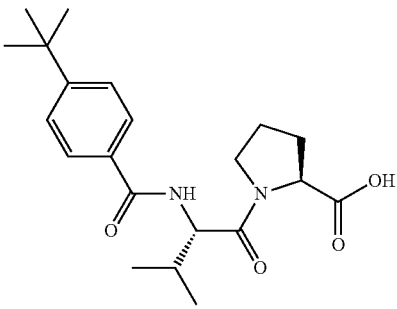<br>(4-(tert-Butyl)benzoyl)-L-valyl-L-proline | (400 MHz, CDCl$_3$): 7.77 (d, 2H), 7.44 (d, 2H), 7.25 (d, 1H), 4.83 (m, 1H), 4.57 (m, 1H), 4.01 (m, 1H), 3.75 (m, 1H), 2.17 (m, 3H), 2.05 (m, 2H), 1.34 (s, 9H), 1.07 (d, 3H), 1.00 (d, 3H) * | 373.32 | DE-162 |
| DA-163 | 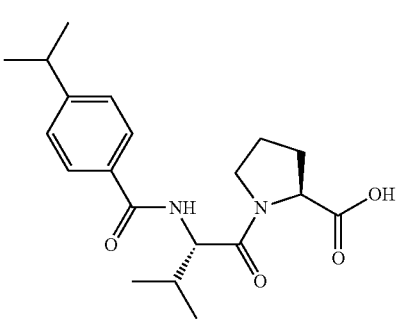<br>(4-Isoprpylbenzoyl)-L-valyl-L-proline | (400 MHz, CDCl$_3$): 7.75 (d, 2H), 7.28 (d, 2H), 6.99 (d, 1H), 4.43 (m, 1H), 4.58 (m, 1H), 3.97 (m, 1H), 3.74 (m, 1H), 2.94 (m, 1H), 2.22 (m, 3H), 2.07 (m, 2H), 1.26 (d, 6H), 1.06 (d, 3H), 1.02 (d, 3H) * | 361.46 | DE-163 |

TABLE E2-continued

| | | | | |
|---|---|---|---|---|
| DA-164 | 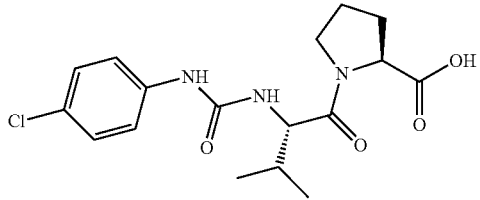<br>((4-Chlorophenyl)carbamoyl)-L-valyl-L-proline | (400 MHz, CDCl$_3$): 9.37 (br, 1H), 7.69 (s, 1H), 7.22 (d, 2H), 7.14 (d, 2H), 6.70 (d, 1H), 4.52 (m, 1H), 4.45 (m, 1H), 3.95 (m, 1H), 3.68 (m, 1H), 2.20 (m, 1H), 2.01 (m, 4H), 1.01 (d, 3H), 0.93 (d, 3H) * | — | DE-164 |
| DA-165 | 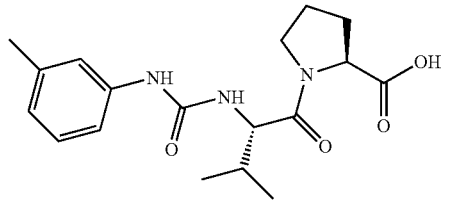<br>((3-Chlorophenyl)carbamoyl)-L-valyl-L-proline | (400 MHz, CDCl$_3$): 7.65 (br, 1H), 7.43 (br, 1H), 7.10 (m, 2H), 6.91 (m, 1H), 6.67 (m, 1H), 4.54 (m, 1H), 4.48 (m, 1H), 3.95 (m, 1H), 3.70 (m, 1H), 2.22 (m, 1H), 2.04 (m, 4H), 1.02 (d, 3H), 0.94 (d, 3H) * | — | DE-165 |
| DA-167 | 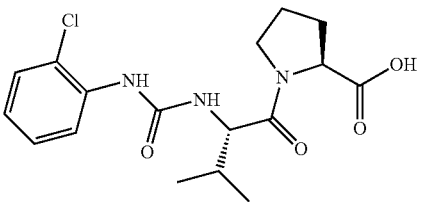<br>((2-Chlorophenyl)carbamoyl)-L-valyl-L-proline | (400 MHz, CDCl$_3$): 8.06 (d, 1H), 7.41 (s, 1H), 7.24 (d, 2H), 7.15 (m, 1H), 6.89 (m, 1H), 4.59 (m, 1H), 4.53 (m, 1H), 3.92 (m, 1H), 3.71 (m, 1H), 2.17 (m, 1H), 2.03 (m, 4H), 1.02 (d, 3H), 0.95 (d, 3H) * | — | DE-167 |
| DA-168 | 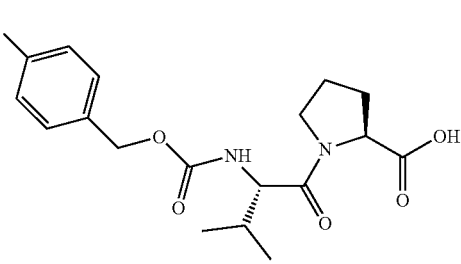<br>(((4-Chlorobenzyl)oxy)carbonyl)-L-valyl-L-proline | (400 MHz, CDCl$_3$): 7.30 (m, 4H), 5.66 (d, 1H), 5.05 (s, 2H), 4.59 (m, 1H), 4.33 (m, 1H), 3.82 (m, 1H), 3.68 (m, 1H), 2.22 (m, 1H), 2.06 (m, 4H), 1.01 (d, 3H), 0.95 (d, 3H) * | 383.52 | DE-168 |
| DA-169 | 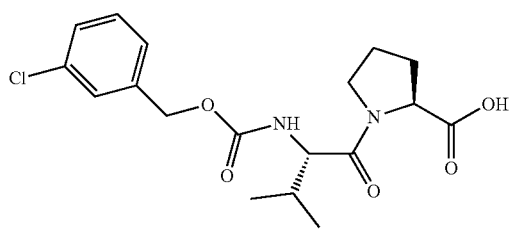<br>(((3-Chlorobenzyl)oxy)carbonyl)-L-valyl-L-proline | (400 MHz, CDCl$_3$): 7.26 (m, 4H), 5.77 (d, 1H), 5.07 (s, 2H), 4.59 (m, 1H), 4.33 (m, 1H), 3.84 (m, 1H), 3.67 (m, 1H), 2.20 (m, 2H), 2.04 (m, 3H), 0.96 (d, 3H), 0.91 (d, 3H) * | 383.52 | DE-169 |

| | | | | |
|---|---|---|---|---|
| DA-170 | (((2-Chlorobenzyl)oxy)carbonyl)-L-valyl-L-proline | (400 MHz, CDCl$_3$): 7.41 (m, 2H), 7.28 (m, 2H), 5.71 (d, 1H), 5.52 (d, 1H), 5.18 (d, 1H), 4.59 (m, 1H), 4.34 (m, 1H), 3.81 (m, 1H), 3.67 (m, 1H), 2.19 (m, 2H), 2.07 (m, 3H), 1.02 (d, 3H), 0.96 (d, 3H) * | 383.53 | DE-170 |
| DA-171 | (2S,4R)-1-((4-Bromobenzoyl)-L-valyl)-4-hydroxypyrrolidene-2-carboxylic acid | 12.47 (br, 1H), 8.64 (d, 1H), 7.85 (d, 2H), 7.67 (d, 2H), 5.19 (br, 1H), 4.49 (m, 1H), 4.36 (m, 1H), 4.26 (m, 1H), 3.81 (m, 1H), 3.73 (m, 1H), 2.14 (m, 2H), 1.89 (m, 1H), 0.98 (d, 3H), 0.93 (d, 3H) * | 413.31 | DE-171 |
| DA-172 | (2S,4R)-1-((S)-2-(4-Bromobenzamido)-2-cyclohexylacetyl)-4-hydroxypyrrolidine-2-carboxylic acid | 12.44 (br, 1H), 8.60 (d, 1H), 7.84 (d, 2H), 7.67 (d, 2H), 5.17 (br, 1H), 4.53 (m, 1H), 4.35 (m, 1H), 4.25 (m, 1H), 3.80 (m, 1H), 3.72 (m, 1H), 2.08 (m, 1H), 1.83 (m, 4H), 1.64 (m, 3H), 1.15 (m, 3H), 0.99 (d, 3H) * | 453.32 | DE-172 |
| DA-173 | ((S)-2-(4-Bromobenzamido)-2-cyclohexylacetyl)-L-serine | 12.52 (br, 1H), 8.40 (d, 1H), 8.20 (d, 1H), 7.82 (d, 2H), 7.67 (d, 2H), 4.95 (br, 1H), 4.43 (m, 1H), 4.26 (m, 1H), 3.69 (m, 2H), 1.54-1.83 (m, 6H), 0.96-1.23 (m, 5H) * | 429.32 | DE-173 |

TABLE E2-continued
| DA-174 | 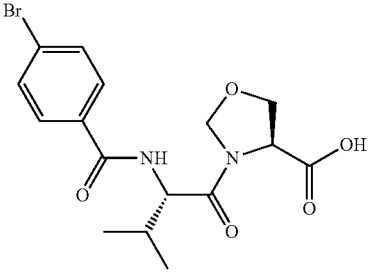<br>(S)-3-((4-Bromobenzoyl)-L-valyl)oxazolidine-4-carboxylic acid | 12.86 (br, 1H), 8.22 (d, 1H), 7.86 (d, 2H), 7.68 (d, 2H), 5.49 (d, 1H), 5.11 (d, 1H), 4.45 (dd, 1H), 4.26 (dd, 1H), 4.11 (dd, 1H), 3.98 (dd, 1H), 2.21-2.12 (m, 1H), 1.02 (d, 3H), 0.98 (d, 3H) * | 400.29 | DE-174 |
|---|---|---|---|---|
| DA-175 | 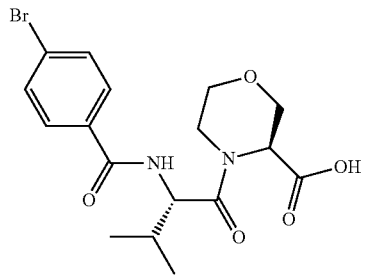<br>(S)-4-((4-Bromobenzoyl)-L-valyl)morpholine-3-carboxylic acid | — | 414.65 | DE-175 |
| DA-176 | 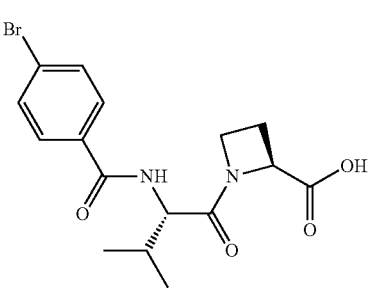<br>(S)-1-((4-Bromobenzoyl)-L-valyl)azetidine-2-carboxylic acid | 12.52 (br, 1H), 8.69 (d, 1H), 7.86 (d, 2H), 7.67 (d, 2H), 4.56 (dd, 1H), 4.39 (m, 1H), 4.26 (m, 1H), 4.13 (m, 1H), 2.58 (m, 1H), 2.13 (m, 2H), 1.01 (d, 3H), 0.96 (d, 3H) * | 383.59 | DE-176 |
| DA-177 | 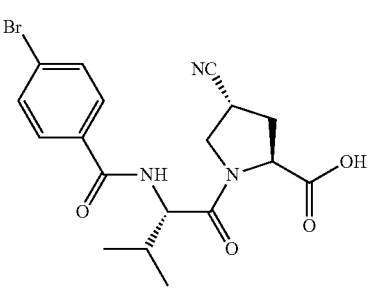<br>(2S,4R)-1-((4-Bromobenzoyl)-L-valyl)-4-cyanopyrrolidine-2-carboxylic acid | — | 422.61 | DE-177 |

TABLE E2-continued
| | | | | |
|---|---|---|---|---|
| DA-178 | 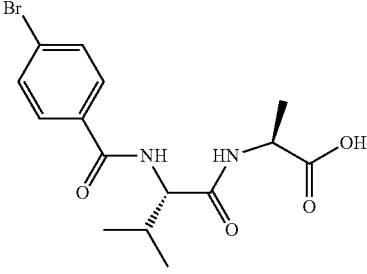<br>(4-Bromobenzoyl)-L-valyl-L-alanine | 12.45 (br, 1H), 8.33 (dd, 2H), 7.83 (d, 2H), 7.67 (d, 2H). 4.33 (m, 1H), 4.18 (m, 1H), 2.11 (m, 1H), 1.28 (d, 3H), 0.96 (d, 3H), 0.91 (d, 3H) * | 371.52 | DE-178 |
| DA-179 | 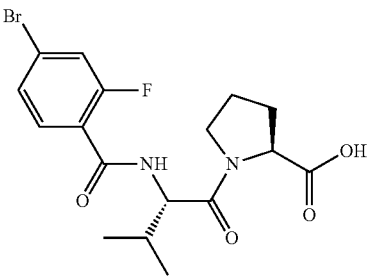<br>(4-Bromo-2-fluorobenzoyl)-L-valyl-L-proline | 12.44 (br s, 1H), 8.47 (d, 1H), 7.64 (d, 1H), 7.51 (m, 2H), 4.52 (m, 1H), 4.26 (dd, 1H), 3.84 (m, 1H), 3.63 (m, 1H), 2.18 (m, 1H), 2.08 (m, 1H), 1.93 (m, 2H), 1.84 (m, 1H), 0.99 (d, 3H), 0.94 (d, 3H) * | 415.5 | DE-179 |
| DA-180 | 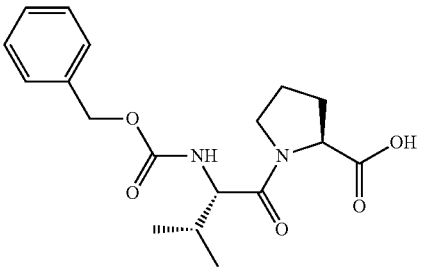<br>((Benzyloxy)carbonyl)-L-isoleucyl-L-proline | 12.42 (br s, 1H), 7.51 (d, 1H), 7.34 (m, 5H), 5.03 (d, 1H), 4.98 (d, 1H), 4.24 (m, 1H), 4.09 (t, 1H), 3.79 (m, 1H), 3.60 (m, 1H), 2.14 (m, 1H), 1.87 (m, 3H), 1.74 (m, 1H), 1.51 (m, 1H), 1.11 (m, 1H), 0.89 (d, 3H), 0.81 (t, 3H) * | 363 | DE-180 |
| DA-181 | 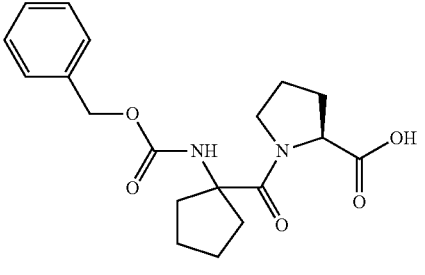<br>(1-(((Benzyloxy)carbonyl)amino)cyclopentane-1-carbonyl)-L-proline | — | 361.3 | DE-181 |

TABLE E2-continued

| | | | | |
|---|---|---|---|---|
| DA-182 | ((Benzyloxy)carbonyl)-L-phenylalanyl-L-proline | 12.50 (br s, 1H), 7.65 (d, 1H), 7.26 (m, 10H), 4.93 (s, 2H), 4.41 (m, 1H), 4.27 (dd, 1H), 3.68 (m, 1H), 3.56 (m, 1H), 2.93 (m, 1H), 2.77 (m, 1H), 2.15 (m, 1H), 1.93 (m, 2H), 1.85 (m, 1H) * | 396.9 | DE-182 |
| DA-183 | (4-Bromo-2-methylbenzoyl)-L-valyl-L-proline | 12.43 (br s, 1H), 8.48 (d, 1H), 7.51 (m, 2H), 7.20 (d, 1H), 4.45 (t, 1H), 4.26 (dd, 1H), 3.89 (m, 1H), 3.63 (m, 1H), 2.29 (s, 3H), 2.17 (m, 1H), 2.07 (m, 1H), 1.94 (m, 2H), 1.85 (m, 1H), 0.99 (d, 3H), 0.95 (d, 3H) * | 411.4 | DE-183 |
| DA-184 | ((Benzyloxy)carbonyl)-L-leucyl-L-proline | 12.42 (br s, 1H), 7.50 (d, 1H), 7.34 (m, 5H), 5.00 (s, 2H), 4.28 (m, 2H), 3.68 (m, 1H), 3.50 (m, 1H), 2.13 (m, 1H), 1.93 (m, 2H), 1.83 (m, 1H), 1.67 (m, 1H), 1.47 (m, 1H), 1.37 (m, 1H), 0.89 (d, 6H) * | 363 | DE-184 |
| DA-185 | (4-Bromobenzoyl)-L-leucyl-L-proline | 12.42 (br s, 1H), 8.68 (d, 1H), 7.84 (d, 2H), 7.67 (d, 2H), 4.74 (m, 1H), 4.26 (m, 1H), 3.78 (m, 1H), 3.56 (m, 1H), 2.16 (m, 1H), 1.93 (m, 2H), 1.83 (m, 1H), 1.71 (m, 2H), 1.47 (m, 1H), 0.91 (m, 6H) * | 411.4 | DE-185 |

TABLE E2-continued

| | | | | |
|---|---|---|---|---|
| DA-186 | 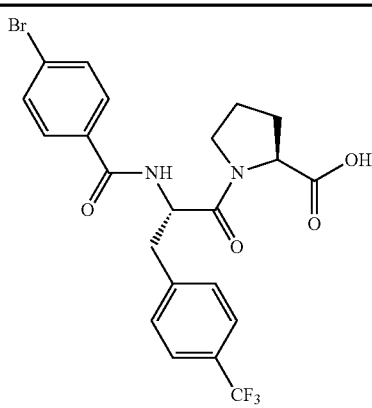<br>((S)-2-(4-Bromobenzamido)-3-(4-trifluoromethyl)phenyl)propanoyl)-L-proline | — | 513.5 | DE-186 |

Dipeptide esters DE-102-DE-105, DE-A1, and DE-A2 were prepared in a similar manner to methyl ((benzyloxy)carbonyl)-L-valyl-L-prolinate (DE-101) from the corresponding acid and methyl L-prolinate. Dipeptide esters DE-107 and DE-108 were prepared from the corresponding acid and methyl (S)-piperidine-2-carboxylate. Dipeptide esters DE-109-DE-111 and DE-140 were prepared from ((benzyloxy)carbonyl)-L-valine and the corresponding proline and serine esters. Dipeptide esters DE-113, DE-115 to DE-139, DE-145 to DE-148, and DE-151 to DE-159 were prepared in a similar manner to methyl (2-bromobenzoyl)-L-valyl-L-prolinate (DE-114) from methyl L-valyl-L-prolinate and the corresponding acid, acid chloride, isocyanate, or sulfonyl chloride. Dipeptide esters DE-142 to DE-144 and DE-149 were prepared from 4-bromobenzoyl chloride and the corresponding esters. Dipeptide esters DE-160, DE-162, DE-163 and DE-171 to DE-186 were prepared in a similar manner to DE-101 or DE-114 from the corresponding amine ester and acid or acid chloride in Table E3.

Dipeptide esters used as intermediates are summarized in Table E3 with characterization data and corresponding starting materials.

TABLE E3

Characterization data for dipeptide ester intermediates.

| Dipeptide Ester | Formula/Name | (ppm; 400 MHz, d$_6$-DMSO) | m/z [M + 1]$^+$ | Starting materials |
|---|---|---|---|---|
| DE-102 | Methyl ((S)-2-(((benzyloxy)carbonyl)amino)-2-cyclohexylacetyl)-L-prolinate | 7.45 (d, 1H), 7.34 (m, 5H), 5.04 (d, 1H), 4.98 (d, 1H), 4.32 (dd, 1H), 4.10 (t, 1H), 3.80 (m, 1H), 3.60 (s, 3H), 3.58 (m, 1H), 2.17 (m, 1H), 1.90 (m, 2H), 1.82 (m, 1H), 1.75 (m, 2H), 1.63 (m, 4H), 1.13 (m, 2H), 0.99 (m, 2H) | 403.5 | (S)-2-(((Benzyloxy)carbonyl)amino)-2-cyclohexylacetic) acid |

TABLE E3-continued

Characterization data for dipeptide ester intermediates.

| Dipeptide Ester | Formula/Name | (ppm; 400 MHz, d$_6$-DMSO) | m/z [M + 1]$^+$ | Starting materials |
|---|---|---|---|---|
| DE-103 | 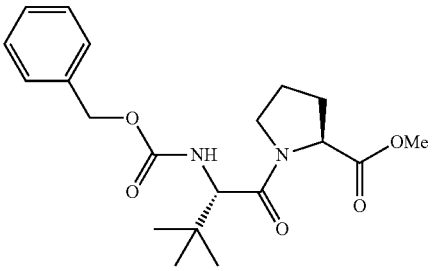<br>Methyl ((S)-2-(((benzyloxy)carbonyl)amino)-3,3-dimethylbutanoyl)-L-prolinate | 7.36 (m, 6H), 5.05 (d, 1H), 4.99 (d, 1H), 4.33 (m, 1H), 4.23 (m, 1H), 3.76 (m, 1H), 3.63 (m, 1H), 3.61 (s, 3H), 2.18 (m, 1H), 1.91 (m, 2H), 1.81 (m, 1H), 0.97 (s, 9H) | 377.4 | 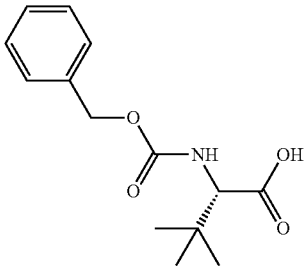<br>Dicyclohexylamine (S)-2-(((benzyloxy)carbonyl)amino)-3,3-dimethylbutanoate |
| DE-104 | 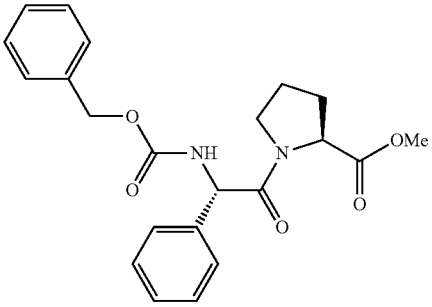<br>Methyl ((S)-2-(((benzyloxy)carbonyl)amino)-2-phenylacetyl)-L-prolinate | — | 397.4 | 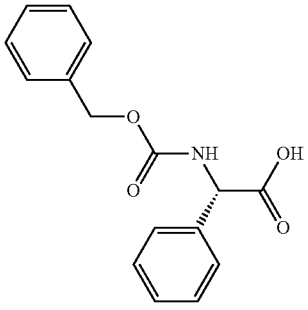<br>(S)-2-((Benzyloxy)carbonyl)amino)-2-phenylacetic acid |
| DE-105 | 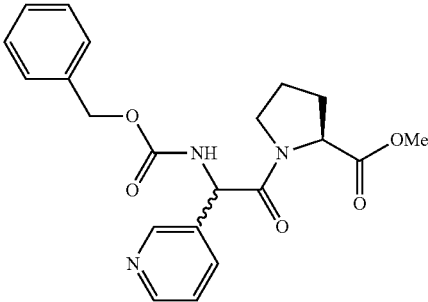<br>Methyl (2-(((benzyloxy)carbonyl)amino)-2-pyridin-3-yl)acetyl-L-prolinate | — | 384.5 | 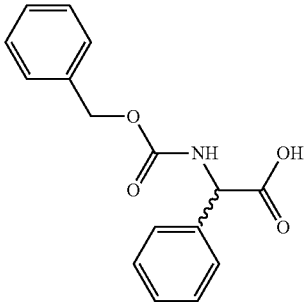<br>2-(((Benzyloxy)carbonyl)amino)-2-(pyridin-3-yl)acetic acid |

TABLE E3-continued

Characterization data for dipeptide ester intermediates.

| Dipeptide Ester | Formula/Name | (ppm; 400 MHz, d₆-DMSO) | m/z [M + 1]⁺ | Starting materials |
|---|---|---|---|---|
| DE-107 | Methyl (S)-1-(((benzyloxy)carbonyl)-L-valyl)piperdine-2-carboxylate | — | 377.3 | ((Benzyloxy)carbonyl)-L-valine |
| DE-108 | Methyl (S)-1-((S)-2-(((benzyloxy)carbonyl)amino-2-cyclohexylacetyl)piperidine-2-carboxylate | — | 417.4 | (S)-2-((((Benzyloxy)carbonyl)amino)-2-cyclohexylacetic acid |
| DE-109 | Methyl (2S,4R)-1-(((benzyloxy)carbonyl)-L-valyl)-4-hydroxypyrrolidine-2-carboxylate | — | 379.3 | Methyl (2S,4R)-4-hydroxypyrrolidine-2-carboxylate |

TABLE E3-continued

Characterization data for dipeptide ester intermediates.

| Di-pep-tide Ester | Formula/Name | (ppm; 400 MHz, d$_6$-DMSO) | m/z [M + 1]$^+$ | Starting materials |
|---|---|---|---|---|
| DE-110 | 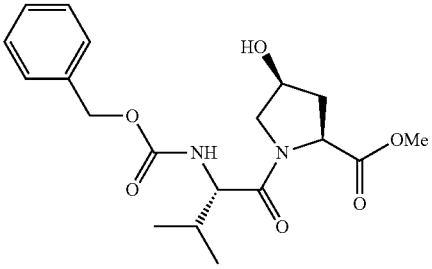<br>Methyl (2S,4R)-1-(((benzyloxy)carbonyl)-L-valyl)-4-hydroxypyrrolidine-2-carboxylate | — | 379.6 | 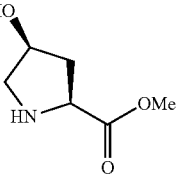<br>Methyl (2S,4R)-4-hydroxypyrrolidine-2-carboxylate |
| DE-111 | 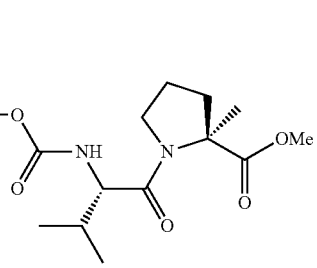<br>Methyl (S)-1-(((benzyloxy)carbonyl)-L-valyl)-2-methylpyrrolidine-2-carboxylate | — | 377.3 | 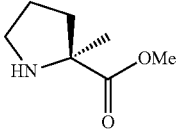<br>Methyl (S)-2-methylpyrrolidine-2-carboxylate |
| DE-112 | 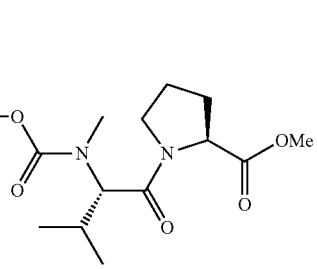<br>Methyl N-((benzyloxy)carbonyl)-N-methyl-L-valyl-L-prolinate | — | 377.3 | — |
| DE-113 | 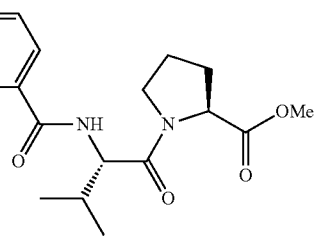<br>Methyl benzoyl-L-valyl-L-prolinate | — | 333.4 | Benzoic acid |

TABLE E3-continued

Characterization data for dipeptide ester intermediates.

| Dipeptide Ester | Formula/Name | ¹H NMR (ppm; 400 MHz, d₆-DMSO) | m/z [M + 1]⁺ | Starting materials |
|---|---|---|---|---|
| DE-114 | 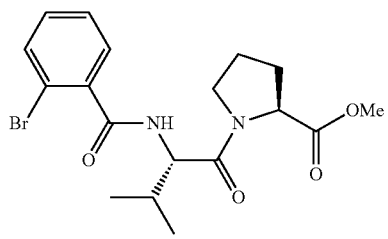<br>Methyl (2-bromobenzoyl)-L-valyl-L-prolinate | 8.65 (d, 1H), 7.63 (dd, 1H), 7.41 (m, 1H), 7.34 (dd, 1H), 7.30 (m, 1H), 4.48 (t, 1H), 4.34 (m, 1H), 3.94 (m, 1H), 3.67 (m, 1H), 3.61 (s, 3H), 2.20 (m, 1H), 2.07 (m, 1H), 1.95 (m, 1H), 1.84 (m, 1H), 0.99 (d, 3H), 0.97 (d, 3H) | 413.3 | 2-Bromobenzoyl chloride |
| DE-115 | 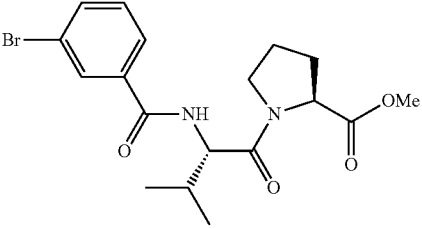<br>Methyl (3-bromobenzoyl)-L-valyl-L-prolinate | 8.72 (d, 1H), 8.11 (s, 1H), 7.89 (m, 1H), 7.75 (m, 1H), 7.44 (t, 1H), 4.47 (m, 1H), 4.34 (m, 1H), 3.96 (m, 1H), 3.67 (m, 1H), 3.63 (s, 3H), 2.19 (m, 2H), 1.95 (m, 1H), 1.85 (m, 1H), 1.00 (d, 3H), 0.97 (d, 3H) | 413.3 | 3-Bromobenzoic acid |
| DE-116 | 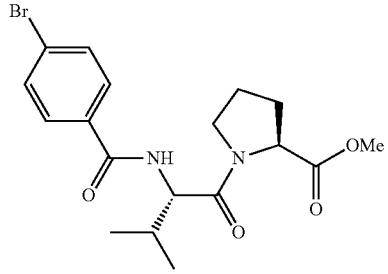<br>Methyl (4-bromobenzoyl)-L-valyl-L-prolinate | — | — | 4-Bromobenzoyl chloride |
| DE-117 | 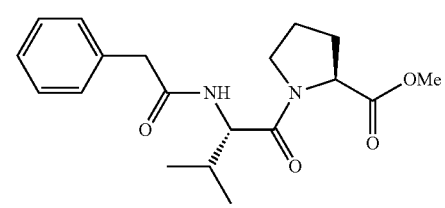<br>Methyl (2-phenylacetyl)-L-valyl-L-prolinate | 8.28 (d, 1H), 7.25 (m, 5H), 4.30 (m, 2H), 3.77 (m, 1H), 3.61 (s, 3H), 3.59 (m, 1H), 3.52 (d, 1H), 3.42 (d, 1H), 2.16 (m, 1H), 1.97 (m, 1H), 1.85 (m, 3H), 0.90 (d, 3H), 0.86 (d, 3H) | 347.4 | 2-Phenylacetic acid |

TABLE E3-continued

Characterization data for dipeptide ester intermediates.

| Di-pep-tide Ester | Formula/Name | (ppm; 400 MHz, $d_6$-DMSO) | m/z [M + 1]$^+$ | Starting materials |
|---|---|---|---|---|
| DE-118 | 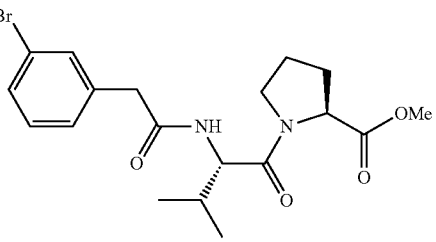<br>Methyl (2-(3-bromophenyl)acetyl)-L-prolinate | 8.36 (d, 1H), 7.47 (s, 1H), 7.41 (m, 1H), 7.25 (m, 2H), 4.31 (m, 2H), 3.75 (m, 1H), 3.61 (s, 3H), 3.59 (m, 1 H), 3.54 (d, 1H), 3.44 (d, 1H), 2.16 (m, 1H), 1.98 (m, 1H), 1.86 (m, 3H), 0.90 (d, 3H), 0.86 (d, 3H) | 427.3 | 2-(3-Bromophenyl)acetic acid |
| DE-119 | 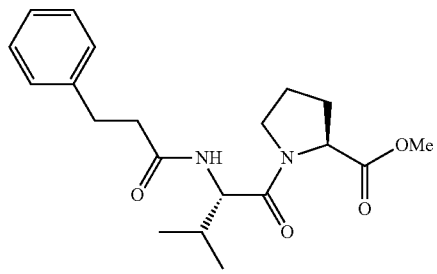<br>Methyl (3-phenylpropanoyl)-L-valyl-L-prolinate | 8.07 (d, 1H), 7.20 (m, 5H), 4.31 (m, 2H), 3.80 (m, 1H), 3.61 (s, 3H), 3.59 (m, 1H), 2.80 (t, 2H), 2.50 (m, 1H), 2.44 (m, 1H), 2.15 (m, 1H), 1.88 (m, 4H), 0.88 (d, 3H), 0.81 (d, 3H) | 361.4 | 3-Phenylpropanoic acid |
| DE-120 | 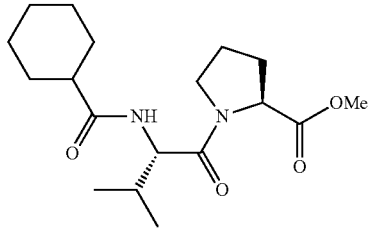<br>Methyl (cyclohexanecarbonyl)-L-valyl-L-prolinate | 7.82 (d, 1H), 4.30 (m, 2H), 3.79 (m, 1H), 3.61 (s, 3H), 3.58 (m, 1H), 2.20 (m, 2H), 1.91 (m, 3H), 1.80 (m, 1H), 1.68 (m, 3H), 1.59 (m, 2H), 1.28 (m, 2H), 1.16 (m, 3H), 0.90 (d, 3H), 0.86 (d, 3H) | 339.3 | Cyclohexanecarboxylic acid |
| DE-121 | 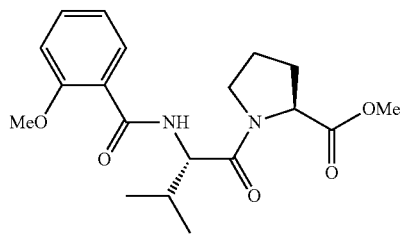<br>Methyl (2-methoxybenzoyl)-L-valyl-L-prolinate | — | 363.5 | 2-Methoxybenzoyl chloride |

TABLE E3-continued

Characterization data for dipeptide ester intermediates.

| Dipeptide Ester | Formula/Name | (ppm; 400 MHz, d₆-DMSO) | m/z [M + 1]⁺ | Starting materials |
|---|---|---|---|---|
| DE-122 | 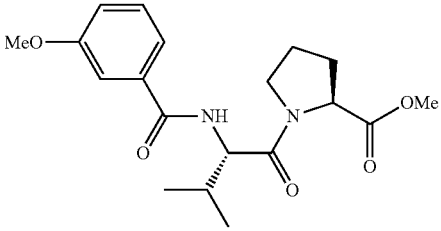 Methyl (3-methoxybenzoyl)-L-valyl-L-prolinate | — | 363.6 | 3-Methoxybenzoyl chloride |
| DE-123 | 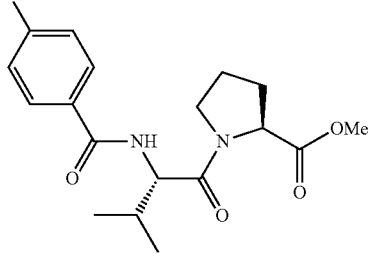 Methyl (4-methoxybenzoyl)-L-valyl-L-prolinate | — | 363.4 | 4-Methoxybenzoyl chloride |
| DE-124 | 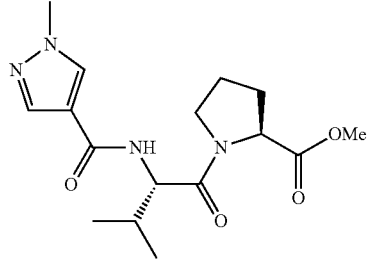 Methyl (1-methyl-1H-pyrazole-4-carbonyl)-L-valyl-L-prolinate | — | 337.4 | 1-Methyl-1H-pyrazole-4-carboxylic acid |
| DE-125 | 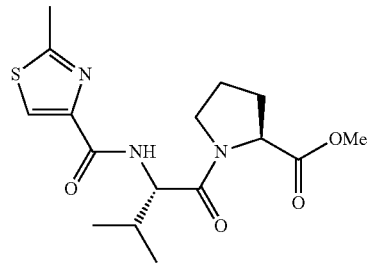 Methyl (2-methylthiazole-4-carbonyl)-L-valyl-L-prolinate | — | 354.5 | 2-Methylthiazole-4-carboxylic acid |

TABLE E3-continued

Characterization data for dipeptide ester intermediates.

| Dipeptide Ester | Formula/Name | (ppm; 400 MHz, $d_6$-DMSO) | m/z [M + 1]$^+$ | Starting materials |
|---|---|---|---|---|
| DE-126 | 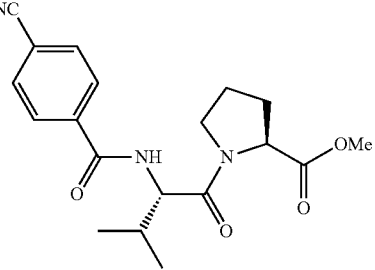<br>Methyl (4-cyanobenzoyl)-L-valyl-L-prolinate | — | 358.6 | 4-Cyanobenzoic acid |
| DE-127 | 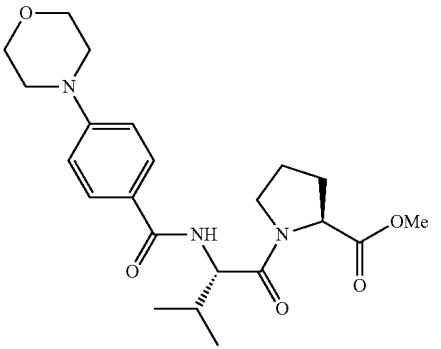<br>Methyl (4-morpholinobenzoyl)-L-valyl-L-prolinate | — | 418.4 | 4-Morpholinobenzoic acid |
| DE-128 | 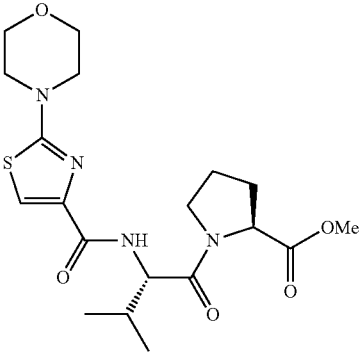<br>Methyl (2-morpholinothiazole)-4-carbonyl)-L-valyl-L-prolinate | — | 425.5 | 2-Morpholinothiazole-4-carboxylic acid |
| DE-129 | 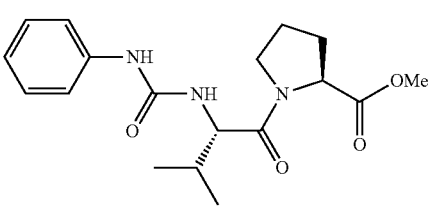<br>Methyl (phenylcarbamoyl-L-valyl-L-prolinate | — | 348.4 | Phenyl isocyanate |

TABLE E3-continued

Characterization data for dipeptide ester intermediates.

| Dipeptide Ester | Formula/Name | (ppm; 400 MHz, d$_6$-DMSO) | m/z [M + 1]$^+$ | Starting materials |
|---|---|---|---|---|
| DE-130 | 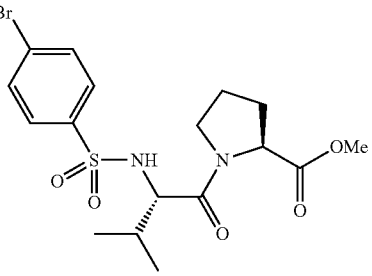  Methyl ((4-bromophenyl)sulfonyl)-L-valyl-L-prolinate | — | 448.8 | 4-Bromobenzenesulfonyl chloride |
| DE-A1 | 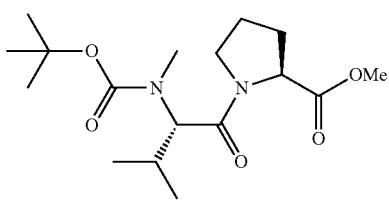  Methyl N-(tert-butoxycarbonyl)-N-methyl-L-valyl-L-prolinate | — | 377.3 | 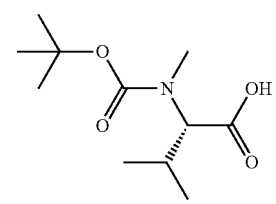  N-(tert-Butoxycarbonyl)-N-methyl-L-valine |
| DE-A2 | 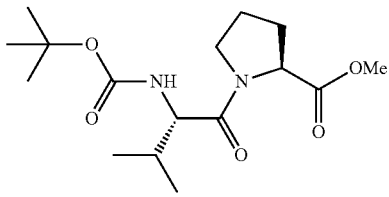  Methyl (tert-butoxycarbonyl)-L-valyl-L-prolinate | — | 329.2 | 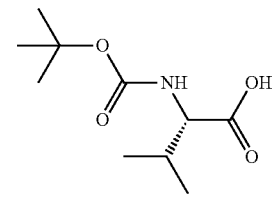  (tert-Butoxycarbonyl)-L-valine |
| DE-A3 | 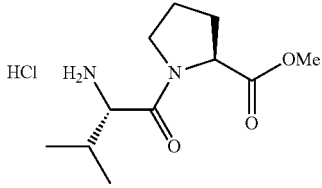  Methyl L-valyl-L-prolinate hydrochloride | — | 229.7 | — |
| DE-131 | 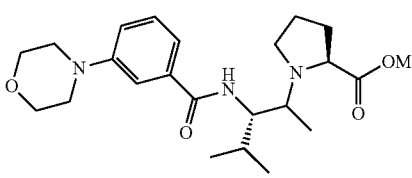  (3-Morpholinobenzoyl)-L-valyl-L-prolinate | — | 418.6 | 3-Morpholinobenzoic acid |

TABLE E3-continued

Characterization data for dipeptide ester intermediates.

| Dipeptide Ester | Formula/Name | (ppm; 400 MHz, d$_6$-DMSO) | m/z [M + 1]$^+$ | Starting materials |
|---|---|---|---|---|
| DE-132 | Methyl (3-(4-methylpiperazin)-1-yl)benzoyl)-L-valyl-L-prolinate | — | 431.7 | 3-(4-Methylpiperazin-1-yl)benzoic acid |
| DE-133 | Methyl (3-acetamidobenzoyl)-L-valyl-L-prolinate | — | 390.6 | 3-Acetamidobenzoic acid |
| DE-134 | Methyl (3-cyanobenzoyl)-L-valyl-L-prolinate | — | 358.4 | 3-Cyanobenzoic acid |
| DE-135 | Methyl (4-trifluoromethyl)benzoyl)-L-valyl-L-prolinate | — | 401.4 | 4-(Trifluoromethyl)benzoyl chloride |
| DE-136 | Methyl (4-chlorobenzoyl)-L-valyl-L-prolinate | — | 367.5 | 4-Chlorobenzoyl chloride |

TABLE E3-continued

Characterization data for dipeptide ester intermediates.

| Dipeptide Ester | Formula/Name | (ppm; 400 MHz, d$_6$-DMSO) | m/z [M + 1]$^+$ | Starting materials |
|---|---|---|---|---|
| DE-137 | 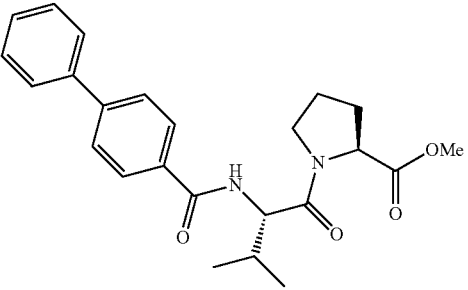<br>Methyl ([1,1′-biphenyl]-4-carbonyl)-L-valyl-L-prolinate | — | 409.5 | [1,1′-Biphenyl]-4-carbonyl chloride |
| DE-138 | 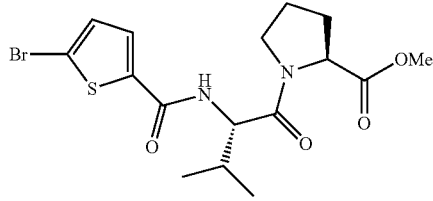<br>Methyl (5-bromothiophene-2-carbonyl)-L-valyl-L-prolinate | — | 419.4 | 5-Bromothiophene-2-carboxylic acid |
| DE-139 | 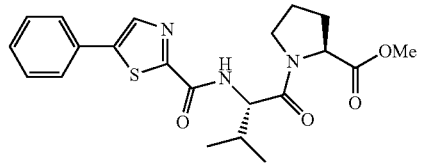<br>Methyl (5-phenylthiazole-2-carbonyl)-L-valyl-L-prolinate | — | 416.6 | 5-Phenylthiazole-2-carboxylic acid |
| DE-140 | 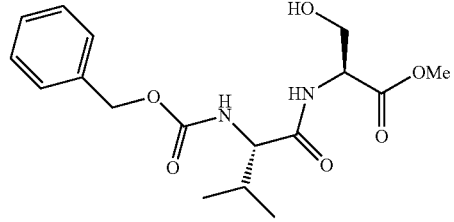<br>Methyl ((benzyloxy)carbonyl)-L-valyl-L-serine | — | 353.7 | 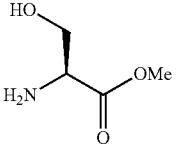<br>Methyl L-serinate |

TABLE E3-continued

Characterization data for dipeptide ester intermediates.

| Dipeptide Ester | Formula/Name | (ppm; 400 MHz, d$_6$-DMSO) | m/z [M + 1]$^+$ | Starting materials |
|---|---|---|---|---|
| DE-142 | 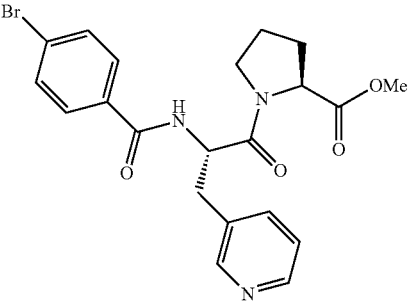<br>Methyl ((S)-2-(4-bromobenzamido)-3-(pyridine-3-yl)propanoyl)-L-prolinate | — | 462.4 | Methyl ((S)-2-amino-3-(pyridin-3-yl)propanoyl)-L-prolinate AE-1 |
| DE-143 | 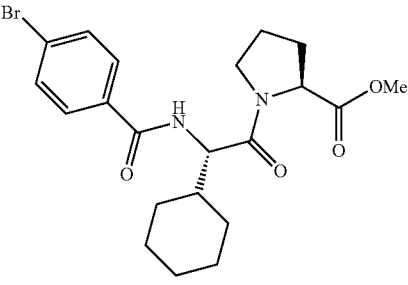<br>Methyl ((S)-2-(4-bromobenzamido)-2-cyclohexylacetyl-L-prolinate | — | 452.6 | Methyl ((S)-2-amino-2-cyclohexylacetyl)-L-prolinate AE-2 |
| DE-144 | 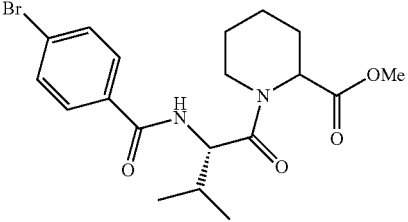<br>Methyl (S)-1-((4-bromobenzoyl)-L-valyl)piperidine-2-carboxylate | — | 426.6 | Methyl (S)-1-(L-valyl)piperidine-2-carboxylate AE-3 |
| DE-145 | 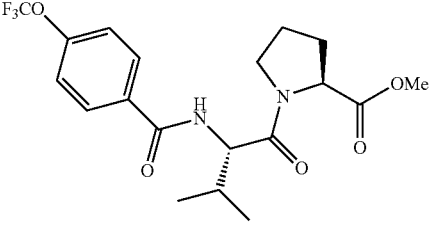<br>Methyl (4-trifluoromethoxy)benzoyl-L-valyl-L-prolinate | — | 417.5 | 4-(Trifluoromethoxy)benzoyl chloride |

TABLE E3-continued

Characterization data for dipeptide ester intermediates.

| Dipeptide Ester | Formula/Name | (ppm; 400 MHz, d$_6$-DMSO) | m/z [M + 1]$^+$ | Starting materials |
| --- | --- | --- | --- | --- |
| DE-146 | Methyl (4-bromo-3-cyanobenzoyl)-L-valyl-L-prolinate | — | 437.9 | 4-Bromo-3-cyanobenzoic acid |
| DE-147 | Methyl (4-chloro-3-cyanobenzoyl)-L-valyl-L-prolinate | — | 392.6 | 4-Chloro-3-cyanobenzoic acid |
| DE-148 | Methyl (3-trifluoromethoxy)benzoyl-L-valyl-L-prolinate | — | 417.3 | 3-(Trifluoromethoxy)benzoyl chloride |
| DE-149 | Methyl (4-bromobenzoyl)-L-valyl-L-serinate | — | 402.6 | Methyl L-valyl-L-serinate AE-4 |

TABLE E3-continued

Characterization data for dipeptide ester intermediates.

| Dipeptide Ester | Formula/Name | (ppm; 400 MHz, d$_6$-DMSO) | m/z [M + 1]$^+$ | Starting materials |
|---|---|---|---|---|
| DE-151 | 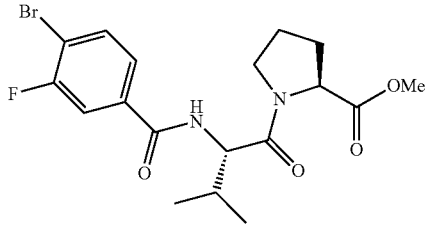
Methyl (4-bromo-3-fluorobenzoyl)-L-valyl-L-prolinate | — | 431.7 | 4-Bromo-3-fluorobenzoic acid |
| DE-152 | 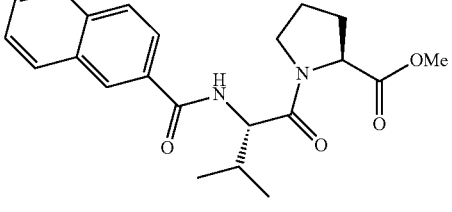
Methyl (2-naphthoyl)-L-valyl-L-prolinate | — | 382.4 | 2-Naphthoyl chloride |
| DE-153 | 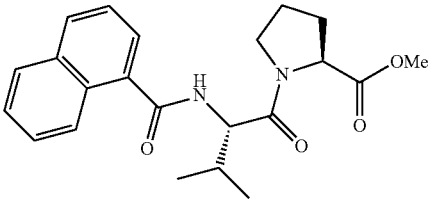
Methyl (1-naphthoyl)-L-valyl-L-prolinate | — | 382.4 | 1-Naphthoyl chloride |
| DE-154 | 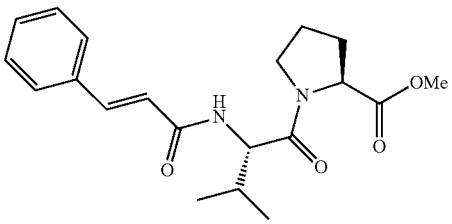
Methyl cinnamoyl-L-valyl-L-prolinate | — | 359.7 | Cinnamoyl chloride |

TABLE E3-continued

Characterization data for dipeptide ester intermediates.

| Dipeptide Ester | Formula/Name | (ppm; 400 MHz, d$_6$-DMSO) | m/z [M + 1]$^+$ | Starting materials |
|---|---|---|---|---|
| DE-155 | 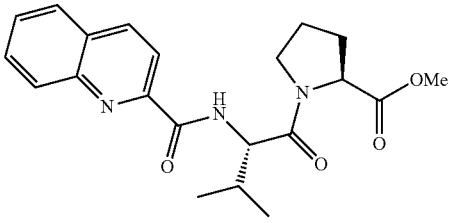 Methyl (quinoline-2-carbonyl)-L-valyl-L-prolinate | — | 384.9 | Quinoline-2-carboxylic acid |
| DE-156 | 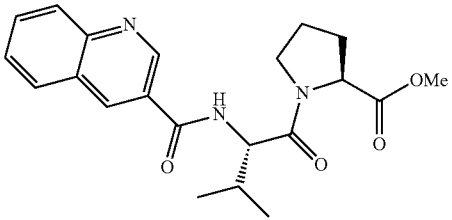 Methyl (quinoline-3-carbonyl)-L-valyl-L-prolinate | — | 384.6 | Quinoline-3-carboxylic acid |
| DE-157 | 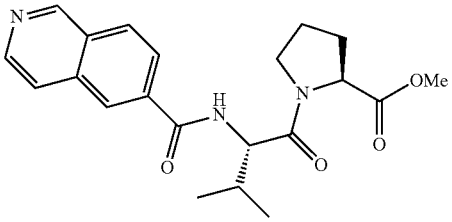 Methyl (isoquinoline-6-carbonyl)-L-valyl-L-prolinate | — | 384.4 | Isoquinoline-6-carboxylic acid |
| DE-158 | 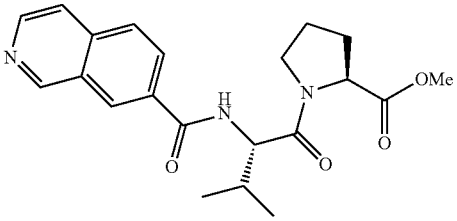 Methyl (isoquinoline-7-carbonyl)-L-valyl-L-prolinate | — | 384.3 | Isoquinoline-7-carboxylic acid |
| DE-159 | 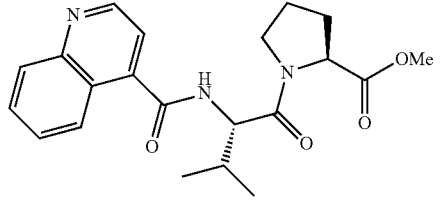 Methyl (quinoline-4-carbonyl)-L-valyl-L-prolinate | — | 384.8 | Quinoline-4-carboxylic acid |

TABLE E3-continued

Characterization data for dipeptide ester intermediates.

| Dipeptide Ester | Formula/Name | (ppm; 400 MHz, $d_6$-DMSO) | m/z [M + 1]$^+$ | Starting materials |
|---|---|---|---|---|
| DE-160 | 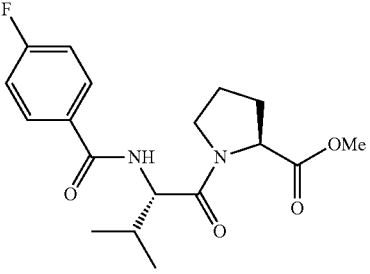<br>Methyl (4-fluorobenzoyl)-L-valyl-L-prolinate | 7.81 (m, 2H), 7.10 (m, 2H), 6.96 (d, 1H), 4.84 (m, 1H), 4.51 (m, 1H), 3.90 (m, 1H), 3.74 (s, 3H), 3.72 (m, 1H), 2.22 (m, 2H), 2.09 (m, 1H), 2.01 (m, 2H), 1.11 (d, 3H), 1.01 (d, 3H) | 351.39 | Methyl L-valyl-L-prolinate (dipeptide ester 32) and 4-fluorobenzoic acid |
| DE-162 | 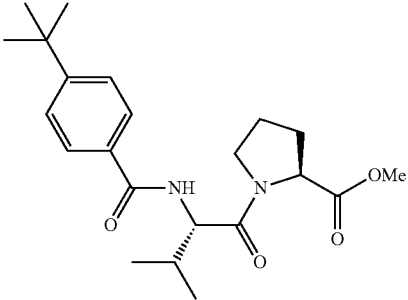<br>Methyl (4-(tert-butyl)benzoyl)-L-valyl-L-prolinate | 7.74 (d, 2H), 7.43 (d, 2H), 6.89 (d, 1H), 4.86 (m, 1H), 4.51 (m, 1H), 3.90 (m, 1H), 3.75 (s, 3H), 3.73 (m, 1H), 2.22 (m, 2H), 2.06 (m, 3H), 1.99 (s, 9H), 1.10 (d, 3H), 1.01 (d, 3H) | 389.58 | Methyl L-valyl-L-prolinate (dipeptide ester 32) and 4-(tert-butyl)benzoic acid |
| DE-163 | 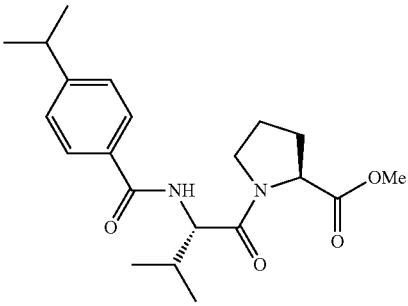<br>Methyl (4-isopropylbenzoyl)-L-valyl-L-prolinate | 7.74 (d, 2H), 7.27 (d, 2H), 6.87 (d, 1H), 4.86 (m, 1H), 4.51 (m, 1H), 3.90 (m, 1H), 3.75 (s, 3H), 3.72 (m, 1H), 2.94 (m, 1H), 2.23 (m, 2H), 2.04 (m, 3H), 1.25 (d, 6H), 1.10 (d, 3H), 1.01 (d, 3H) | 375.46 | Methyl L-valyl-L-prolinate (dipeptide ester 32) and 4-isopropylbenzoic acid |
| DE-171 | 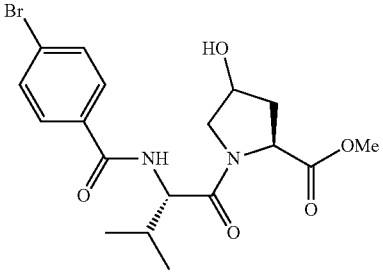<br>Methyl (2S,4R)-1-((4-bromobenzoyl)-L-valyl)-4-hydroxypyrrolidine-2-carboxylate | 7.61 (d, 2H), 7.54 (dd, 2H), 7.04 (br, 1H), 4.69 (m, 2H), 4.58 (m, 1H), 4.13 (m, 1H), 3.79 (m, 1H), 3.75 (s, 3H), 2.36 (m, 1H), 2.20 (m, 1H), 2.04 (m, 1H), 1.09 (d, 3H), 1.02 (d, 3H) | 426.71 | AE-5 Methyl (2S,4R)-1-(L-valyl)-4-hydroxypyrrolidine-2-carboxylate and 4-bromobenzoic acid |

TABLE E3-continued

Characterization data for dipeptide ester intermediates.

| Dipeptide Ester | Formula/Name | (ppm; 400 MHz, d<sub>6</sub>-DMSO) | m/z [M + 1]⁺ | Starting materials |
|---|---|---|---|---|
| DE-172 | 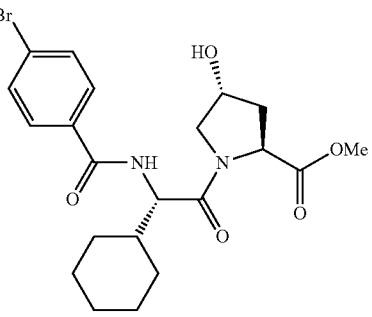<br>Methyl (2S,4R)-1-((S)-2-(4-bromobenzamido)-2-cyclohexylacetyl)-4-hydroxypyrrolidine-2-carboxylate | 7.57 (dd, 2H), 7.50 (d, 2H), 7.16 (br, 1H), 4.68 (m, 2H), 4.58 (m, 1H), 4.18 (m, 1H), 3.77 (m, 1H), 3.75 (s, 3H), 2.38 (m, 2H), 2.04 (m, 1H), 1.73-1.96 (m, 5H), 1.04-1.28 (m, 5H) | 468.55 | AE-6<br>Methyl (2S,4R)-1-((S)-2-amino-2-cyclohexylacetyl)-4-hydroxypyrrolidine-2-carboxylate and 4-bromobenzoic acid |
| DE-173 | 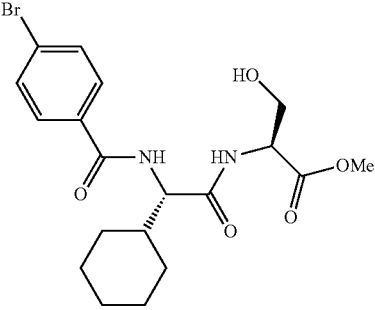<br>Methyl ((S)-2-(4-bromobenzamido)-2-cyclohexylacetyl)-L-serinate | 8.39 (m, 2H), 7.82 (d, 2H), 7.67 (d, 2H), 5.05 (br, 1H), 4.43 (m, 1H), 4.34 (m, 1H), 3.72 (m, 1H), 3.65 (s, 1H), 3.61 (s, 3H), 1.57-1.86 (m, 6H), 0.95-1.22 (m, 5H) | 443.32 | AE-7<br>Methyl ((S)-2-amino-2-cyclohexylacetyl)-L-serinate and 4-bromobenzoic acid |
| DE-174 | 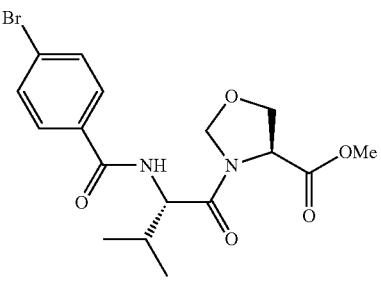<br>Methyl (S)-3-((4-bromobenzoyl)-L-valyl)oxazolidine-4-carboxylate | — | 413.73 | AE-8<br>Methyl (S)-3-(L-valyl)oxazolidine-4-carboxylate and 4-bromobenzoyl chloride |

TABLE E3-continued

Characterization data for dipeptide ester intermediates.

| Dipeptide Ester | Formula/Name | (ppm; 400 MHz, d<sub>6</sub>-DMSO) | m/z [M + 1]⁺ | Starting materials |
|---|---|---|---|---|
| DE-175 | Methyl (S)-4-((4-bromobenzoyl)-L-valyl)morpholine-3-carboxylate | — | 427.35 | AE-9 Methyl (S)-4-(L-valyl)morpholine-3-carboxylate and 4-bromobenzoyl chloride |
| DE-176 | Methyl (S)-1-((4-bromobenzoyl)-L-valyl)azetidine-2-carboxylate | — | 397.86 | AE-10 Methyl (S)-1-(L-valyl)azetidine-2-carboxylate and 4-bromobenzoyl chloride |
| DE-177 | Methyl (2S,4R)-1-((4-bromobenzoyl)-L-valyl)-4-cyanopyrrolidene-2-carboxylate | — | 436.48 | AE-11 Methyl (2S,4R)-1-(L-valyl)-4-cyanopyrrolidine-2-carboxylate and 4-bromobenzoyl chloride |
| DE-178 | Methyl (4-bromobenzoyl)-L-valyl)-L-alaninate | — | 385.74 | Acid 1 (4-Bromobenzoyl)-L-valine and methyl L-alaninate |

TABLE E3-continued

Characterization data for dipeptide ester intermediates.

| Dipeptide Ester | Formula/Name | (ppm; 400 MHz, $d_6$-DMSO) | m/z [M + 1]$^+$ | Starting materials |
| --- | --- | --- | --- | --- |
| DE-179 | 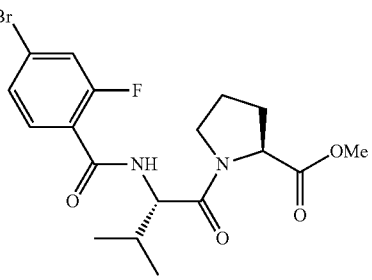<br>Methyl (4-bromo-2-fluorobenzyl)-L-valyl)-L-prolinate | — | 429.4 | Methyl L-valyl-L-prolinate (dipeptide ester 32) and 4-bromo-2-fluorobenzoic acid |
| DE-180 | 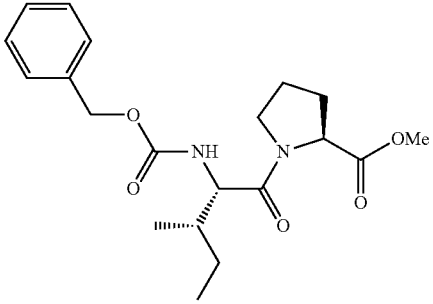<br>Methyl ((benzyloxy)carbonyl)-L-isoleucyl-L-prolinate | — | 377.2 | (((Benzyloxy)carbonyl)-L-isoleucine and methyl L-prolinate |
| DE-181 | 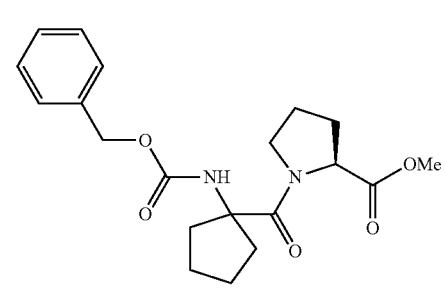<br>Methyl (1-(((benzyloxy)carbonyl)amino)cyclopentane-1-carbonyl)-L-prolinate | — | 375.2 | 1-(((Benzyloxy)carbonyl)amino)cyclopentane-1-carboxylic acid and methyl L-prolinate |

TABLE E3-continued

Characterization data for dipeptide ester intermediates.

| Dipeptide Ester | Formula/Name | (ppm; 400 MHz, $d_6$-DMSO) | m/z [M + 1]$^+$ | Starting materials |
| --- | --- | --- | --- | --- |
| DE-182 | 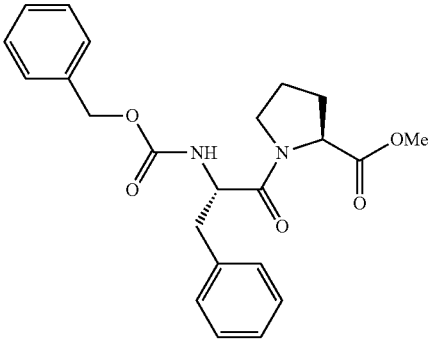<br>Methyl ((benzyloxy)carbonyl)-L-phenylalanyl-L-prolinate | — | 412.4 | ((Benzyloxy)carbonyl)-L-phenylalanine and methyl L-prolinate |
| DE-183 | 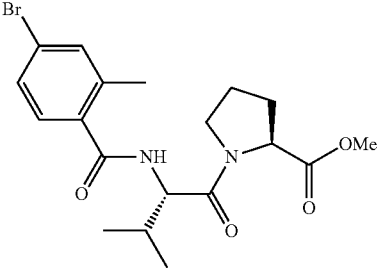<br>Methyl (4-bromo-2-metylbenzoyl)-L-valyl-L-prolinate | — | 425.5 | Methyl L-valyl-L-prolinate (dipeptide ester 32) and 4-bromo-2-fluorobenzoic acid |
| DE-184 | 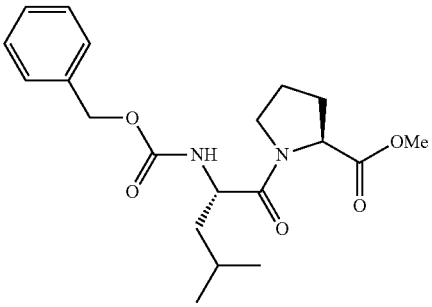<br>Methyl ((benzyloxy)carbonyl)-L-leucyl-L-prolinate | — | 377.3 | ((Benzyloxy)carbonyl)-L-leucine and methyl L-prolinate |

TABLE E3-continued

Characterization data for dipeptide ester intermediates.

| Dipeptide Ester | Formula/Name | (ppm; 400 MHz, $d_6$-DMSO) | m/z [M + 1]⁺ | Starting materials |
|---|---|---|---|---|
| DE-185 | Methyl (4-bromobenzoyl)-L-leucyl-L-prolinate | — | 425.4 | Acid 2 (4-Bromobenzoyl)-L-leucine and methyl L-prolinate |
| DE-186 | Methyl ((S)-2-(4-bromobenzamido)-3-(4-trifluoromethyl)phenyl)propanoyl)-L-prolinate | — | 527.4 | Acid 3 (S)-2-(4-Bromobenzamido)-3-(4-(trifluoromethyl)phenyl) propanoic acid and methyl L-prolinate |

Methyl N-((benzyloxy)carbonyl)-N-methyl-L-valyl-L-prolinate (DE-112)

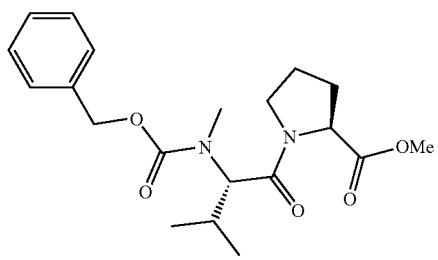 [SMILES: COC(=O)[C@@H]1CCCN1C(=O)[C@H](C(C)C)N(C)C(=O)OCc1ccccc1]

Methyl (tert-butoxycarbonyl)-L-valyl-L-prolinate (856 mg) was dissolved in 1,4-dioxane (10 mL). HCl in 1,4-dioxane (4 M, 5 mL) was added and the reaction stirred for 1 hour. The solvent was removed under reduced pressure to give a white solid (700 mg), used directly without purification. This compound was dissolved in DCM (50 mL) and cooled to 0° C. Benzyl chloroformate (0.48 mL) and triethylamine (2.14 mL) were added, and the mixture stirred for 1 hour. The reaction mixture was quenched with sat. aq. NaHCO₃ and extracted with DCM (3×50 mL). The combined organic layer was washed with brine, dried (MgSO₄) and concentrated, and the residue purified by column chromatography (50 to 70% EtOAc in hexanes) to give a colorless oil. MS (m/z): 377.3 [M+1]⁺. Methyl (2-bromobenzoyl)-L-valyl-L-prolinate (DE-114)

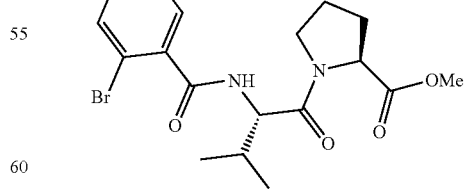

Triethylamine (1.21 mL, 8.76 mmol) was added to a solution of methyl L-valyl-L-prolinate (1.00 g, 4.38 mmol) and 2-bromobenzoyl chloride (961 mg, 4.38 mmol) in DCM (20 mL) at 0° C. After 30 minutes, the reaction mixture was diluted with DCM and washed with 1M HCl. The organic layer was dried (MgSO$_4$), concentrated, and the residue purified by column chromatography (EtOAc in Hexanes, gradient) to give 1.20 g product. $^1$H NMR (400 MHz, d$_6$-DMSO) δ 8.65 (d, 1H), 7.63 (dd, 1H), 7.41 (m, 1H), 7.34 (dd, 1H), 7.30 (m, 1H), 4.48 (t, 1H), 4.34 (m, 1H), 3.94 (m, 1H), 3.67 (m, 1H), 3.61 (s, 3H), 2.20 (m, 1H), 2.07 (m, 1H), 1.95 (m, 1H), 1.84 (m, 1H), 0.99 (d, 3H), 0.97 (d, 3H); MS (m/z): 413.3 [M+1]$^+$.

Methyl (phenylcarbamoyl)-L-valyl-L-prolinate (DE-129)

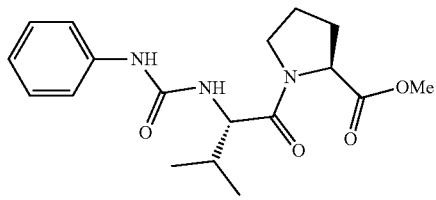 [SMILES: COC(=O)[C@@H]1CCCN1C(=O)[C@@H](NC(=O)Nc1ccccc1)C(C)C]

Phenyl isocyanate (0.23 mL, 1.89 mmol) and triethylamine (0.79 mL, 5.67 mmol) were added to a solution of methyl L-valyl-L-prolinate (0.50 g, 1.89 mmol) in DCM (25 mL) at 0° C. The mixture was warmed to RT and stirred for 1 hour. The reaction was quenched with H$_2$O (10 mL) and extracted with DCM (3×50 mL). The combined organic layer was washed with brine, dried (MgSO$_4$) and concentrated, and the residue purified by column chromatography (10-50% EtOAc in Hexanes) to give a colorless oil (0.57 g, 88% yield). MS (m/z): 348.4 [M+1]$^+$.

Methyl ((4-bromophenyl)sulfonyl)-L-valyl-L-prolinate (DE-130)

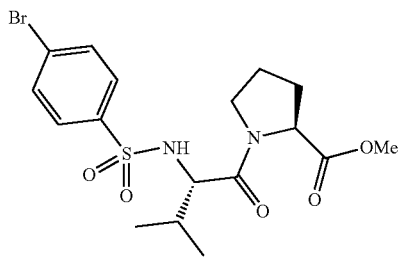 [SMILES: COC(=O)[C@@H]1CCCN1C(=O)[C@@H](NS(=O)(=O)c1ccc(Br)cc1)C(C)C]

4-Bromobenzenesulfonyl chloride (0.48 g, 1.89 mmol) and triethylamine (0.79 mL, 5.67 mmol) were added to a solution of methyl L-valyl-L-prolinate (0.50 g, 1.89 mmol) in DCM (25 mL) at 0° C. The mixture was warmed to RT and stirred for 1 hour. The reaction was quenched with H$_2$O (10 mL) and extracted with DCM (3×50 mL). The combined organic layer was washed with brine, dried (MgSO$_4$) and concentrated, and the residue purified by column chromatography (10-50% EtOAc in Hexanes) to give a colorless oil (0.80 g, 95% yield). MS (m/z): 448.8 [M+1]$^+$.

Methyl L-valyl-L-prolinate HCl (DE-A3)

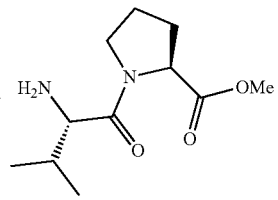

Methyl (tert-butoxycarbonyl)-L-valyl-L-prolinate (1.0 g, 3.04 mmol) was dissolved in anhydrous 1,4-dioxane (10 mL) under an inert atmosphere. HCl in 1,4-dioxane (4 M, 7.5 mL, 30.4 mmol) was added and the mixture heated to 60° C. After 5 hours the solvent was removed under reduced pressure to give a white solid (0.8 g, 99% yield). MS (m/z): 229.7 [M+1]$^+$.

Methyl ((4-chlorophenyl)carbamoyl)-L-valyl-L-prolinate (DE-164)

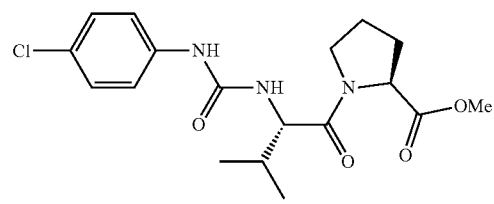 [SMILES: COC(=O)[C@@H]1CCCN1C(=O)[C@@H](NC(=O)Nc1ccc(Cl)cc1)C(C)C]

Triphosgene (0.28 g, 0.94 mmol) was added to a solution of 3-chloroaniline (0.27 g, 2.1 mmol) and triethylamine (0.96 g, 9.5 mmol) in dichloromethane (10 mL) at 5° C. The reaction was stirred for 30 min at 5° C. and methyl L-valyl-L-prolinate (0.5 g, 1.9 mmol) was added. The reaction was stirred for another 30 min at 5° C., quenched with water (20 mL) and extracted with dichloromethane (3×20 mL). The organic extracts were combined, dried over anhydrous sodium sulfate, and concentrated. The residue was purified by silica chromatography (Hexanes:EA=3:1) to give the title compound (440 mg, 61% yield). MS (m/z): 382.39 [M+1]$^+$.

Dipeptide Esters DE-165 and DE-167 were prepared in a similar manner to DE-164 from the corresponding aniline and methyl L-valyl-L-prolinate.

TABLE E4

Characterization of Dipeptide Esters DE-165 and DE-167.

| Dipeptide Ester | Formula/Name | ¹H NMR (ppm; 400 MHz, CDCl₃) | m/z [M + 1]⁺ | Aniline Starting Material |
|---|---|---|---|---|
| DE-165 | 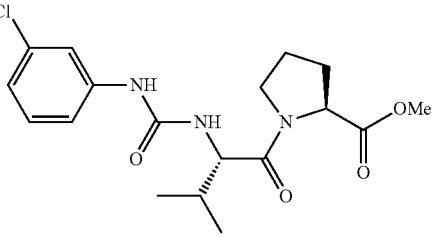<br>Methyl ((3-chlorophenyl)carbamoyl)-L-valyl-L-prolinate | δ: 7.81 (br, 1H), 7.50 (s, 1H), 7.15 (m, 2H), 6.92 (m, 2H), 4.55 (m, 2H), 4.09 (m, 1H), 3.78 (m, 1H), 3.64 (s, 3H), 2.28 (m, 1H), 2.06 (m, 4H), 1.11 (d, 3H), 1.03 (d, 3H) | 382.4 | 3-Chloroaniline |
| DE-167 | 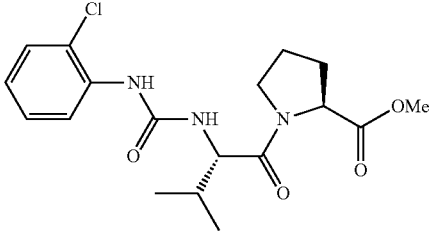<br>Methyl ((2-chlorophenyl)carbamoyl)-L-valyl-L-prolinate | δ: 7.88 (d, 1H), 7.40 (s, 1H), 7.25 (m, 1H), 7.21 (d, 1H), 7.06 (m, 1H), 6.86 (m, 1H), 4.62 (m, 1H), 4.57 (m, 1H), 3.96 (m, 1H), 3.71 (m, 1H), 3.64 (s, 3H), 2.23 (m, 1H), 2.04 (m, 4H), 1.11 (d, 3H), 1.02 (d, 3H) | 382.4 | 2-Chloroaniline |

Methyl (((4-chlorobenzyl)oxy)carbonyl)-L-valyl-L-prolinate (DE-168)

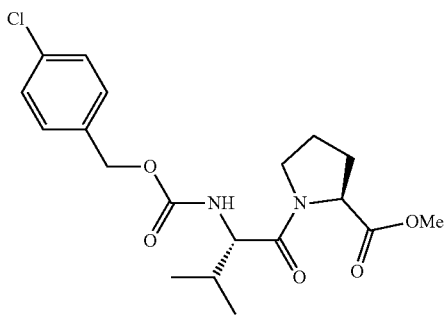 [SMILES: COC(=O)[C@@H]1CCCN1C(=O)[C@@H](NC(=O)OCc1ccc(Cl)cc1)C(C)C]

A solution of methyl ((S)-2-isocyanato-3-methylbutanoyl)-L-prolinate (0.93 g, 3.6 mmol), 4-chlorobenzyl alcohol (0.54 g, 3.9 mmol), and triethylamine (0.75 g, 7.4 mmol) in acetonitrile (20 mL) was refluxed for 2 hours. The solvent was removed under reduced pressure, and the residue dissolved in ethyl acetate (20 mL) and washed with 5% KHSO₄ solution. The organic layer was dried over anhydrous sodium sulfate, concentrated and the residue purified by silica chromatography (PE:EA=4:1) to give the title compound (0.78 g, 52%). ¹H NMR (CDCl₃, 400 MHz) δ: 7.32 (d, 2H), 7.28 (d, 2H), 5.47 (d, 1H), 5.04 (m, 2H), 4.52 (m, 1H), 4.33 (m, 1H), 3.73 (m, 1H), 3.71 (s, 3H), 3.66 (m, 1H), 2.24 (m, 1H), 2.03 (m, 4H), 1.05 (d, 3H), 0.94 (d, 3H). MS (m/z): 397.08 [M+1]⁺.

Dipeptide Esters DE-169 and DE-170 were prepared in a similar manner to DE-168 from the corresponding alcohol and methyl ((S)-2-isocyanato-3-methylbutanoyl)-L-prolinate.

TABLE E5

Characterization of Dipeptide Esters DE-169 and DE-170.

| Dipeptide Ester | Formula/Name | $^1$H NMR (ppm; 400 MHz, CDCl$_3$) | m/z [M + 1]$^+$ | Alcohol Starting Material |
|---|---|---|---|---|
| DE-169 | 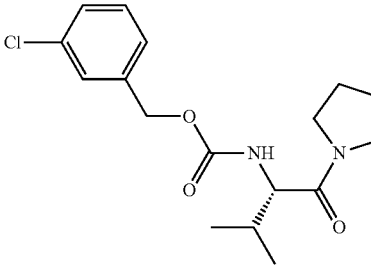<br>Methyl (((3-chlorobenzyl)oxy)carbonyl)-L-valyl-L-prolinate | δ: 7.34 (s, 1H), 7.28 (m, 2H), 7.22 (m, 1H), 5.53 (d, 1H), 5.05 (m, 2H), 4.53 (m, 1H), 4.33 (m, 1H), 3.78 (m, 1H), 3.73 (s, 3H), 3.70 (m, 1H), 2.23 (m, 1H), 2.01 (m, 4H), 1.05 (d, 3H), 0.95 (d, 3H) | 397.09 | 3-Chlorobenzyl alcohol |
| DE-170 | 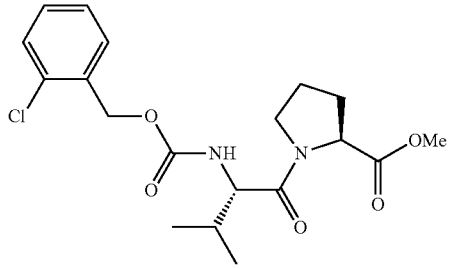<br>Methyl (((2-chlorobenzyl)oxy)carbonyl-L-valyl-L-prolinate | δ: 7.39 (m, 2H), 7.25 (m, 2H), 5.53 (d, 1H), 5.24 (d, 1H), 5.18 (d, 1H), 4.53 (m, 1H), 4.35 (m, 1H), 3.76 (m, 1H), 3.73 (s, 3H), 3.70 (m, 1H), 2.23 (m, 1H), 2.02 (m, 4H), 1.06 (d, 3H), 0.97 (d, 3H) | 397.08 | 2-Chlorobenzyl alcohol |

Methyl ((S)-2-isocyanato-3-methylbutanoyl)-L-prolinate

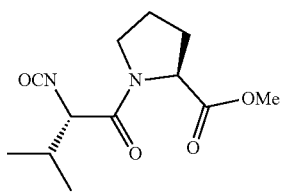

Triphosgene (1.11 g, 3.7 mmol) was added in portions to a mixture of methyl L-valyl-L-prolinate (3 g, 11.4 mmol) and sodium bicarbonate (4.8 g, 56.8 mmol) in DCM/water (60 mL/45 mL) at 5° C. The reaction was stirred for 5 min at 5° C. The organic layer was separated and the water phase was re-extracted with dichloromethane (50 mL×2). The organic extracts were combined, dried over anhydrous sodium sulfate, and concentrated to give the title compound (2.8 g, 97%), which was used without further purification.

Amino Esters AE-1 to AE-11 were prepared in a similar manner to methyl L-valyl-L-prolinate (DE-A3), by deprotection of the coupling products of the corresponding acid starting materials and amine starting materials are shown in Table E6.

TABLE E6

Characterization of Amino Esters AE-1 to AE-4.

| Amino Ester | Formula/Name | m/z [M + 1]⁺ | Starting materials |
|---|---|---|---|
| AE-1 | Methyl ((S)-2-amino-3-(pyridin-3-yl)propanoyl)-L-prolinate | 277.08 | (S)-2-((tert-Butoxycarbonyl)amino)-3-(pyridin-3-yl)propanoic acid and methyl-L-prolinate |
| AE-2 | Methyl ((S)-2-amino-2-cyclohexylacetyl)-L-prolinate | — | (S)-2-((tert-Butoxycarbonyl)amino)-2-cyclohexylacetic acid and methyl L-prolinate |
| AE-3 | Methyl ((S)-1-(L-valyl)piperidine-2-carboxylate | 243.46 | (tert-Butoxycarbonyl)-L-valine and methyl (S)-piperidine-2-carboxylate |
| AE-4 | Methyl (L-valyl)-L-serinate | 219.28 | (tert-Butoxycarbonyl)-L-valine and methyl L-serinate |
| AE-5 | Methyl (2S,4R)-1-(L-valyl)-4-hydroxypyrrolidine-2-carboxylate | — | (tert-Butoxycarbonyl)-L-valine and methyl (2S,4R)-4-hydroxypyrrolidine-2-carboxylate |

TABLE E6-continued

Characterization of Amino Esters AE-1 to AE-4.

| Amino Ester | Formula/Name | m/z [M + 1]+ | Starting materials |
|---|---|---|---|
| AE-6 | 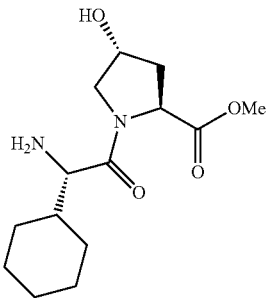<br>Methyl (2S,4R)-1-((S)-2-amino-2-cyclohexylacetyl)-4-hydroxypyrrolidine-2-carboxylate | — | (S)-2-((tert-Butoxycarbonyl)amino)-2-cyclohexylacetic acid and methyl (2S,4R)-4-hydroxypyrrolidine-2-carboxylate |
| AE-7 | 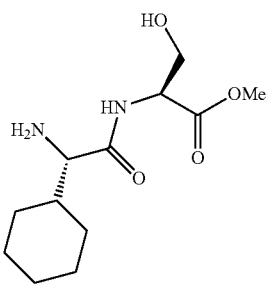<br>Methyl ((S)-2-amino-2-cyclohexylacetyl)-L-serinate | — | (S)-2-((tert-Butoxycarbonyl)amino)-2-cyclohexylacetic acid and methyl L-serinate |
| AE-8 | 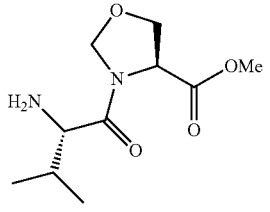<br>Methyl ((S)-3-(L-valyl)oxazolidine-4-carboxylate | 231.05 | (tert-Butoxycarbonyl)-L-valine and methyl (S)-oxazolidine-4-carboxylate |
| AE-9 | 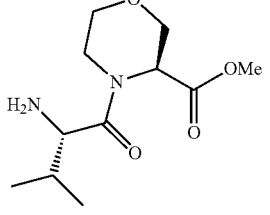<br>Methyl ((S)-4-(L-valyl)morpholine-3-carboxylate | 245.14 | (tert-Butoxycarbonyl)-L-valine and methyl (S)-morpholine-3-carboxylate |

TABLE E6-continued

Characterization of Amino Esters AE-1 to AE-4.

| Amino Ester | Formula/Name | m/z [M + 1]⁺ | Starting materials |
|---|---|---|---|
| AE-10 | Methyl ((S)-1-(L-valyl)azetidine-2-carboxylate | 215.01 | (tert-Butoxycarbonyl)-L-valine and methyl (S)-azetidine-2-carboxylate |
| AE-11 | Methyl (2S,4R)-1-(L-valyl)-4-cyanopyrrolidine-2-carboxylate | 254.18 | (tert-Butoxycarbonyl)-L-valine and methyl (2S,4R)-4-cyanopyrrolidine-2-carboxylate |

Acids 1 to 3 were prepared by coupling of 4-bromobenzoyl chloride and the corresponding amines, followed by hydrolysis of the methyl ester in the case of acid 1.

TABLE E7

Characterization of Acids 1 to 3.

| Acid | Formula/Name | m/z [M + 1]⁺ | Starting material |
|---|---|---|---|
| Acid 1 | (4-Bromobenzoyl)-L-valine | 300.16 | Methyl L-valinate |
| Acid 2 | (4-Bromobenzoyl)-L-leucine | 314.1 | L-Leucine |

TABLE E7-continued

Characterization of Acids 1 to 3.

| Acid | Formula/Name | m/z [M + 1]+ | Starting material |
|---|---|---|---|
| Acid 3 | 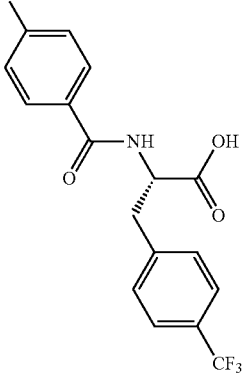<br>(S)-2-(4-Bromobenzamido)-3-(4-(trifluoromethyl)phenyl)propanoic acid | 415.9 | (S)-2-Amino-3-(4-(trifluoromethyl)phenyl) propanoic acid |

(S)-1-((S)-2-Amino-3-cyclohexylpropanoyl)-N—((S)-1-fluoro-2-oxo-6-(3-((2,2,4,6,7-pentamethyl-2,3-dihydrobenzofuran-5-yl)sulfonyl)guanidino) hexan-3-yl)pyrrolidine-2-carboxamide

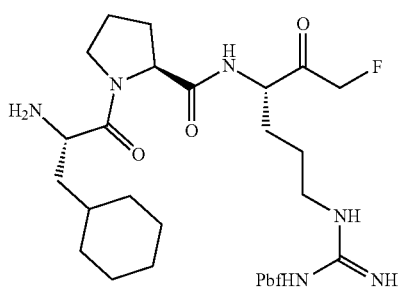

The title compound was prepared by coupling of ((S)-2-(((benzyloxy)carbonyl)amino)-3-cyclohexylpropanoyl)-L-proline (Acid 4) and (S)—N—(N-(4-amino-6-fluoro-5-oxo-hexyl)carbamimidoyl)-2,2,4,6,7-pentamethyl-2,3-dihydrobenzofuran-5-sulfonamide. MS (m/z): 693.5 [M+1]+.

((S)-2-(((Benzyloxy)carbonyl)amino)-3-cyclohexyl-propanoyl)-L-proline (Acid 4)

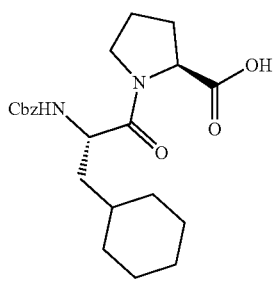 [SMILES: O=C(N[C@@H](CC1CCCCC1)C(=O)N1CCC[C@H]1C(=O)O)OCc1ccccc1]

Acid 4 was prepared by coupling of (S)-2-(((benzyloxy)carbonyl)amino)-3-cyclohexylpropanoic acid (Acid 5) and methyl L-prolinate, followed by ester hydrolysis. MS (m/z): 403.2 [M+1]+.

(S)-2-(((Benzyloxy)carbonyl)amino)-3-cyclohexyl-propanoic acid (Acid 5)

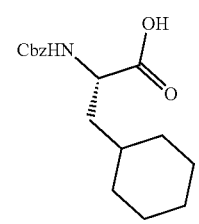 [SMILES: O=C(N[C@@H](CC1CCCCC1)C(=O)O)OCc1ccccc1]

Acid 5 was prepared by Cbz protection of (S)-2-amino-3-cyclohexylpropanoic acid. MS (m/z): 306.4 [M+1]+.

Figure 5:
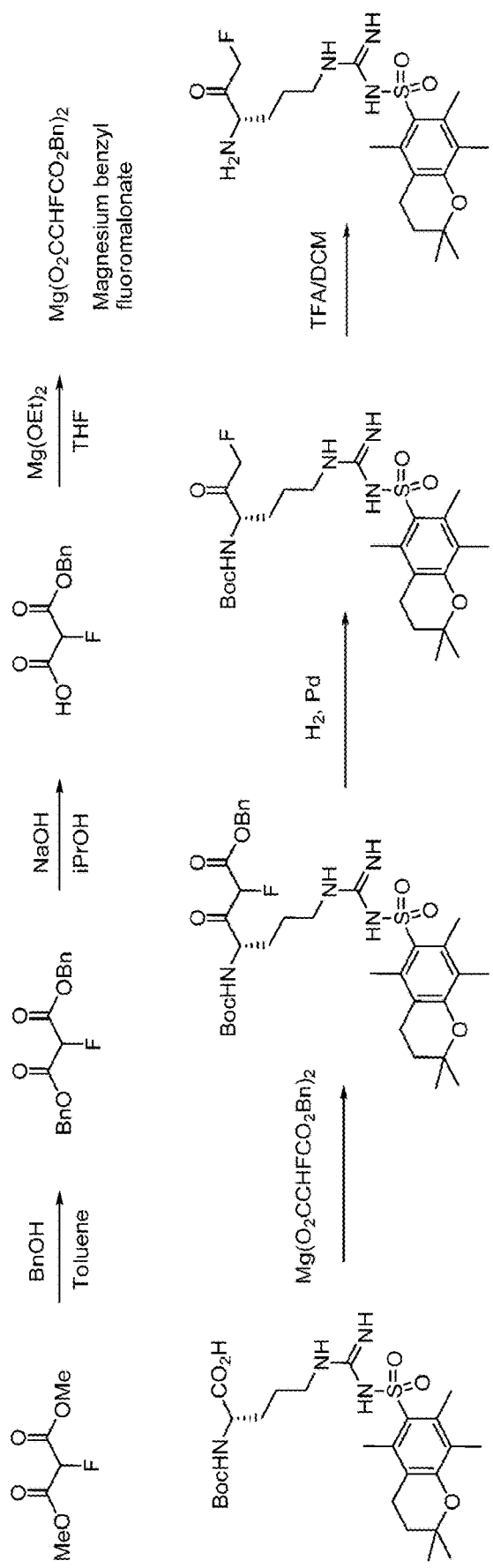
FIG. 5 shows Scheme E4.

The synthesis of (Pmc)arginine-fmk is shown in Scheme E4 (FIG. 5), and described below. The reagent magnesium benzyl fluoromalonate is further described in U.S. Pat. No. 5,210,272 which is incorporated herein by reference.

(S)—N—(N-(4-Amino-6-fluoro-5-oxohexyl)car-bamimidoyl)-2,2,5,7,8-pentamethylchromane-6-sulfonamide 2,2,2-trifluoroacetate

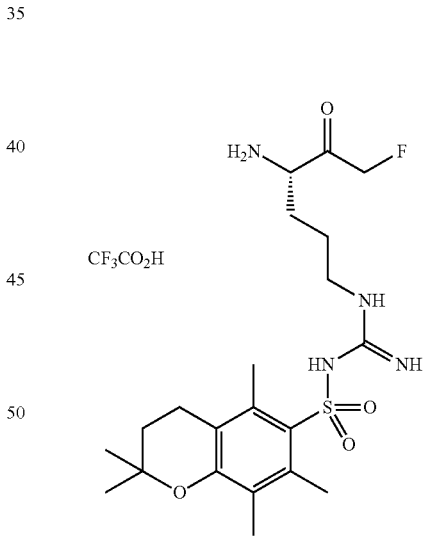

tert-Butyl (S)-(1-fluoro-2-oxo-6-(3-((2,2,5,7,8-pentamethylchroman-6-yl)sulfonyl)guanidino) hexan-3-yl)carbamate (0.125 g, 0.225 mmol) was dissolved in DCM (10 mL). TFA (1 mL) was added and the mixture was stirred for 30 minutes. The solvent was removed under reduced pressure to give a brown oil (0.1 g, 98% yield). MS (m/z): 457.4 [M+1]+.

tert-Butyl (S)-(1-fluoro-2-oxo-6-(3-((2,2,5,7,8-pentamethylchroman-6-yl)sulfonyl)guanidino)hexan-3-yl)carbamate

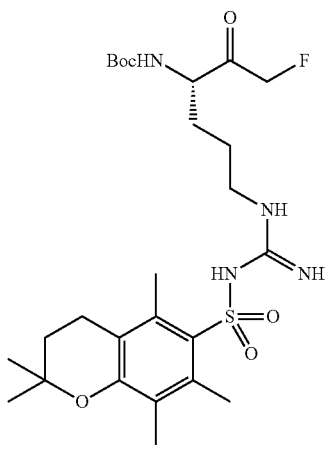 [SMILES: Cc1c(C)c(S(=O)(=O)NC(=N)NCCC[C@H](NC(=O)OC(C)(C)C)C(=O)CF)c(C)c2c1OC(C)(C)CC2]

$N^2$-(tert-Butoxycarbonyl)-$N^\omega$-((2,2,5,7,8-pentamethylchroman-6-yl)sulfonyl)-L-arginine (1.0 g, 1.85 mmol) was dissolved in THF (75 mL) and cooled to 0° C. CDI (0.75 g, 4.63 mmol) was added and the reaction was stirred under $N_2$ for 2 hours. Magnesium benzyl fluoromalonate (2.39 g, 5.55 mmol) was added and the mixture stirred at RT overnight. The reaction was quenched with sat. aq. $NaHCO_3$ and extracted with EtOAc (3×100 mL). The combined organic layer was washed with brine, dried (MgSO4) and concentrated. The crude product was dissolved in EtOH (100 mL), Pd/C (0.25 g) was added and the reaction vessel was evacuated to hydrogen using a balloon. The mixture was stirred under hydrogen for 24 hours, then filtered through Celite, washing with EtOH (150 mL) and concentrated. The residue was purified by column chromatography (10-70% EtOAc in Hexanes) to give a colorless oil (0.63 g, 61% yield). $^1$H NMR (400 MHz, $d_6$-DMSO) δ 7.28 (d, 1H), 6.68 (br s, 1H), 6.41 (br s, 2H), 5.18 (dd, 1H), 5.12 (dd, 1H), 4.00 (m, 1H), 3.02 (m, 2H), 2.59 (t, 2H), 2.47 (s, 6H), 2.03 (s, 3H), 1.78 (t, 2H), 1.64 (m, 1H), 1.41 (m, 3H), 1.39 (s, 9H), 1.26 (s, 6H); MS (m/z): 557.4 $[M+1]^+$.

X-Ray Co-Crystal Structure of Compound 101 and MALT1

Figure 3:
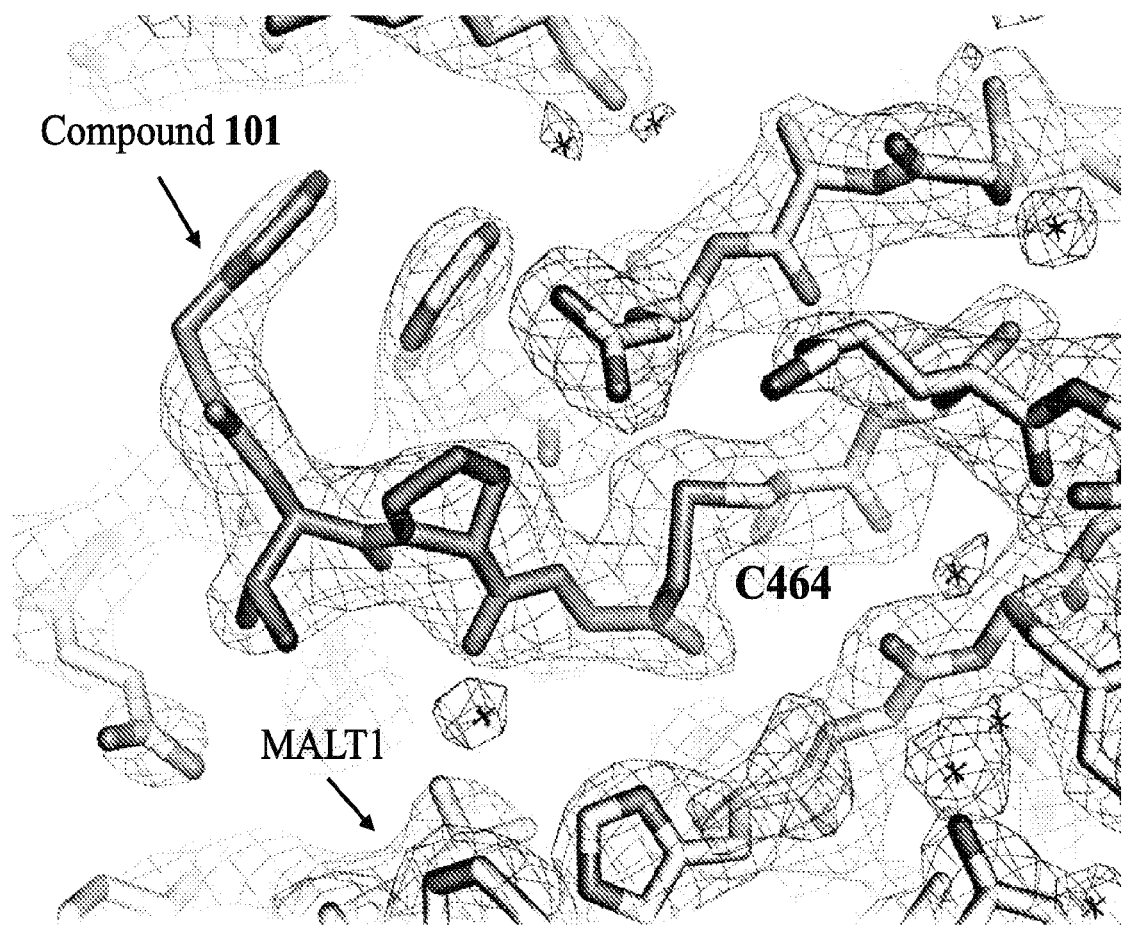
FIG. 3 shows a co-crystal structure of compound 101 and MALT1. Compound 101 is in the MALT1 paracaspase pocket.

Compound 101 was incubated with MALT1 to form a complex, and the complex was purified and crystallized for structure determination. X-ray diffraction data was collected, and the compound 101-MALT1 structure was solved in 2.0 angstrom resolution. Exemplary results are shown in FIG. 3. FIG. 3 indicates the formation of a covalent bond between: (1) the carbon atom to which the fluorine atom is directly attached in compound 101; and (2) the sulfur atom of the Cys464 residue of MALT1. Exemplary evidence for the formation of the covalent bond is the existence of continuous electron density from compound 101 to the Cys464 residue of MALT1. The electron density is 2Fo–Fc map contoured at 1.0 sigma.

Biological Assays of the Compounds

Inhibition Constants ($K_i$'s)

For exemplary compounds of the disclosure, $K_i$ for inhibition of MALT1 was measured (Table E11). A concentration of 100 nM MALT1 was used for the assay.

Cell Growth Inhibition Assays

DLBCL cell lines were grown in exponential growth conditions during the 96 hours of treatment. Cells were treated twice: at t=0 and t=48 hours, and cell viability was determined by ATP quantification using a luminescent method (CELLTITER-GLO, Promega, Madison, Wis.). Cell viability in drug-treated cells was normalized to vehicle controls (fractional viability) and results are given as 1-fractional viability. PRISM GRAPHPAD software (Biosoft, Cambridge, UK) was used to determine the drug concentration that inhibits the growth of cell lines by 50% compared to control ($GI_{50}$).

Experiments were Performed in Triplicate.

Western blot: OCI-Ly3 cells (a line of human diffuse large B-cell lymphoma (ABC type)) were pre-treated for 30 minutes with indicated doses of MALT1 inhibitors followed by a 2-hour treatment with proteasome inhibitor MG-132 at 5 μM. Protein was then extracted in a PBS-based lysis buffer containing 1% NP-40. Equal amounts of total protein (50 to 75 μg) were separated on sodium dodecyl sulfate-polyacrylamide gel electrophoresis (SDS-PAGE), and electrotransferred onto nitrocellulose membranes. Membranes were incubated with primary antibodies (MALT1, from Santa Cruz Biotechnologies, Santa Cruz, Calif.; RELB from Cell Signaling, Danvers, Mass., and α-Tubulin from Sigma), followed by secondary antibodies conjugated to horseradish peroxidase, which were detected by chemiluminescence (Pierce, Thermo Scientific, Rockford, Ill.).

Exemplary results of the cell growth inhibition assays are shown in Table E11.

TABLE E11

Enzyme $K_i$ and OCI-LY3 $GI_{50}$ of exemplary compounds

| Compound | MALT1 $K_i$ (nM) | OCI-LY3 $GI_{50}$ (μM) |
|---|---|---|
| 101 | 40 | 8.52 |
| 102 | 44 | 1.45 |
| 103 | 43 | 1.44 |
| 104 | 154 | 8.05 |
| 105 | 55 | 4.26 |
| 106 | 146 | 8.43 |
| 107 | 40 | 0.73 |
| 108 | 37 | 1.33 |
| 109 | 53 | 0.29 |
| 110 | 49 | 1.07 |
| 111 | 158 | 10.5 |
| 112 | 808 | >20 |
| 113 | 40 | 0.66 |
| 114 | 105 | 4.24 |
| 115 | 41 | 0.53 |
| 116 | 10 | 0.13 |
| 117 | 42 | 3.37 |
| 118 | 46 | 2.91 |
| 119 | 43 | 1.88 |
| 120 | 56 | 0.94 |
| 121 | 109 | 7.29 |
| 122 | 75 | 2 |
| 123 | 50 | 1.67 |
| 124 | 100 | 16.8 |
| 125 | 52 | 9.65 |
| 126 | 60 | 6.66 |
| 127 | 75 | >20 |
| 128 | 111 | >20 |
| 129 | 52 | 1.52 |
| 130 | 66 | 3.72 |
| 201 | — | >5 |
| 202 | 90 | 1.05 |
| 203 | — | 0.819 |
| 204 | 120 | — |
| 205 | >200 | — |
| 131 | 58 | 14.5 |
| 132 | 175 | >20 |
| 133 | 54 | >20 |
| 134 | 39 | 3.69 |
| 135 | 132 | 0.12 |
| 136 | 67 | 1.24 |

TABLE E11-continued

Enzyme K_i and OCI-LY3 GI_50 of exemplary compounds

| Compound | MALT1 $K_i$ (nM) | OCI-LY3 $GI_{50}$ (µM) |
|---|---|---|
| 137 | 30 | 0.55 |
| 138 | — | 1.24 |
| 139 | 121 | 1.75 |
| 140 | 64 | 0.29 |
| 141 | — | — |
| 142 | >1000 | 14.1 |
| 143 | 45 | 0.13 |
| 144 | 79 | 0.46 |
| 145 | 27 | 0.7 |
| 146 | 13 | 0.5 |
| 147 | 24 | 0.55 |
| 148 | 15 | 0.53 |
| 149 | 64 | — |
| 150 | — | — |
| 151 | 78 | — |
| 152 | 47 | — |
| 153 | 102 | 0.16 |
| 154 | 36 | 0.11 |
| 155 | 55 | 0.57 |
| 156 | 40 | 3.88 |
| 157 | 59 | 0.63 |
| 158 | 110 | 1.7 |
| 159 | 139 | 4.22 |
| 160 | 13 | 2.34 |
| 161 | 346 | 0.91 |
| 162 | 45 | 0.98 |
| 163 | 22 | 0.27 |
| 164 | 62 | 0.78 |
| 165 | 27 | 0.52 |
| 166 | 557 | — |
| 167 | 24 | — |
| 168 | 32 | — |
| 169 | 22 | — |
| 170 | 27 | — |
| 171 | 50 | 0.07 |
| 172 | 34 | 0.06 |
| 173 | 46 | 0.24 |
| 174 | 20 | 0.12 |
| 175 | 70 | 0.46 |
| 176 | 118 | 0.77 |
| 177 | 28 | — |
| 178 | 38 | — |
| 179 | 71 | 0.81 |
| 180 | 30 | 2.44 |
| 181 | 1185 | 4.31 |
| 182 | 76 | 2.30 |
| 183 | 40 | 0.85 |
| 184 | 93 | 5.49 |
| 185 | 182 | 1.10 |
| 186 | 448 | 1.37 |
| 187 | 122 | — |

Maximum Killing Effects on Select Cell-Lines

The maximum killing effects on cell-lines OCI-LY3, TMD8, and OCI-LY1 were also measured for select compounds at inhibitor concentration of 20 µM and 5 µM. TMD8 is another line of ABC type diffuse large-B cell lymphoma, while OCI-LY1 is a DLBCL line of the germinal center B-cell subtype. Table E12 lists the measured killing effect for Z-VRPR-fmk, mepazine, and exemplary compounds of the disclosure at concentration of 20 µM or 5 µM.

TABLE E12

Maximum killing effect for exemplary compounds with DLBCL cell lines.

| Compound | OCI-LY3 | | TMD8 | | OCI-LY1 | |
|---|---|---|---|---|---|---|
|  | 20 µM | 5 µM | 20 µM | 5 µM | 20 µM | 5 µM |
| Z-VRPR-fmk | 62% | 42% | 67% | 27% | <0% | <0% |
| mepazine | 97% | 35% | 99% | 32% | 82% | 6% |
| 101 | 79% | 70% | 63% | 50% | 7% | <0% |
| 102 | 85% | — | 54% | — | 19% | — |
| 107 | 85% | 38% | 58% | 29% | 11% | 3% |
| 112 | 51% | 28% | 66% | — | 2% | 5% |
| 114 | 80% | — | 40% | — | 9% | — |
| 115 | 84% | — | 64% | — | 15% | — |
| 116 | 90% | — | 76% | — | 19% | — |
| 120 | 81% | — | 52% | — | <0% | — |
| 202 | 87% | 71% | 59% | — | <0% | 6% |
| 203 | 79% | — | 59% | — | 3% | — |

Figure 1B:
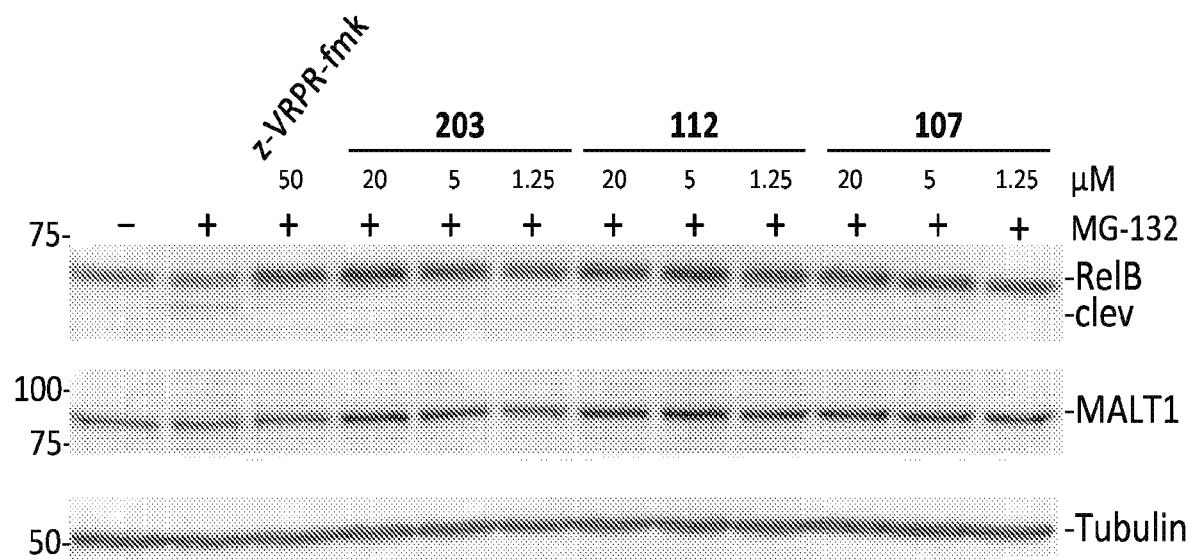
FIG. 1B. Western blots for RelB with indicated doses of compounds or vehicle in OCI-LY3.
Figure 2:
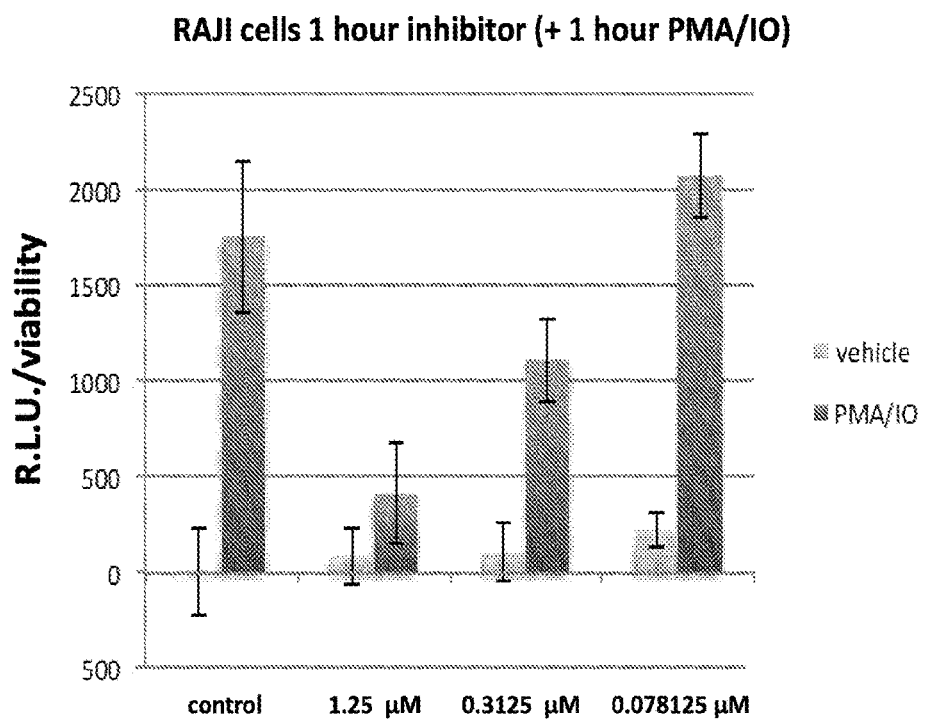
FIG. 2. Dose-response effect of compound 202 in luciferase activity of MALT1 GLOSENSOR™ reporter. Luciferase activity is increased by MALT1 cleavage of the reporter protein. RAJI (Burkitt's lymphoma) cells were treated with different concentrations of 202 for 1 hour, and subsequently stimulated with phorbol myristate acetate+ionomycin (PMA/IO) for 1 hour.

Western blots for RelB and MALT1 show inhibition of RelB cleavage by inhibitors 202, 109, 116, 203, 112, and 107. OCI-LY3 cells were pretreated with the an inhibitor at the desired concentration and subsequently treated with 5 µM MG-132, a proteasome inhibitor, for 2 hours. Results are shown in FIGS. 1A and 1B.

REFERENCES

1. Swerdlow, S. H., Campo, E., Harris, N. L., Jaffe, E. S., Pileri, S. A., Stein, H., Thiele, J., Vardiman, J. W (2008). World Health Organization Classification of Tumours of Haematopoietic and Lymphoid Tissues, (Lyon: IARC Press).
2. Alizadeh, A. A., Eisen, M. B., Davis, R. E., Ma, C, Lossos, I. S., Rosenwald, A., Boldrick, J. C., Sabet, H., Tran, T., Yu, X., et al. (2000). Distinct types of diffuse large B-cell lymphoma identified by gene expression profiling. Nature. 403, 503-511.
3. Rosenwald, A., Wright, G., Chan, W. C, Connors, J. M., Campo, E., Fisher, R. I., Gascoyne, R. D., Muller-Hermelink, H. K., Smeland, E. B., Giltnane, J. M., et al. (2002). The use of molecular profiling to predict survival after chemotherapy for diffuse large-B-cell lymphoma. New Eng. J. Med. 346, 1937-1947.
4. Davis, R. E., Ngo, V. N., Lenz, G., Tolar, P., Young, R. M., Romesser, P. B., Kohlhammer, H., Lamy, L., Zhao, H., Yang, Y., et al. (2010). Chronic active B-cell-receptor signalling in diffuse large B-cell lymphoma. Nature. 463, 88-92.
5. Afonina, I. S., Elton, L. Carpentier, I., Beyaert, R. (2015). FEBS Journal. DOI: 10.1111/febs.13325.
6. Ruefli-Brasse, A. A., French, D. M., and Dixit, V. M. (2003). Regulation of NF-κB-dependent lymphocyte activation and development by paracaspase. Science. 302, 1581-1584.
7. Ruland, J., Duncan, G. S., Wakeham, A., and Mak, T. W. (2003). Differential requirement for MALT1 in T and B cell antigen receptor signaling. Immunity. 19, 749-758.
8. Rebeaud, F., Hailfinger, S., Posevitz-Fejfar, A., Tapernoux, M., Moser, R., Rueda, D., Gaide, O., Guzzardi, M., Iancu, E. M., Rufer, N., et al. (2008). The proteolytic activity of the paracaspase MALT1 is key in T cell activation. Nat Immunol 9, 272-281.
9. Coornaert, B., Baens, M., Heyninck, K., Bekaert, T., Haegman, M., Staal, J., Sun, L., Chen, Z. J., Marynen, P., Beyaert, R. (2008) T cell antigen receptor stimulation induces MALT1 paracaspase-mediated cleavage of the NF-kappaB inhibitor A20. Nat Immunol. 9, 263-271.
10. Staal, J., Driege, Y., Bekaert, T., Demeyer, A., Muyllaert, D., Van Damme, P., Gevaert, K., Beyaert, R. (2011) T-cell receptor-induced JNK activation requires proteolytic inactivation of CYLD by MALT1. *EMBO J.* 30, 1742-1752.
11. Hailfinger, S., Nogai, H., Pelzer, C., Jaworski, M., Cabalzar, K., Charton, J. E., Guzzardi, M., Decaillet, C., Grau, M., Dorken, B., et al. (2011) Malt1-dependent RelB cleavage promotes canonical NF-kappaB activation in lymphocytes and lymphoma cell lines. *PNAS.* 108, 14596-14601.
12. Jeltsch, K. M., Hu, D., Brenner, S., Zoller, J., Heinz, G. A., Nagel, D., Vogel, K. U., Rehage, N., Warth, S. C., Edelmann, S. L. et al., (2014) Cleavage of roquin and regnase-1 by the paracaspase MALT1 releases their cooperatively repressed targets to promote T(H)17 differentiation. *Nat. Immunol.* 15, 1079-1089.
13. Uehata, T., Iwasaki, H., Vandenbon, A., Matsushita, K., Hernandez-Cuellar, E., Kuniyoshi, K., Satoh, T., Mino, T., Suzuki, Y., Standley, D. M. et al., (2013) Malt1-induced cleavage of regnase-1 in CD4(+) helper T cells regulates immune activation. *Cell.* 153, 1036-1049.
14. Rosebeck, S., Madden, L., Jin, X., Gu, S., Apel, I. J., Appert, A., Hamoudi, R. A., Noels, H., Sagaert, X., Van Loo, P. et al., (2011) Cleavage of NIK by the API2-MALT1 fusion oncoprotein leads to noncanonical NF-kappaB activation. *Science.* 331, 468-472.
15. Nie, Z., Du, M. Q., McAllister-Lucas, L. M., Lucas, P. C., Bailey, N. G., Hogaboam, C. M., Lim, M. S., Elenitoba-Johnson, K. S. (2015) Conversion of the LIMA1 tumour suppressor into an oncogenic LMO-like protein by API2-MALT1 in MALT lymphoma. *Nat. Commun.* 6, 5908.
16. Baens, M., Bonsignore, L., Somers, R., Vanderheydt, C., Weeks, S. D., Gunnarsson, J., Nilsson, E., Roth, R. G., Thome, M., Marynen, P. (2014) MALT1 autoproteolysis is essential for NF-κB-dependent gene transcription in activated lymphocytes. *PLoS ONE.* 9, e103774.
17. Farinha, P., Gascoyne, R. D. (2005). Molecular pathogenesis of mucosa-associated lymphoid tissue lymphoma. *J. Clinical Oncology.* 23, 6370-6378.
18. Hailfinger, S., Lenz, G., Ngo, V., Posvitz-Fejfar, A., Rebeaud, F., Guzzardi, M., Penas, E. M., Dierlamm, J., Chan, W. C, Staudt, L. M., Thome, M. (2009). Essential role of MALT1 protease activity in activated B cell-like diffuse large B-cell lymphoma. *PNAS.* 106, 19946-19951.
19. Nagel, D., Spranger, S., Vincendeau, M., Grau, M., Raffegerst, S., Kloo, B., Hlahla, D., Neuenschwander, M., von Kries J. P., Hadian, K., Dorken, B., Lenz, P., Lenz, G., Schendel, D., Krappmann, D. (2012) Pharmacologic inhibition of MALT1 protease by phenothiazines as a therapeutic approach for the treatment of aggressive ABC-DLBCL. *Cancer Cell.* 22, 825-837.
20. Fontan, L., Yang, C., Kabaleeswaran, V., Volpon, L., Osborne, M. J., Beltran, E., Garcia, M., Cerchietti, L., Shaknovich, R., Yang, S. N., Fang, F., Gascoyne, R. D., Martinez-Climent, J. A., Glickman, J. F., Borden, K., Wu, H., Melnick, A. (2012) MALT1 small molecule inhibitors specifically suppress ABC-DLBCL in vitro and in vivo. *Cancer Cell.* 22, 812-824.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(S) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The dipeptide acid intermediates were prepared in a similar manner to ((benzyloxy)carbonyl)-L-valyl-L-proline (DA-101), and are listed in Table E2, along with characterization data and the corresponding dipeptide ester from which they were prepared.

Dipeptide esters DE-102-DE-105, DE-A1, and DE-A2 were prepared in a similar manner to methyl ((benzyloxy)carbonyl)-L-valyl-L-prolinate (DE-101) from the corresponding acid and methyl L-prolinate. Dipeptide esters DE-107 and DE-108 were prepared from the corresponding acid and methyl (S)-piperidine-2-carboxylate. Dipeptide esters DE-109-DE-111 and DE-140 were prepared from ((benzyloxy)carbonyl)-L-valine and the corresponding proline and serine esters. Dipeptide esters DE-113, DE-115 to DE-139, DE-145 to DE-148, and DE-151 to DE-159 were prepared in a similar manner to methyl (2-bromobenzoyl)-L-valyl-L-prolinate (DE-114) from methyl L-valyl-L-prolinate and the corresponding acid, acid chloride, isocyanate, or sulfonyl chloride. Dipeptide esters DE-142 to DE-144 and DE-149 were prepared from 4-bromobenzoyl chloride and the corresponding esters. Dipeptide esters DE-160, DE-162, DE-163 and DE-171 to DE-186 were prepared in a similar manner to DE-101 or DE-114 from the corresponding amine ester and acid or acid chloride in Table E3.

Dipeptide esters used as intermediates are summarized in Table E3 with characterization data and corresponding starting materials.

solvent was removed under reduced pressure to give a white solid (0.8 g, 99% yield). MS (m/z): 229.7 [M+1]$^+$.

Methyl ((4-chlorophenyl)carbamoyl)-L-valyl-L-prolinate (DE-164)

Triphosgene (0.28 g, 0.94 mmol) was added to a solution of 3-chloroaniline (0.27 g, 2.1 mmol) and triethylamine (0.96 g, 9.5 mmol) in dichloromethane (10 mL) at 5° C. The reaction was stirred for 30 min at 5° C. and methyl L-valyl-L-prolinate (0.5 g, 1.9 mmol) was added. The reaction was stirred for another 30 min at 5° C., quenched with water (20 mL) and extracted with dichloromethane (3×20 mL). The organic extracts were combined, dried over anhydrous sodium sulfate, and concentrated. The residue was purified by silica chromatography (Hexanes:EA=3:1) to give the title compound (440 mg, 61% yield). MS (m/z): 382.39 [M+1]$^+$.

Dipeptide Esters DE-165 and DE-167 were prepared in a similar manner to DE-164 from the corresponding aniline and methyl L-valyl-L-prolinate.

Methyl (((4-chlorobenzyl)oxy)carbonyl)-L-valyl-L-prolinate (DE-168)

A solution of methyl ((S)-2-isocyanato-3-methylbutanoyl)-L-prolinate (0.93 g, 3.6 mmol), 4-chlorobenzyl alcohol (0.54 g, 3.9 mmol), and triethylamine (0.75 g, 7.4 mmol) in acetonitrile (20 mL) was refluxed for 2 hours. The solvent was removed under reduced pressure, and the residue dissolved in ethyl acetate (20 mL) and washed with 5% KHSO$_4$ solution. The organic layer was dried over anhydrous sodium sulfate, concentrated and the residue purified by silica chromatography (PE:EA=4:1) to give the title compound (0.78 g, 52%). $^1$H NMR (CDCl$_3$, 400 MHz) δ: 7.32 (d, 2H), 7.28 (d, 2H), 5.47 (d, 1H), 5.04 (m, 2H), 4.52 (m, 1H), 4.33 (m, 1H), 3.73 (m, 1H), 3.71 (s, 3H), 3.66 (m, 1H), 2.24 (m, 1H), 2.03 (m, 4H), 1.05 (d, 3H), 0.94 (d, 3H). MS (m/z): 397.08 [M+1]$^+$.

Dipeptide Esters DE-169 and DE-170 were prepared in a similar manner to DE-168 from the corresponding alcohol and methyl ((S)-2-isocyanato-3-methylbutanoyl)-L-prolinate.

Methyl ((S)-2-isocyanato-3-methylbutanoyl)-L-prolinate

Triphosgene (1.11 g, 3.7 mmol) was added in portions to a mixture of methyl L-valyl-L-prolinate (3 g, 11.4 mmol) and sodium bicarbonate (4.8 g, 56.8 mmol) in DCM/water (60 mL/45 mL) at 5° C. The reaction was stirred for 5 min at 5° C. The organic layer was separated and the water phase was re-extracted with dichloromethane (50 mL×2). The organic extracts were combined, dried over anhydrous sodium sulfate, and concentrated to give the title compound (2.8 g, 97%), which was used without further purification.

Amino Esters AE-1 to AE-11 were prepared in a similar manner to methyl L-valyl-L-prolinate (DE-A3), by deprotection of the coupling products of the corresponding acid starting materials and amine starting materials are shown in Table E6.

Acids 1 to 3 were prepared by coupling of 4-bromobenzoyl chloride and the corresponding amines, followed by hydrolysis of the methyl ester in the case of acid 1.

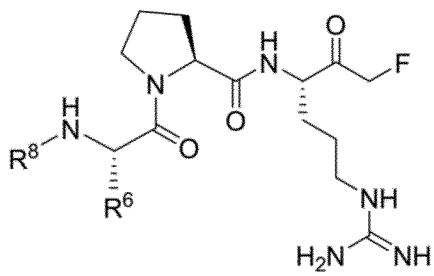

What is claimed is:

1. A compound of Formula (I):

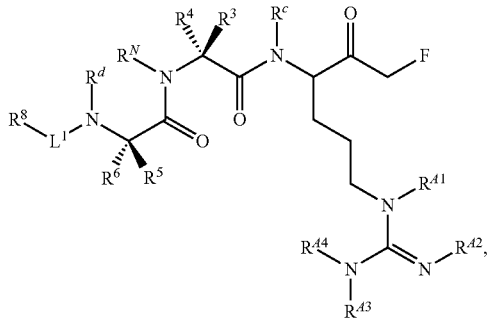

or a pharmaceutically acceptable salt, stereoisomer, or tautomer thereof, wherein:

$R^3$ is hydrogen, halogen, optionally substituted alkyl, optionally substituted carbocyclyl, optionally substituted heterocyclyl, optionally substituted aryl, or optionally substituted heteroaryl;

$R^4$ is hydrogen, halogen, or optionally substituted alkyl;

$R^N$ is hydrogen, optionally substituted alkyl, optionally substituted acyl, or a nitrogen protecting group;

or $R^N$ and either $R^3$ or $R^4$ are joined to form an optionally substituted heterocyclic ring, or $R^3$ and $R^4$ are joined to form an optionally substituted carbocyclic or optionally substituted heterocyclic ring;

$R^5$ is hydrogen, halogen, optionally substituted alkyl, optionally substituted carbocyclyl, optionally substituted heterocyclyl, optionally substituted aryl, or optionally substituted heteroaryl;

$R^6$ is hydrogen, halogen, optionally substituted alkyl, optionally substituted carbocyclyl, optionally substituted heterocyclyl, optionally substituted aryl, or optionally substituted heteroaryl;

or $R^5$ and $R^6$ are joined to form an optionally substituted carbocyclic or optionally substituted heterocyclic ring;

$R^8$ is optionally substituted alkyl, optionally substituted carbocyclyl, optionally substituted heterocyclyl, —C(=O)$R^{8b}$, —C(=O)N($R^{8a}$)$_2$, —S(=O)$_2R^{8a}$, or of formula

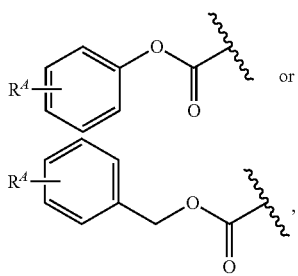

wherein each instance of $R^A$ is independently hydrogen, halogen, optionally substituted alkyl, optionally substituted carbocyclyl, cyano, optionally substituted heterocyclyl, optionally substituted aryl, optionally substituted heteroaryl, or optionally substituted acyl;

each occurrence of $R^{8a}$ and $R^{8b}$ is independently hydrogen, optionally substituted alkyl, optionally substituted alkenyl, optionally substituted carbocyclyl, optionally substituted heterocyclyl, optionally substituted aryl, optionally substituted heteroaryl, optionally substituted acyl, an oxygen protecting group when attached to an oxygen atom, or a nitrogen protecting group when attached to a nitrogen atom, or two $R^{8a}$ are joined to form an optionally substituted heterocyclic or optionally substituted heteroaryl ring;

$L^1$ is a bond, an amino acid, or a dipeptide;

each of $R^c$ and $R^d$ is independently hydrogen, optionally substituted alkyl, optionally substituted acyl, or a nitrogen protecting group;

$R^{A1}$ is hydrogen, optionally substituted alkyl, optionally substituted acyl, optionally substituted sulfonyl, or a nitrogen protecting group; and each of $R^{A2}$, $R^{A3}$, and $R^{A4}$ is independently hydrogen, unsubstituted methyl, methyl substituted with one or more halogen, optionally substituted $C_{2-10}$ alkyl, —C(=O)$R^f$, —C(=O)NH($R^f$), —C(=O)N($R^f$)$_2$, optionally substituted sulfonyl, or a nitrogen protecting group selected from the group consisting of formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, phenacylsulfonamide, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys), wherein each occurrence of $R^f$ is independently hydrogen, optionally substituted alkyl, optionally substituted carbocyclyl, optionally substituted heterocyclyl, optionally substituted aryl, optionally substituted heteroaryl, optionally substituted acyl, or a nitrogen protecting group when attached to a nitrogen atom, or two $R^f$ are joined to form an optionally substituted heterocyclic or optionally substituted heteroaryl ring;

or any two of $R^{41}$, $R^{42}$, $R^{43}$, and $R^{44}$ are joined to form an optionally substituted heterocyclic or optionally substituted heteroaryl ring;

provided the compound is not of formula:

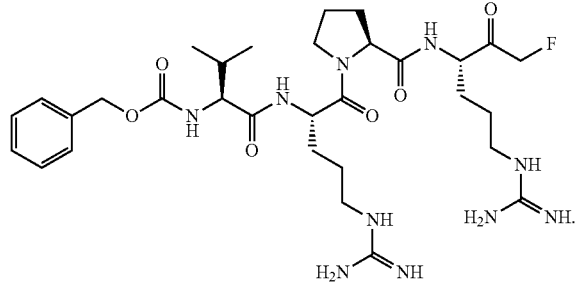 [SMILES: CC(C)[C@H](NC(=O)OCc1ccccc1)C(=O)N[C@@H](CCCNC(=N)N)C(=O)N1CCC[C@H]1C(=O)N[C@@H](CCCNC(=N)N)C(=O)CF]

2. The compound of claim 1, or a pharmaceutically acceptable salt, stereoisomer, or tautomer thereof, wherein $R^5$ is hydrogen, halogen, or optionally substituted alkyl.

3. The compound of claim 1, or a pharmaceutically acceptable salt, stereoisomer, or tautomer thereof, wherein:

$R^5$ is hydrogen, halogen, or optionally substituted alkyl;

each occurrence of $R^{8a}$ and $R^{8b}$ is independently hydrogen, optionally substituted alkyl, optionally substituted carbocyclyl, optionally substituted heterocyclyl, optionally substituted aryl, optionally substituted heteroaryl, optionally substituted acyl, an oxygen protecting group when attached to an oxygen atom, or a nitrogen protecting group when attached to a nitrogen atom, or two $R^{8a}$ are joined to form an optionally substituted heterocyclic or optionally substituted heteroaryl ring.

4. The compound of claim 1, wherein the compound is of Formula (I-A), (I-B), or (I-D):

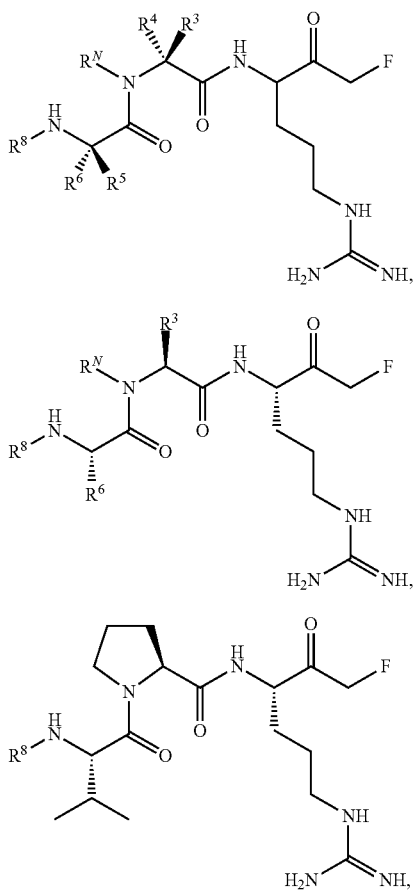

(I-A)

(I-B)

or (I-D)

or a pharmaceutically acceptable salt or tautomer thereof.

5. The compound of claim 1, or a pharmaceutically acceptable salt, stereoisomer, or tautomer thereof, wherein $R^3$ and $R^N$ are joined to form an optionally substituted 4-6-membered heterocyclic ring.

6. The compound of claim 1, or a pharmaceutically acceptable salt, stereoisomer, or tautomer thereof, wherein $R^3$ is of formula:

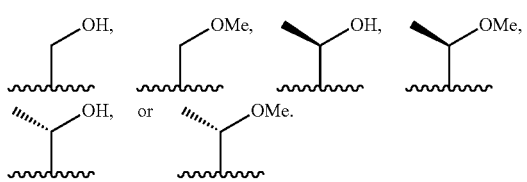

7. The compound of claim 1, or a pharmaceutically acceptable salt, stereoisomer, or tautomer thereof, wherein $R^4$ and $R^N$ are joined to form an optionally substituted 5-membered heterocyclic ring.

8. The compound of claim 1, or a pharmaceutically acceptable salt, stereoisomer, or tautomer thereof, wherein $R^4$ is hydrogen.

9. The compound of claim 1, or a pharmaceutically acceptable salt, stereoisomer, or tautomer thereof, wherein $R^5$ and $R^6$ are each unsubstituted $C_{1-12}$ alkyl.

10. The compound of claim 1, or a pharmaceutically acceptable salt, stereoisomer, or tautomer thereof, wherein $R^5$ and $R^6$ are joined to form an optionally substituted 3-6-membered carbocyclic or optionally substituted 3-6-membered heterocyclic ring.

11. The compound of claim 1, or a pharmaceutically acceptable salt, stereoisomer, or tautomer thereof, wherein $R^6$ is optionally substituted 5-6-membered carbocyclyl or optionally substituted 5-6-membered heterocyclyl.

12. The compound of claim 1, or a pharmaceutically acceptable salt, stereoisomer, or tautomer thereof, wherein $R^6$ is unsubstituted $C_{1-12}$ alkyl.

13. The compound of claim 1, or a pharmaceutically acceptable salt, stereoisomer, or tautomer thereof, wherein $R^6$ is of formula:

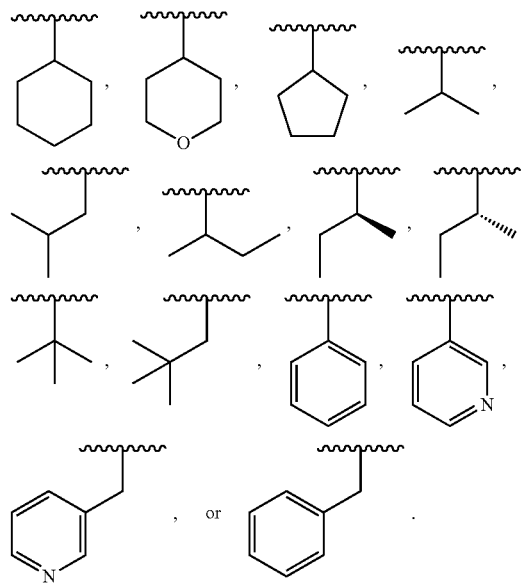

14. The compound of claim 1, or a pharmaceutically acceptable salt, stereoisomer, or tautomer thereof, wherein $R^8$ is —C(=O)$R^{8b}$, —C(=O)N($R^{8a}$)$_2$, or of formula

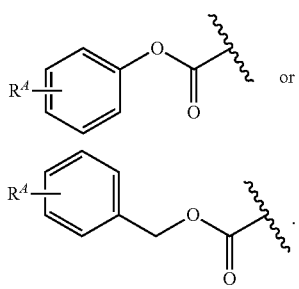

15. The compound of claim 1, wherein the compound is of formula:

337
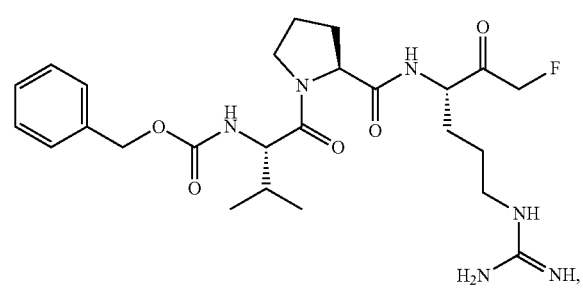
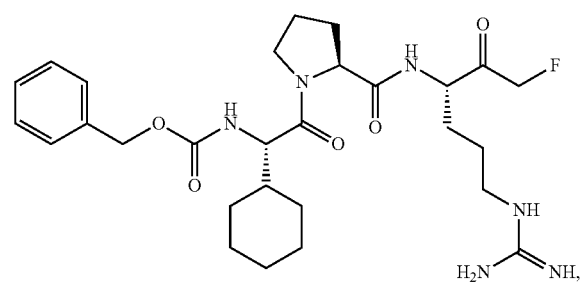
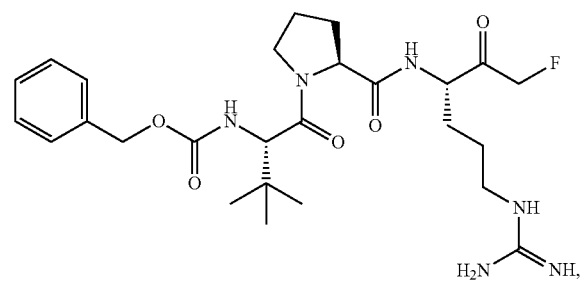
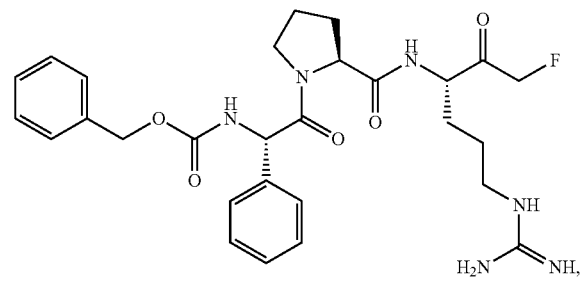
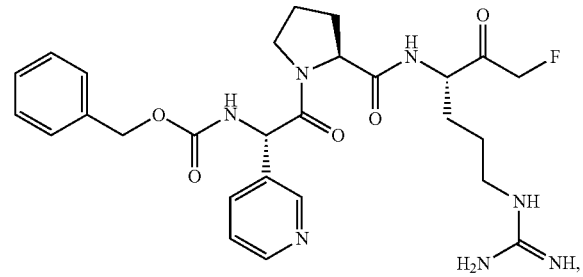
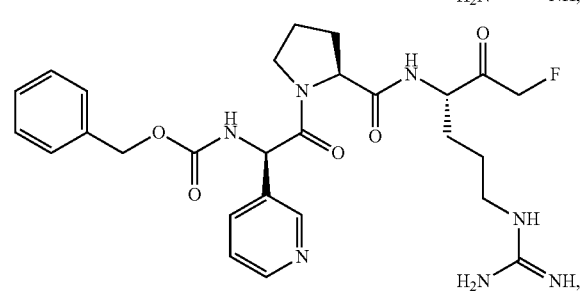
338
-continued
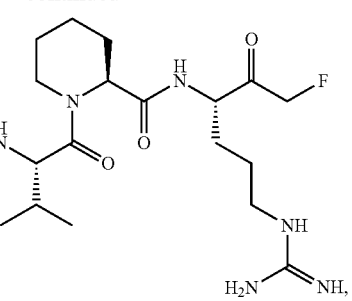
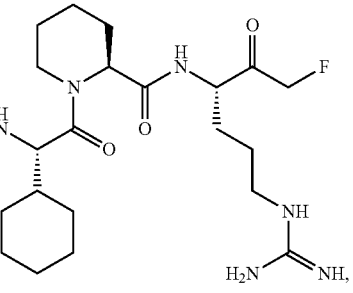
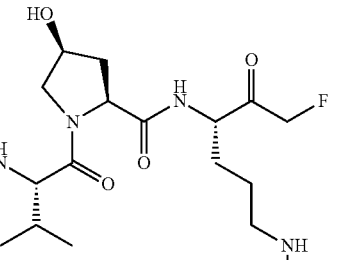
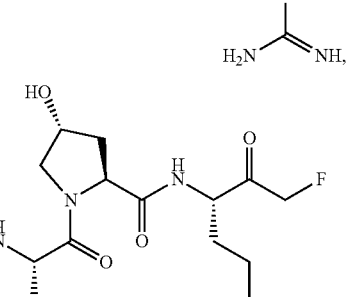
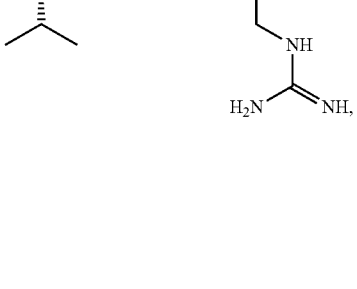

339
-continued
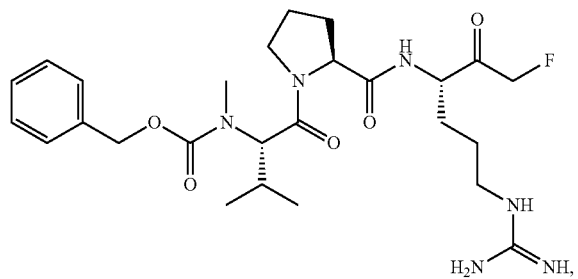
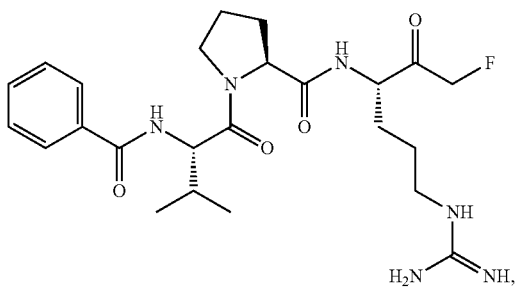
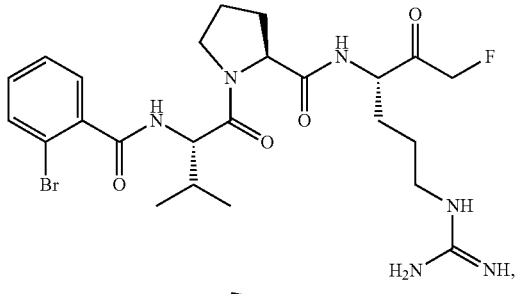
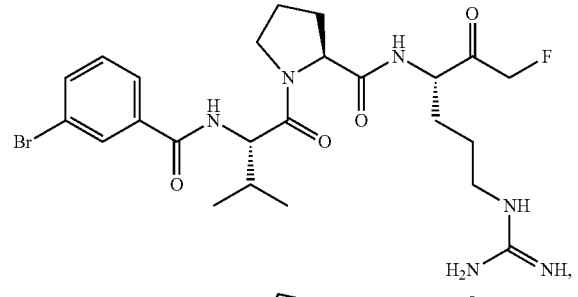
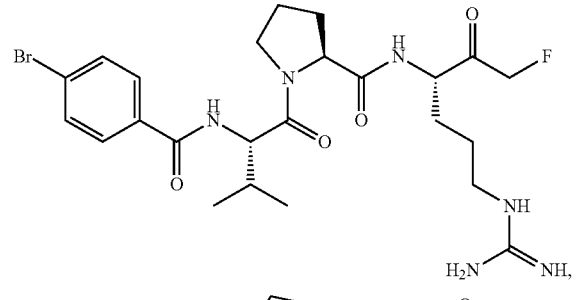
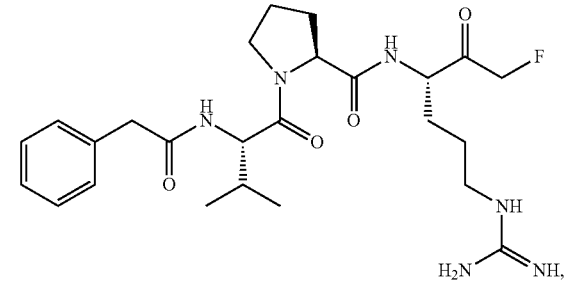
340
-continued
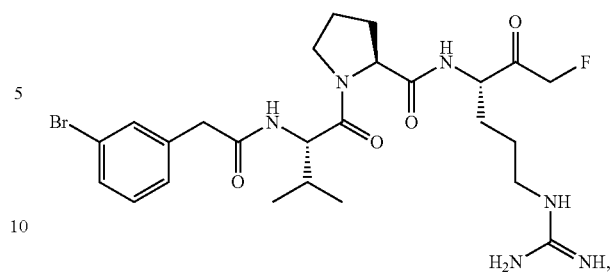
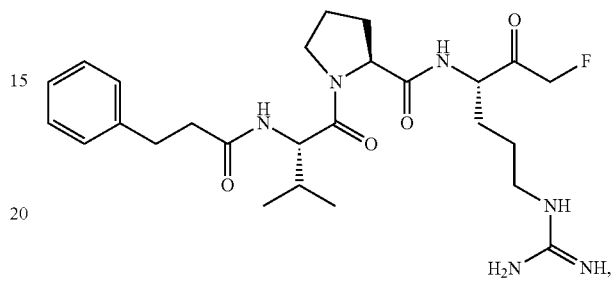
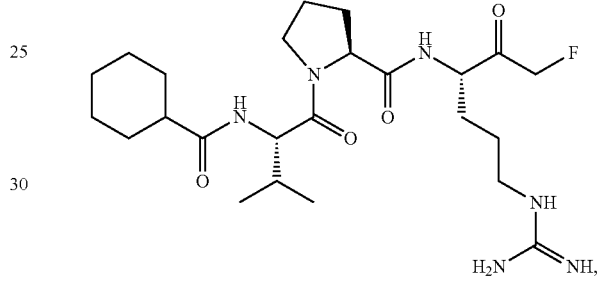
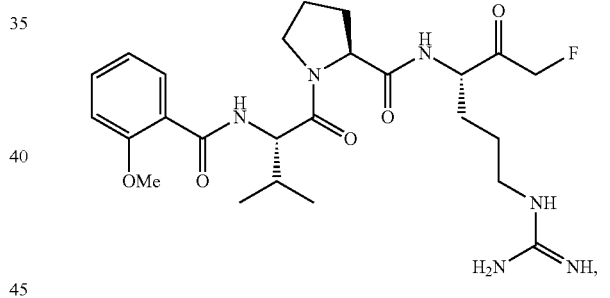
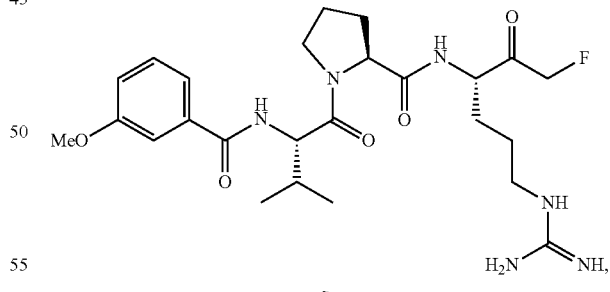
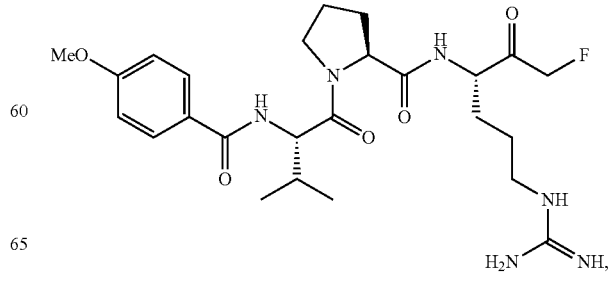

341
-continued
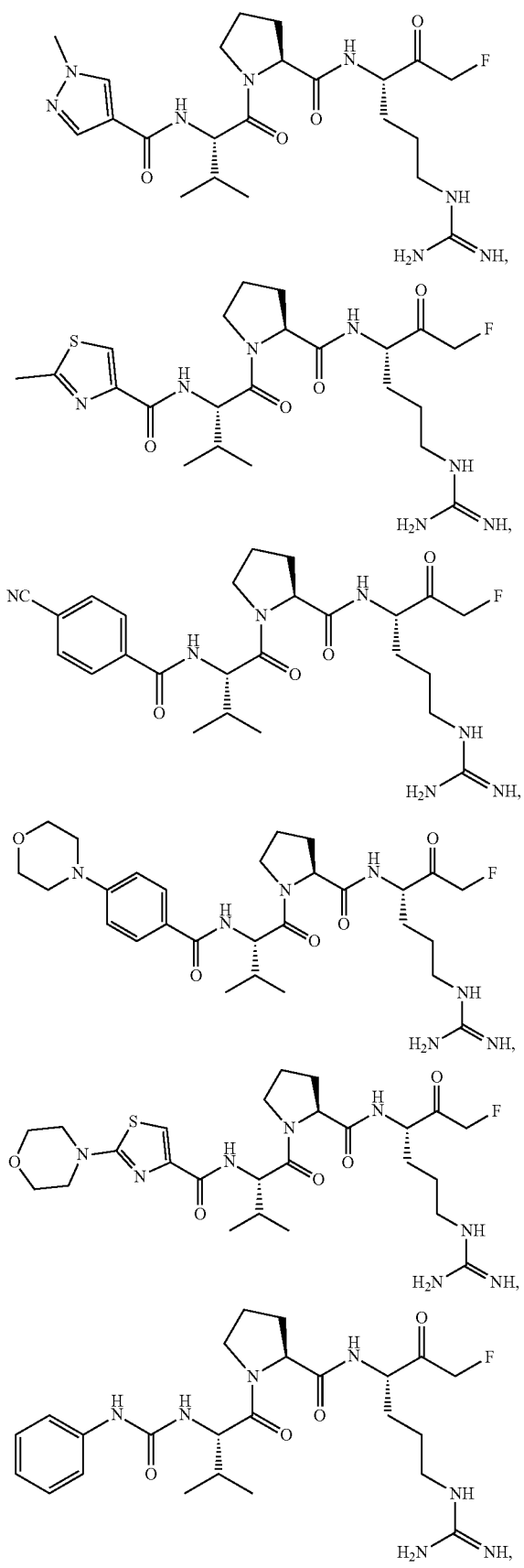
342
-continued
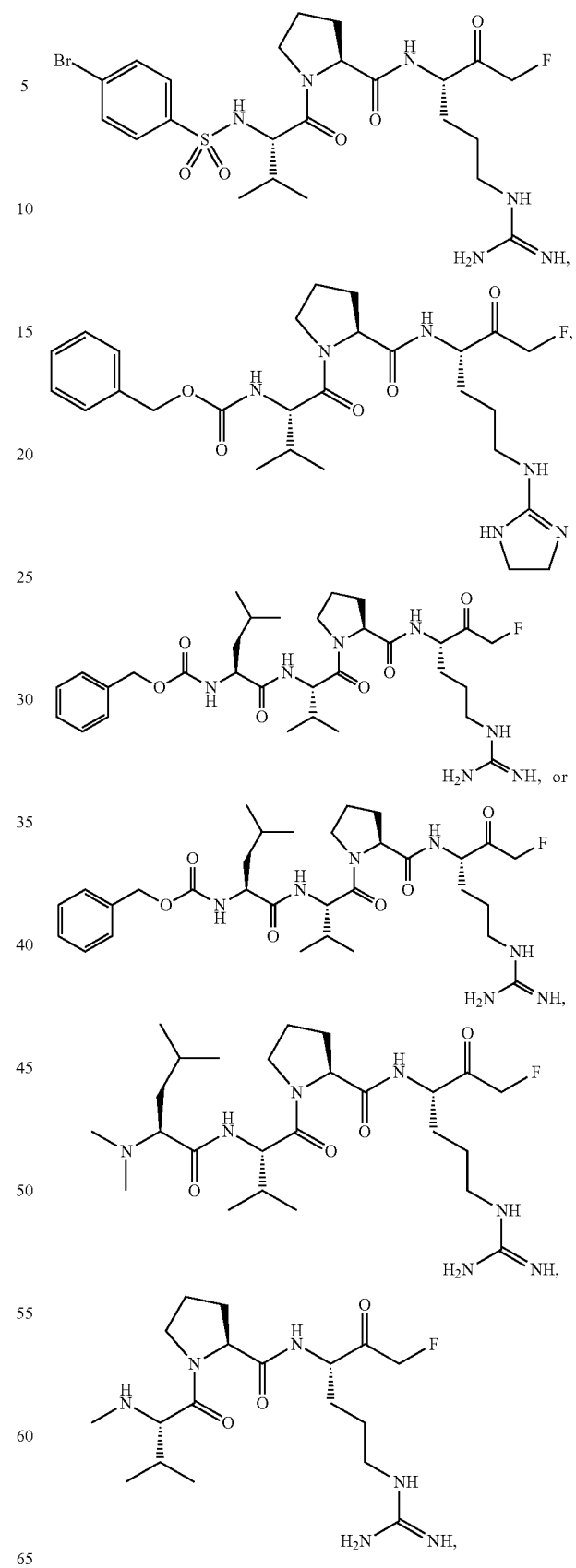

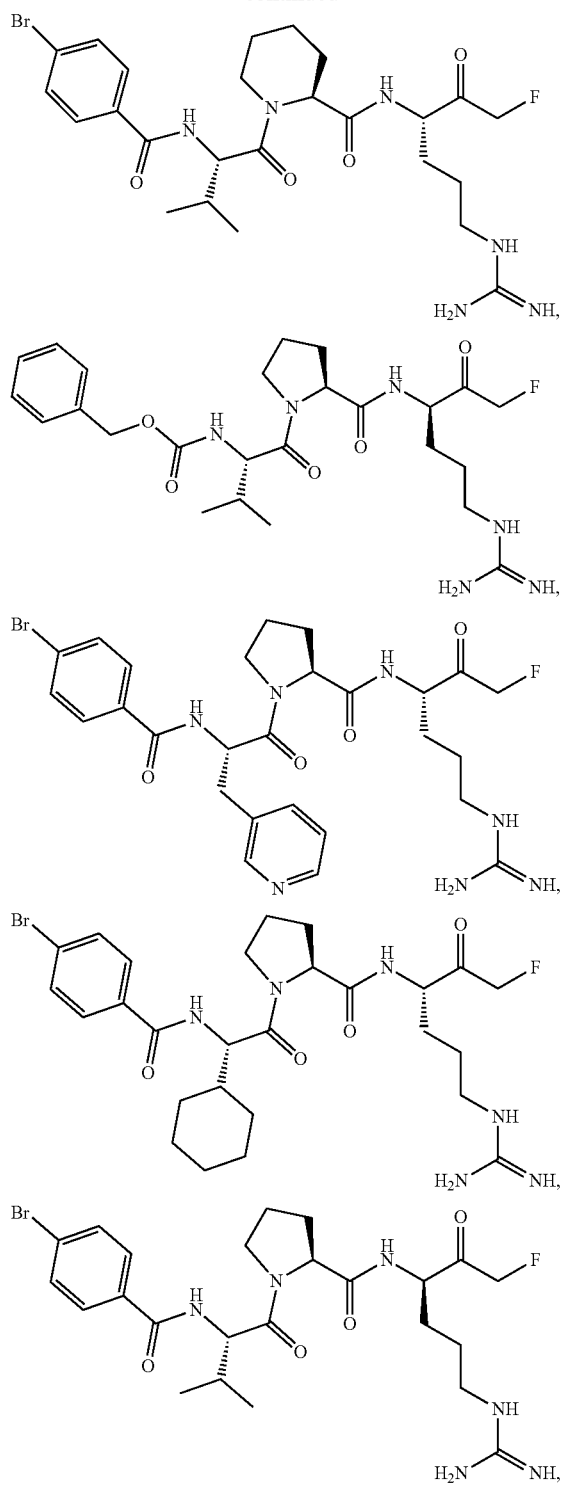
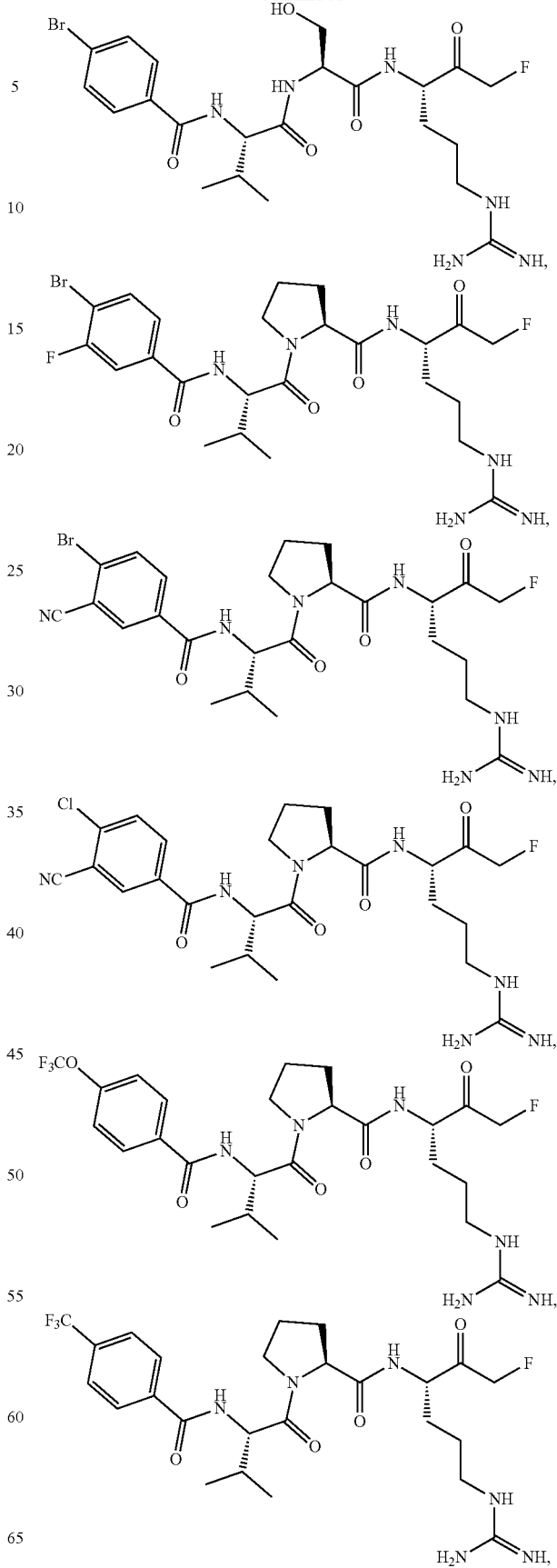

345
-continued
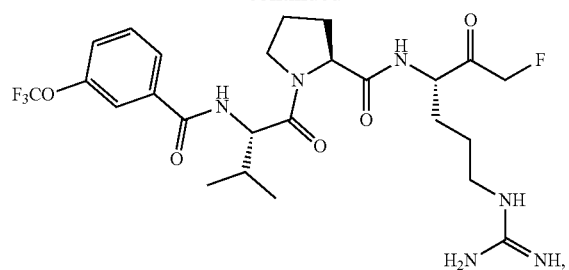
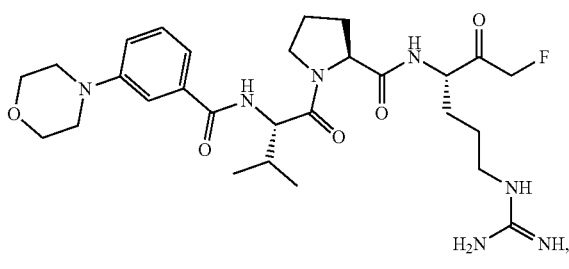
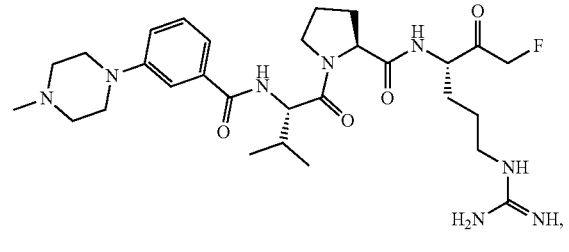
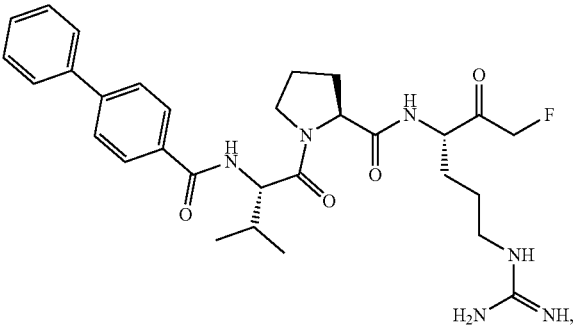
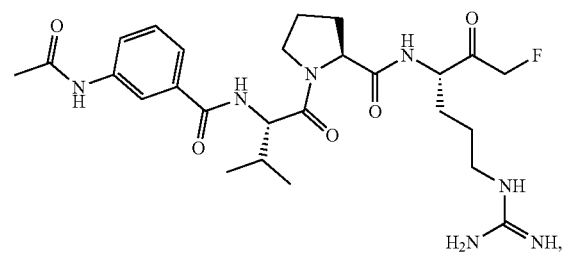
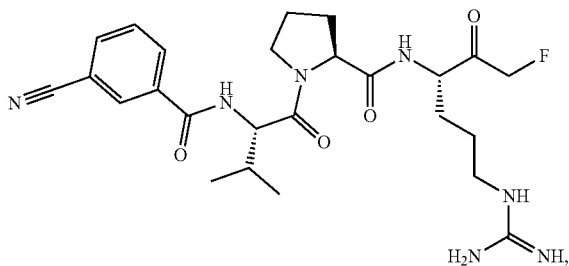
346
-continued
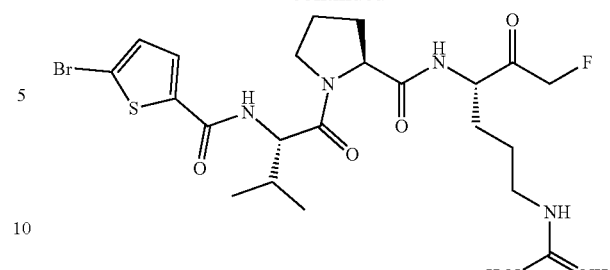
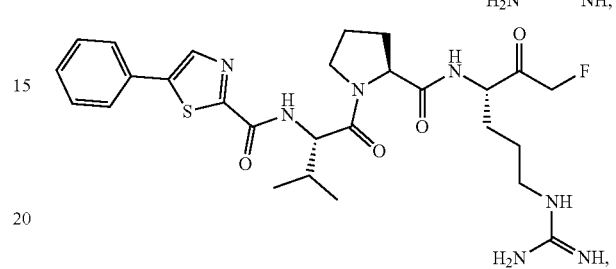
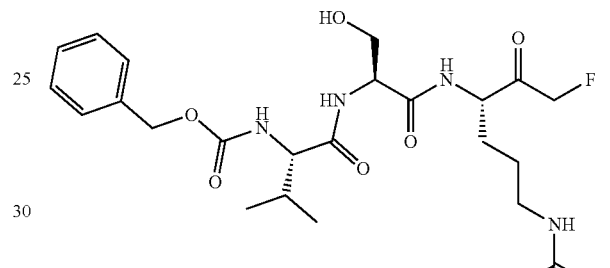
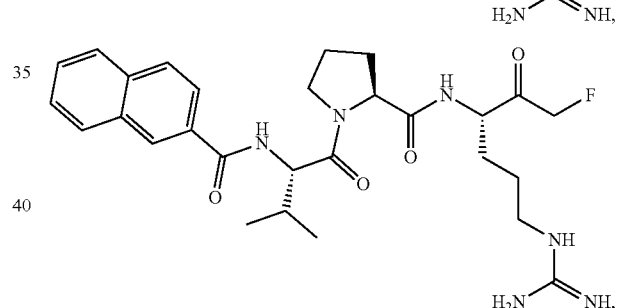
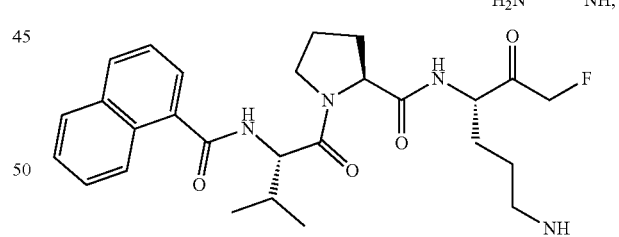
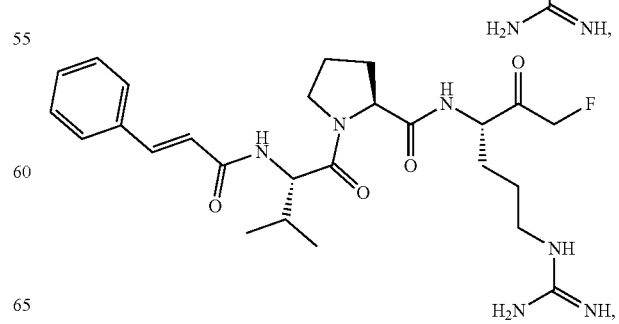

347
-continued
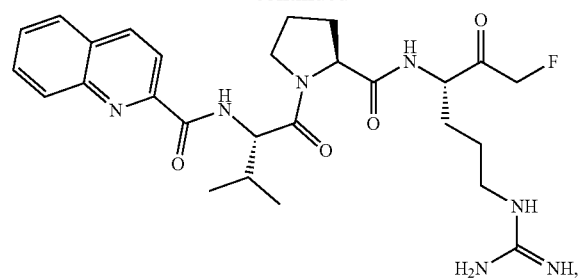
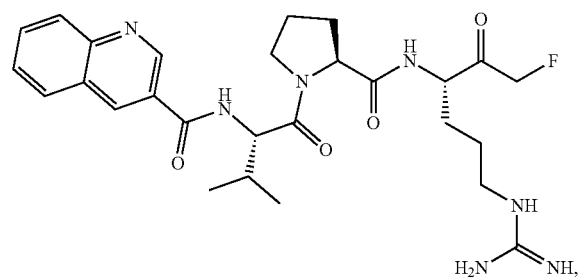
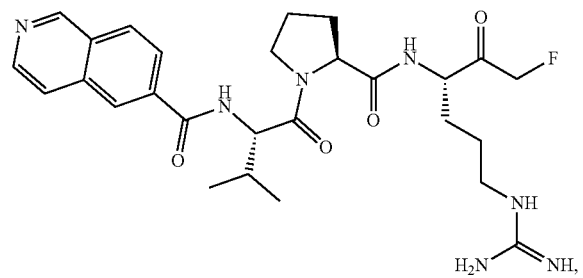
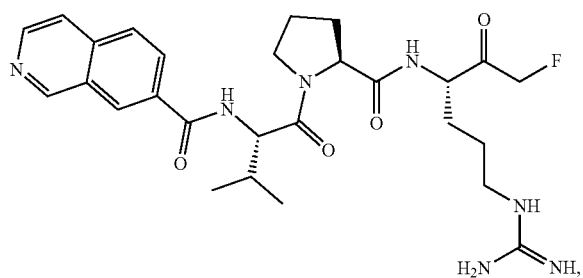
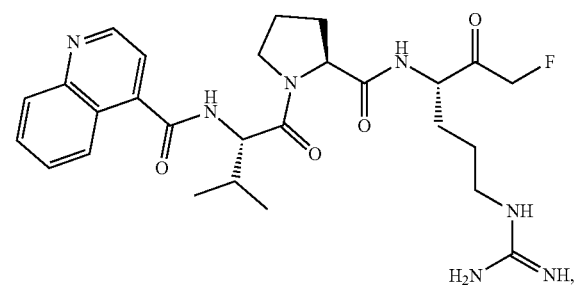
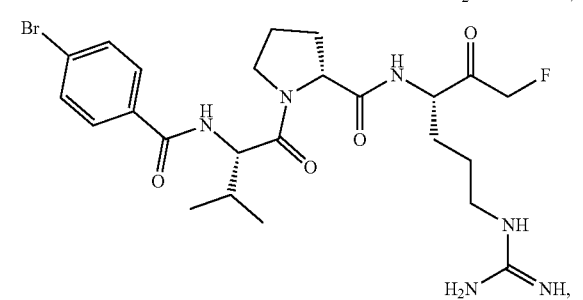
348
-continued
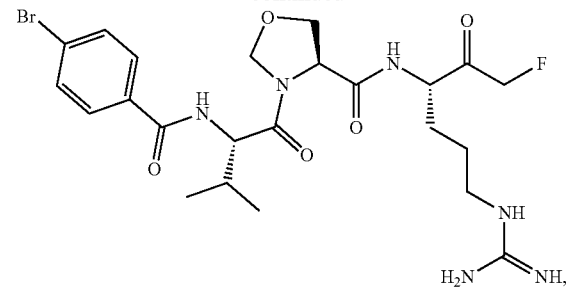
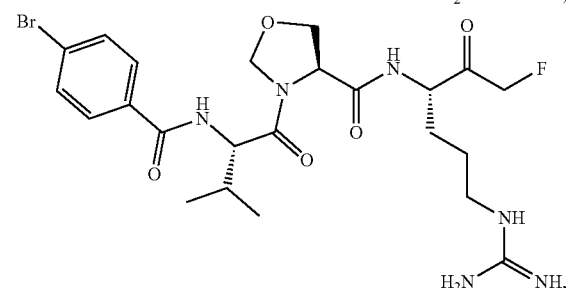
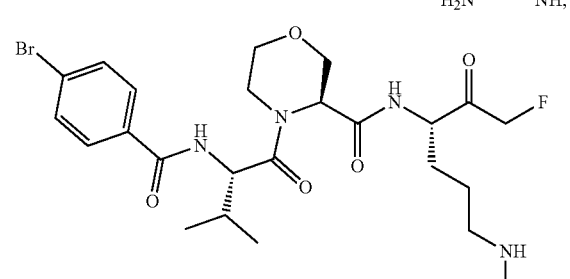
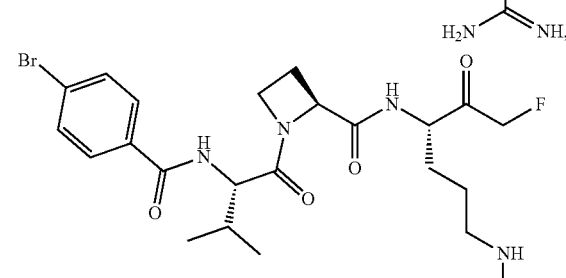
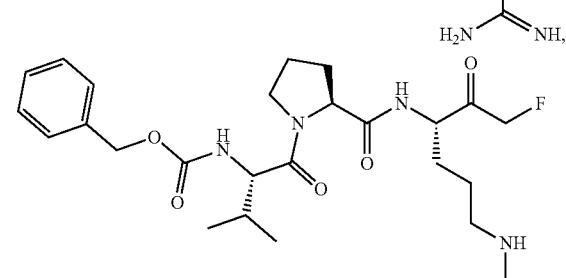
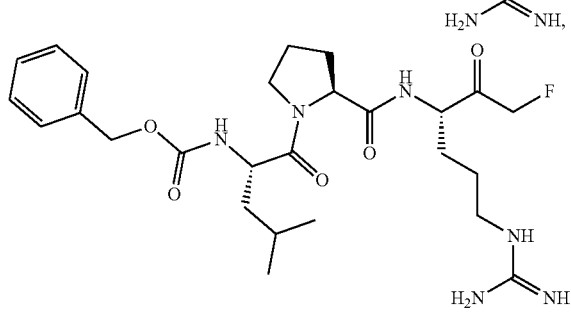

349
-continued
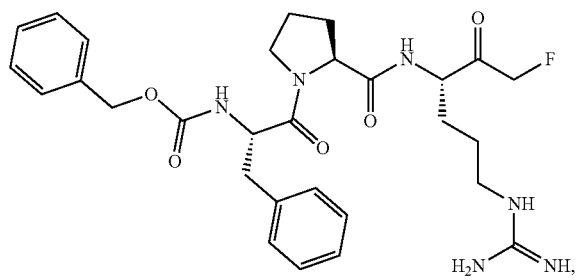
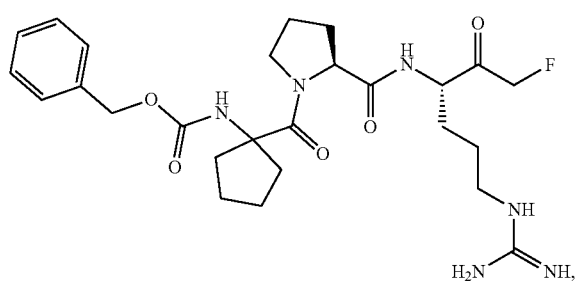
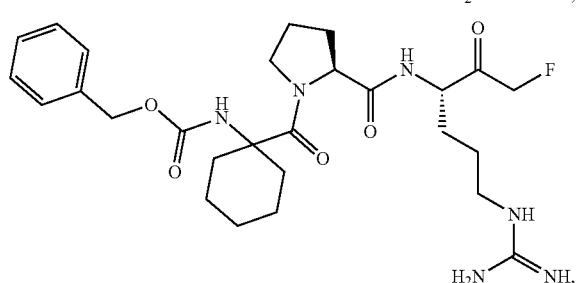
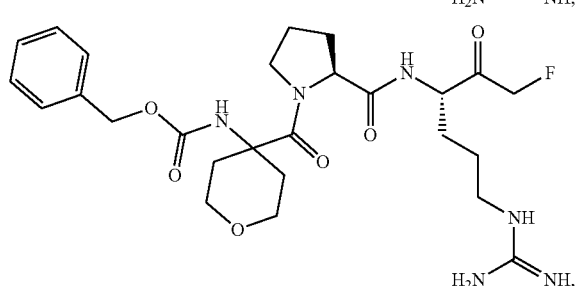
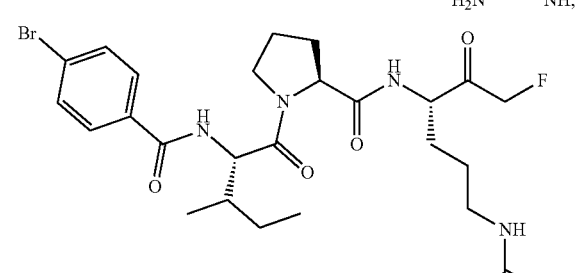
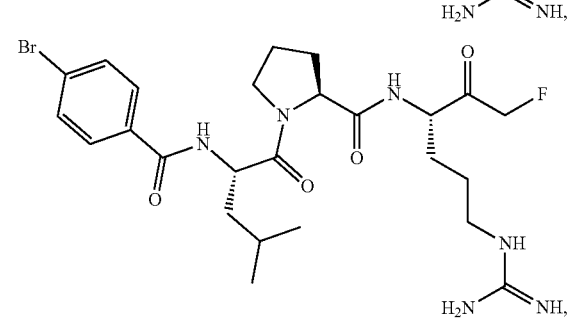
350
-continued
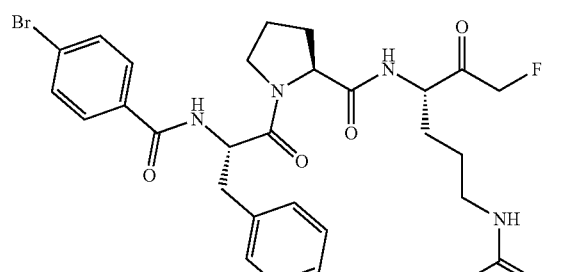
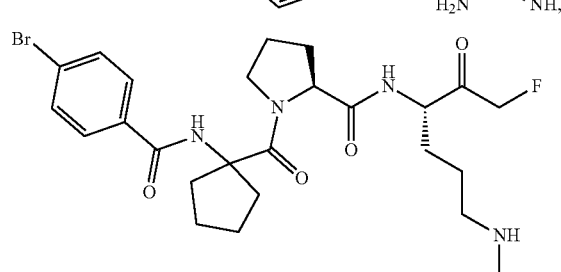
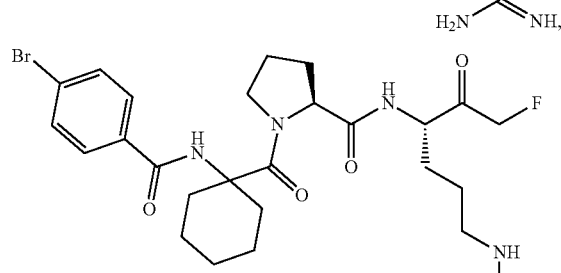
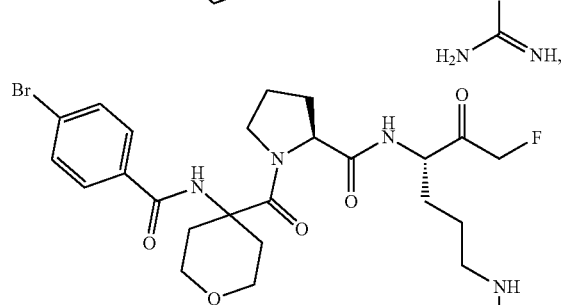
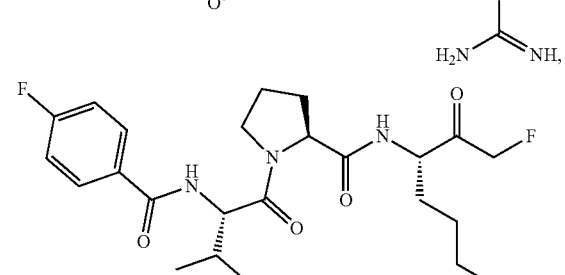
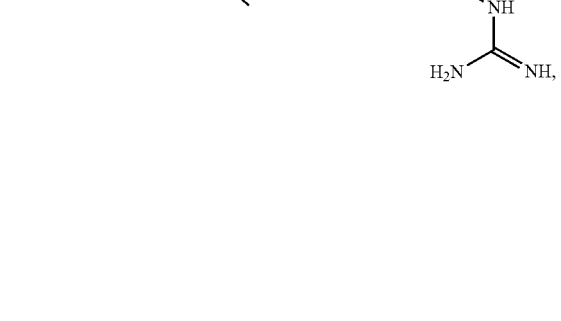

351
-continued
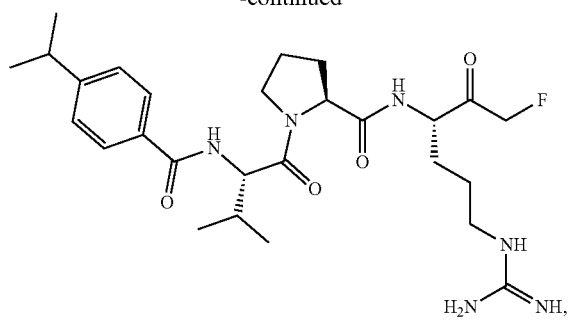
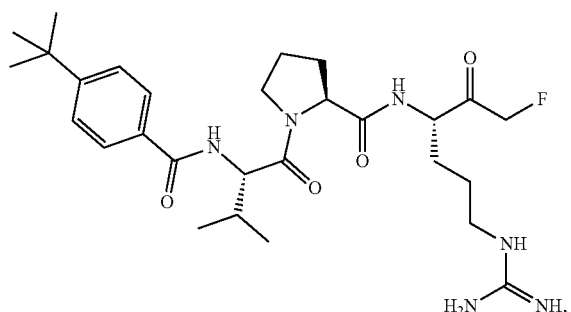
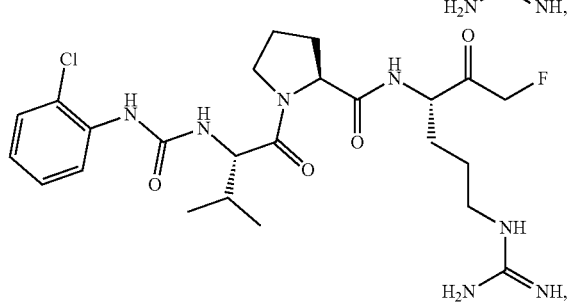
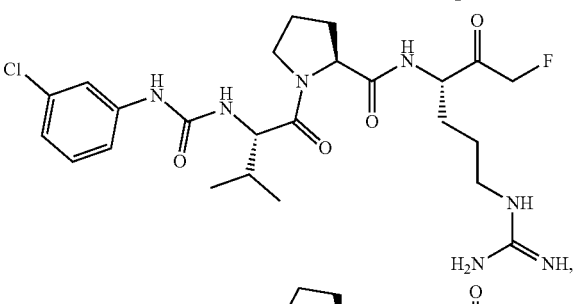
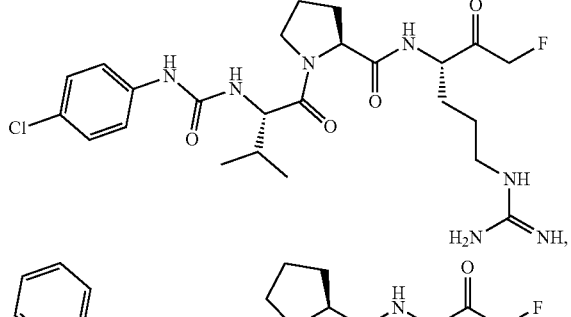
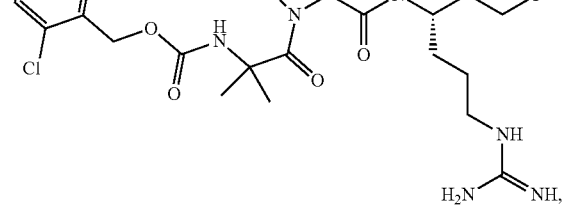
352
-continued
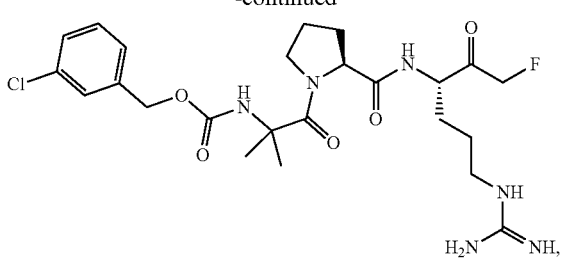
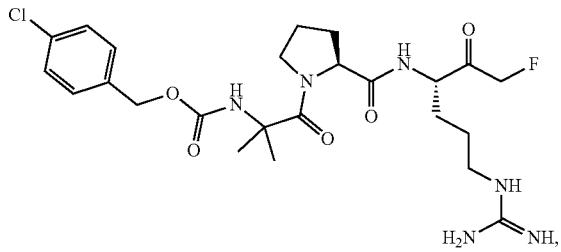
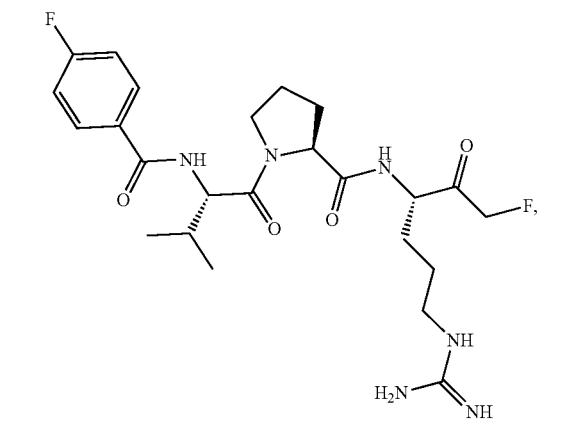
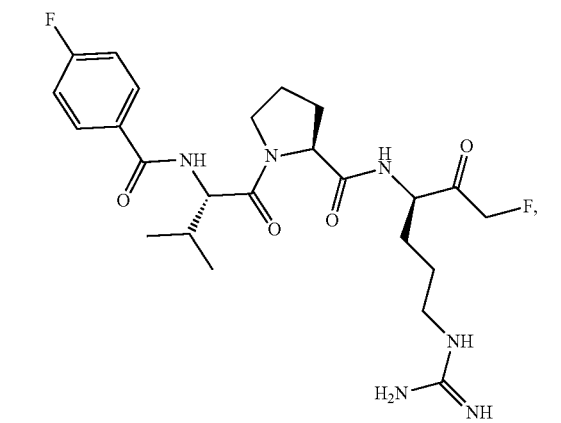

353
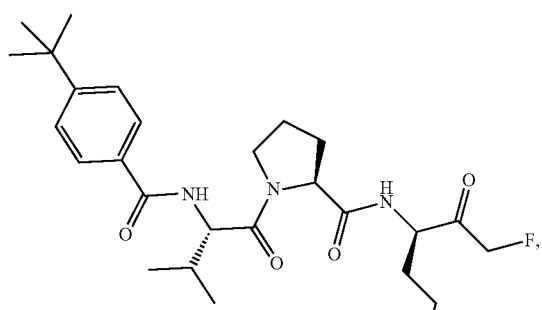
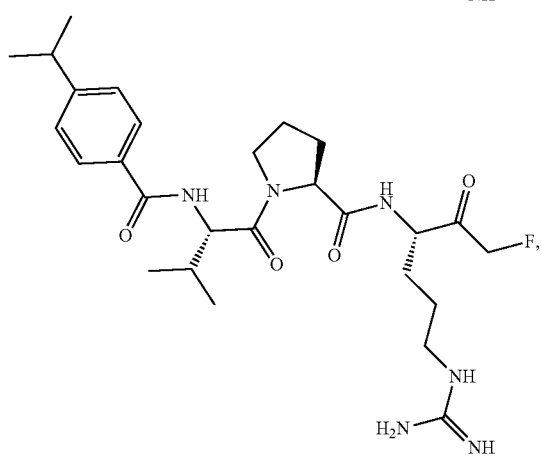
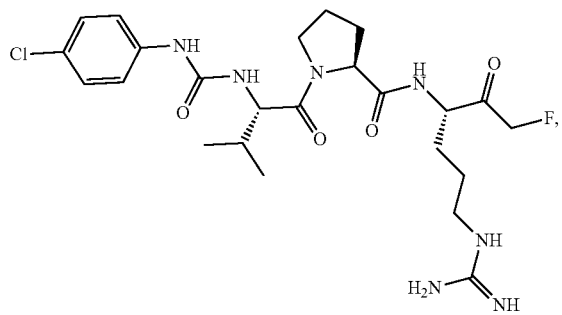
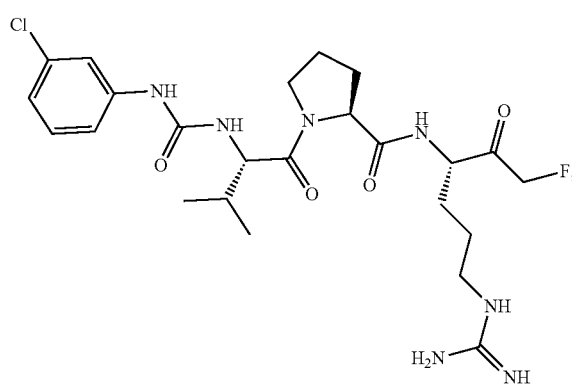
354
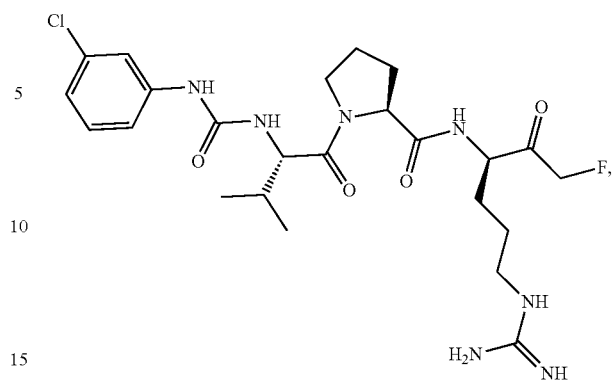
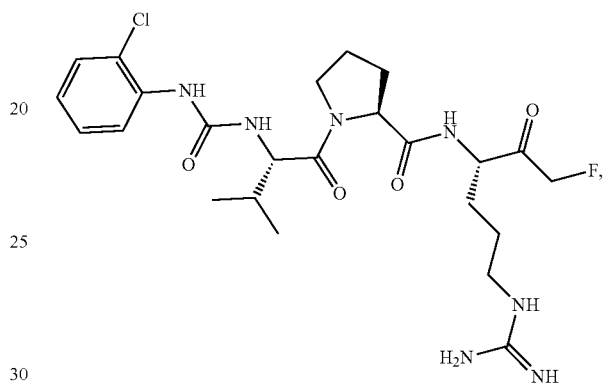
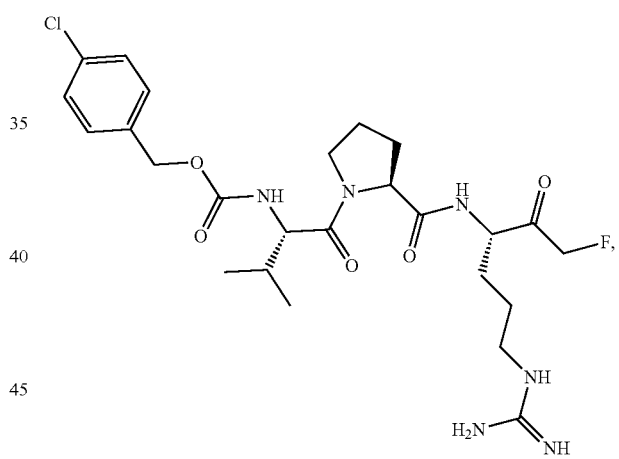
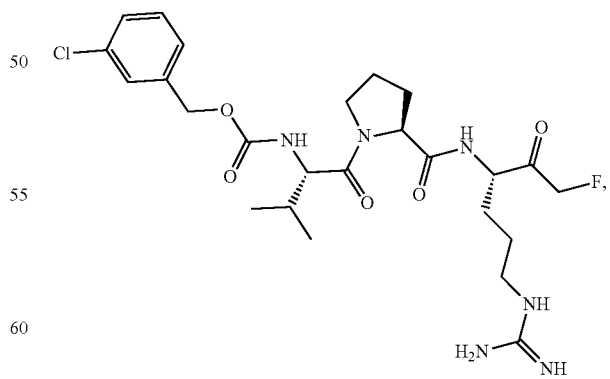

355
-continued
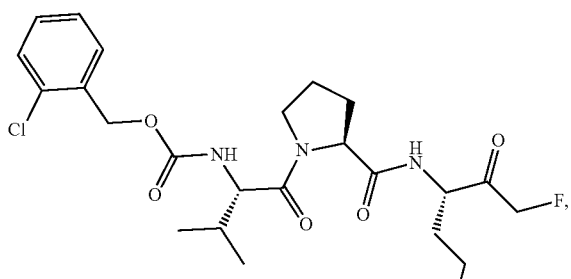
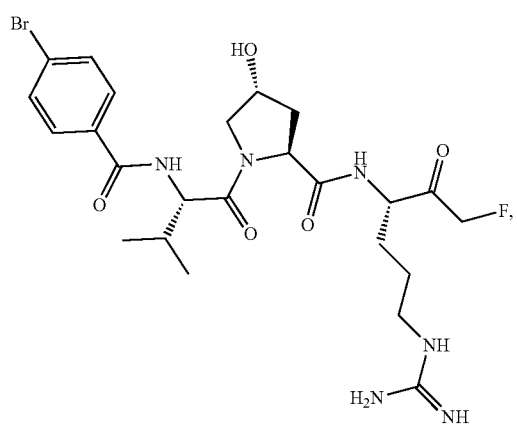
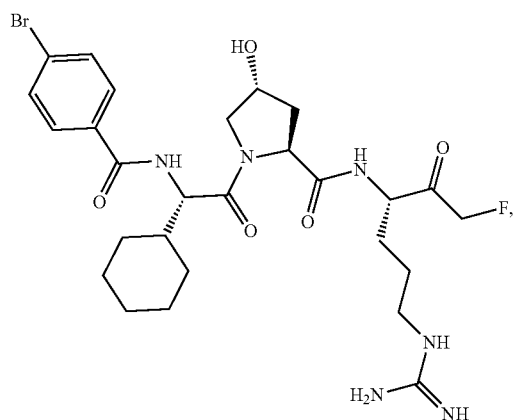
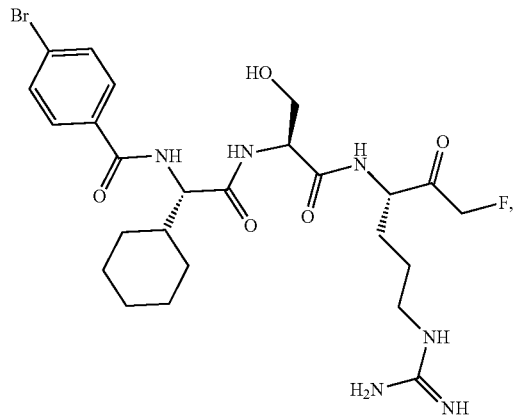
356
-continued
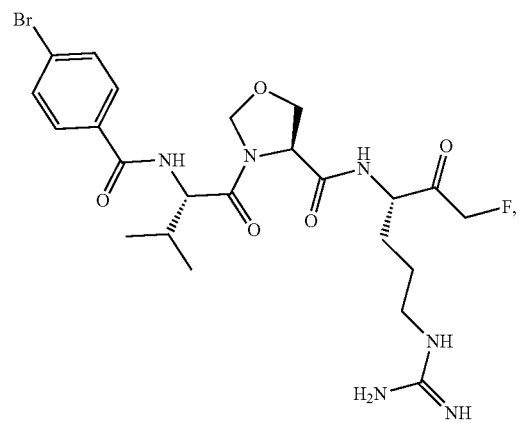
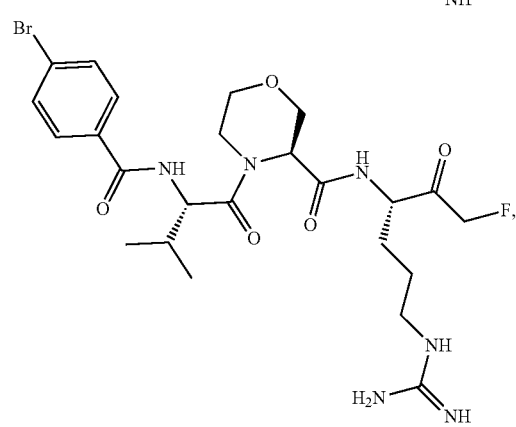
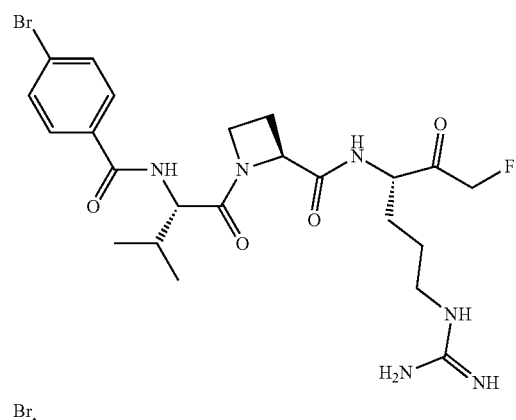
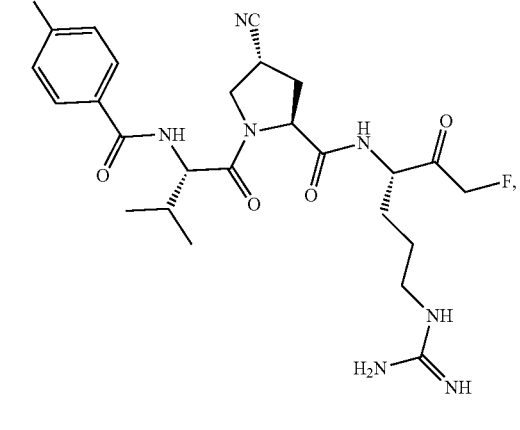

357
-continued
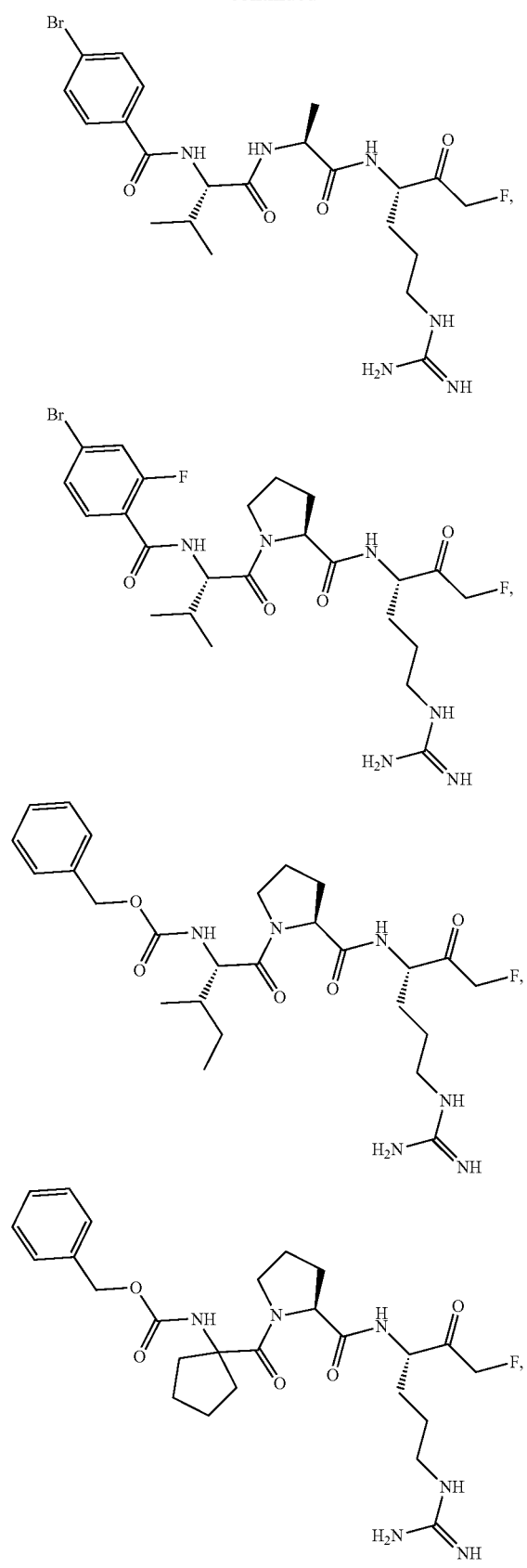
358
-continued
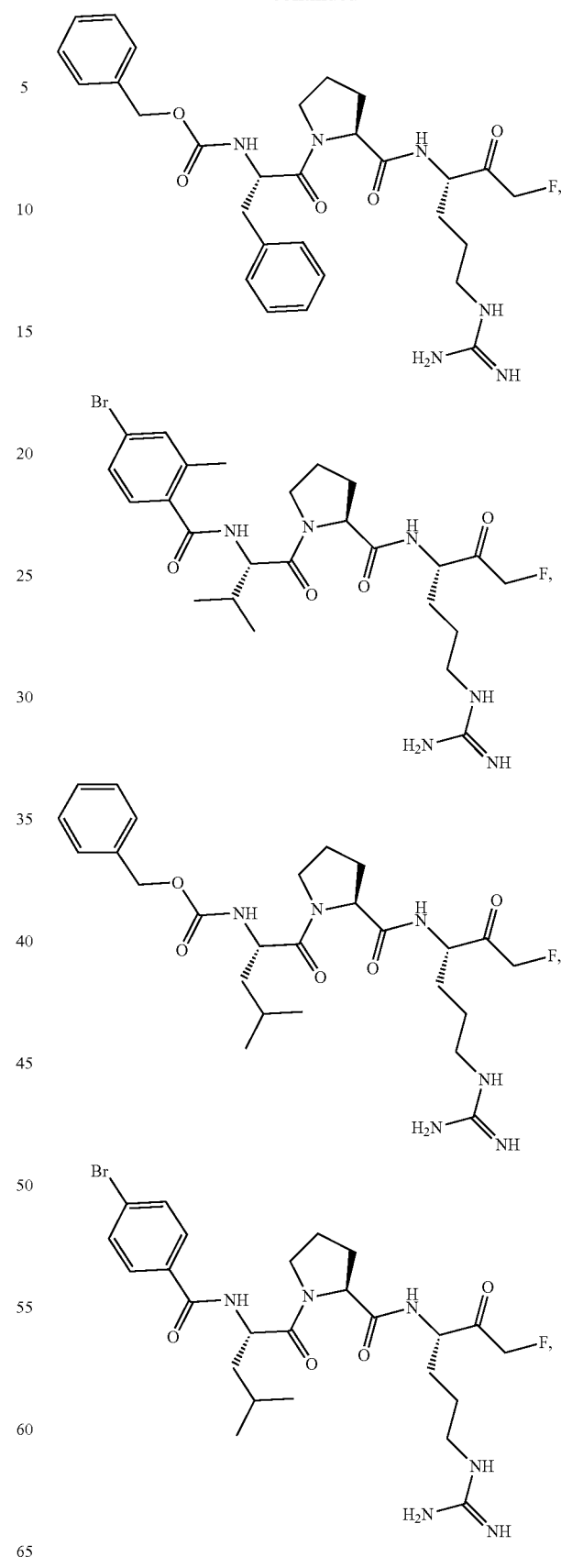

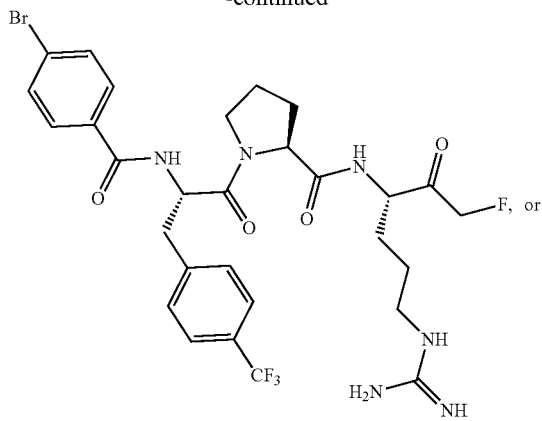

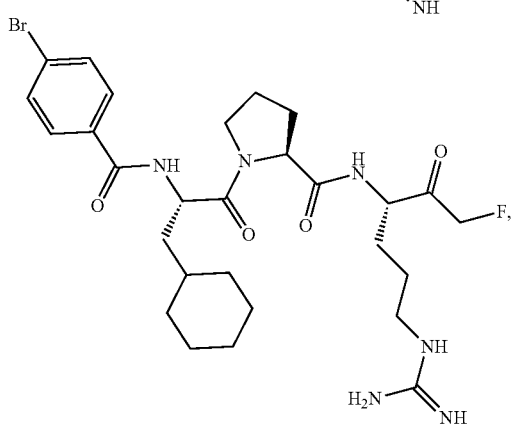

or a pharmaceutically acceptable salt or tautomer thereof.

16. The compound of claim 1, or a pharmaceutically acceptable salt, stereoisomer, or tautomer thereof, wherein $L^1$ is a bond.

17. The compound of claim 1, or a pharmaceutically acceptable salt, stereoisomer, or tautomer thereof, wherein $R^5$ is hydrogen.

18. The compound of claim 1, or a pharmaceutically acceptable salt, stereoisomer, or tautomer thereof, wherein $R^3$ and $R^N$ are joined to form an optionally substituted pyrrolidine ring.

19. The compound of claim 1, wherein the compound is of the formula:

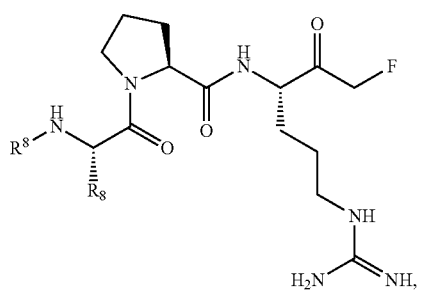

(I-C)

or a pharmaceutically acceptable salt or tautomer thereof.

20. The compound of claim 1, wherein the compound is of the formula:

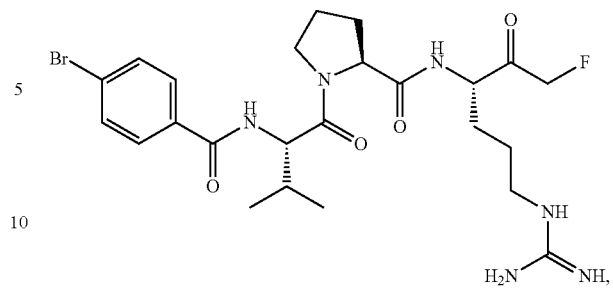

or a pharmaceutically acceptable salt or tautomer thereof.

21. A pharmaceutical composition comprising a compound of claim 1, or a pharmaceutically acceptable salt, stereoisomer, or tautomer thereof, and a pharmaceutically acceptable excipient.

22. A method of treating a proliferative disease comprising administering an effective amount of a compound of claim 1, or a pharmaceutically acceptable salt, stereoisomer, or tautomer thereof, to a subject in need thereof, wherein the proliferative disease is a cancer or autoimmune disease.

23. The method of claim 22, wherein the proliferative disease is a cancer.

24. The method of claim 23, wherein the cancer is lymphoma.

25. The method of claim 23, wherein the cancer is diffuse large B-cell lymphoma.

26. The method of claim 23, wherein the cancer is mantle cell lymphoma, primary effusion lymphoma, or MALT lymphoma.

27. The method of claim 23, wherein the cancer is leukemia.

28. The method of claim 23, wherein the cancer is chronic lymphocytic leukemia.

29. The method of claim 23, wherein the cancer is lung cancer.

30. The method of claim 22, wherein the proliferative disease is an autoimmune disease.

31. The method of claim 30, wherein the autoimmune disease is multiple sclerosis.

32. A method of inhibiting MALT1 or API2-MALT1 in a subject, the method comprising administering to the subject a compound of claim 1, or a pharmaceutically acceptable salt, stereoisomer, or tautomer thereof, wherein the subject is in need of treatment of a cancer or autoimmune disease.

33. A method of inhibiting cleavage of A20, RelB, Bcl10, CYLD, regnase-1, roquin-1, roquin-2, NIK, LIMA1α, or MALT1 in a subject, the method comprising administering to the subject a compound of claim 1, or a pharmaceutically acceptable salt, stereoisomer, or tautomer thereof, wherein the subject is in need of treatment of a cancer or autoimmune disease.

34. A method of preparing a compound of claim 1,
or a pharmaceutically acceptable salt, stereoisomer, or tautomer thereof, the method comprising coupling a carboxylic acid of Formula (D):

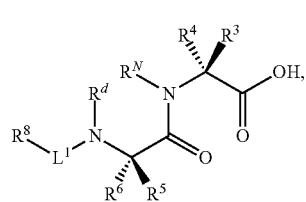
(D)
or a salt thereof, and a compound of Formula (E):
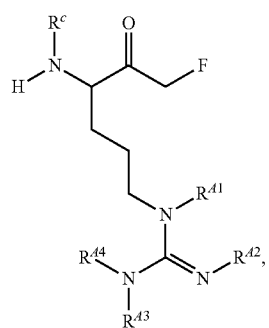
(E)
or a salt thereof.
* * * * *

UNITED STATES PATENT AND TRADEMARK OFFICE
CERTIFICATE OF CORRECTION

| | |
|---|---|
| PATENT NO. | : 10,711,036 B2 |
| APPLICATION NO. | : 15/755951 |
| DATED | : July 14, 2020 |
| INVENTOR(S) | : Nathanael S. Gray et al. |

It is certified that error appears in the above-identified patent and that said Letters Patent is hereby corrected as shown below:

In the Claims

In Claim 15, at Column 342, Lines 34-43, formula:

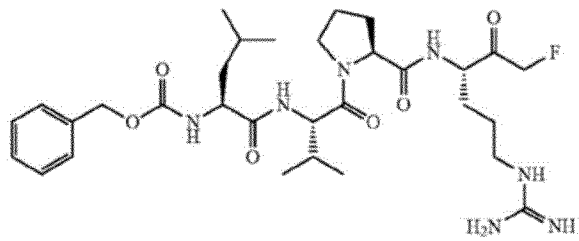

Should be replaced with the formula:

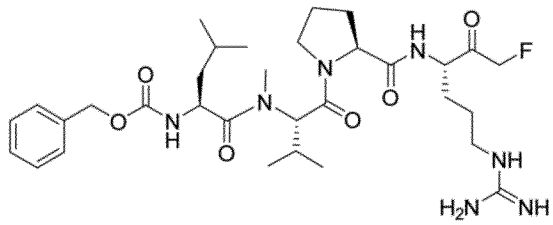

In Claim 15, at Column 348, Lines 12-23, formula:

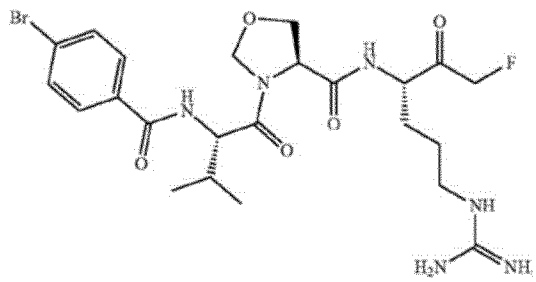

Signed and Sealed this
Sixth Day of October, 2020

Andrei Iancu
*Director of the United States Patent and Trademark Office*

Should be replaced with the formula:
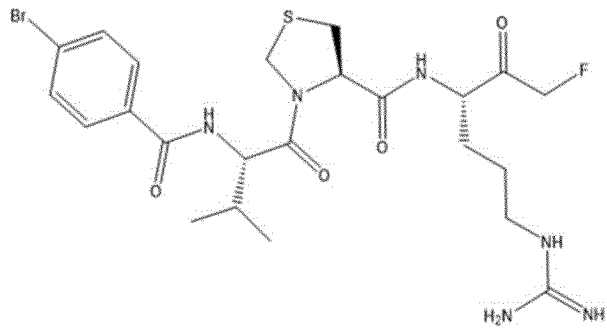
In Claim 15, at Column 348, in Lines 46-55, the formula:
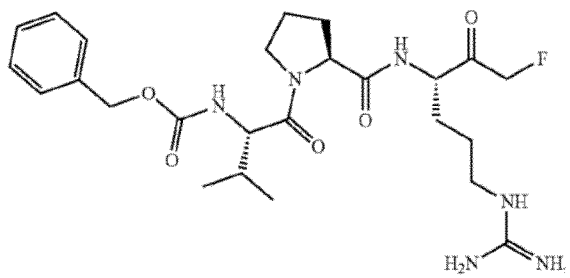
Should be replaced with the formula:
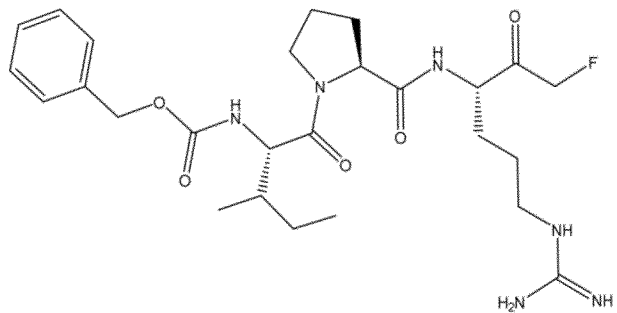
In Claim 15, at Column 353, in Lines 1-19, the formula:
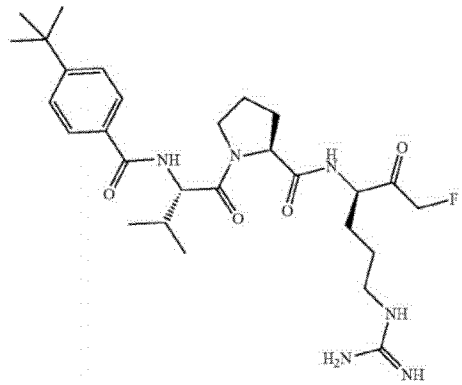
Should be replaced with the formula:

CERTIFICATE OF CORRECTION (continued)
U.S. Pat. No. 10,711,036 B2

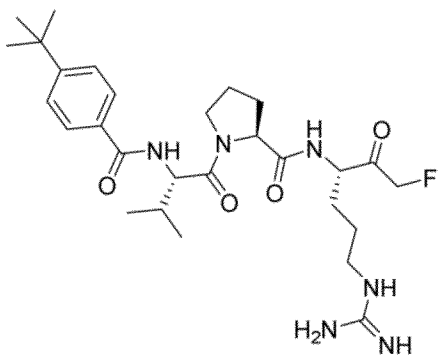

In Claim 19, at Column 359, in Lines 50-64, in formula (I-C), the formula:

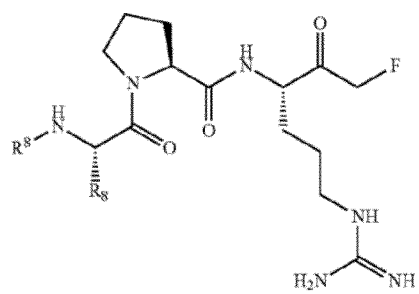

Should be replaced with the formula: